United States Patent
Rutaganira et al.

(10) Patent No.: US 11,208,411 B2
(45) Date of Patent: Dec. 28, 2021

(54) COMPOSITIONS AND METHODS FOR TREATING PARASITIC DISEASES

(71) Applicants: THE REGENTS OF THE UNIVERSITY OF CALIFORNIA, Oakland, CA (US); Washington University, St. Louis, MO (US)

(72) Inventors: Florentine Rutaganira, Woodland, CA (US); Kevan M. Shokat, San Francisco, CA (US); Laurence David Sibley, St. Louis, MO (US); James W. Janetka, St. Louis, MO (US)

(73) Assignees: The Regents of the University of California, Oakland, CA (US); Washington University, St. Louis, MO (US)

( * ) Notice: Subject to any disclaimer, the term of this patent is extended or adjusted under 35 U.S.C. 154(b) by 33 days.

(21) Appl. No.: 16/085,981

(22) PCT Filed: Mar. 17, 2017

(86) PCT No.: PCT/US2017/023085
§ 371 (c)(1),
(2) Date: Sep. 17, 2018

(87) PCT Pub. No.: WO2017/161344
PCT Pub. Date: Sep. 21, 2017

(65) Prior Publication Data
US 2020/0291030 A1     Sep. 17, 2020

Related U.S. Application Data
(60) Provisional application No. 62/309,803, filed on Mar. 17, 2016.

(51) Int. Cl.
*C07D 487/04* (2006.01)
*A61P 33/02* (2006.01)
*A61K 31/42* (2006.01)
*A61K 31/505* (2006.01)
*A61K 31/7056* (2006.01)

(52) U.S. Cl.
CPC ............ *C07D 487/04* (2013.01); *A61P 33/02* (2018.01); *A61K 31/42* (2013.01); *A61K 31/505* (2013.01); *A61K 31/7056* (2013.01)

(58) Field of Classification Search
CPC ....... C07D 487/04; A61P 33/02; A61K 31/42; A61K 31/505; A61K 31/7056
See application file for complete search history.

(56) References Cited

U.S. PATENT DOCUMENTS

| | | |
|---|---|---|
| 2010/0331297 A1 | 12/2010 | Bulawa et al. |
| 2011/0275651 A1 | 11/2011 | Dar et al. |
| 2013/0018040 A1 | 1/2013 | Van Voorhis et al. |

OTHER PUBLICATIONS

STN Registry database entry for CAS RN 1604800-88-5, entry date of May 14, 2014, Accessed Apr. 10, 2021.*
Extended European Search Report dated Jul. 11, 2019, for EP Patent Application No. 17767680.6, 7 pages.
Traxler, P. et al. (Oct. 24, 1997). "Use of a pharmacophore model for the design of EGF-R tyrosine kinase inhibitors: 4-(phenylamino)pyrazolo[3,4-d]pyrimidines," *J Med Chem* 40(22):3601-3616.
Larson, E.T. et al. (Mar. 22, 2012, e-published Mar. 13, 2012). "Multiple determinants for selective inhibition of apicomplexan calcium-dependent protein kinase CDPK1," *J Med Chem* 55(6):2803-2810.
International Search Report dated Jul. 27, 2017, for PCT Application No. PCT/US2017/23085, filed Mar. 17, 2017, 4 pages.
Written Opinion dated Jul. 27, 2017, for PCT Application No. PCT/US2017/23085, filed Mar. 17, 2017, 7 pages.

* cited by examiner

*Primary Examiner* — Alicia L Otton
(74) *Attorney, Agent, or Firm* — Mintz, Levin, Cohn, Ferris, Glovsky and Popeo, P.C.

(57) ABSTRACT

Disclosed herein, inter alia, are compositions and methods for treating parasitic diseases.

20 Claims, No Drawings

COMPOSITIONS AND METHODS FOR TREATING PARASITIC DISEASES

CROSS-REFERENCES TO RELATED APPLICATIONS

This application claims the benefit of International Application No. PCT/US2017/023085 filed Mar. 17 2017, U.S. Provisional Application No. 62/309,803, filed Mar. 17, 2017, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant no. R01 AI094098, awarded by the National Institutes of Health. The government has certain rights in the invention.

BACKGROUND

The Apicomplexa is a large phylum containing parasites that are the causative agents for many serious human and animal diseases. Apicomplexa are unicellular spore-forming organisms that have multiple life stages. In the case of *Toxoplasma gondii*, infectious sporozoites contained in oocysts, which are shed from cats, and bradyzoites found in undercooked meat, are infectious for humans. Human pathogens within the Apicomplexa include *Plasmodium* spp., (e.g. *Plasmodium falciparum, Plasmodium vivax*) *Toxoplasma gondii, Babesia* spp. (e.g. *Babesia microti, Babesia bigemina*), *Cyclospora cayetanensis, Isospora belli, Sarcocystis neurona*, and *Cryptosporidium* spp. (e.g., *Cryptosporidium parvum* or *Cryptosporidium hominis*), which cause malaria, toxoplasmosis, babesiosis, cyclosporiasis, isosporiasis, sarcocystosis, and cryptosporidiosis respectively. Treatment and prevention of these and other Apicomplexa-associated diseases have been challenging and additional treatments are needed. Disclosed herein, inter alia, are solutions to these and other problems in the art.

BRIEF SUMMARY OF THE INVENTION

In an aspect is provided a compound having the formula:

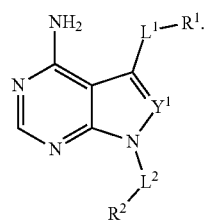

(I)

$Y^1$ is —N═ or —CH═. $R^1$ is substituted or unsubstituted aryl or substituted or unsubstituted heteroaryl. $R^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^1$ is —SO—, —SO$_2$—, —O—, —S—, —N(R$^3$)—, —B(R$^6$)— (i.e. $L^1$ includes a boron), or substituted or unsubstituted $C_1$-$C_3$ alkylene. $L^2$ is a bond, —O—, —S—, —N(R$^7$)—, —B(R$^8$)— (i.e. $L^2$ includes a boron), substituted or unsubstituted alkylene, or substituted or unsubstituted heteroalkylene. $R^3$ is hydrogen, halogen, —SO$_2$CH$_3$, —CN, —COOH, —COCH$_3$, —CX$^3_3$, substituted or unsubstituted alkyl, or substituted or unsubstituted heteroalkyl; $X^3$ is independently halogen. $R^6$ is hydrogen, halogen, —CX$^6_3$, —CHX$^6_2$, —CH$_2$X$^6$, —OCX$^6_3$, —OCH$_2$X$^6$, —OCHX$^6_2$, —CN, —SH, —SO$_2$NH$_2$, —NHC(O)NH$_2$, —N(O), —N(O)$_2$, —NH$_2$, —C(O)H, —C(O)O H, —C(O)NH$_2$, —OH, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen, —CN, —COOH, —CX$^7_3$, substituted or unsubstituted alkyl (e.g., $C_1$-$C_8$ alkyl, $C_1$-$C_6$ alkyl, $C_1$-$C_4$ alkyl, $C_1$-$C_2$ alkyl, unsubstituted $C_1$-$C_8$ alkyl, unsubstituted $C_1$-$C_6$ alkyl, unsubstituted $C_1$-$C_4$ alkyl, or unsubstituted $C_1$-$C_2$ alkyl), or substituted or unsubstituted heteroalkyl (e.g., 2 to 8 membered heteroalkyl, 2 to 6 membered heteroalkyl, 2 to 4 membered heteroalkyl, 2 to 3 membered heteroalkyl, unsubstituted 2 to 8 membered heteroalkyl, unsubstituted 2 to 6 membered heteroalkyl, unsubstituted 2 to 4 membered heteroalkyl, or unsubstituted 2 to 3 membered heteroalkyl). $R^8$ is hydrogen, halogen, —CX$^8_3$, —CHX$^8_2$, —CH$_2$X$^8$, —OCX$^8_3$, —OCH$_2$X$^8$, —OCHX$^8_2$, —CN, —SH, —SO$_2$NH$_2$, —NHC(O)NH$_2$, —N(O), —N(O)$_2$, —NH$_2$, —C(O)H, —C(O)OH, —C(O)NH$_2$, —OH, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $X^6$ is independently —F, —Cl, —Br, or —I. $X^7$ is independently —F, —Cl, —Br, or —I. $X^8$ is independently —F, —Cl, —Br, or —I.

In another aspect is provided a pharmaceutical composition including a pharmaceutically acceptable excipient and a compound, or pharmaceutically acceptable salt thereof, as described herein.

In an aspect is provided a method of treating an apicomplexan infection (e.g., *Babesia* spp., *Plasmodium* spp., *Cryptosporidium parvum, Cryptosporidium hominis, Cyclospora cayetanensis, Isospora belli, Neospora caninum, Sarcocystis neurona*, or *Toxoplasma gondii* infection), the method including administering to a subject in need thereof an effective amount of a compound described herein.

In an aspect is provided a method of treating an apicomplexan associated disease, the method including administering to a subject in need thereof an effective amount of a compound described herein.

In an aspect is provided a method of inhibiting calcium dependent protein kinase (CDPK) activity, the method including contacting the calcium dependent protein kinase with an effective amount of a compound described herein.

In an aspect is provided a method of inhibiting *Toxoplasma gondii* calcium dependent protein kinase 1 (TgCDPK1) activity, the method including contacting the calcium dependent protein kinase 1 with an effective amount of a compound described herein.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, B, or S), and wherein the nitrogen and sulfur atoms may optionally be oxidized, and the nitrogen heteroatom may optionally be quaternized. The heteroatom(s) (e.g., O, N, P, S, B, or Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, B, or P). A heteroalkyl moiety may include two optionally different heteroatoms (e.g., O, N, S, Si, B, or P). A heteroalkyl moiety may include three optionally different heteroatoms (e.g., O, N, S, Si, B, or P). A heteroalkyl moiety may include four optionally different heteroatoms (e.g., O, N, S, Si, B, or P). A heteroalkyl moiety may include five optionally different heteroatoms (e.g., O, N, S, Si, B, or P). A heteroalkyl moiety may include up to 8 optionally different heteroatoms (e.g., O, N, S, Si, B, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, B, or P). A heterocycloalkyl moiety may include two optionally different ring heteroatoms (e.g., O, N, S, Si, B, or P). A heterocycloalkyl moiety may include three optionally different ring heteroatoms (e.g., O, N, S, Si, B, or P). A heterocycloalkyl moiety may include four optionally different ring heteroatoms (e.g., O, N, S, Si, B, or P). A heterocycloalkyl moiety may include five optionally different ring heteroatoms (e.g., O, N, S, Si, B, or P). A heterocycloalkyl moiety may include up to 8 optionally different ring heteroatoms (e.g., O, N, S, Si, B, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S($O_2$)R', —S($O_2$)NR'R", —NRSO$_2$R', —NR'NR"R''', —ONR'R", —NR'C=(O)NR''NR'''R'''', —CN, —NO$_2$, in a number ranging from zero to (2 m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —NR'NR''R''', —ONR'R'', —NR'C=(O)NR''NR'''R'''', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R'', R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C''R''R''')$_d$—, where s and d are independently—Integers of from 0 to 3, and X' is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), boron (B), and silicon (Si).

A substituent group, as used herein, may be a group selected from the following moieties:

(A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted alkyl, unsubstituted heteroalkyl, unsubstituted cycloalkyl, unsubstituted heterocycloalkyl, unsubstituted aryl, unsubstituted heteroaryl and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_5$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cell, in the extracellular space near a cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)-for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol " ⌇ " denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with Apicomplexa infection (e.g., *Plasmodium* spp., *Toxoplasma gondii*, or *Cryptosporidium parvum, Cryptosporidium hominis*). Certain methods described herein may treat diseases associated with Apicomplexa infection (e.g., *Plasmodium* spp., *Toxoplasma gondii*, or *Cryptosporidium parvum, Cryptosporidium hominis*) by inhibiting an Apicomplexa (e.g., *Plasmodium* spp., *Toxoplasma gondii*, or *Cryptosporidium parvum, Cryptosporidium hominis*) protein activity (e.g. CDPK1 (e.g., TgCDPK1)). Certain methods described herein may treat diseases associated with CDPK1 (e.g., TgCDPK1) activity by inhibiting CDPK1 (e.g., TgCDPK1) activity. For example, certain methods herein treat toxoplasmosis. For example certain methods herein treat toxoplasmosis by decreasing a symptom of toxoplasmosis. Symptoms of toxoplasmosis would be known or may be determined by a person of ordinary skill in the art. For example, certain methods herein treat an infectious disease (e.g., Apicomplexa infection, *Toxoplasma gondii* infection, or toxoplasmosis). The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A therapeutically effective amount may be administered in one or more administrations. A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. toxoplasmosis or apicomplexan infection) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with CDPK1 (e.g., TgCDPK1) activity may be treated with an agent (e.g. compound as described herein) effective for decreasing the level of CDPK1 (e.g., TgCDPK1) activity. For example, a disease associated with Apicomplexa infection (e.g., *Plasmodium* spp., *Toxoplasma gondii*, *Cryptosporidium parvum*, or *Cryptosporidium hominis*) may be treated with an agent (e.g. compound as described herein) effective for reducing the viability, proliferation, survival, or spread of an Apicomplexa organism (e.g., *Plasmodium* spp., *Toxoplasma gondii*, *Cryptosporidium parvum*, or *Cryptosporidium hominis*).

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule. In embodiments, a modulator is an anti-infectious disease agent. In embodiments, a modulator is a modulator of an Apicomplexa infection (e.g., *Plasmodium* spp., *Toxoplasma gondii*, *Cryptosporidium parvum*, or *Cryptosporidium hominis*). In embodiments, a modulator is a modulator of the level of CDPK1 (e.g., TgCDPK1) activity. In embodiments, a modulator is a CDPK1 (e.g., TgCDPK1) activity inhibitor.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having a symptom of Apicomplexa infection (e.g., *Plasmodium* spp., *Toxoplasma gondii*, *Cryptosporidium parvum*, or *Cryptosporidium hominis*). Cryptosporidiosis is associated with diarrheal disease especially in immunocompromised patients and young children. Symptoms include fluid loss, chronic wasting, failure to thrive and malnutrition. Acute toxoplasmosis is associated with swollen lymph nodes, muscle aches, fever, and fatigue. In those with weakened immune systems, symptoms can be more severe including headache, confusion, poor motor coordination, seizures, and impaired vision. In infants that are infected congenitally, symptoms can include intracranial calcification, chorioretinitis leading to later development of impaired vision, hydrocephalus, and neurological sequelae (seizures, delayed development of cognitive or motor skills). Chronic toxoplasmosis is associated with tissue cysts that are found in muscle and the central nervous system. Chronic toxoplasmosis has been associated with increased risk of schizophrenia, obsessive compulsive disorder, addiction, and biopolar disorder. Chronic infection also posses a risk of reactivation with loss of immunity resulting in development of toxoplasmic encephalitis, a potentially life threatening condition. Malaria is associated with high fever, shaking chills, sweating, headache, diarrhea, anemia, and seizures. Pregnancy associated malaria can lead to low birth weight and failure to thrive. Cerebral malaria can lead to coma and sudden death. In embodiments, the disease is toxoplasmosis. In some embodiments, the disease is malaria. In some embodiments, the disease is cryptosporidiosis.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. Nucleic acids containing one or more carbocyclic sugars are also included within one definition of nucleic acids.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to modify conformation and function of a protein.

Example of Amino Acid Classification

Small/Aliphatic residues: Gly, Ala, Val, Leu, Ile
Cyclic Imino Acid: Pro
Hydroxyl-containing Residues: Ser, Thr
Acidic Residues: Asp, Glu
Amide Residues: Asn, Gln
Basic Residues: Lys, Arg
Imidazole Residue: His
Aromatic Residues: Phe, Tyr, Trp
Sulfur-containing Residues: Met, Cys In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, 2nd ed. Lubert Stryer ed. (Stanford University); Henikoff et al., *Proc. Nat'l Acad. Sci. USA* (1992) 89:10915-10919; Lei et al., *J. Biol. Chem.* (1995) 270(20):11882-11886).

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

Following expression, the proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a cell expressing the proteins. Typically, a polypeptide is purified when it constitutes at least 60 (e.g., at least 65, 70, 75, 80, 85, 90, 92, 95, 97, or 99) %, by weight, of the total protein in a sample.

An amino acid residue in a protein "corresponds" to a given residue when it occupies the same essential structural position within the protein as the given residue. For example, a selected residue in a selected protein corresponds to a residue when the selected residue occupies the same essential spatial or other structural relationship as a specified residue relative the rest of the protein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, anti-neurodegenerative disease agent, anti-inflammatory disease agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer or neurodegenerative disease). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of toxoplasmosis or an apicomplexa infection), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

The term "calcium-dependent protein kinase" or "CDPK" refers to the calcium-dependent protein kinase of an Apicomplexa species. Included in the term "calcium-dependent protein kinase" or "CDPK" are the wildtype, natural variants, and mutant forms of the protein. In embodiments, "calcium-dependent protein kinase" or "CDPK" refers to the protein associated with UniProt KB-P62343, UniProt S7UHK8, UniProt KB S7UHK8 TOXGO, UniProt KB-Q6S4W0, UniProt KB-S8EXE8, or UniProtKB-S8EQY1. In embodiments, the reference numbers immediately above refer to the protein, and associated nucleic acids, known as of the date of filing of this application. In embodiments, the CDPK is CDPK1, CPKD2, or CDPK6.

The term "calcium-dependent protein kinase 1" or "CDPK1" refers to the calcium-dependent protein kinase of Apicomplexa. In embodiments, "calcium-dependent protein kinase 1" or "CDPK1" or refers to the *Toxoplasma gondii* protein (TgCDPK1). Included in the term "calcium-dependent protein kinase 1" or "CDPK1" are the wildtype, natural variants, and mutant forms of the protein. In embodiments, "calcium-dependent protein kinase 1" or "CDPK1" refers to the protein associated with UniProt S7UHK8 and/or UniProtKB S7UHK8_TOXGO. In embodiments, the reference numbers immediately above refer to the protein, and associated nucleic acids, known as of the date of filing of this application. In embodiments, the CDPK1 is a CDPK1 protein from *Pasmodium falciparum* (e.g., UniProt KB-P62343). In embodiments, the CDPK1 is a CDPK1 protein from *Cryptosporidium parvum* (e.g., UniProt KB-Q6S4W0). In embodiments, the CDPK1 is a CDPK1 protein from *Toxoplasma gondii* (e.g., UniProt S7UHK8, or S7UHK8_TOXGO).

As used herein, the term "infectious disease" refers to a disease or condition related to the presence of an organism (the agent or infectious agent) within or contacting the subject or patient. Examples include a bacterium, protozoa, protist, fungus, virus, or other microorganism. A "protist infectious disease" is an infectious disease wherein the organism is a protist. The terms "parasitic infectious disease," "parasitic disease," and "parasite infectious disease" are interchangeable and refer to a disease caused by an infectious agent that is a parasite, such as a protist or protozoa. In embodiments, a parasitic infectious disease is caused by an Apicomplexa (e.g., *Babesia, Plasmodium* spp., *Cryptosporidium parvum, Cryptosporidium hominis, Cyclospora cayetanensis, Isospora belli, Neospora caninum, Sarcocystis neurona*, or *Toxoplasma gondii*). Examples of parasitic infectious diseases include babesiosis, malaria, neosporosis, cryptosporidiosis, cyclosporiasis, isosporiasis, neosporosis, sarcocystosis, and toxoplasmosis. In embodiments, the infectious agent is *Toxoplasma gondii* and the infectious disease is toxoplasmosis.

The term "Apicomplexa infection" as used herein is used in accordance with its plain ordinary meaning and refers to a disease or condition related to the presence of an Apicomplexa organism (the agent or infectious agent) within or contacting the subject or patient. Apicomplexa organism are eukaryotic organism (e.g., parasite or protist) which may be characterized according to cytoskeletal structures such as an apical complex or structures during their life cycle (e.g., the tachyzoites, bradyzoites, oocysts, sporocysts, sporozoites, or enteroepithelial) stage.

Non-limiting examples of apicomplexan genera include *Babesia* (e.g., *Babesia bigemina, Babesia bovis, Babesia caballi, Babesia canis, Babesia cati, Babesia crassa, Babesia divergens, Babesia duncani, Babesia felis, Babesia gibsoni, Babesia herpailuri, Babesia jakimovi, Babesia major, Babesia microti, Babesia motasi, Babesia ovate, Babesia ovis, Babesia pantherae,* or *Babesia* sp. 'north carolina dog'), *Plasmodium* (e.g., *Plasmodium accipiteris, Plasmodium achiotense, Plasmodium achromaticum, Plasmodium acuminatum, Plasmodium adleri, Plasmodium adunyinkai, Plasmodium aegyptensis, Plasmodium aeuminatum, Plasmodium agamae, Plasmodium alaudae, Plasmodium alloelongatum, Plasmodium anasum, Plasmodium anomaluri, Plasmodium arachniformis, Plasmodium ashfordi, Plasmodium atheruri, Plasmodium audaciosum, Plasmodium auffenbergi, Plasmodium aurulentum, Plasmodium australis, Plasmodium attenuatum, Plasmodium azurophilum, Plasmodium billbrayi, Plasmodium billcollinsi, Plasmodium balli, Plasmodium bambusicolai, Plasmodium basilisci, Plasmodium beaucournui, Plasmodium beebei, Plasmodium beltrani, Plasmodium berghei, Plasmodium bertii, Plasmodium bigueti, Plasmodium bioccai, Plasmodium biziurae, Plasmodium blacklocki, Plasmodium booliati, Plasmodium bouillize, Plasmodium bowiei, Plasmodium brodeni, Plasmodium brasilianum, Plasmodium brumpti, Plasmodium brygooi, Plasmodium bubalis, Plasmodium bucki, Plasmodium buteonis, Plasmodium caloti, Plasmodium capistrani, Plasmodium carmelinoi, Plasmodium cathemerium, Plasmodium caucasica, Plasmodium cephalophi, Plasmodium cercopitheci, Plasmodium chabaudi, Plasmodium chiricahuae, Plasmodium circularis, Plasmodium circumflexum, Plasmodium clelandi, Plasmodium cnemaspi, Plasmodium cnemidophori, Plasmodium coatneyi, Plasmodium coggeshalli, Plasmodium coluzzii, Plasmodium colombiense, Plasmodium columbae, Plasmodium cordyli, Plasmodium corradettii, Plasmodium coturnixi, Plasmodium coulangesi, Plasmodium cuculus, Plasmodium cyclopsi, Plasmodium cynomolgi bastianelli, Plasmodium cynomolgi ceylonensis, Plasmodium cynomolgi cynomolgi, Plasmodium dherteae, Plasmodium diminutivum, Plasmodium diploglossi, Plasmodium dissanaikei, Plasmodium dominicana, Plasmodium dorsti, Plasmodium draconis, Plasmodium durae, Plasmodium egerniae, Plasmodium elongatum, Plasmodium eylesi, Plasmodium fairchildi, Plasmodium falciparum, Plasmodium fallax, Plasmodium fieldi, Plasmodium fischeri, Plasmodium foleyi, Plasmodium formosanum, Plasmodium forresteri, Plasmodium floridense, Plasmodium fragile, Plasmodium gaboni, Plasmodium gabaldoni, Plasmodium garnhami, Plasmodium gallinaceum, Plasmodium gemini, Plasmodium georgesi, Plasmodium ghadiriani, Plasmodium giganteum, Plasmodium giovannolai, Plasmodium ginsburgi, Plasmodium girardi, Plasmodium globularis, Plasmodium gloriai, Plasmodium gologoense, Plasmodium golvani, Plasmodium gonatodi, Plasmodium gonderi, Plasmodium gracilis, Plasmodium griffithsi, Plasmodium guangdong, Plasmodium gundersi, Plasmodium guyannense, Plasmodium heischi, Plasmodium hegneri, Plasmodium hermani, Plasmodium heroni, Plasmodium heteronucleare, Plasmodium hexamerium, Plasmodium hispaniolae, Plasmodium hoionucleophilum, Plasmodium holaspi, Plasmodium holti, Plasmodium homocircumflexum, Plasmodium homopolare, Plasmodium huffi, Plasmodium hydrochaeri, Plasmodium hylobati, Plasmodium incertae, Plasmodium icipeensis, Plasmodium iguanae, Plasmodium inopinatum, Plasmodium inui, Plasmodium japonicum, Plasmodium jeanriouxi, Plasmodium jefferyi, Plasmodium jiangi, Plasmodium josephinae, Plasmodium joyeuxi, Plasmodium juxtanucleare, Plasmodium kachelibaensis, Plasmodium kadogoi, Plasmodium kaninii, Plasmodium kempi, Plasmodium kentropyxi, Plasmodium knowlesi knowlesi, Plasmodium knowlesi edesoni, Plasmodium koreafense, Plasmodium kyaii, Plasmodium lacertiliae, Plasmodium lagopi, Plasmodium lainsoni, Plasmodium landauae, Plasmodium lemuris, Plasmodium lenoblei, Plasmodium lepidoptiformis, Plasmodium lionatum, Plasmodium lophurae, Plasmodium loveridgei, Plasmodium lucens, Plasmodium lutzi, Plasmodium lygosomae, Plasmodium mabuiae, Plasmodium mackerrasae, Plasmodium mackiei, Plasmodium maculilabre, Plasmodium maior, Plasmodium majus, Plasmodium malagasi, Plasmodium malariae, Plasmodium multivacuolaris, Plasmodium marginatum, Plasmodium matutinum, Plasmodium megaglobularis, Plasmodium megalotrypa, Plasmodium melanoleuca, Plasmodium melanipherum, Plasmodium merulae, Plasmodium mexicanum, Plasmodium michikoa, Plasmodium minasense, Plasmodium minuoviride, Plasmodium modestum, Plasmodium mohammedi, Plasmodium morulum, Plasmodium multiformis, Plasmodium narayani, Plasmodium necatrix, Plasmodium neusticuri, Plasmodium nucleophilium, Plasmodium octamerium, Plasmodium odhiamboi, Plasmodium odocoilei, Plasmodium ovale curtisi, Plasmodium ovale wallikeri, Plasmodium pachysomum, Plasmodium paddae, Plasmodium papernai, Plasmodium parahexamerium, Plasmodium paranucleophilum, Plasmodium parvulum, Plasmodium pedioecetii, Plasmodium pelaezi, Plasmodium percygarnhami, Plasmodium pessoai, Plasmodium petersi, Plasmodium pifanoi, Plasmodium pinotti, Plasmodium pitheci, Plasmodium pitmani, Plasmodium polare, Plasmodium polymorphum, Plasmodium pulmophilium, Plasmodium pythonias, Plasmodium quelea, Plasmodium reichenowi, Plasmodium relictum, Plasmodium reniai, Plasmodium rhadinurum, Plasmodium rhodaini, Plasmodium robinsoni, Plasmodium rousetti, Plasmodium rousseloti, Plasmodium rouxi, Plasmodium sandoshami, Plasmodium sapaaensis, Plasmodium sasai, Plasmodium saurocaudatum, Plasmodium schwetzi, Plasmodium sergentorum, Plasmodium scelopori, Plasmodium scorzai, Plasmodium semiovale, Plasmodium semnopitheci, Plasmodium silvaticum, Plasmodium simium, Plasmodium simplex, Plasmodium smirnovi, Plasmodium snounoui, Plasmodium stellatum, Plasmodium stuthionis, Plasmodium tanzaniae, Plasmodium tenue, Plasmodium tejerai, Plasmodium telfordi, Plasmodium tomodoni, Plasmodium torrealbai, Plasmodium toucani, Plasmodium traguli, Plasmodium tranieri, Plasmodium tribolonti, Plasmodium tropiduri, Plasmodium tumbayaensis, Plasmodium tyrio, Plasmodium uilenbergi, Plasmodium uluguruense, Plasmodium uncinatum, Plasmodium unalis, Plasmodium uzungwiense, Plasmodium watteni, Plasmodium wenyoni, Plasmodium vacuolatum, Plasmodium valkiunasi, Plasmodium vastator, Plasmodium vaughani, Plasmodium vautieri, Plasmodium venkataramiahii, Plasmodium vinckei, Plasmodium vivax, Plasmodium volans, Plasmodium voltaicum, Plasmodium wenyoni, Plasmodium yoelii, Plasmodium youngi,* or *Plasmodium zonuriae*), *Cryptosporidium* (e.g., *Cryptosporidium andersoni, Cryptosporidium bailey, Cryptosporidium bovis, Cryptosporidium cervine, Cryptosporidium canis, Cryptosporidium cuniculus, Cryptosporidium ducismarci, Cryptosporidium fayeri, Cryptosporidium felis, Cryptosporidium fragile, Cryptosporidium galli, Cryptosporidium hominis, Cryptosporidium marcopodum, Cryptosporidium meleagridis, Cryptosporidium molnari, Cryptosporidium muris, Cryptosporidium parvum, Cryptosporidium ryanae, Cryptosporidium saurophilum, Cryptosporidium serpentis, Cryptosporidium suis,*

*Cryptosporidium ubiquitum, Cryptosporidium wrairi,* or *Cryptosporidium xiaoi*), *Cyclospora* (e.g., *Cyclospora cayetanensis*), *Isospora belli* (e.g., *Iaspora almaataensis, Iaspora anseris, Iaspora ashmoonensis, Iaspora bahiensis, Iaspora belli, Iaspora bigemina, Iaspora bronchocelae, Iaspora buteonis, Iaspora buteonis, Iaspora canis, Iaspora felis, Iaspora hammondi, Iaspora heydorni, Iaspora hominis, Iaspora mandari, Iaspora mejiro, Iaspora neorivolta, Iaspora ohioensis, Iaspora peromysci, Iaspora rara, Iaspora ratti, Iaspora rivolta, Iaspora suis, Iaspora thibetana,* or *Iaspora wallacei*), *Neospora* (e.g., *Neospora caninum* or *Neospora hughesi*) or *Toxoplasma gondii*. In embodiments, the apicomplexan is an apicomplexan species found in humans. In embodiments, the apicomplexan is an apicomplexan species found in mammals. In embodiments, the apicomplexan is disease causing apicomplexan species in mammals.

As used herein the abbreviation "sp." for species means at least one species (e.g., 1, 2, 3, 4, 5, or more species) of the indicated genus. The abbreviation "spp." for species means 2 or more species (e.g., 2, 3, 4, 5, 6, 7, 8, 9, 10 or more) of the indicated genus. In embodiments, methods and compositions provided herein comprise a single species within an indicated genus or indicated genera, or 2 or more (e.g., a plurality comprising more than 2) species within an indicated genus or indicated genera. In embodiments, 1, 2, 3, 4, 5, or more or all of the indicated species is or are isolated.

II. Compositions

In an aspect is provided a compound having the formula:

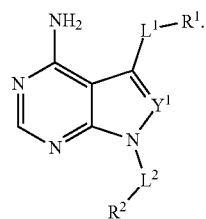

(I)

$Y^1$ is —N= or —CH=. $R^1$ is substituted or unsubstituted aryl or substituted or unsubstituted heteroaryl. $R^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^1$ is —SO—, —SO$_2$—, —O—, —S—, —N(R$^3$)—, —B(R$^6$)— (i.e. $L^1$ includes a boron), or substituted or unsubstituted C$_1$-C$_3$ alkylene (e.g., C$_1$-C$_2$ alkylene, C$_2$-C$_3$ alkylene, n-propylene, isopropylene, ethylene, or methylene). $L^2$ is a bond, —O—, —S—, —N(R$^7$)—, —B(R$^8$)— (i.e. $L^2$ includes a boron), substituted or unsubstituted alkylene, or substituted or unsubstituted heteroalkylene. $R^3$ is hydrogen, halogen, —SO$_2$CH$_3$, —CN, —COOH, —COCH$_3$, —CX$^3$$_3$, —CHX$^3$$_2$, —CH$_2$X$^3$, substituted or unsubstituted alkyl, or substituted or unsubstituted heteroalkyl; $X^3$ is independently halogen. $R^6$ is hydrogen, halogen, —CX$^6$$_3$, —CHX$^6$$_2$, —CH$_2$X$^6$, —OCX$^6$$_3$, —OCH$_2$X$^6$, —OCHX$^6$$_2$, —CN, —SH, —SO$_2$NH$_2$, —NHC(O)NH$_2$, —N(O), —N(O)$_2$, —NH$_2$, —C(O)H, —C(O)OH, —C(O)NH$_2$, —OH, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen, —CN, —COOH, —CX$^7$$_3$, substituted or unsubstituted alkyl (e.g., C$_1$-C$_8$ alkyl, C$_1$-C$_6$ alkyl, C$_1$-C$_4$ alkyl, C$_1$-C$_2$ alkyl, unsubstituted C$_1$-C$_8$ alkyl, unsubstituted C$_1$-C$_6$ alkyl, unsubstituted C$_1$-C$_4$ alkyl, or unsubstituted C$_1$-C$_2$ alkyl), or substituted or unsubstituted heteroalkyl (e.g., 2 to 8 membered heteroalkyl, 2 to 6 membered heteroalkyl, 2 to 4 membered heteroalkyl, 2 to 3 membered heteroalkyl, unsubstituted 2 to 8 membered heteroalkyl, unsubstituted 2 to 6 membered heteroalkyl, unsubstituted 2 to 4 membered heteroalkyl, or unsubstituted 2 to 3 membered heteroalkyl). $R^8$ is hydrogen, halogen, —CX$^8$$_3$, —CHX$^8$$_2$, —CH$_2$X$^8$, —OCX$^8$$_3$, —OCH$_2$X$^8$, —OCHX$^8$ 2, —CN, —SH, —SO$_2$NH$_2$, —NHC(O)NH$_2$, —N(O), —N(O)$_2$, —NH$_2$, —C(O)H, —C(O)OH, —C(O)NH$_2$, —OH, —NHSO$_2$H, —NHC(O)H, —NHC(O)OH, —NHO H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $X^6$ is independently —F, —Cl, —Br, or —I. Each $X^7$ is independently —F, —Cl, —Br, or —I. Each $X^8$ is independently —F, —Cl, —Br, or —I.

In embodiments, $R^1$ is substituted or unsubstituted aryl or substituted or unsubstituted heteroaryl. In embodiments, $R^2$ is substituted or unsubstituted heterocycloalkyl or substituted or unsubstituted heteroaryl. In embodiments, L is —O—, —S—, or —N(R$^3$)—. In embodiments, $L^2$ is a bond, substituted or unsubstituted alkylene, or substituted or unsubstituted heteroalkylene. In embodiments, $R^3$ is hydrogen, —CN, —COOH, —CF$_3$, substituted or unsubstituted alkyl, or substituted or unsubstituted heteroalkyl.

In embodiments, $Y^1$ is —N=. In embodiments, $Y^1$ is —CH=.

In embodiments, $R^1$ is substituted or unsubstituted C$_6$-C$_{10}$ aryl or substituted or unsubstituted 5 to 10 membered heteroaryl. In embodiments, $R^1$ is substituted or unsubstituted C$_6$-C$_{10}$ aryl or substituted or unsubstituted 5 to 9 membered heteroaryl. In embodiments, $R^1$ is substituted or unsubstituted phenyl or substituted or unsubstituted 5 to 6 membered heteroaryl.

In embodiments, $R^1$ is substituted or unsubstituted aryl. In embodiments, $R^1$ is substituted aryl. In embodiments, $R^1$ is unsubstituted aryl. In embodiments, $R^1$ is substituted or unsubstituted C$_6$-C$_{10}$ aryl. In embodiments, $R^1$ is substituted C$_6$-C$_{10}$ aryl. In embodiments, $R^1$ is unsubstituted C$_6$-C$_{10}$ aryl. In embodiments, $R^1$ is substituted or unsubstituted C$_{10}$ aryl. In embodiments, $R^1$ is substituted C$_{10}$ aryl. In embodiments, $R^1$ is unsubstituted C$_{10}$ aryl. In embodiments, $R^1$ is substituted or unsubstituted phenyl. In embodiments, $R^1$ is substituted phenyl. In embodiments, $R^1$ is unsubstituted phenyl.

In embodiments, $R^1$ is substituted or unsubstituted heteroaryl. In embodiments, $R^1$ is substituted heteroaryl. In embodiments, $R^1$ is unsubstituted heteroaryl. In embodiments, $R^1$ is substituted or unsubstituted 5 to 10 membered heteroaryl. In embodiments, $R^1$ is substituted 5 to 10 membered heteroaryl. In embodiments, $R^1$ is unsubstituted 5 to 10 membered heteroaryl. In embodiments, $R^1$ is substituted or unsubstituted 5 to 9 membered heteroaryl. In embodiments, $R^1$ is substituted 5 to 9 membered heteroaryl. In embodiments, $R^1$ is unsubstituted 5 to 9 membered heteroaryl. In embodiments, $R^1$ is substituted or unsubstituted 5 to 6 membered heteroaryl. In embodiments, $R^1$ is substituted 5 to 6 membered heteroaryl. In embodiments, $R^1$ is unsubstituted 5 to 6 membered heteroaryl. In embodiments, $R^1$ is substituted or unsubstituted 5 membered heteroaryl. In embodiments, $R^1$ is substituted 5 membered heteroaryl. In embodiments, $R^1$ is unsubstituted 5 membered heteroaryl. In embodiments, $R^1$ is substituted or unsubstituted 6 membered heteroaryl. In embodiments, $R^1$ is substituted 6 membered heteroaryl. In embodiments, $R^1$ is unsubstituted 6 membered heteroaryl. In embodiments, $R^1$ is substituted or unsubstituted 9 membered heteroaryl. In embodiments, $R^1$ is substituted 9 membered heteroaryl. In embodiments, $R^1$ is unsubstituted 9 membered heteroaryl. In embodiments, $R^1$ is substituted or unsubstituted 10 membered heteroaryl. In embodiments, $R^1$ is substituted 10 membered heteroaryl. In embodiments, $R^1$ is unsubstituted 10 membered heteroaryl.

In embodiments, $R^1$ is substituted or unsubstituted phenyl. In embodiments, $R^1$ is substituted or unsubstituted napththyl. In embodiments, $R^1$ is substituted or unsubstituted benzofuranyl. In embodiments, $R^1$ is substituted or unsubstituted isobenzofuranyl. In embodiments, $R^1$ is substituted or unsubstituted indolyl. In embodiments, $R^1$ is substituted or unsubstituted isoindolyl. In embodiments, $R^1$ is substituted or unsubstituted benzothienyl. In embodiments, $R^1$ is substituted or unsubstituted benzo[c]thienyl. In embodiments, $R^1$ is substituted or unsubstituted benzimidazolyl. In embodiments, $R^1$ is substituted or unsubstituted benzoisoxazolyl. In embodiments, $R^1$ is substituted or unsubstituted azaindolyl. In embodiments, $R^1$ is substituted or unsubstituted pyrrolopyridinyl. In embodiments, $R^1$ is substituted or unsubstituted purinyl. In embodiments, $R^1$ is substituted or unsubstituted indazolyl. In embodiments, $R^1$ is substituted or unsubstituted benzoxazolyl. In embodiments, $R^1$ is substituted or unsubstituted benzisoxazolyl. In embodiments, $R^1$ is substituted or unsubstituted benzothiazolyl. In embodiments, $R^1$ is substituted or unsubstituted quinolinyl. In embodiments, $R^1$ is substituted or unsubstituted isoquinolinyl. In embodiments, $R^1$ is substituted or unsubstituted quinoxalinyl. In embodiments, $R^1$ is substituted or unsubstituted quinazolinyl. In embodiments, $R^1$ is substituted or unsubstituted cinnolinyl. In embodiments, $R^1$ is substituted or unsubstituted or phthalazinyl. In embodiments, $R^1$ is substituted or unsubstituted furanyl. In embodiments, $R^1$ is substituted or unsubstituted pyrrolyl. In embodiments, $R^1$ is substituted or unsubstituted thienyl. In embodiments, $R^1$ is substituted or unsubstituted imidazolyl. In embodiments, $R^1$ is substituted or unsubstituted pyrazolyl. In embodiments, $R^1$ is substituted or unsubstituted oxazolyl. In embodiments, $R^1$ is substituted or unsubstituted isoxazolyl. In embodiments, $R^1$ is substituted or unsubstituted thiazolyl. In embodiments, $R^1$ is substituted or unsubstituted isothiazolyl. In embodiments, $R^1$ is substituted or unsubstituted triazolyl. In embodiments, $R^1$ is substituted or unsubstituted oxadiazolyl. In embodiments, $R^1$ is substituted or unsubstituted thiadiazolyl. In embodiments, $R^1$ is substituted or unsubstituted tetrazolyl. In embodiments, $R^1$ is substituted or unsubstituted pyridinyl. In embodiments, $R^1$ is substituted or unsubstituted pyrazinyl. In embodiments, $R^1$ is substituted or unsubstituted pyrimidinyl. In embodiments, $R^1$ is substituted or unsubstituted pyridazinyl. In embodiments, $R^1$ is substituted or unsubstituted triazinyl.

In embodiments, $R^1$ is substituted phenyl. In embodiments, $R^1$ is substituted napththyl. In embodiments, $R^1$ is substituted benzofuranyl. In embodiments, $R^1$ is substituted isobenzofuranyl. In embodiments, $R^1$ is substituted indolyl. In embodiments, $R^1$ is substituted isoindolyl. In embodiments, $R^1$ is substituted benzothienyl. In embodiments, $R^1$ is substituted benzo[c]thienyl. In embodiments, $R^1$ is substituted benzimidazolyl. In embodiments, $R^1$ is substituted azaindolyl. In embodiments, $R^1$ is substituted benzoisoxazolyl. In embodiments, $R^1$ is substituted pyrrolopyridinyl. In embodiments, $R^1$ is substituted purinyl. In embodiments, $R^1$ is substituted indazolyl. In embodiments, $R^1$ is substituted benzoxazolyl. In embodiments, $R^1$ is substituted benzisoxazolyl. In embodiments, $R^1$ is substituted benzothiazolyl. In embodiments, $R^1$ is substituted quinolinyl. In embodiments, $R^1$ is substituted isoquinolinyl. In embodiments, $R^1$ is substituted quinoxalinyl. In embodiments, $R^1$ is substituted quinazolinyl. In embodiments, $R^1$ is substituted cinnolinyl. In embodiments, $R^1$ is substituted or phthalazinyl. In embodiments, $R^1$ is substituted furanyl. In embodiments, $R^1$ is substituted pyrrolyl. In embodiments, $R^1$ is substituted thienyl. In embodiments, $R^1$ is substituted imidazolyl. In embodiments, $R^1$ is substituted pyrazolyl. In embodiments, $R^1$ is substituted oxazolyl. In embodiments, $R^1$ is substituted isoxazolyl. In embodiments, $R^1$ is substituted thiazolyl. In embodiments, $R^1$ is substituted isothiazolyl. In embodiments, $R^1$ is substituted triazolyl. In embodiments, $R^1$ is substituted oxadiazolyl. In embodiments, $R^1$ is substituted thiadiazolyl. In embodiments, $R^1$ is substituted tetrazolyl. In embodiments, $R^1$ is substituted pyridinyl. In embodiments, $R^1$ is substituted pyrazinyl. In embodiments, $R^1$ is substituted pyrimidinyl. In embodiments, $R^1$ is substituted pyridazinyl. In embodiments, $R^1$ is substituted triazinyl.

In embodiments, $R^1$ is unsubstituted phenyl. In embodiments, $R^1$ is unsubstituted napththyl. In embodiments, $R^1$ is unsubstituted benzofuranyl. In embodiments, $R^1$ is unsubstituted isobenzofuranyl. In embodiments, $R^1$ is unsubstituted indolyl. In embodiments, $R^1$ is unsubstituted isoindolyl. In embodiments, $R^1$ is unsubstituted benzothienyl. In embodiments, $R^1$ is unsubstituted benzo[c]thienyl. In embodiments, $R^1$ is unsubstituted benzimidazolyl. In embodiments, $R^1$ is unsubstituted azaindolyl. In embodiments, $R^1$ is unsubstituted benzoisoxazolyl. In embodiments, $R^1$ is unsubstituted pyrrolopyridinyl. In embodiments, $R^1$ is unsubstituted purinyl. In embodiments, $R^1$ is unsubstituted indazolyl. In embodiments, $R^1$ is unsubstituted benzoxazolyl. In embodiments, $R^1$ is unsubstituted benzisoxazolyl. In embodiments, $R^1$ is unsubstituted benzothiazolyl. In embodiments, $R^1$ is unsubstituted quinolinyl. In embodiments, $R^1$ is unsubstituted isoquinolinyl. In embodiments, $R^1$ is unsubstituted quinoxalinyl. In embodiments, $R^1$ is unsubstituted quinazolinyl. In embodiments, $R^1$ is unsubstituted cinnolinyl. In embodiments, $R^1$ is unsubstituted or phthalazinyl. In embodiments, $R^1$ is unsubstituted furanyl. In embodiments, $R^1$ is unsubstituted pyrrolyl. In embodiments, $R^1$ is unsubstituted thienyl. In embodiments, $R^1$ is unsubstituted imidazolyl. In embodiments, $R^1$ is unsubstituted pyrazolyl. In embodiments, $R^1$ is unsubstituted oxazolyl. In embodiments, $R^1$ is unsubstituted isoxazolyl. In embodiments, $R^1$ is unsubstituted thiazolyl. In embodiments, $R^1$ is unsubstituted isothiazolyl. In embodiments, $R^1$ is unsubstituted triazolyl. In embodiments, $R^1$ is unsubstituted oxadiazolyl. In embodiments, $R^1$ is unsubstituted thiadiazolyl. In embodiments, $R^1$ is unsubstituted tetrazolyl. In embodiments, $R^1$ is unsubstituted pyridinyl. In embodiments, $R^1$ is unsubstituted pyrazinyl. In embodiments, $R^1$ is unsubstituted pyrimidinyl. In embodiments, $R^1$ is unsubstituted pyridazinyl. In embodiments, $R^1$ is unsubstituted triazinyl.

In embodiments, $R^1$ is $R^{20}$-substituted or unsubstituted aryl or $R^{20}$-substituted or unsubstituted heteroaryl. In embodiments, $R^1$ is $R^{20}$-substituted or unsubstituted phenyl or $R^{20}$-substituted or unsubstituted 5 to 6 membered heteroaryl.

$R^{20}$ is independently halogen, $-CX^{20}_3$, $-CHX^{20}_2$, $-CH_2X^{20}$, $-OCH_2X^{20}$, $-OCX^{20}_3$, $-OCHX^{20}_2$, $-CN$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, R$^{21}$-substituted or unsubstituted alkyl, R$^{21}$-substituted or unsubstituted heteroalkyl, R$^{21}$-substituted or unsubstituted cycloalkyl, R$^{21}$-substituted or unsubstituted heterocycloalkyl, R$^{21}$-substituted or unsubstituted aryl, or R$^{21}$-substituted or unsubstituted heteroaryl. X$^{20}$ is halogen. In embodiments, X$^{20}$ is F.

In embodiments, R$^{20}$ is independently halogen, —CX$^{20}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{20}_3$, —OCHX$^{20}_2$, R$^{21}$-substituted or unsubstituted C$_1$-C$_8$ alkyl, R$^{21}$-substituted or unsubstituted 2 to 8 membered heteroalkyl, R$^{21}$-substituted or unsubstituted C$_3$-C$_8$ cycloalkyl, R$^{21}$-substituted or unsubstituted 3 to 8 membered heterocycloalkyl, R$^{21}$-substituted or unsubstituted phenyl, or R$^{21}$-substituted or unsubstituted 5 to 6 membered heteroaryl. X$^{20}$ is —F, —Cl, —Br, or —I. In embodiments, R$^{20}$ is independently halogen, unsubstituted C$_1$-C$_3$ alkyl, or unsubstituted 2 to 4 membered heteroalkyl. In embodiments, R$^{20}$ is independently halogen, unsubstituted methyl, or —OCH$_3$. In embodiments, R$^{20}$ is —Br. In embodiments, R$^{20}$ is —Cl. In embodiments, R$^{20}$ is —F. In embodiments, R$^{20}$ is —OCH$_3$. In embodiments, R$^{20}$ is —CH$_3$. In embodiments, R$^{20}$ is —CF$_3$.

R$^{21}$ is independently oxo, halogen, —CX$^{21}_3$, —CHX$^{21}_2$, —CH$_2$X$^{21}$, —OCH$_2$X$^{21}$, —OCX$^{21}_3$, —OCHX$^{21}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, R$^{22}$-substituted or unsubstituted alkyl, R$^{22}$-substituted or unsubstituted heteroalkyl, R$^{22}$-substituted or unsubstituted cycloalkyl, R$^{22}$-substituted or unsubstituted heterocycloalkyl, R$^{22}$-substituted or unsubstituted aryl, or R$^{22}$-substituted or unsubstituted heteroaryl. In embodiments, R$^{21}$ is independently oxo, halogen, —CX$^{21}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{21}_3$, —OCHX$^{21}_2$, R$^{22}$-substituted or unsubstituted C$_1$-C$_5$ alkyl, R$^{22}$-substituted or unsubstituted 2 to 8 membered heteroalkyl, R$^{22}$-substituted or unsubstituted C$_3$-C$_8$ cycloalkyl, R$^{22}$-substituted or unsubstituted 3 to 8 membered heterocycloalkyl, R$^{22}$-substituted or unsubstituted phenyl, or R$^{22}$-substituted or unsubstituted 5 to 6 membered heteroaryl. X$^{21}$ is —F, —Cl, —Br, or —I.

R$^{22}$ is independently hydrogen, oxo, halogen, —CCl$_3$, —CBr$_3$, —CF$_3$, —CL$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_5$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{22}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{22}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted C$_1$-C$_8$ alkyl, unsubstituted 2 to 8 membered heteroalkyl, unsubstituted C$_3$-C$_8$ cycloalkyl, unsubstituted 3 to 6 membered heterocycloalkyl, unsubstituted phenyl, or unsubstituted 5 to 6 membered heteroaryl.

In embodiments R$^2$ is substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_5$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments R$^2$ is hydrogen.

In embodiments, R$^2$ is substituted or unsubstituted alkyl. In embodiments, R$^2$ is substituted alkyl. In embodiments, R$^2$ is unsubstituted alkyl. In embodiments, R$^2$ is substituted or unsubstituted C$_1$-C$_8$ alkyl. In embodiments, R$^2$ is substituted C$_1$-C$_8$ alkyl. In embodiments, R$^2$ is unsubstituted C$_1$-C$_8$ alkyl. In embodiments, R$^2$ is substituted or unsubstituted C$_1$-C$_4$ alkyl. In embodiments, R$^2$ is substituted C$_1$-C$_4$ alkyl. In embodiments, R$^2$ is unsubstituted C$_1$-C$_4$ alkyl. In embodiments, R$^2$ is R$^{23}$-substituted or unsubstituted alkyl. In embodiments, R$^2$ is R$^{23}$-substituted or unsubstituted C$_1$-C$_8$ alkyl. In embodiments, R$^2$ is hydrogen. In embodiments, R$^2$ is unsubstituted methyl. In embodiments, R$^2$ is unsubstituted ethyl. In embodiments, R$^2$ is unsubstituted n-propyl. In embodiments, R$^2$ is unsubstituted isopropyl. In embodiments, R$^2$ is unsubstituted n-butyl. In embodiments, R$^2$ is unsubstituted isobutyl. In embodiments, R$^2$ is unsubstituted tert-butyl. In embodiments, R$^2$ is unsubstituted pentyl.

In embodiments, R$^2$ is substituted or unsubstituted heteroalkyl (e.g., 2 to 8 membered heteroalkyl, 2 to 6 membered heteroalkyl, or 2 to 4 membered heteroalkyl). In embodiments, R$^2$ is substituted heteroalkyl (e.g., 2 to 8 membered heteroalkyl, 2 to 6 membered heteroalkyl, or 2 to 4 membered heteroalkyl).

In embodiments, R$^2$ is R$^{23}$-substituted or unsubstituted heteroalkyl (e.g., 2 to 8 membered heteroalkyl, 2 to 6 membered heteroalkyl, or 2 to 4 membered heteroalkyl). In embodiments, R$^2$ is R$^{23}$-substituted heteroalkyl (e.g., 2 to 8 membered heteroalkyl, 2 to 6 membered heteroalkyl, or 2 to 4 membered heteroalkyl). In embodiments, R$^2$ is an unsubstituted heteroalkyl (e.g., 2 to 8 membered heteroalkyl, 2 to 6 membered heteroalkyl, or 2 to 4 membered heteroalkyl).

In embodiments, R$^2$ is substituted or unsubstituted cycloalkyl (e.g., C$_3$-C$_5$ cycloalkyl, C$_3$-C$_6$ cycloalkyl, or C$_5$-C$_6$ cycloalkyl). In embodiments, R$^2$ is substituted cycloalkyl (e.g., $C_3$-$C_5$ cycloalkyl, $C_3$-$C_6$ cycloalkyl, or $C_5$-$C_6$ cycloalkyl). In embodiments, $R^2$ is substituted or unsubstituted cycloheptanyl. In embodiments, $R^2$ is substituted or unsubstituted cyclohexanyl. In embodiments, $R^2$ is substituted or unsubstituted cyclopentanyl. In embodiments, $R^2$ is substituted or unsubstituted cyclooctanyl.

In embodiments, $R^2$ is substituted or unsubstituted $C_3$-$C_8$ cycloalkyl. In embodiments, $R^2$ is substituted or unsubstituted $C_3$-$C_6$ cycloalkyl. In embodiments, $R^2$ is substituted or unsubstituted $C_5$-$C_6$ cycloalkyl. In embodiments, $R^2$ is substituted $C_3$-$C_8$ cycloalkyl. In embodiments, $R^2$ is substituted $C_3$-$C_6$ cycloalkyl. In embodiments, $R^2$ is substituted $C_5$-$C_6$ cycloalkyl. In embodiments, $R^2$ is unsubstituted $C_3$-$C_8$ cycloalkyl. In embodiments, $R^2$ is unsubstituted $C_3$-$C_6$ cycloalkyl. In embodiments, $R^2$ is unsubstituted $C_5$-$C_6$ cycloalkyl.

In embodiments, $R^2$ is $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is $R^{23}$-substituted cycloalkyl (e.g., $C_3$-$C_8$ cycloalkyl, $C_3$-$C_6$ cycloalkyl, or $C_5$-$C_6$ cycloalkyl). In embodiments, $R^2$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is $R^{23}$-substituted or unsubstituted cyclooctanyl. In embodiments, $R^2$ is $R^{23}$-substituted or unsubstituted cycloheptanyl. In embodiments, $R^2$ is $R^{23}$-substituted or unsubstituted cyclohexanyl. In embodiments, $R^2$ is $R^{23}$-substituted or unsubstituted cyclopentanyl. In embodiments, $R^2$ is $R^{23}$-substituted cyclooctanyl. In embodiments, $R^2$ is $R^{23}$-substituted cycloheptanyl. In embodiments, $R^2$ is $R^{23}$-substituted cyclohexanyl. In embodiments, $R^2$ is $R^{23}$-substituted cyclopentanyl. In embodiments, $R^2$ is unsubstituted cyclooctanyl. In embodiments, $R^2$ is unsubstituted cycloheptanyl. In embodiments, $R^2$ is unsubstituted cyclohexanyl. In embodiments, $R^2$ is unsubstituted cyclopentanyl. In embodiments, $R^2$ is $R^{23}$-substituted cycloheptanyl. In embodiments, $R^2$ is $R^{23}$-substituted cyclohexanyl. In embodiments, $R^2$ is $R^{23}$-substituted cyclopentanyl.

In embodiments, $R^2$ is substituted or unsubstituted 3 to 7 membered heterocycloalkyl or substituted or unsubstituted 5 to 10 membered heteroaryl. In embodiments, $R^2$ is substituted or unsubstituted heterocycloalkyl. In embodiments, $R^2$ is substituted heterocycloalkyl. In embodiments, $R^2$ is unsubstituted heterocycloalkyl. In embodiments, $R^2$ is substituted or unsubstituted 3 to 7 membered heterocycloalkyl. In embodiments, $R^2$ is substituted 3 to 7 membered heterocycloalkyl. In embodiments, $R^2$ is unsubstituted 3 to 7 membered heterocycloalkyl. In embodiments, $R^2$ is substituted or unsubstituted 3 to 6 membered heterocycloalkyl. In embodiments, $R^2$ is substituted 3 to 6 membered heterocycloalkyl. In embodiments, $R^2$ is unsubstituted 3 to 6 membered heterocycloalkyl. In embodiments, $R^2$ is substituted or unsubstituted 3 to 5 membered heterocycloalkyl. In embodiments, $R^2$ is substituted 3 to 5 membered heterocycloalkyl. In embodiments, $R^2$ is unsubstituted 3 to 5 membered heterocycloalkyl. In embodiments, $R^2$ is substituted or unsubstituted 5 to 6 membered heterocycloalkyl. In embodiments, $R^2$ is substituted 5 to 6 membered heterocycloalkyl. In embodiments, $R^2$ is unsubstituted 5 to 6 membered heterocycloalkyl. In embodiments, $R^2$ is substituted or unsubstituted 3 membered heterocycloalkyl. In embodiments, $R^2$ is substituted 3 membered heterocycloalkyl. In embodiments, $R^2$ is unsubstituted 3 membered heterocycloalkyl. In embodiments, $R^2$ is substituted or unsubstituted 4 membered heterocycloalkyl. In embodiments, $R^2$ is substituted 4 membered heterocycloalkyl. In embodiments, $R^2$ is unsubstituted 4 membered heterocycloalkyl. In embodiments, $R^2$ is substituted or unsubstituted 5 membered heterocycloalkyl. In embodiments, $R^2$ is substituted 5 membered heterocycloalkyl. In embodiments, $R^2$ is unsubstituted 5 membered heterocycloalkyl. In embodiments, $R^2$ is substituted or unsubstituted 6 membered heterocycloalkyl. In embodiments, $R^2$ is substituted 6 membered heterocycloalkyl. In embodiments, $R^2$ is unsubstituted 6 membered heterocycloalkyl. In embodiments, $R^2$ is substituted or unsubstituted 7 membered heterocycloalkyl. In embodiments, $R^2$ is substituted 7 membered heterocycloalkyl. In embodiments, $R^2$ is unsubstituted 7 membered heterocycloalkyl.

In embodiments, $R^2$ is substituted or unsubstituted heteroaryl. In embodiments, $R^2$ is substituted heteroaryl. In embodiments, $R^2$ is unsubstituted heteroaryl. In embodiments, $R^2$ is substituted or unsubstituted 5 to 10 membered heteroaryl. In embodiments, $R^2$ is substituted 5 to 10 membered heteroaryl. In embodiments, $R^2$ is unsubstituted 5 to 10 membered heteroaryl. In embodiments, $R^2$ is substituted or unsubstituted 5 to 9 membered heteroaryl. In embodiments, $R^2$ is substituted 5 to 9 membered heteroaryl. In embodiments, $R^2$ is unsubstituted 5 to 9 membered heteroaryl. In embodiments, $R^2$ is substituted or unsubstituted 5 to 6 membered heteroaryl. In embodiments, $R^2$ is substituted 5 to 6 membered heteroaryl. In embodiments, $R^2$ is unsubstituted 5 to 6 membered heteroaryl. In embodiments, $R^2$ is substituted or unsubstituted 5 membered heteroaryl. In embodiments, $R^2$ is substituted 5 membered heteroaryl. In embodiments, $R^2$ is unsubstituted 5 membered heteroaryl. In embodiments, $R^2$ is substituted or unsubstituted 6 membered heteroaryl. In embodiments, $R^2$ is substituted 6 membered heteroaryl. In embodiments, $R^2$ is unsubstituted 6 membered heteroaryl. In embodiments, $R^2$ is substituted or unsubstituted 9 membered heteroaryl. In embodiments, $R^2$ is substituted 9 membered heteroaryl. In embodiments, $R^2$ is unsubstituted 9 membered heteroaryl. In embodiments, $R^2$ is substituted or unsubstituted 10 membered heteroaryl. In embodiments, $R^2$ is substituted 10 membered heteroaryl. In embodiments, $R^2$ is unsubstituted 10 membered heteroaryl.

In embodiments, $R^2$ is substituted or unsubstituted aziridinyl. In embodiments, $R^2$ is substituted or unsubstituted azirinyl. In embodiments, $R^2$ is substituted or unsubstituted diaziridinyl. In embodiments, $R^2$ is substituted or unsubstituted diazirinyl. In embodiments, $R^2$ is substituted or unsubstituted oxaziridinyl. In embodiments, $R^2$ is substituted or unsubstituted azetidinyl. In embodiments, $R^2$ is substituted or unsubstituted azetyl. In embodiments, $R^2$ is substituted or unsubstituted diazetidinyl. In embodiments, $R^2$ is substituted or unsubstituted diazetyl. In embodiments, $R^2$ is substituted or unsubstituted pyrrolidinyl. In embodiments, $R^2$ is substituted or unsubstituted pyrazolidinyl. In embodiments, $R^2$ is substituted or unsubstituted oxazolidinyl. In embodiments, $R^2$ is substituted or unsubstituted isoxazolidinyl. In embodiments, $R^2$ is substituted or unsubstituted thiazolidinyl. In embodiments, $R^2$ is substituted or unsubstituted isothiazolidinyl. In embodiments, $R^2$ is substituted or unsubstituted furazanyl. In embodiments, $R^2$ is substituted or unsubstituted dithiazolyl. In embodiments, $R^2$ is substituted or unsubstituted piperidinyl. In embodiments, $R^2$ is substituted or unsubstituted piperazinyl. In embodiments, $R^2$ is substituted or unsubstituted morpholinyl. In embodiments, $R^2$ is substituted or unsubstituted thiomorpholinyl.

In embodiments, $R^2$ is substituted aziridinyl. In embodiments, $R^2$ is substituted azirinyl. In embodiments, $R^2$ is substituted diaziridinyl. In embodiments, $R^2$ is substituted diazirinyl. In embodiments, $R^2$ is substituted oxaziridinyl. In embodiments, $R^2$ is substituted azetidinyl. In embodiments, $R^2$ is substituted azetyl. In embodiments, $R^2$ is substituted diazetidinyl. In embodiments, $R^2$ is substituted diazetyl. In embodiments, $R^2$ is substituted pyrrolidinyl. In embodiments, $R^2$ is substituted pyrazolidinyl. In embodiments, $R^2$ is substituted oxazolidinyl. In embodiments, $R^2$ is substituted isoxazolidinyl. In embodiments, $R^2$ is substituted thiazolidinyl. In embodiments, $R^2$ is substituted isothiazolidinyl. In embodiments, $R^2$ is substituted furazanyl. In embodiments, $R^2$ is substituted dithiazolyl. In embodiments, $R^2$ is substituted piperidinyl. In embodiments, $R^2$ is substituted piperazinyl. In embodiments, $R^2$ is substituted morpholinyl. In embodiments, $R^2$ is substituted thiomorpholinyl.

In embodiments, $R^2$ is unsubstituted aziridinyl. In embodiments, $R^2$ is unsubstituted azirinyl. In embodiments, $R^2$ is unsubstituted diaziridinyl. In embodiments, $R^2$ is unsubstituted diazirinyl. In embodiments, $R^2$ is unsubstituted oxaziridinyl. In embodiments, $R^2$ is unsubstituted azetidinyl. In embodiments, $R^2$ is unsubstituted azetyl. In embodiments, $R^2$ is unsubstituted diazetidinyl. In embodiments, $R^2$ is unsubstituted diazetyl. In embodiments, $R^2$ is unsubstituted pyrrolidinyl. In embodiments, $R^2$ is unsubstituted pyrazolidinyl. In embodiments, $R^2$ is unsubstituted oxazolidinyl. In embodiments, $R^2$ is unsubstituted isoxazolidinyl. In embodiments, $R^2$ is unsubstituted thiazolidinyl. In embodiments, $R^2$ is unsubstituted isothiazolidinyl. In embodiments, $R^2$ is unsubstituted furazanyl. In embodiments, $R^2$ is unsubstituted dithiazolyl. In embodiments, $R^2$ is unsubstituted piperidinyl. In embodiments, $R^2$ is unsubstituted piperazinyl. In embodiments, $R^2$ is unsubstituted morpholinyl. In embodiments, $R^2$ is unsubstituted thiomorpholinyl.

In embodiments, $R^2$ is substituted or unsubstituted piperidinyl. In embodiments, $R^2$ is substituted or unsubstituted piperazinyl. In embodiments, $R^2$ is substituted or unsubstituted benzofuranyl. In embodiments, $R^2$ is substituted or unsubstituted isobenzofuranyl. In embodiments, $R^2$ is substituted or unsubstituted indolyl. In embodiments, $R^2$ is substituted or unsubstituted isoindolyl. In embodiments, $R^2$ is substituted or unsubstituted benzothienyl. In embodiments, $R^2$ is substituted or unsubstituted benzo[c]thienyl. In embodiments, $R^2$ is substituted or unsubstituted benzimidazolyl. In embodiments, $R^2$ is substituted or unsubstituted azaindolyl. In embodiments, $R^2$ is substituted or unsubstituted benzoisoxazolyl. In embodiments, $R^2$ is substituted or unsubstituted pyrrolopyridinyl. In embodiments, $R^2$ is substituted or unsubstituted purinyl. In embodiments, $R^2$ is substituted or unsubstituted indazolyl. In embodiments, $R^2$ is substituted or unsubstituted benzoxazolyl. In embodiments, $R^2$ is substituted or unsubstituted benzisoxazolyl. In embodiments, $R^2$ is substituted or unsubstituted benzothiazolyl. In embodiments, $R^2$ is substituted or unsubstituted quinolinyl. In embodiments, $R^2$ is substituted or unsubstituted isoquinolinyl. In embodiments, $R^2$ is substituted or unsubstituted quinoxalinyl. In embodiments, $R^2$ is substituted or unsubstituted quinazolinyl. In embodiments, $R^2$ is substituted or unsubstituted cinnolinyl. In embodiments, $R^2$ is substituted or unsubstituted phthalazinyl. In embodiments, $R^2$ is substituted or unsubstituted furanyl. In embodiments, $R^2$ is substituted or unsubstituted pyrrolyl. In embodiments, $R^2$ is substituted or unsubstituted thienyl. In embodiments, $R^2$ is substituted or unsubstituted imidazolyl. In embodiments, $R^2$ is substituted or unsubstituted pyrazolyl. In embodiments, $R^2$ is substituted or unsubstituted oxazolyl. In embodiments, $R^2$ is substituted or unsubstituted isoxazolyl. In embodiments, $R^2$ is substituted or unsubstituted thiazolyl. In embodiments, $R^2$ is substituted or unsubstituted isothiazolyl. In embodiments, $R^2$ is substituted or unsubstituted triazolyl. In embodiments, $R^2$ is substituted or unsubstituted oxadiazolyl. In embodiments, $R^2$ is substituted or unsubstituted thiadiazolyl. In embodiments, $R^2$ is substituted or unsubstituted tetrazolyl. In embodiments, $R^2$ is substituted or unsubstituted pyridinyl. In embodiments, $R^2$ is substituted or unsubstituted pyrazinyl. In embodiments, $R^2$ is substituted or unsubstituted pyrimidinyl. In embodiments, $R^2$ is substituted or unsubstituted pyridazinyl. In embodiments, $R^2$ is substituted or unsubstituted triazinyl. In embodiments, $R^2$ is substituted or unsubstituted 6 membered heteroaryl. In embodiments, $R^2$ is substituted or unsubstituted pyridinyl. In embodiments, $R^2$ is substituted or unsubstituted pyrazinyl. In embodiments, $R^2$ is substituted or unsubstituted pyrimidinyl. In embodiments, $R^2$ is substituted or unsubstituted pyridazinyl.

In embodiments, $R^2$ is substituted piperidinyl. In embodiments, $R^2$ is substituted piperazinyl. In embodiments, $R^2$ is substituted benzofuranyl. In embodiments, $R^2$ is substituted isobenzofuranyl. In embodiments, $R^2$ is substituted indolyl. In embodiments, $R^2$ is substituted isoindolyl. In embodiments, $R^2$ is substituted benzothienyl. In embodiments, $R^2$ is substituted benzo[c]thienyl. In embodiments, $R^2$ is substituted benzimidazolyl. In embodiments, $R^2$ is substituted azaindolyl. In embodiments, $R^2$ is substituted benzoisoxazolyl. In embodiments, $R^2$ is substituted pyrrolopyridinyl. In embodiments, $R^2$ is substituted purinyl. In embodiments, $R^2$ is substituted indazolyl. In embodiments, $R^2$ is substituted benzoxazolyl. In embodiments, $R^2$ is substituted benzisoxazolyl. In embodiments, $R^2$ is substituted benzothiazolyl. In embodiments, $R^2$ is substituted quinolinyl. In embodiments, $R^2$ is substituted isoquinolinyl. In embodiments, $R^2$ is substituted quinoxalinyl. In embodiments, $R^2$ is substituted quinazolinyl. In embodiments, $R^2$ is substituted cinnolinyl. In embodiments, $R^2$ is substituted phthalazinyl. In embodiments, $R^2$ is substituted furanyl. In embodiments, $R^2$ is substituted pyrrolyl. In embodiments, $R^2$ is substituted thienyl. In embodiments, $R^2$ is substituted imidazolyl. In embodiments, $R^2$ is substituted pyrazolyl. In embodiments, $R^2$ is substituted oxazolyl. In embodiments, $R^2$ is substituted isoxazolyl. In embodiments, $R^2$ is substituted thiazolyl. In embodiments, $R^2$ is substituted isothiazolyl. In embodiments, $R^2$ is substituted triazolyl. In embodiments, $R^2$ is substituted oxadiazolyl. In embodiments, $R^2$ is substituted thiadiazolyl. In embodiments, $R^2$ is substituted tetrazolyl. In embodiments, $R^2$ is substituted pyridinyl. In embodiments, $R^2$ is substituted pyrazinyl. In embodiments, $R^2$ is substituted pyrimidinyl. In embodiments, $R^2$ is substituted pyridazinyl. In embodiments, $R^2$ is substituted triazinyl. In embodiments, $R^2$ is substituted 6 membered heteroaryl. In embodiments, $R^2$ is substituted pyridinyl. In embodiments, $R^2$ is substituted pyrazinyl. In embodiments, $R^2$ is substituted pyrimidinyl. In embodiments, $R^2$ is substituted pyridazinyl.

In embodiments, $R^2$ is unsubstituted piperidinyl. In embodiments, $R^2$ is unsubstituted piperazinyl. In embodiments, $R^2$ is unsubstituted benzofuranyl. In embodiments, $R^2$ is unsubstituted isobenzofuranyl. In embodiments, $R^2$ is unsubstituted indolyl. In embodiments, $R^2$ is unsubstituted isoindolyl. In embodiments, $R^2$ is unsubstituted benzothienyl. In embodiments, $R^2$ is unsubstituted benzo[c]thienyl. In embodiments, $R^2$ is unsubstituted benzimidazolyl. In embodiments, $R^2$ is unsubstituted azaindolyl. In embodiments, $R^2$ is unsubstituted benzoisoxazolyl. In embodiments, $R^2$ is unsubstituted pyrrolopyridinyl. In embodiments, $R^2$ is unsubstituted purinyl. In embodiments, $R^2$ is unsubstituted indazolyl. In embodiments, $R^2$ is unsubstituted benzoxazolyl. In embodiments, $R^2$ is unsubstituted benzisoxazolyl. In embodiments, R² is unsubstituted benzothiazolyl. In embodiments, R² is unsubstituted quinolinyl. In embodiments, R² is unsubstituted isoquinolinyl. In embodiments, R² is unsubstituted quinoxalinyl. In embodiments, R² is unsubstituted quinazolinyl. In embodiments, R² is unsubstituted cinnolinyl. In embodiments, R² is unsubstituted phthalazinyl. In embodiments, R² is unsubstituted furanyl. In embodiments, R² is unsubstituted pyrrolyl. In embodiments, R² is unsubstituted thienyl. In embodiments, R² is unsubstituted imidazolyl. In embodiments, R² is unsubstituted pyrazolyl. In embodiments, R² is unsubstituted oxazolyl. In embodiments, R² is unsubstituted isoxazolyl. In embodiments, R² is unsubstituted thiazolyl. In embodiments, R² is unsubstituted isothiazolyl. In embodiments, R² is unsubstituted triazolyl. In embodiments, R² is unsubstituted oxadiazolyl. In embodiments, R² is unsubstituted thiadiazolyl. In embodiments, R² is unsubstituted tetrazolyl. In embodiments, R² is unsubstituted pyridinyl. In embodiments, R² is unsubstituted pyrazinyl. In embodiments, R² is unsubstituted pyrimidinyl. In embodiments, R² is unsubstituted pyridazinyl. In embodiments, R² is unsubstituted triazinyl. In embodiments, R² is unsubstituted 6 membered heteroaryl. In embodiments, R² is unsubstituted pyridinyl. In embodiments, R² is unsubstituted pyrazinyl. In embodiments, R² is unsubstituted pyrimidinyl. In embodiments, R² is unsubstituted pyridazinyl.

In embodiments, R² is —CX²³, —CHX²², or —CH₂X². In embodiments, R² is —CF₃, —CHF₂, or —CH₂F. In embodiments, R² is substituted cyclopropyl In embodiments, R² is R²³-substituted cyclopropyl. In embodiments, R² is unsubstituted cyclopropyl. In embodiments, R² is unsubstituted methyl. In embodiments, R² is —CF₃. In embodiments, R² is —CHF₂. In embodiments, R² is —CH₂F. X² is a halogen. In embodiments, X² is F.

In embodiments, L²-R² is unsubstituted isopropyl. In embodiments, -L²-R² is unsubstituted tert-butyl. In embodiments, -L²-R² is hydrogen. In embodiments, -L²-R² is

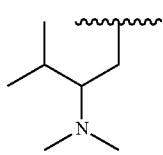

In embodiments, -L²-R² is

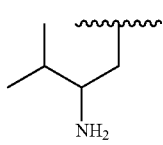

In embodiments, -L²-R² is

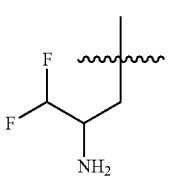

In embodiments, -L²-R² is

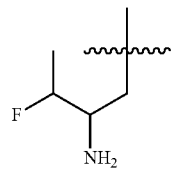

In embodiments, L²-R² is

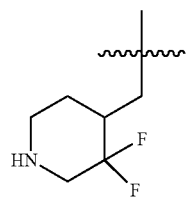

In embodiments, L²-R² is

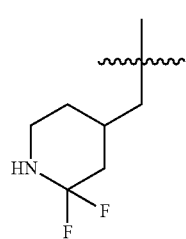

In embodiments, L²-R² is

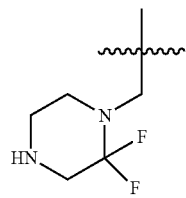

In embodiments, L²-R² is

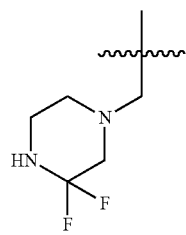

In embodiments, $L^2$-$R^2$ is
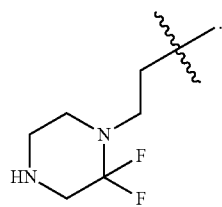
In embodiments, $L^2$-$R^2$ is
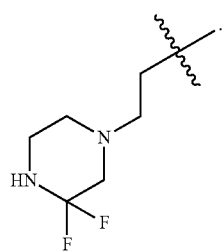
In embodiments, $L^2$-$R^2$ is
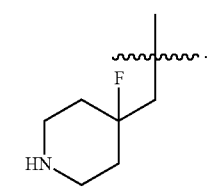
In embodiments, $L^2$-$R^2$ is
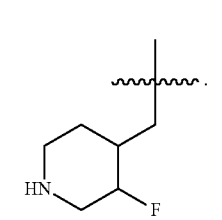
In embodiments, $L^2$-$R^2$ is
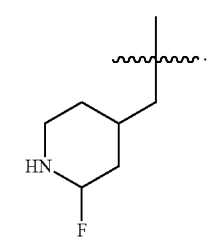 [SMILES: *CC1CCNC(F)C1]
In embodiments, $L^2$-$R^2$ is
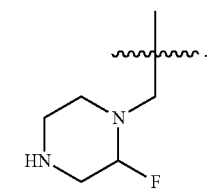
In embodiments, $L^2$-$R^2$ is
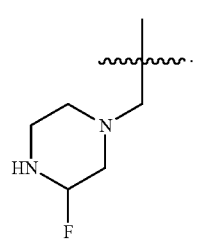
In embodiments, $L^2$-$R^2$ is
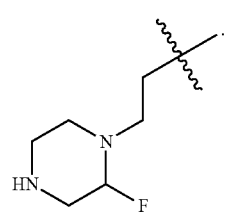
In embodiments, $L^2$-$R^2$ is
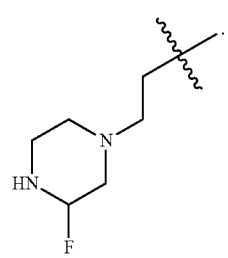
In embodiments, $L^2$-$R^2$ is
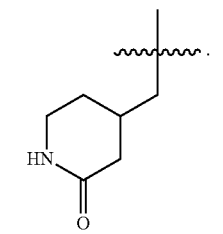 [SMILES: *CC1CCNC(=O)C1]
In embodiments, $L^2$-$R^2$ is
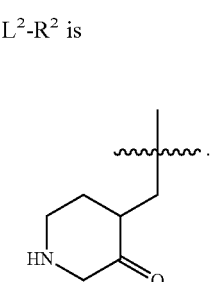

In embodiments, L²-R² is
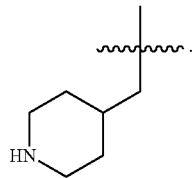
In embodiments, L²-R² is
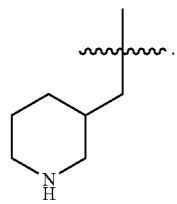 [SMILES: *CC1CCCNC1]
In embodiments, L²-R² is
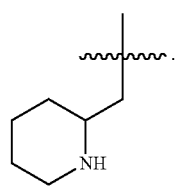 [SMILES: *CC1CCCCN1]
In embodiments, L²R² is
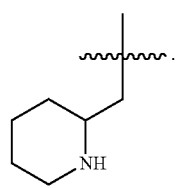
In embodiments, L²-R² is
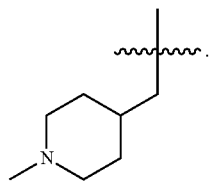
In embodiments, L²-R² is
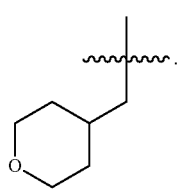
In embodiments, L²-R² is
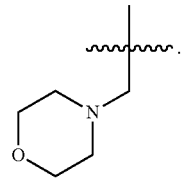
In embodiments, L²-R² is
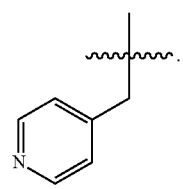
In embodiments, L²-R² is
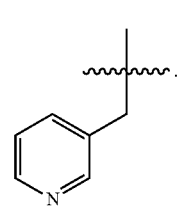 [SMILES: *Cc1cccnc1]
In embodiments, L²-R² is
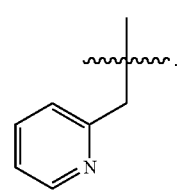 [SMILES: *Cc1ccccn1]
In embodiments, L²-R² is
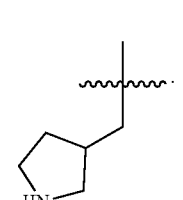
In embodiments, L²-R² is
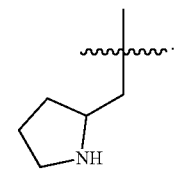

In embodiments, $L^2$-$R^2$ is

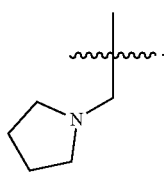 [SMILES: *CN1CCCC1]

In embodiments, -$L^2$-$R^2$ is

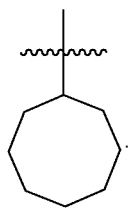

In embodiments, $L^2$-$R^2$ is

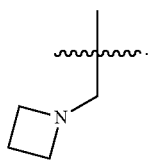 [SMILES: *CN1CCC1]

In embodiments, -$L^2$-$R^2$ is

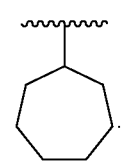

In embodiments, $L^2$-$R^2$ is

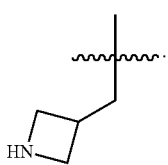

In embodiments, -$L^2$-$R^2$ is

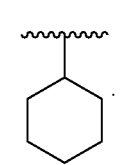

In embodiments, $L^2$-$R^2$ is

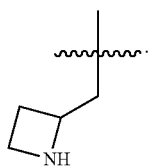 [SMILES: *CC1CCN1]

In embodiments, -$L^2$-$R^2$ is

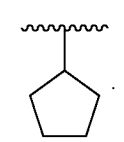

In embodiments, $L^2$-$R^2$ is

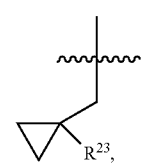

In embodiments, -$L^2$-$R^2$ is

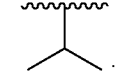

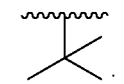

wherein $R^{23}$ is as described herein. In embodiments, $L^2$-$R^2$ is

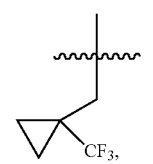

wherein $R^{23}$ is as described herein. In embodiments, -$L^2$-$R^2$ is

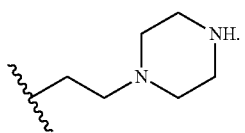 [SMILES: *CCN1CCNCC1]

In embodiments -L²-R² is
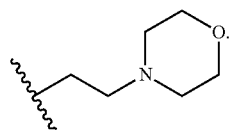 [SMILES: *CCN1CCOCC1]
In embodiments, -L²-R² is
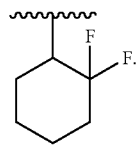 [SMILES: *C1CCCCC1(F)F]
In embodiments, -L²-R² is
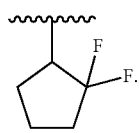
In embodiments, -L²-R² is
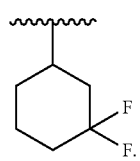
In embodiments, -L²-R² is
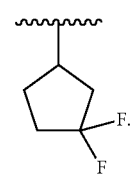 [SMILES: *C1CCC(F)(F)C1]
In embodiments -L²-R² is
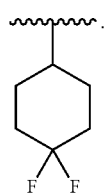
In embodiments, -L²-R² is
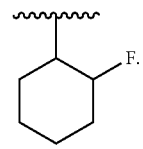
In embodiments, -L²-R² is
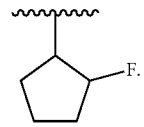
In embodiments, -L²-R²
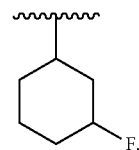
In embodiments, -L²-R²
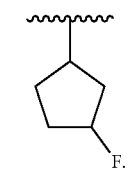 [SMILES: *C1CCC(F)C1]
In embodiments, -L²-R² is
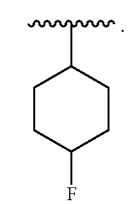
In embodiments, L²-R² is
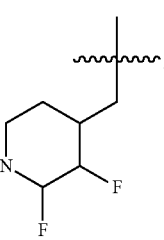

In embodiments, L²-R² is
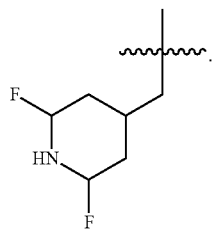
In embodiments, L²-R² is
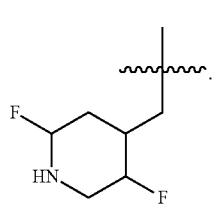
In embodiments, L²-R² is
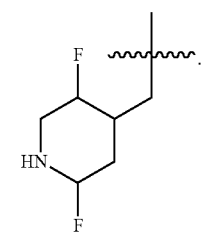
In embodiments, -L²-R²
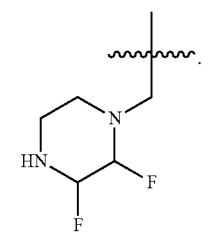
In embodiments, -L²-R²
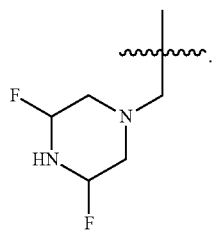
In embodiments, -L²-R²
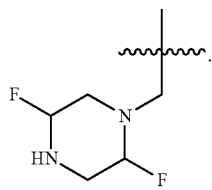
In embodiments, -L²-R²
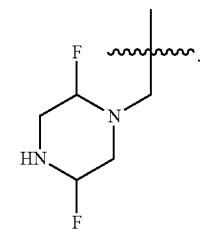
In embodiments, -L²-R²
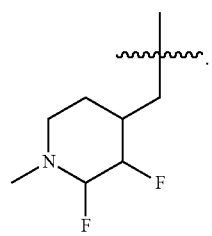 [SMILES: *CC1CCN(C)C(F)C1F]
In embodiments, -L²-R²
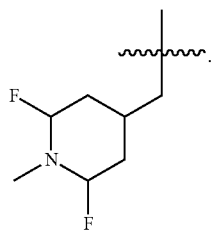 [SMILES: *CN1CC(F)N(C)C(F)C1]
In embodiments, -L²-R²
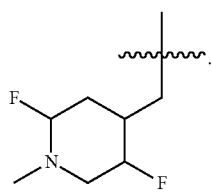 [SMILES: *CN1CC(F)N(C)CC1F]

In embodiments, -L²-R²
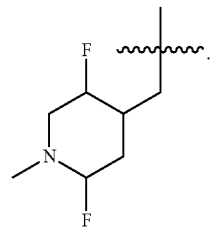 [SMILES: *CN1CC(F)N(C)CC1F]
In embodiments, -L²-R²
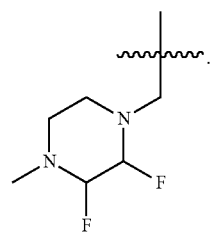
In embodiments, -L²-R²
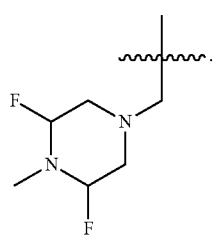
In embodiments, -L²-R²
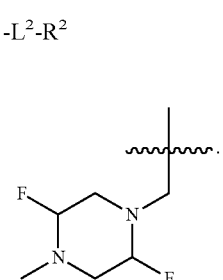
In embodiments, -L²-R²
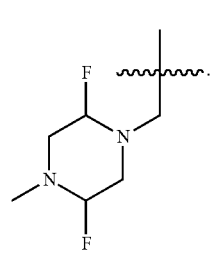
In embodiments, -L²-R²
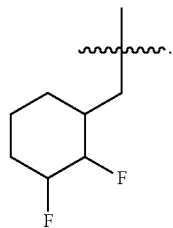 [SMILES: *CC1CCCC(F)C1F]
In embodiments, -L²-R²
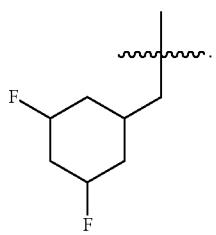 [SMILES: *CC1CC(F)CC(F)C1]
In embodiments, -L²-R²
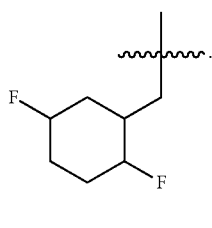 [SMILES: *CC1CC(F)CCC1F]
In embodiments, -L²-R²
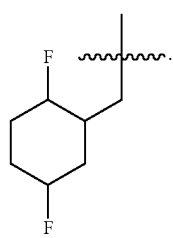 [SMILES: *CC1CC(F)CCC1F]
In embodiments, -L²-R²
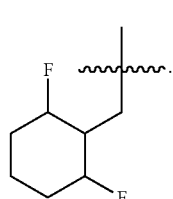

In embodiments, L²-R² is

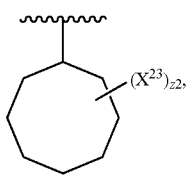

wherein X²³ is a halogen; z2 is an integer from 0 to 15. In embodiments, z2 is 2. In embodiments, -L²-R² is

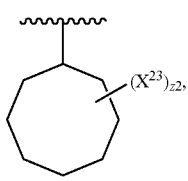

wherein X²³ is a halogen; z2 is an integer from 0 to 13. In embodiments, z2 is 2. In embodiments, -L²-R² is

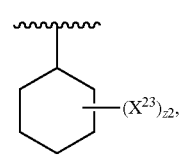

wherein X²³ is a halogen; z2 is an integer from 0 to 11. In embodiments, z2 is 2. In embodiments, -L²-R² is

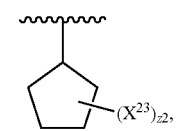

wherein X²³ is a halogen; z2 is an integer from 0 to 9. In embodiments, z2 is 2.

In embodiments, -L²-R²

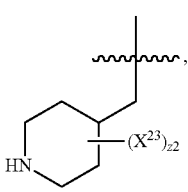

wherein X²³ is a halogen; z2 is an integer from 0 to 9. In embodiments, z2 is 2. In embodiments, L²-R² is

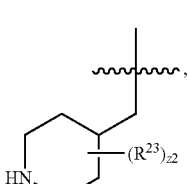

wherein R²³ is as described herein; z2 is an integer from 0 to 9. In embodiments, z2 is 2. In embodiments, L²-R² is

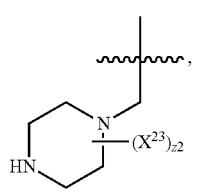

wherein X²³ is as described herein; z2 is an integer from 0 to 8. In embodiments, z² is 2. In embodiments, L²-R² is

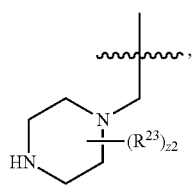

wherein R²³ is as described herein; z2 is an integer from 0 to 8. In embodiments, z2 is 2. In embodiments, L²-R² is

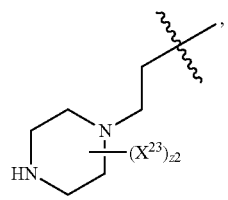

wherein X²³ is as described herein; z2 is an integer from 0 to 8. In embodiments, L²-R²R² is

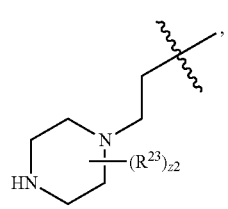

wherein R²³ is as described herein; z2 is an integer from 0 to 8. In embodiments, z2 is 2. In embodiments, X²³ is F.

In embodiments, L²-R² is

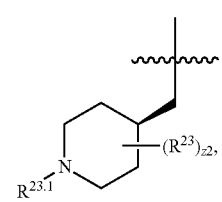

wherein R²³·¹ is R²³ at a fixed position (e.g., non-floating as shown in the formula described herein) and may independently be any R²³ substituent; and wherein R²³ is as described herein and z2 is an integer from 0 to 9. In embodiments, z2 is 2. In embodiments, $R^{23.1}$ is hydrogen, substituted or unsubstituted alkyl, substituted or unsubstituted cyclopropyl, —C(O)-(substituted or unsubstituted alkyl), —C(O)-(substituted or unsubstituted cyclopropyl), —C(N)-alkyl, —C(N)-cyclopropyl. In embodiments, $R^{23}$ is —OH, oxo, —F, or —COOH.

In embodiments, $L^2$-$R^2$ is

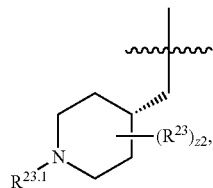

wherein $R^{23.1}$ is $R^{23}$ at a fixed position (e.g., non-floating as shown in the formula described herein) and may independently be any $R^{23}$ substituent; and wherein $R^{23}$ is as described herein and z2 is an integer from 0 to 9. In embodiments, z2 is 2. In embodiments, $R^{23.1}$ is hydrogen, substituted or unsubstituted alkyl, substituted or unsubstituted cyclopropyl, —C(O)-(substituted or unsubstituted alkyl), —C(O)-(substituted or unsubstituted cyclopropyl), —C(N)-alkyl, —C(N)-cyclopropyl. In embodiments, $R^{23}$ is —OH, oxo, —F, or —COOH.

In embodiments, $L^2$-$R^2$ is

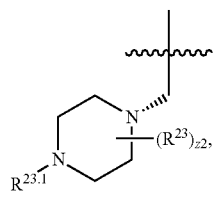

wherein $R^{23.1}$ is $R^{23}$ at a fixed position (e.g., non-floating as shown in the formula described herein) and may independently be any $R^{23}$ substituent; and wherein $R^{23}$ is as described herein and z2 is an integer from 0 to 9. In embodiments, z2 is 2. In embodiments, $R^{23.1}$ is hydrogen, substituted or unsubstituted alkyl, substituted or unsubstituted cyclopropyl, —C(O)-(substituted or unsubstituted alkyl), —C(O)-(substituted or unsubstituted cyclopropyl), —C(N)-alkyl, —C(N)-cyclopropyl. In embodiments, $R^{23}$ is —OH, oxo, —F, or —COOH.

In embodiments, $L^2$-$R^2$ is

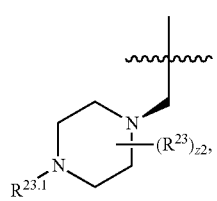

wherein $R^{23.1}$ is $R^{23}$ at a fixed position (e.g., non-floating as shown in the formula described herein) and may independently be any $R^{23}$ substituent; and wherein $R^{23}$ is as described herein and z2 is an integer from 0 to 9. In embodiments, z2 is 2. In embodiments, $R^{23.1}$ is hydrogen, substituted or unsubstituted alkyl, substituted or unsubstituted cyclopropyl, —C(O)-(substituted or unsubstituted alkyl), —C(O)-(substituted or unsubstituted cyclopropyl), —C(N)-alkyl, —C(N)-cyclopropyl. In embodiments, $R^{23}$ is —OH, oxo, —F, or —COOH.

In embodiments, $R^{23}$ is independently oxo. In embodiments, $R^{23}$ is independently halogen. In embodiments, $R^{23}$ is independently —F. In embodiments, $R^{23}$ is independently —Cl. In embodiments, $R^{23}$ is independently —COOH. In embodiments, $R^{23}$ is independently —C(O)NR$^{23A}$R$^{23B}$.

In embodiments, $R^{23.1}$ is hydrogen. In embodiments, $R^{23.1}$ is substituted or unsubstituted alkyl. In embodiments, $R^{23.1}$ is independently substituted or unsubstituted alkyl. In embodiments, $R^{23.1}$ is $R^{24}$-substituted or unsubstituted alkyl (e.g., $C_1$-$C_8$ alkyl, $C_1$-$C_6$ alkyl, or $C_1$-$C_4$ alkyl). In embodiments, $R^{23.1}$ is $R^{24}$-substituted alkyl (e.g., $C_1$-$C_8$ alkyl, $C_1$-$C_6$ alkyl, or $C_1$-$C_4$ alkyl). In embodiments, $R^{23.1}$ is an unsubstituted alkyl (e.g., $C_1$-$C_8$ alkyl, $C_1$-$C_6$ alkyl, or $C_1$-$C_4$ alkyl). In embodiments, $R^{23.1}$ is independently substituted or unsubstituted cycloalkyl. In embodiments, $R^{23.1}$ is $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{23.1}$ is $R^{24}$-substituted cycloalkyl (e.g., $C_3$-$C_8$ cycloalkyl, $C_3$-$C_6$ cycloalkyl, or $C_5$-$C_6$ cycloalkyl). In embodiments, $R^{23.1}$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{23.1}$ is unsubstituted cyclopropyl.

In embodiments, $R^{23.1}$ is $R^{24}$-substituted cyclopropyl. In embodiments, $R^{23.1}$ is —C(O)NH$_2$. In embodiments, $R^{23.1}$ is —C(O)NR$^{23A}$R$^{23B}$,

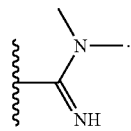

In embodiments, $R^{23.1}$ is

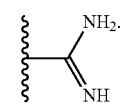

In embodiments, $R^{23.1}$ is

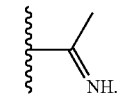

In embodiments, $R^{23.1}$ is

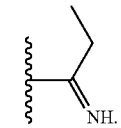

In embodiments, $R^{23.1}$ is

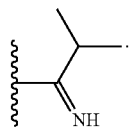 [SMILES: *C(=N)C(C)C]

In embodiments, $R^{23.1}$ is

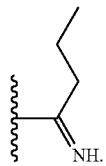 [SMILES: *C(=N)CCC]

In embodiments $R^{23.1}$ is

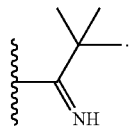 [SMILES: *C(=N)C(C)(C)C]

In embodiments, $R^{23.1}$ is —C(N)-(substituted or unsubstituted alkyl). In embodiments, $R^{23.1}$ is —C(N)-(substituted or unsubstituted $C_1$-$C_8$ alkyl). In embodiments, $R^{23.1}$ is —C(N)-(substituted or unsubstituted $C_1$-$C_6$ alkyl). In embodiments, $R^{23.1}$ is —C(N)-(substituted or unsubstituted $C_1$-$C_4$ alkyl). In embodiments, $R^{23.1}$ is —C(N)—($R^{24}$-substituted or unsubstituted alkyl). In embodiments, $R^{23.1}$ is —C(N)-(unsubstituted alkyl). In embodiments, $R^{23.1}$ is —C(N)—($R^{24}$-substituted alkyl).

In embodiments, $R^{23.1}$ is —C(N)-(substituted or unsubstituted cycloalkyl). In embodiments, $R^{23.1}$ is —C(N)-(substituted or unsubstituted $C_3$-$C_8$ cycloalkyl). In embodiments, $R^{23.1}$ is —C(N)-(substituted or unsubstituted $C_3$-$C_6$ cycloalkyl). In embodiments, $R^{23.1}$ is —C(N)-(substituted or unsubstituted $C_5$-$C_6$ cycloalkyl). In embodiments, $R^{23.1}$ is —C(N)—($R^{24}$-substituted or unsubstituted cycloalkyl). In embodiments, $R^{23.1}$ is —C(N)-(unsubstituted cycloalkyl). In embodiments, $R^{23.1}$ is —C(N)—($R^{24}$-substituted cycloalkyl).

In embodiments, $R^{23.1}$ is —C(O)-(substituted or unsubstituted alkyl). In embodiments, $R^{23.1}$ is —C(O)-(substituted or unsubstituted $C_1$—C alkyl). In embodiments, $R^{23.1}$ is —C(O)-(substituted or unsubstituted $C_1$-$C_6$ alkyl). In embodiments, $R^{23.1}$ is —C(O)-(substituted or unsubstituted $C_1$-$C_4$ alkyl). In embodiments, $R^{23.1}$ is —C(O)—($R^{24}$-substituted or unsubstituted alkyl). In embodiments, $R^{23.1}$ is —C(O)-(unsubstituted alkyl). In embodiments, $R^{23.1}$ is —C(O)—($R^{24}$-substituted alkyl).

In embodiments, $R^{23.1}$ is —C(O)-(substituted or unsubstituted cycloalkyl). In embodiments, $R^{23.1}$ is —C(O)-(substituted or unsubstituted $C_3$—C cycloalkyl). In embodiments, $R^{23.1}$ is —C(O)-(substituted or unsubstituted $C_3$-$C_6$ cycloalkyl). In embodiments, $R^{23.1}$ is —C(O)-(substituted or unsubstituted $C_5$-$C_6$ cycloalkyl). In embodiments, $R^{23.1}$ is —C(O)—($R^{24}$-substituted or unsubstituted cycloalkyl). In embodiments, $R^{23.1}$ is —C(O)-(unsubstituted cycloalkyl). In embodiments, $R^{23.1}$ is —C(O)—($R^{24}$-substituted cycloalkyl).

In embodiments, z4 and z5 are independently an integer from 0 to 2. In embodiments z4 is 0. In embodiments z4 is 1. In embodiments z4 is 2. In embodiments z5 is 0. In embodiments z5 is 1. In embodiments z5 is 2.

In embodiments, $L^2$-$R^2$ is

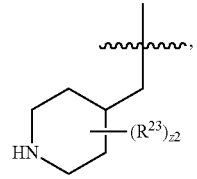

wherein $R^{23}$ is as described herein; z2 is an integer from 0 to 9. In embodiments z2 is 2.

In embodiments, $L^2$-$R^2$ is

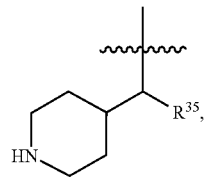

wherein $R^{35}$ is as described herein. In embodiments, $L^2$-$R^2$ is

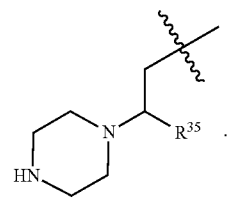

In embodiments, $L^2$-$R^2$ is

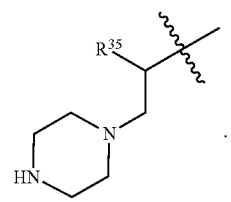

In embodiments, $L^2$-$R^2$ is

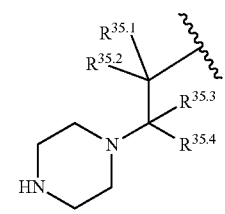

wherein $R^{35.1}$, $R^{35.2}$, $R^{35.3}$, and $R^{35.4}$ are each independently $R^{35}$ at a fixed position (e.g., non-floating as shown in the formula described herein) and may independently be any $R^{35}$ substituent. In embodiments, $L^2$-$R^2$ is

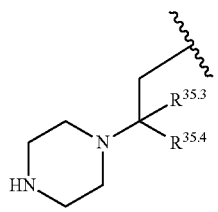

wherein $R^{35.3}$ and $R^{3.4}$ are each independently $R^{35}$ at a fixed position (e.g., non-floating as shown in the formula described herein) and may independently be any $R^{35}$ substituent. In embodiments, $L^2$-$R^2$ is

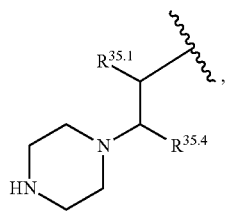

wherein $R^{35.1}$ and $R^{35.4}$ are each independently $R^{35}$ at a fixed position (e.g., non-floating as shown in the formula described herein) and may independently be any $R^{35}$ substituent. In embodiments, $R^{35.1}$ is halogen. In embodiments, $R^{35.1}$ is F.

In embodiments, $L^2$-$R^2$ is

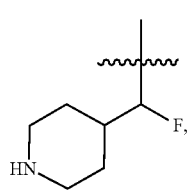

wherein $R^{35}$ is as described herein. In embodiments, $L^2$-$R^2$ is

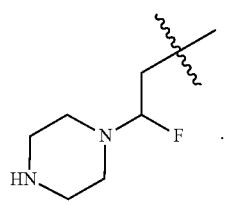

In embodiments, $L^2$-$R^2$ is

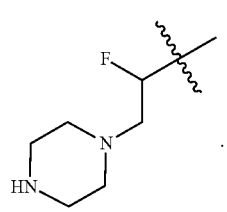 [SMILES: *C(F)CN1CCNCC1]

In embodiments, $L^2$-$R^2$ is

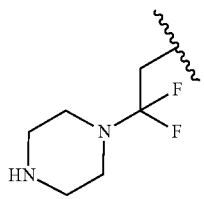 [SMILES: *CC(F)(F)N1CCNCC1]

wherein $R^{35.1}$, $R^{35.2}$, $R^{35.3}$, and $R^{35.4}$ are each independently $R^{35}$ at a fixed position (e.g., non-floating as shown in the formula described herein) and may independently be any $R^{35}$ substituent. In embodiments, $L^2$-$R^2$ is

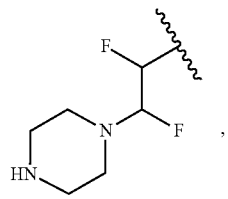

wherein $R^{35.1}$ and $R^{35.4}$ are each independently $R^{35}$ at a fixed position (e.g., non-floating as shown in the formula described herein) and may independently be any $R^{35}$ substituent. In embodiments, $R^{35.1}$ is halogen. In embodiments, $R^{35.1}$ is F. In embodiments, $L^2$-$R^2$ is

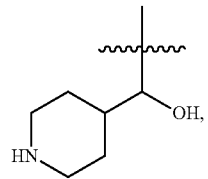

wherein $R^{35}$ is as described herein. In embodiments, $L^2$-$R^2$ is

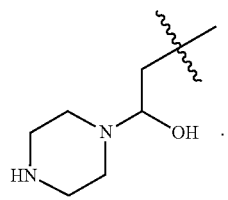

In embodiments, $L^2$-$R^2$ is

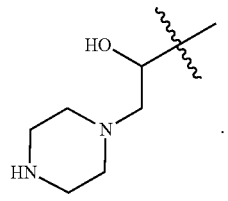

In embodiments, $R^2$ is $R^{23}$-substituted or unsubstituted heterocycloalkyl or $R^{23}$-substituted or unsubstituted heteroaryl. In embodiments, $R^2$ is $R^{23}$-substituted or unsubstituted 3 to 6 membered heterocycloalkyl or $R^{23}$-substituted or unsubstituted 5 to 6 membered heteroaryl.

$R^{23}$ is independently oxo, halogen, —$CX^{23}_3$, —$CHX^{23}_2$, —$CH_2X^{23}$, —$OCH_2X^{23}$, —$OCX^{23}_3$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{23}_3$, —$OCHX^{23}_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl. In embodiments, $R^{23}$ is a halogen. In embodiments, $R^{23}$ is $R^{24}$-substituted or unsubstituted alkyl. $X^{23}$ is halogen. In embodiments, $X^{23}$ is F. In embodiments, $R^{23}$ is unsubstituted alkyl. In embodiments, $R^{23}$ is —F. In embodiments, $R^{23}$ is a —Cl. In embodiments, $R^{23}$ is —$CX^{23}_3$. In embodiments, $R^{23}$ is —$CHX^{23}_2$. In embodiments, $R^{23}$ is —$CH_2X^{23}$. In embodiments, $R^{23}$ is —$OCH_2X^{23}$. In embodiments, $R^{23}$ is —$OCX^{23}_3$. In embodiments, $R^{23}$ is or —$OCHX^{23}_2$.

In embodiments, $R^{23}$ is independently oxo, halogen, —$CX^{23}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, $R^{24}$-substituted or unsubstituted $C_1$-$C_8$ alkyl, $R^{24}$-substituted or unsubstituted 2 to 8 membered heteroalkyl, $R^{24}$-substituted or unsubstituted $C_3$-$C_8$ cycloalkyl, $R^{24}$-substituted or unsubstituted 3 to 8 membered heterocycloalkyl, $R^{24}$-substituted or unsubstituted phenyl, or $R^{24}$ substituted or unsubstituted 5 to 6 membered heteroaryl. $X^{23}$ is —F, —Cl, —Br, or —I. In embodiments, $R^{23}$ is —$CX^{23}_3$, —$CHX^{23}_2$, —$CH_2X^{23}$, —$OCH_2X^{23}$, —$OCX^{23}_3$, or —$OCHX^{23}_2$. In embodiments, $R^{23}$ is —$CF_3$, —$CHF_2$, —$CH_2F$, —$OCH_2F$, —$OCF_3$, or —$OCHF_2$. In embodiments, $R^{23}$ is unsubstituted cyclopropyl. In embodiments, $R^{23}$ is unsubstituted methyl. In embodiments, $R^{23}$ is —$CF_3$. In embodiments, $R^{23}$ is —$CHF_2$. In embodiments, $R^{23}$ is —$CH_2F$. In embodiments, $R^{23}$ is —$OCH_2F$. In embodiments, $R^{23}$ is —$OCF_3$. In embodiments, $R^{23}$ is —$OCHF_2$.

$R^{24}$ is independently oxo, halogen, —$CX^{24}_3$, —$CHX^{24}2$, —$CH_2X^{24}$, —$OCH_2X^{24}$, —$OCX^{24}_3$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, $R^{25}$-substituted or unsubstituted alkyl, $R^{25}$-substituted or unsubstituted heteroalkyl, $R^{25}$ substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl. In embodiments, $R^{24}$ is independently oxo, halogen, —$CX^{24}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{24}_3$, —$OCHX^{24}_2$, $R^{25}$-substituted or unsubstituted $C_1$-$C_8$ alkyl, $R^{25}$-substituted or unsubstituted 2 to 8 membered heteroalkyl, $R^{25}$-substituted or unsubstituted $C_3$-$C_8$ cycloalkyl, $R^{25}$-substituted or unsubstituted 3 to 68 membered heterocycloalkyl, $R^{25}$-substituted or unsubstituted phenyl, or $R^{25}$-substituted or unsubstituted 5 to 6 membered heteroaryl. $X^{24}$ is —F, —Cl, —Br, or —I.

$R^{25}$ is independently hydrogen, oxo, halogen, —$CCl_3$, —$CBr_3$, —$CF_3$, —$CL_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{25}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{25}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted phenyl, or unsubstituted 5 to 6 membered heteroaryl.

In embodiments, $R^3$ is hydrogen, —CN, —COOH, —$CX^3_3$, substituted or unsubstituted alkyl, or substituted or unsubstituted heteroalkyl. In embodiments, $R^3$ is hydrogen, —CN, —COOH, —$CX^3_3$, substituted or unsubstituted $C_1$-$C_4$ alkyl, or substituted or unsubstituted 2 to 4 membered heteroalkyl. In embodiments, $R^3$ is hydrogen. In embodiments, $R^3$ is hydrogen, —$SO_2CH_3$, —CN, —$COCH_3$, —$CX^3_3$, substituted or unsubstituted alkyl, or substituted or unsubstituted heteroalkyl.

In embodiments, $R^3$ is hydrogen. In embodiments, $R^3$ is —$CX^3_3$. In embodiments, $R^3$ is —$CHX^{32}$. In embodiments, $R^3$ is —$CH_2X^3$. In embodiments, $R^3$ is —CN. In embodiments, $R^3$ is —COOH. In embodiments, $R^3$ is substituted or unsubstituted alkyl. In embodiments, $R^3$ is substituted or unsubstituted heteroalkyl. In embodiments, $R^3$ is substituted alkyl. In embodiments, $R^3$ is substituted heteroalkyl. In embodiments, $R^3$ is unsubstituted alkyl. In embodiments, $R^3$ is unsubstituted heteroalkyl. In embodiments, $R^3$ is substituted or unsubstituted $C_1$-$C_8$alkyl. In embodiments, $R^3$ is substituted or unsubstituted 2 to 8 membered heteroalkyl. In embodiments, $R^3$ is substituted $C_1$-$C_8$ alkyl. In embodiments, $R^3$ is substituted 2 to 8 membered heteroalkyl. In embodiments, $R^3$ is unsubstituted $C_1$-$C_5$ alkyl. In embodiments, $R^3$ is unsubstituted 2 to 8 membered heteroalkyl. In embodiments, $R^3$ is substituted or unsubstituted $C_1$-$C_4$ alkyl. In embodiments, $R^3$ is substituted or unsubstituted 2 to 4 membered heteroalkyl. In embodiments, $R^3$ is substituted $C_1$-$C_4$ alkyl. In embodiments, $R^3$ is substituted 2 to 4 membered heteroalkyl. In embodiments, $R^3$ is unsubstituted $C_1$-$C_4$ alkyl. In embodiments, $R^3$ is unsubstituted 2 to 4 membered heteroalkyl. In embodiments, $R^3$ is unsubstituted methyl. In embodiments, $R^3$ is unsubstituted ethyl. In embodiments, $R^3$ is unsubstituted propyl. In embodiments, $R^3$ is unsubstituted isopropyl. In embodiments, $R^3$ is unsubstituted butyl. In embodiments, $R^3$ is unsubstituted tert-butyl.

In embodiments, $R^3$ is hydrogen, —CN, —COOH, —CX$^3_3$, $R^{26}$-substituted or unsubstituted alkyl or $R^{26}$-substituted or unsubstituted heteroalkyl. In embodiments, $R^3$ is hydrogen, —CN, —COOH, —CX$^3_3$, $R^{26}$-substituted or unsubstituted $C_1$-$C_5$ alkyl or $R^{26}$-substituted or unsubstituted 2 to 8 membered heteroalkyl. $X^3$ is —F, —Cl, —Br, or —I. In embodiments, $R^3$ is independently hydrogen. In embodiments, $R^3$ is independently unsubstituted methyl. In embodiments, $R^3$ is independently unsubstituted ethyl.

$R^{26}$ is independently oxo, halogen, —CX$^{26}_3$, —CHX$^{26}_2$, —CH$_2$X$^{26}$, —OCH$_2$X$^{26}$, —OCX$^{26}_3$, —OCHX$^{26}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{26}_3$, —OCHX$^{26}_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl. In embodiments, $R^{26}$ is independently oxo, halogen, —CX$^{26}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{26}_3$, —OCHX$^{26}_2$, $R^{27}$-substituted or unsubstituted $C_1$-$C_8$ alkyl, $R^{27}$-substituted or unsubstituted 2 to 8 membered heteroalkyl, $R^{27}$-substituted or unsubstituted $C_3$-$C_8$ cycloalkyl, $R^{27}$-substituted or unsubstituted 3 to 8 membered heterocycloalkyl, $R^{27}$-substituted or unsubstituted phenyl, or $R^{27}$-substituted or unsubstituted 5 to 6 membered heteroaryl. $X^{26}$ is —F, —Cl, —Br, or —I.

$R^{27}$ is independently oxo, halogen, —CX$^{27}_3$, —CHX$^{27}_2$, —CH$_2$X$^{27}$, —OCH$_2$X$^{27}$, —OCX$^{27}_3$, —OCHX$^{27}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{27}_3$, —OCHX$^{27}_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl. In embodiments, $R^{27}$ is independently oxo, halogen, —CX$^{27}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{27}_3$, —OCHX$^{27}_2$, $R^{28}$-substituted or unsubstituted $C_1$-$C_5$ alkyl, $R^{28}$-substituted or unsubstituted 2 to 8 membered heteroalkyl, $R^{28}$-substituted or unsubstituted $C_3$-$C_8$ cycloalkyl, $R^{28}$-substituted or unsubstituted 3 to 8 membered heterocycloalkyl, $R^{28}$-substituted or unsubstituted phenyl, or $R^{28}$-substituted or unsubstituted 5 to 6 membered heteroaryl. $X^{27}$ is —F, —Cl, —Br, or —I.

$R^{28}$ is independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{28}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{28}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted $C_1$-$C_5$ alkyl, unsubstituted 2 to 8 membered heteroalkyl, unsubstituted $C_3$-$C_8$ cycloalkyl, unsubstituted 3 to 8 membered heterocycloalkyl, unsubstituted phenyl, or unsubstituted 5 to 6 membered heteroaryl.

In embodiments, $X^3$ is independently halogen. In embodiments, $X^3$ is independently —F. In embodiments, $X^3$ is independently —Cl. In embodiments, $X^3$ is independently —Br. In embodiments, $X^3$ is independently —I.

In embodiments, $L^1$ is —O—. In embodiments, $L^1$ is —S—. In embodiments, $L^1$ is —N(R$^3$)—. In embodiments, $L^1$ is —SO—. In embodiments, $L^1$ is —SO$_2$—. In embodiments, $L^1$ is —N(H)—. In embodiments, L is —SO—, —SO$_2$—, —O—, —S—, —N(R$^3$)—, —B(R$^6$)— (i.e. $L^1$ includes a boron), or $R^6$-substituted or unsubstituted $C_1$-$C_3$ alkylene. In embodiments, $L^1$ is $R^6$-substituted or unsubstituted $C_1$-$C_3$ alkylene. In embodiments, $L^1$ is $R^6$-substituted $C_1$-$C_3$ alkylene. In embodiments, $L^1$ is unsubstituted $C_1$-$C_3$ alkylene. In embodiments, $L^1$ is unsubstituted methylene. In embodiments, $L^1$ is —O—, —S—, —N(R$^3$)—, or substituted or unsubstituted $C_1$-$C_3$ alkylene.

In embodiments, $L^2$ is a bond, substituted or unsubstituted alkylene, or substituted or unsubstituted heteroalkylene. In embodiments, $L^2$ is a bond. In embodiments, $L^2$ is substituted or unsubstituted alkylene. In embodiments, $L^2$ is substituted or unsubstituted heteroalkylene. In embodiments, $L^2$ is a bond, —N(R$^7$)—, substituted or unsubstituted alkylene, or substituted or unsubstituted heteroalkylene. In embodiments, $L^2$ is a bond, —O—, —S—, —N(R$^7$)—, substituted or unsubstituted alkylene, or substituted or unsubstituted heteroalkylene.

In embodiments, $L^2$ is a bond, substituted or unsubstituted $C_1$-$C_5$ alkylene, or substituted or unsubstituted 2 to 5 membered heteroalkylene. In embodiments, $L^2$ is a bond, —CH$_2$—, —CH$_2$CH$_2$—, —CH$_2$O—, —CH$_2$S—, or —CH$_2$NH—. In embodiments, $L^2$ is a bond. In embodiments, $L^2$ is —CH$_2$—. In embodiments, $L^2$ is —CH$_2$CH$_2$—. In embodiments, $L^2$ is —CH$_2$O—. In embodiments, $L^2$ is —CH$_2$S—. In embodiments, $L^2$ is —CH$_2$NH—.

In embodiments, $L^2$ is a substituted or unsubstituted alkylene. In embodiments, $L^2$ is a substituted or unsubstituted heteroalkylene. In embodiments, $L^2$ is a substituted alkylene. In embodiments, $L^2$ is a substituted heteroalkylene. In embodiments, $L^2$ is a unsubstituted alkylene. In embodiments, $L^2$ is a unsubstituted heteroalkylene. In embodiments, $L^2$ is a substituted or unsubstituted $C_1$-$C_8$ alkylene. In embodiments, $L^2$ is a substituted or unsubstituted 2 to 8 membered heteroalkylene. In embodiments, $L^2$ is a substituted $C_1$-$C_5$ alkylene. In embodiments, $L^2$ is a substituted 2 to 8 membered heteroalkylene. In embodiments, $L^2$ is a unsubstituted $C_1$-$C_5$ alkylene. In embodiments, $L^2$ is a unsubstituted 2 to 8 membered heteroalkylene. In embodiments, $L^2$ is a substituted or unsubstituted $C_1$-$C_4$ alkylene. In embodiments, $L^2$ is a substituted or unsubstituted 2 to 4 membered heteroalkylene. In embodiments, $L^2$ is a substituted $C_1$-$C_4$ alkylene. In embodiments, $L^2$ is a substituted 2 to 4 membered heteroalkylene. In embodiments, $L^2$ is a unsubstituted $C_1$-$C_4$ alkylene. In embodiments, $L^2$ is a unsubstituted 2 to 4 membered heteroalkylene. In embodiments, $L^2$ is a unsubstituted methylene. In embodiments, $L^2$ is a unsubstituted ethylene. In embodiments, $L^2$ is a substituted $C_2$-$C_8$ alkylene. In embodiments, $L^2$ is a unsubstituted $C_2$—C alkylene. In embodiments, $L^2$ is a substituted $C_3$-$C_5$ alkylene. In embodiments, $L^2$ is a unsubstituted $C_3$-$C_8$ alkylene. In embodiments, $L^2$ is a substituted $C_4$-$C_8$ alkylene. In embodiments, $L^2$ is an unsubstituted $C_4$-$C_8$ alkylene. In embodiments, $L^2$ is a substituted $C_2$-$C_3$ alkylene. In embodiments, $L^2$ is an unsubstituted $C_2$-$C_3$ alkylene.

In embodiments, $L^2$ is a bond, $R^{35}$-substituted or unsubstituted alkylene or $R^{35}$-substituted or unsubstituted heteroalkylene. In embodiments, $L^2$ is a bond, $R^{35}$-substituted or unsubstituted $C_1$-$C_5$ alkylene or $R^{35}$-substituted or unsubstituted 2 to 8 membered heteroalkylene. In embodiments, $L^2$ is a bond, $R^{35}$-substituted or unsubstituted $C_1$-$C_4$ alkylene or $R^{35}$-substituted or unsubstituted 2 to 4 membered heteroalkylene. In embodiments, $L^2$ is a bond, $R^{35}$-substituted or unsubstituted $C_1$-$C_3$ alkylene or $R^{35}$-substituted or unsubstituted 2 to 3 membered heteroalkylene. In embodiments, $L^2$ is a bond, $R^{35}$-substituted or unsubstituted $C_1$-$C_2$ alkylene or $R^{35}$-substituted or unsubstituted 2 membered heteroalkylene. In embodiments, $L^2$ is $R^{35}$-substituted or unsubstituted alkylene or $R^{35}$-substituted or unsubstituted heteroalkylene. In embodiments, $L^2$ is $R^{35}$-substituted or unsubstituted $C_1$-$C_8$ alkylene or $R^{35}$-substituted or unsubstituted 2 to 8 membered heteroalkylene. In embodiments, $L^2$ is $R^{35}$-substituted or unsubstituted $C_1$-$C_4$ alkylene or $R^{35}$-substituted or unsubstituted 2 to 4 membered heteroalkylene. In embodiments, $L^2$ is a bond, $R^{35}$-substituted or unsubstituted $C_1$-$C_3$ alkylene or $R^{35}$-substituted or unsubstituted 2 to 3 membered heteroalkylene. In embodiments, $L^2$ is $R^{35}$-substituted or unsubstituted $C_1$-$C_2$ alkylene or $R^{35}$-substituted or unsubstituted 2 membered heteroalkylene.

$R^{35}$ is independently oxo, halogen, —$CX^{35.3}$, —$CHX^{35.2}$, —$CH_2X^{35}$, —$OCH_2X^{35}$, —$OCX^{35.3}$, —$OCHX^{35.2}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl. In embodiments, $R^{35}$ is independently oxo, halogen, —$CX^{35.3}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{35.3}$, —$OCHX^{35.2}$, $R^{36}$-substituted or unsubstituted $C_1$-$C_8$ alkyl, $R^{36}$-substituted or unsubstituted 2 to 8 membered heteroalkyl, $R^{36}$-substituted or unsubstituted $C_3$-$C_8$ cycloalkyl, $R^{36}$-substituted or unsubstituted 3 to 8 membered heterocycloalkyl, $R^{36}$-substituted or unsubstituted phenyl, or $R^{36}$-substituted or unsubstituted 5 to 6 membered heteroaryl. $X^{35}$ is —F, —Cl, —Br, or —I. In embodiments, $R^{35}$ is —$CX^{35.3}$, —$CHX^{35.2}$, —$CH_2X^{35}$, —$OCH_2X^{35}$, —$OCX^{35.3}$, or —$OCHX^{35.2}$. In embodiments, $R^{35}$ is —$CF_3$, —$CHF_2$, —$CH_2F$, —$OCH_2F$, —$OCF_3$, or —$OCHF_2$. In embodiments, $R^{35}$ is unsubstituted cyclopropyl. In embodiments, $R^{35}$ is unsubstituted methyl. In embodiments, $R^{35}$ is —$CF_3$. In embodiments, $R^{35}$ is —$CHF_2$. In embodiments, $R^{35}$ is —$CH_2F$. In embodiments, $R^{35}$ is —$OCH_2F$. In embodiments, $R^{35}$ is —$OCF_3$. In embodiments, $R^{35}$ is —$OCHF_2$. In embodiments, $R^{35}$ is halogen. In embodiments, $R^{35}$ is F. In embodiments, $R^{35}$ is —OH.

$R^{36}$ is independently oxo, halogen, —$CX^{36}_3$, —$CHX^{36}_2$, —$CH_2X^{36}$, —$OCH_2X^{36}$, —$OCX^{36}_3$, —$OCHX^{36}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl. In embodiments, $R^{36}$ is independently oxo, halogen, —$CX^{36}_3$, —$CHX^{36}_2$, —$CH_2X^{36}$, —$OCH_2X^{36}$, —$OCX^{36}_3$, —$OCHX^{36}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, $R^{37}$-substituted or unsubstituted $C_1$-$C_8$ alkyl, $R^{37}$-substituted or unsubstituted 2 to 8 membered heteroalkyl, $R^{37}$-substituted or unsubstituted $C_3$-$C_8$ cycloalkyl, $R^{37}$-substituted or unsubstituted 3 to 8 membered heterocycloalkyl, $R^{37}$-substituted or unsubstituted phenyl, or $R^{37}$-substituted or unsubstituted 5 to 6 membered heteroaryl. $X^{36}$ is —F, —Cl, —Br, or —I.

$R^{37}$ is independently hydrogen, oxo, halogen, —$CCl_3$, —$CBr_3$, —$CF_3$, —$CL_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{37}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{37}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted phenyl, or unsubstituted 5 to 6 membered heteroaryl.

In embodiments, $R^6$ is halogen, —$CX^6_3$, —$CHX^6_2$, —$CH_2X^6$, —$OCX^6_3$, —$OCH_2X^6$, —$OCHX^6_2$, —CN, —SH, —SO$_2$NH$_2$, —NHC(O)NH$_2$, —N(O), —N(O)$_2$, —NH$_2$, —C(O)H, —C(O)O H, —C(O)NH$_2$, —OH, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is —CX$^6_3$, —CHX$^6_2$, —CH$_2$X$^6$, —OCX$^6_3$, —OCH$_2$X$^6$, —OCHX$^6_2$, —CN, —SH, —SO$_2$NH$_2$, —NHC(O)NH$_2$, —N(O), —N(O)$_2$, —NH$_2$, —C(O)H, —C(O)O H, —C(O)NH$_2$, —OH, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is hydrogen.

In embodiments, $R^6$ is halogen, —CX$^6_3$, —CHX$^6_2$, —CH$_2$X$^6$, —OCX$^6_3$, —OCH$_2$X$^6$, —OCHX$^6_2$, —CN, —SH, —SO$_2$NH$_2$, —NHC(O)NH$_2$, —N(O), —N(O)$_2$, —NH$_2$, —C(O)H, —C(O)O H, —C(O)NH$_2$, —OH, —NHSO$_2$H, —NHC(O)H, —NHC(O)OH, —NHOH, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

In embodiments, $R^7$ is —CN, —COOH, —CX$^7_3$, substituted or unsubstituted alkyl (e.g., $C_1$-$C_5$ alkyl, $C_1$-$C_6$ alkyl, $C_1$-$C_4$ alkyl, $C_1$-$C_2$ alkyl, unsubstituted $C_1$-$C_8$ alkyl, unsubstituted $C_1$-$C_6$ alkyl, unsubstituted $C_1$-$C_4$ alkyl, or unsubstituted $C_1$-$C_2$ alkyl), or substituted or unsubstituted heteroalkyl (e.g., 2 to 8 membered heteroalkyl, 2 to 6 membered heteroalkyl, 2 to 4 membered heteroalkyl, 2 to 3 membered heteroalkyl, unsubstituted 2 to 8 membered heteroalkyl, unsubstituted 2 to 6 membered heteroalkyl, unsubstituted 2 to 4 membered heteroalkyl, or unsubstituted 2 to 3 membered heteroalkyl). In embodiments, $R^7$ is —CN, —COOH, —CX$^7_3$, $R^{35}$-substituted or unsubstituted alkyl (e.g., $C_1$-$C_8$ alkyl, $C_1$-$C_6$ alkyl, $C_1$-$C_4$ alkyl, $C_1$-$C_2$ alkyl, unsubstituted $C_1$-$C_8$ alkyl, unsubstituted $C_1$-$C_6$ alkyl, unsubstituted $C_1$-$C_4$ alkyl, or unsubstituted $C_1$-$C_2$ alkyl), or $R^{35}$-substituted or unsubstituted heteroalkyl (e.g., 2 to 8 membered heteroalkyl, 2 to 6 membered heteroalkyl, 2 to 4 membered heteroalkyl, 2 to 3 membered heteroalkyl, unsubstituted 2 to 8 membered heteroalkyl, unsubstituted 2 to 6 membered heteroalkyl, unsubstituted 2 to 4 membered heteroalkyl, or unsubstituted 2 to 3 membered heteroalkyl).

In embodiments, $R^7$ is —CN, —CX$^7_3$, substituted or unsubstituted alkyl (e.g., $C_1$-$C_8$ alkyl, $C_1$-$C_6$ alkyl, $C_1$-$C_4$ alkyl, $C_1$-$C_2$ alkyl, unsubstituted $C_1$-$C_8$ alkyl, unsubstituted $C_1$-$C_6$ alkyl, unsubstituted $C_1$-$C_4$ alkyl, or unsubstituted $C_1$-$C_2$ alkyl), or substituted or unsubstituted heteroalkyl (e.g., 2 to 8 membered heteroalkyl, 2 to 6 membered heteroalkyl, 2 to 4 membered heteroalkyl, 2 to 3 membered heteroalkyl, unsubstituted 2 to 8 membered heteroalkyl, unsubstituted 2 to 6 membered heteroalkyl, unsubstituted 2 to 4 membered heteroalkyl, or unsubstituted 2 to 3 membered heteroalkyl).

In embodiments, $R^8$ is halogen, —CX$^8_3$, —CHX$^8_2$, —CH$_2$X$^8$, —OCX$^8_3$, —OCH$_2$X, —OCHX$^8_2$, —CN, —SH, —SO$_2$NH$_2$, —NHC(O)NH$_2$, —N(O), —N(O)$_2$, —NH$_2$, —C(O)H, —C(O)OH, —C(O)NH$_2$, —OH, —NHSO$_2$H, —NHC(O)H, —NHO H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^8$ is halogen, —CX$^8_3$, —CHX$^8_2$, —CH$_2$X$^8$, —OCX$^8_3$, —OCH$_2$X$^8$, —OCHX$^8_2$, —CN, —SH, —SO$_2$NH$_2$, —NHC(O)NH$_2$, —N(O), —N(O)$_2$, —NH$_2$, —C(O)H, —C(O)OH, —C(O)NH$_2$, —OH, —NHSO$_2$H, —NHC(O) H, —NHC(O)OH, —NHOH, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

Each $X^6$ is independently —F, —Cl, —Br, or —I. Each $X^7$ is independently —F, —Cl, —Br, or —I. Each $X^8$ is independently —F, —Cl, —Br, or —I.

In embodiments, the compound has the formula:

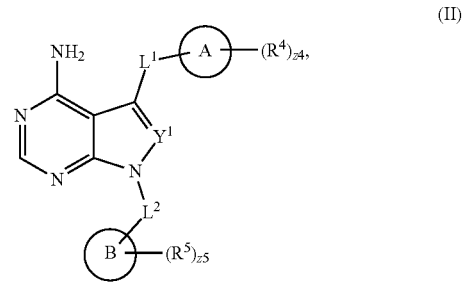

(II)

wherein $L^1$, $L^2$, and $Y^1$ are as described herein. It is understood that when $R^1$ is a substituted or unsubstituted aryl or substituted or unsubstituted heteroaryl it may be written as Ring A and all substitutions of $R^1$ may be assumed by substitutions to Ring A. For example, when $R^1$ is $R^{20}$-substituted aryl or $R^{20}$-substituted heteroaryl, it may be written as $R^4$-substituted Ring A. It is understood that when $R^2$ is a substituted or unsubstituted heterocycloalkyl or substituted or unsubstituted heteroaryl, it may be written as Ring B and all substitutions of $R^2$ may be assumed by substitutions to Ring B. For example, when $R^2$ is $R^{23}$-substituted aryl or $R^{23}$-substituted heteroaryl, it may be written as $R^5$-substituted Ring B.

Ring A is $C_6$-$C_{10}$ aryl or 5 to 10 membered heteroaryl. Ring B is 3 to 7 membered heterocycloalkyl, 5 to 10 membered heteroaryl, or $C_3$-$C_8$ cycloalkyl. $R^4$ is halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl. $R^5$ is halogen, —CX$^5_3$, —CHX$^5_2$, —CH$_2$X$^5$, —OCX$^5_3$, —OCH$_2$X$^5$, —OCHX$^5_2$, —CN, —SO$_{n5}$R$^{5D}$, —SO$_{v5}$NR$^{5A}$R$^{5B}$, —NHC(O)NR$^{5A}$R$^{5B}$, —N(O)$_{m5}$, —NR$^{5A}$R$^{5B}$, —C(O)R$^{5C}$, —C(O)—OR$^{5C}$, —C(O)NR$^{5A}$R$^{5B}$, —OR$^{5D}$, —NR$^{5A}$SO$_2$R$^{5D}$, NR$^{5A}$C(O)R$^{5C}$NR$^{5A}$C(O)OR$^{5C}$_NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^5$ substituents may optionally be joined to form a substituted or unsubstituted cycloalkyl, substituted or unsubstituted heterocycloalkyl, substituted or unsubstituted aryl, or substituted or unsubstituted heteroaryl. Each $R^{4A}$, $R^{4B}$, $R^{4C}$, $R^{4D}$, $R^{5A}$, $R^{5B}$, $R^{5C}$, and $R^{5D}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{4A}$ and $R^{4B}$ substituents bonded to the same nitrogen atom may optionally be joined to form a substituted or unsubstituted heterocycloalkyl or substituted or unsubstituted heteroaryl. $R^{5A}$ and $R^{5B}$ substituents bonded to the same nitrogen atom may optionally be joined to form a substituted or unsubstituted heterocycloalkyl or substituted or unsubstituted heteroaryl. Each X, $X^4$, and $X^5$ is independently —F, —Cl, —Br, or —I. The symbols n4 and n5 are independently an integer from 0 to 4. The symbols m4, m5, v4, and v5 are independently an integer from 1 to 2. The symbol z4 is an integer from 0 to 9. The symbol z5 is an integer from 0 to 6.

In embodiments, Ring A is phenyl. In embodiments, Ring A is napththyl. In embodiments, Ring A is 5 to 10 membered heteroaryl. In embodiments, Ring A is benzofuranyl, isobenzofuranyl, indolyl, isoindolyl, benzothienyl, benzo[c]thienyl, benzimidazolyl, azaindolyl, benzoisoxazolyl, pyrrolopyridinyl, purinyl, indazolyl, benzoxazolyl, benzisoxazolyl, benzothiazolyl, quinolinyl, isoquinolinyl, quinoxalinyl, quinazolinyl, cinnolinyl, or phthalazinyl. In embodiments, Ring A is 5 to 9 membered heteroaryl. In embodiments, Ring A is 5 to 6 membered heteroaryl. In embodiments, Ring A is furanyl, pyrrolyl, thienyl, imidazolyl, pyrazolyl, oxazolyl, isoxazolyl, thiazolyl, isothiazolyl, triazolyl, oxadiazolyl, thiadiazolyl, tetrazolyl, pyridinyl, pyrazinyl, pyrimidinyl, pyridazinyl, or triazinyl.

In embodiments, Ring A is $C_6$-$C_{10}$ aryl or 5 to 10 membered heteroaryl. In embodiments, Ring A is $C_6$-$C_{10}$ aryl or 5 to 9 membered heteroaryl. In embodiments, Ring A is phenyl or 5 to 6 membered heteroaryl. In embodiments, Ring A is aryl. In embodiments, Ring A is $C_6$-$C_{10}$ aryl. In embodiments, Ring A is $C_{10}$ aryl. In embodiments, Ring A is phenyl.

In embodiments, Ring A is heteroaryl. In embodiments, Ring A is 5 to 10 membered heteroaryl. In embodiments, Ring A is 5 to 9 membered heteroaryl. In embodiments, Ring A is 5 to 6 membered heteroaryl. In embodiments, Ring A is 5 membered heteroaryl. In embodiments, Ring A is 6 membered heteroaryl. In embodiments, Ring A is 9 membered heteroaryl. In embodiments, Ring A is 10 membered heteroaryl.

In embodiments, Ring A is phenyl. In embodiments, Ring A is napththyl. In embodiments, Ring A is benzofuranyl. In embodiments, Ring A is isobenzofuranyl. In embodiments, Ring A is indolyl. In embodiments, Ring A is isoindolyl. In embodiments, Ring A is benzothienyl. In embodiments, Ring A is benzo[c]thienyl. In embodiments, Ring A is benzimidazolyl. In embodiments, Ring A is azaindolyl. In embodiments, Ring A is benzoisoxazolyl. In embodiments, Ring A is pyrrolopyridinyl. In embodiments, Ring A is purinyl. In embodiments, Ring A is indazolyl. In embodiments, Ring A is benzoxazolyl. In embodiments, Ring A is benzisoxazolyl. In embodiments, Ring A is benzothiazolyl. In embodiments, Ring A is quinolinyl. In embodiments, Ring A is isoquinolinyl. In embodiments, Ring A is quinoxalinyl. In embodiments, Ring A is quinazolinyl. In embodiments, Ring A is cinnolinyl. In embodiments, Ring A is or phthalazinyl. In embodiments, Ring A is furanyl. In embodiments, Ring A is pyrrolyl. In embodiments, Ring A is thienyl. In embodiments, Ring A is imidazolyl. In embodiments, Ring A is pyrazolyl. In embodiments, Ring A is oxazolyl. In embodiments, Ring A is isoxazolyl. In embodiments, Ring A is thiazolyl. In embodiments, Ring A is isothiazolyl. In embodiments, Ring A is triazolyl. In embodiments, Ring A is oxadiazolyl. In embodiments, Ring A is thiadiazolyl. In embodiments, Ring A is tetrazolyl. In embodiments, Ring A is pyridinyl. In embodiments, Ring A is pyrazinyl. In embodiments, Ring A is pyrimidinyl. In embodiments, Ring A is pyridazinyl. In embodiments, Ring A is triazinyl.

In embodiments, (Ring A)-$(R^4)_{z4}$ is

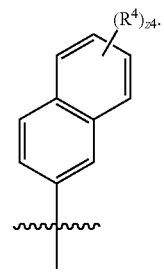

In embodiments, (Ring A)-$(R^4)_{z4}$ is

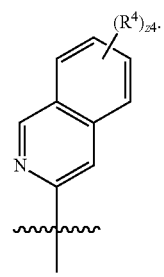

In embodiments, (Ring A)-$(R^4)_{z4}$ is

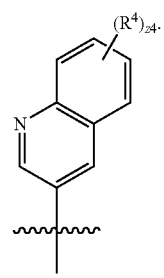

In embodiments, (Ring A)-$(R^4)_{z4}$ is

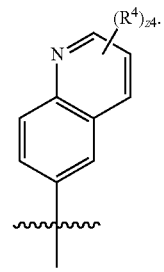

In embodiments, (Ring A)-(R⁴)_{z4} is
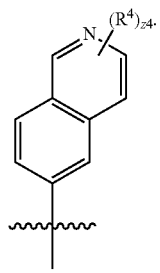
In embodiments, (Ring A)-(R⁴)_{z4} is
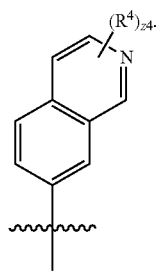
In embodiments, (Ring A)-(R⁴)_{z4} is
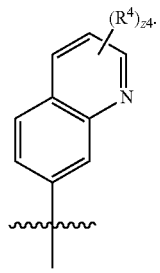
In embodiments, (Ring A)-(R⁴)_{z4} is
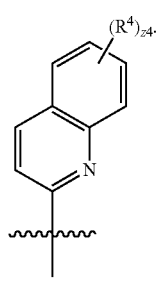
In embodiments, (Ring A)-(R⁴)_{z4} is
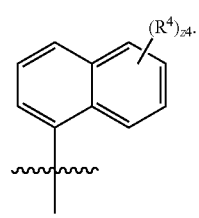
In embodiments, (Ring A)-(R⁴)_{z4} is
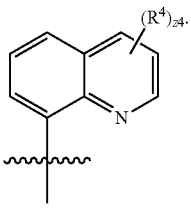
In embodiments, (Ring A)-(R⁴)_{z4} is
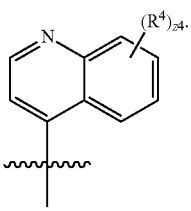
In embodiments, (Ring A)-(R⁴)_{z4} is
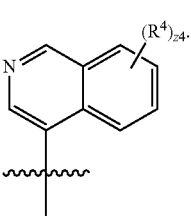
In embodiments, (Ring A)-(R⁴)_{z4} is
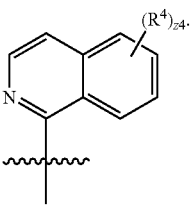
In embodiments, (Ring A)-(R⁴)_{z4} is
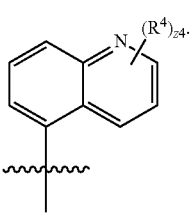

In embodiments, (Ring A)-(R⁴)_{z4} is
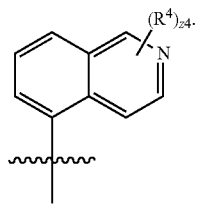
In embodiments, (Ring A)-(R⁴)_{z4} is
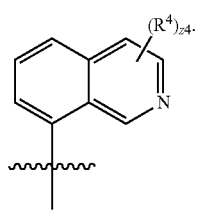
In embodiments, (Ring A)-(R⁴)_{z4} is
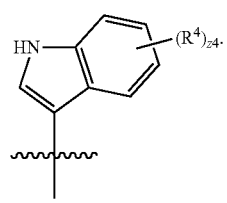
In embodiments, (Ring A)-(R⁴)_{z4} is
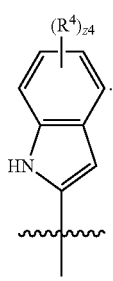
In embodiments, (Ring A)-(R⁴)_{z4} is
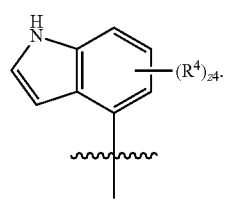
In embodiments, (Ring A)-(R⁴)_{z4} is
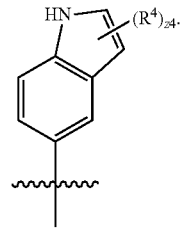
In embodiments, (Ring A)-(R⁴)_{z4} is
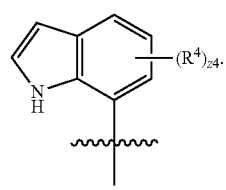
In embodiments, (Ring A)-(R⁴)_{z4} is
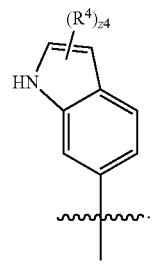
In embodiments, (Ring A)-(R⁴)_{z4} is
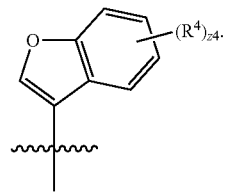
In embodiments, (Ring A)-(R⁴)_{z4} is
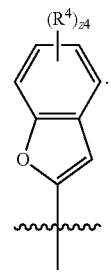

In embodiments, (Ring A)-(R⁴)$_{z4}$ is
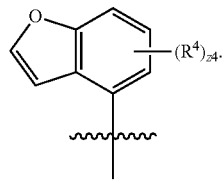
In embodiments, (Ring A)-(R⁴)$_{z4}$ is
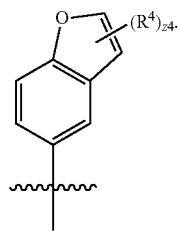
In embodiments, (Ring A)-(R⁴)$_{z4}$ is
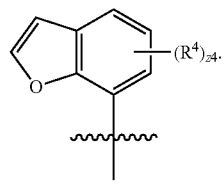
In embodiments, (Ring A)-(R⁴)$_{z4}$ is
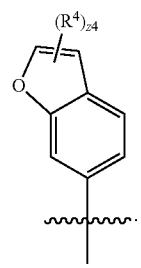
In embodiments, (Ring A)-(R⁴)$_{z4}$ is
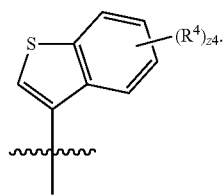
In embodiments, (Ring A)-(R⁴)$_{z4}$ is
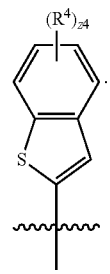
In embodiments, (Ring A)-(R⁴)$_{z4}$ is
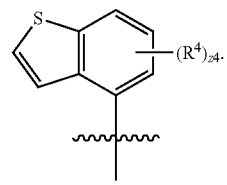
In embodiments, (Ring A)-(R⁴)$_{z4}$ is
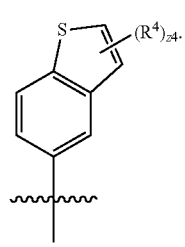
In embodiments, (Ring A)-(R⁴)$_{z4}$ is
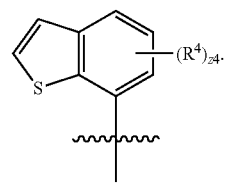
In embodiments, (Ring A)-(R⁴)$_{z4}$ is
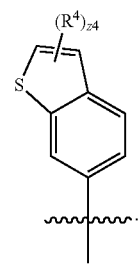

In embodiments, (Ring A)-(R⁴)$_{z4}$ is
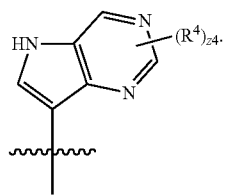
In embodiments, (Ring A)-(R⁴)$_{z4}$ is
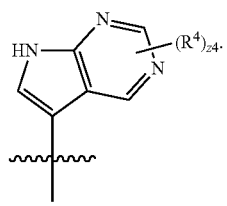
In embodiments, (Ring A)-(R⁴)$_{z4}$ is
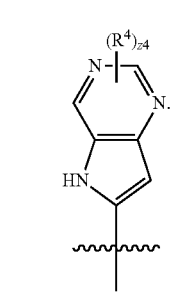
embodiments, (Ring A)-(R⁴)$_{z4}$ is
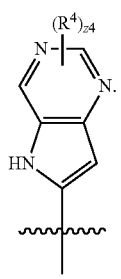
In embodiments, (Ring A)-(R⁴)$_{z4}$ is
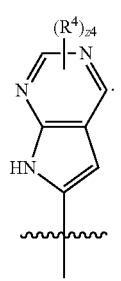
In embodiments, (Ring A)-(R⁴)$_{z4}$ is
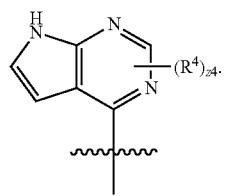
In embodiments, (Ring A)-(R⁴)$_{z4}$ is
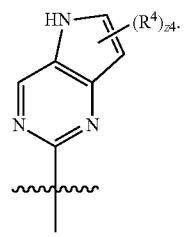
In embodiments, (Ring A)-(R⁴)$_{z4}$ is
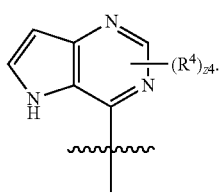
In embodiments, (Ring A)-(R⁴)$_{z4}$ is
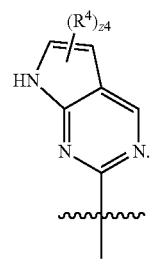
In embodiments, (Ring A)-(R⁴)$_{z4}$ is
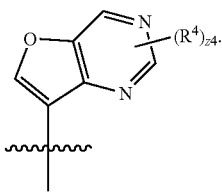
In embodiments, (Ring A)-(R⁴)$_{z4}$ is
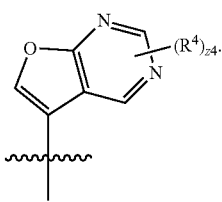

In embodiments, (Ring A)-(R⁴)_{z4} is
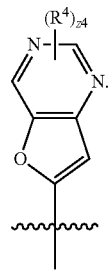
In embodiments, (Ring A)-(R⁴)_{z4} is
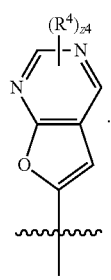
In embodiments, (Ring A)-(R⁴)_{z4} is
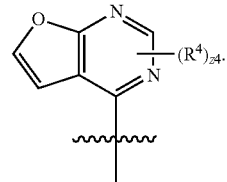
In embodiments, (Ring A)-(R⁴)_{z4} is
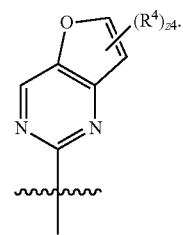
In embodiments, (Ring A)-(R⁴)_{z4} is
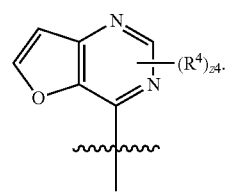
In embodiments, (Ring A)-(R⁴)_{z4} is
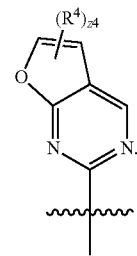
In embodiments, (Ring A)-(R⁴)_{z4} is
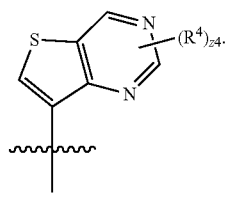
In embodiments, (Ring A)-(R⁴)_{z4} is
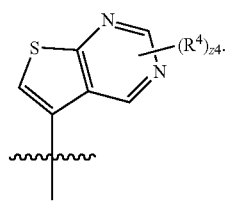
In embodiments, (Ring A)-(R⁴)_{z4} is
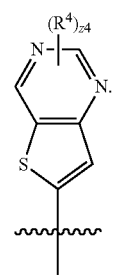
In embodiments, (Ring A)-(R⁴)_{z4} is
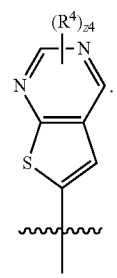

In embodiments, (Ring A)-(R⁴)_{z4} is
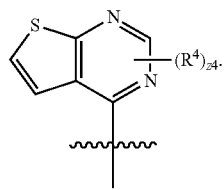
In embodiments, (Ring A)-(R⁴)_{z4} is
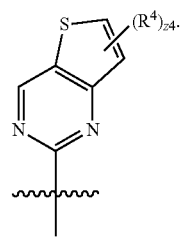
In embodiments, (Ring A)-(R⁴)_{z4} is
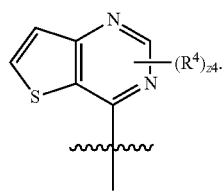
In embodiments, (Ring A)-(R⁴)_{z4} is
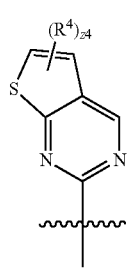
In embodiments, (Ring A)-(R⁴)_{z4} is
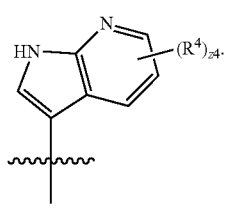
In embodiments, (Ring A)-(R⁴)_{z4} is
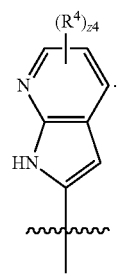
In embodiments, (Ring A)-(R⁴)_{z4} is
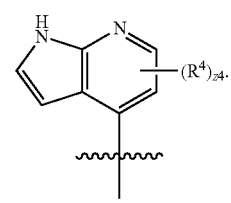
In embodiments, (Ring A)-(R⁴)_{z4} is
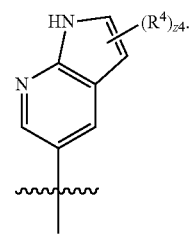
In embodiments, (Ring A)-(R⁴)_{z4} is
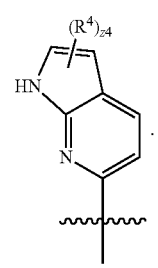
In embodiments, (Ring A)-(R⁴)_{z4} is
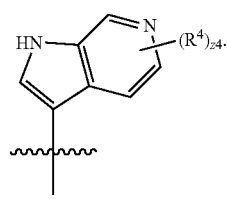

| 79 | 80 |
In embodiments, (Ring A)-(R$^4$)$_{z4}$ is
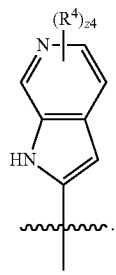
In embodiments, (Ring A)-(R$^4$)$_{z4}$ is
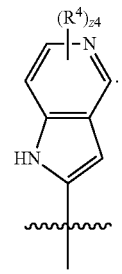
In embodiments, (Ring A)-(R$^4$)$_{z4}$ is
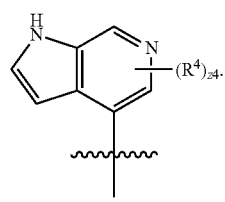
In embodiments, (Ring A)-(R$^4$)$_{z4}$ is
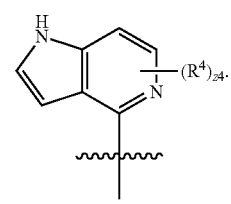
In embodiments, (Ring A)-(R$^4$)$_{z4}$ is
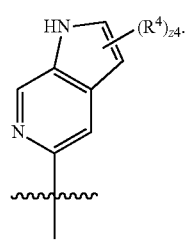
In embodiments, (Ring A)-(R$^4$)$_{z4}$ is
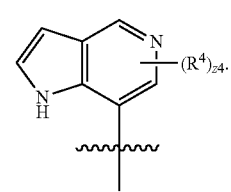
In embodiments, (Ring A)-(R$^4$)$_{z4}$ is
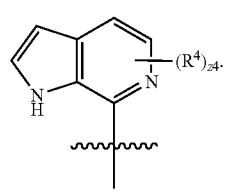
In embodiments, (Ring A)-(R$^4$)$_{z4}$ is
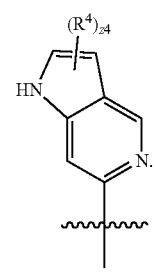
In embodiments, (Ring A)-(R$^4$)$_{z4}$ is
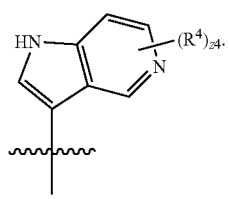
In embodiments, (Ring A)-(R$^4$)$_{z4}$ is
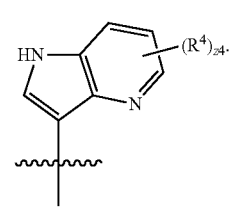

In embodiments, (Ring A)-(R⁴)_{z4} is
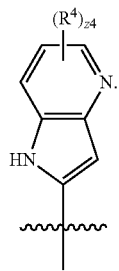
In embodiments, (Ring A)-(R⁴)_{z4} is
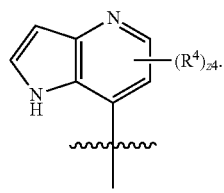
In embodiments, (Ring A)-(R⁴)_{z4} is
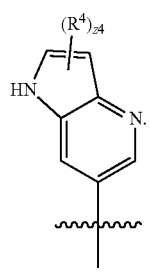
In embodiments, (Ring A)-(R⁴)_{z4} is
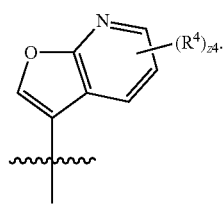
In embodiments, (Ring A)-(R⁴)_{z4} is
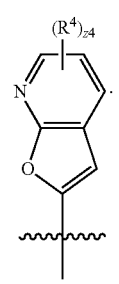
In embodiments, (Ring A)-(R⁴)_{z4} is
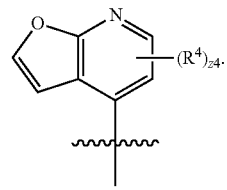
In embodiments, (Ring A)-(R⁴)_{z4} is
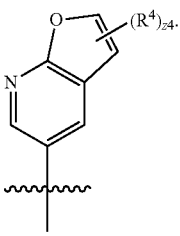
In embodiments, (Ring A)-(R⁴)_{z4} is
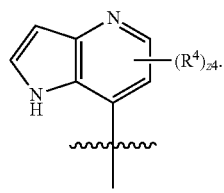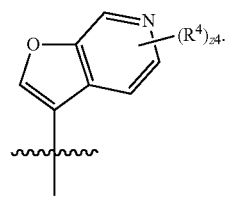
In embodiments, (Ring A)-(R⁴)_{z4} is
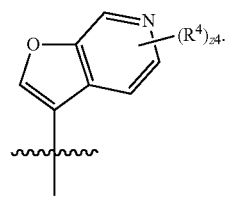
In embodiments, (Ring A)-(R⁴)_{z4} is
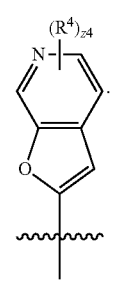

In embodiments, (Ring A)-(R⁴)_{z4} is
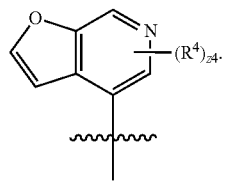
In embodiments, (Ring A)-(R⁴)_{z4} is
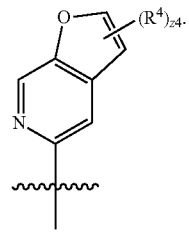
In embodiments, (Ring A)-(R⁴)_{z4} is
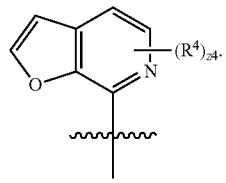
In embodiments, (Ring A)-(R⁴)_{z4} is
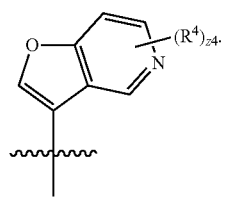
In embodiments, (Ring A)-(R⁴)_{z4} is
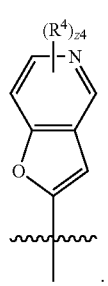
In embodiments, (Ring A)-(R⁴)_{z4} is
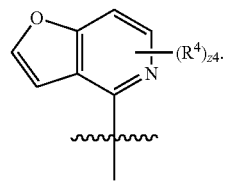
In embodiments, (Ring A)-(R⁴)_{z4} is
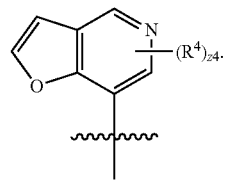
In embodiments, (Ring A)-(R⁴)_{z4} is
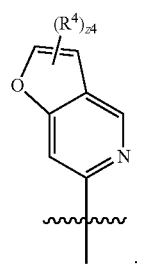
In embodiments, (Ring A)-(R⁴)_{z4} is
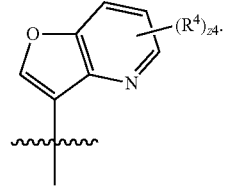
In embodiments, (Ring A)-(R⁴)_{z4} is
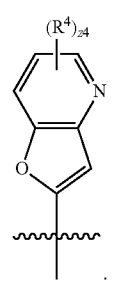

In embodiments, (Ring A)-(R⁴)_{z4} is
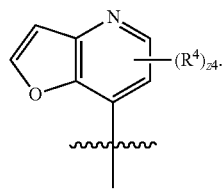
In embodiments, (Ring A)-(R⁴)_{z4} is
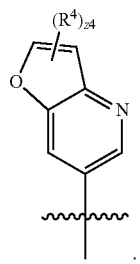
In embodiments, (Ring A)-(R⁴)_{z4} is
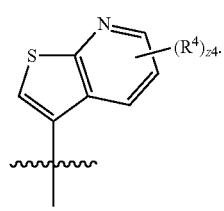
In embodiments, (Ring A)-(R⁴)_{z4} is
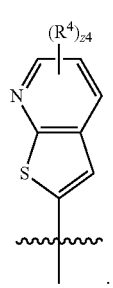
In embodiments, (Ring A)-(R⁴)_{z4} is
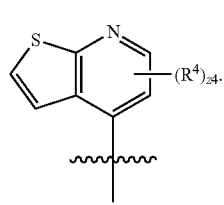
In embodiments, (Ring A)-(R⁴)_{z4} is
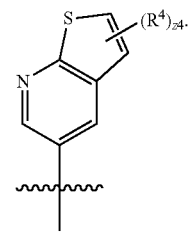
In embodiments, (Ring A)-(R⁴)_{z4} is
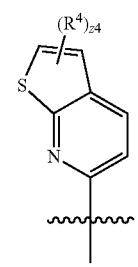
In embodiments, (Ring A)-(R⁴)_{z4} is
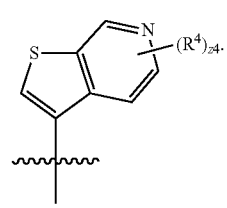
In embodiments, (Ring A)-(R⁴)_{z4} is
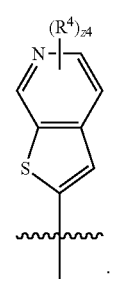
In embodiments, (Ring A)-(R⁴)_{z4} is
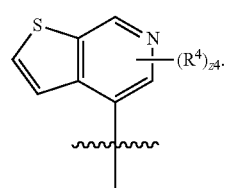

In embodiments, (Ring A)-(R⁴)_{z4} is
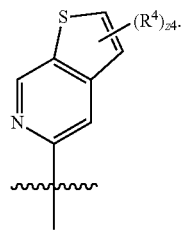
In embodiments, (Ring A)-(R⁴)_{z4} is
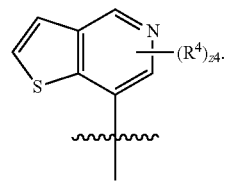
In embodiments, (Ring A)-(R⁴)_{z4} is
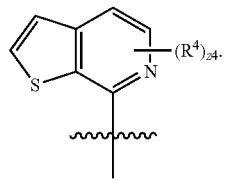
In embodiments, (Ring A)-(R⁴)_{z4} is
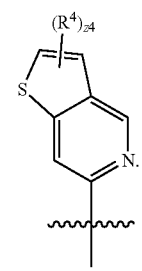
In embodiments, (Ring A)-(R⁴)_{z4} is
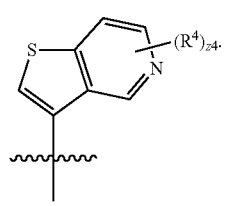
In embodiments, (Ring A)-(R⁴)_{z4} is
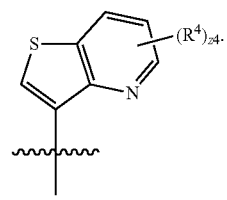
In embodiments, (Ring A)-(R⁴)_{z4} is
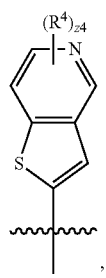
In embodiments, (Ring A)-(R⁴)_{z4} is
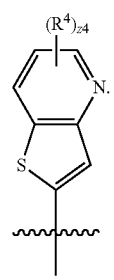
In embodiments, (Ring A)-(R⁴)_{z4} is
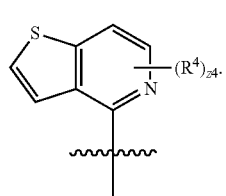
In embodiments, (Ring A)-(R⁴)_{z4} is
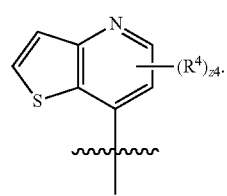

In embodiments, (Ring A)-(R⁴)_{z4} is
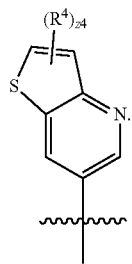
In embodiments, (Ring A)-(R⁴)_{z4} is
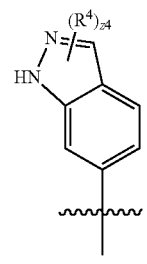
In embodiments, (Ring A)-(R⁴)_{z4} is
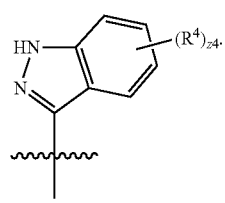
In embodiments, (Ring A)-(R⁴)_{z4} is
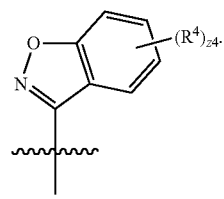
In embodiments, (Ring A)-(R⁴)_{z4} is
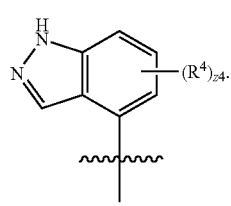
In embodiments, (Ring A)-(R⁴)_{z4} is
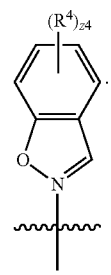
In embodiments, (Ring A)-(R⁴)_{z4} is
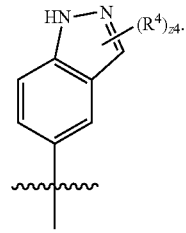
In embodiments, (Ring A)-(R⁴)_{z4} is
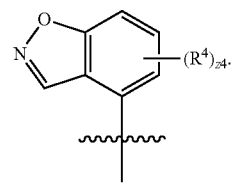
In embodiments, (Ring A)-(R⁴)_{z4} is
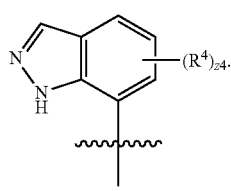
In embodiments, (Ring A)-(R⁴)_{z4} is
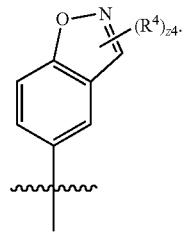

In embodiments, (Ring A)-(R⁴)_{z4} is
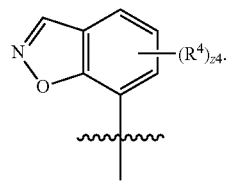
In embodiments, (Ring A)-(R⁴)_{z4} is
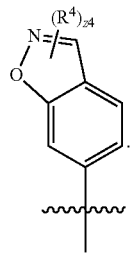
In embodiments, (Ring A)-(R⁴)_{z4} is
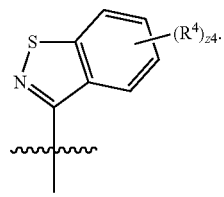
In embodiments, (Ring A)-(R⁴)_{z4} is
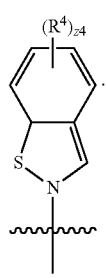
In embodiments, (Ring A)-(R⁴)_{z4} is
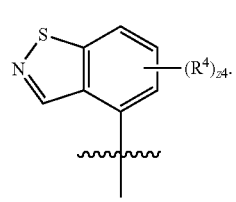
In embodiments, (Ring A)-(R⁴)_{z4} is
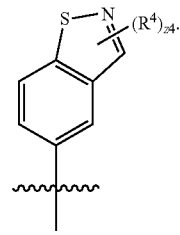
In embodiments, (Ring A)-(R⁴)_{z4} is
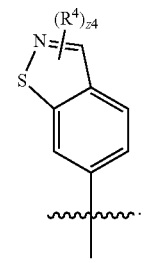
In embodiments, (Ring A)-(R⁴)_{z4} is
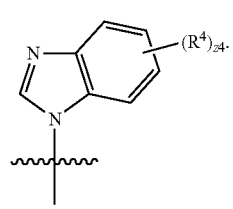
In embodiments, (Ring A)-(R⁴)_{z4} is
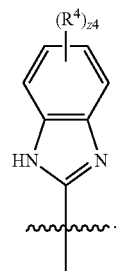
In embodiments, (Ring A)-(R⁴)_{z4} is In embodiments, (Ring A)-(R$^4$)$_{z4}$ is
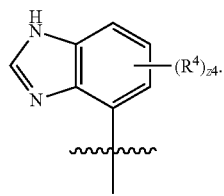
In embodiments, (Ring A)-(R$^4$)$_{z4}$ is
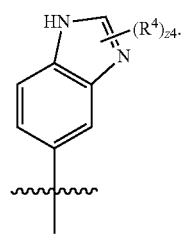
In embodiments, (Ring A)-(R$^4$)$_{z4}$ is
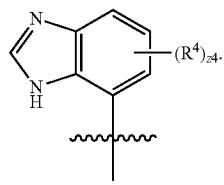
In embodiments, (Ring A)-(R$^4$)$_{z4}$ is
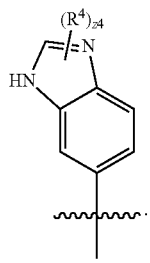
In embodiments, (Ring A)-(R$^4$)$_{z4}$ is
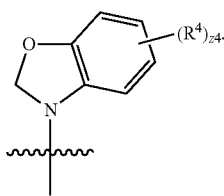
In embodiments, (Ring A)-(R$^4$)$_{z4}$ is
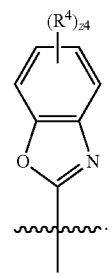
In embodiments, (Ring A)-(R$^4$)$_{z4}$ is
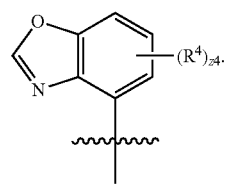
In embodiments, (Ring A)-(R$^4$)$_{z4}$ is
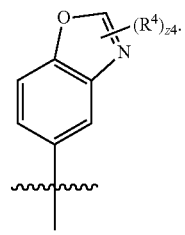
In embodiments, (Ring A)-(R$^4$)$_4$ is
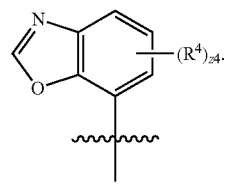
In embodiments, (Ring A)-(R$^4$)$_{z4}$ is
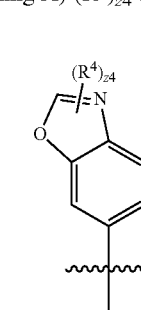
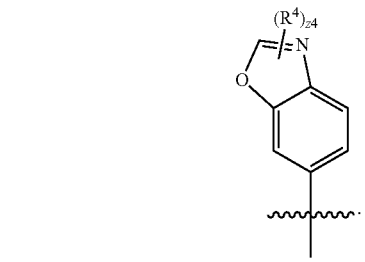

In embodiments, (Ring A)-(R⁴)_{z4} is

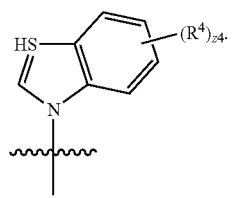

In embodiments, (Ring A)-(R⁴)_{z4} is

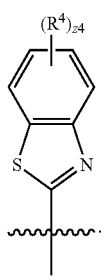

In embodiments, (Ring A)-(R⁴)_{z4} is

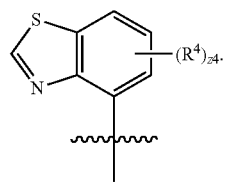

In embodiments, (Ring A)-(R⁴)_{z4} is

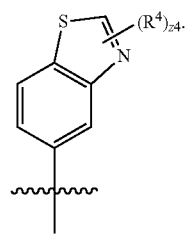

In embodiments, (Ring A)-(R⁴)_{z4} is

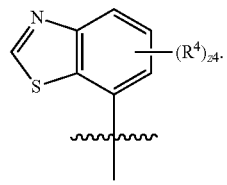

In embodiments, (Ring A)-(R⁴)_{z4} is

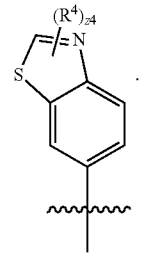

In embodiments, (Ring A)-(R⁴)_{z4} is

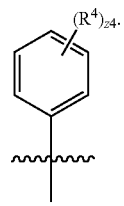

In embodiments, (Ring A)-(R⁴)_{z4} is

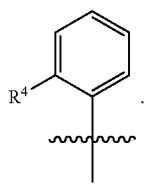

In embodiments, (Ring A)-(R⁴)_{z4} is

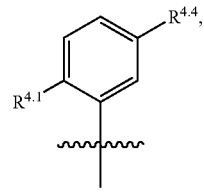

wherein $R^{4.1}$ and $R^{4.4}$ are each independently $R^4$ at a fixed position (e.g., non-floating as shown in the formula described herein) and may independently be any $R^4$ substituent. In embodiments, (Ring A)-(R⁴)_{z4} is

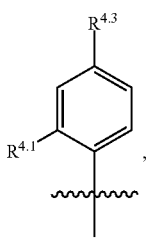

wherein $R^{4.1}$ and $R^{4.3}$ are each independently $R^4$ at a fixed position (e.g., non-floating as shown in the formula described herein) and may independently be any $R^4$ substituent. In embodiments, (Ring A)-(R⁴)_{z4}

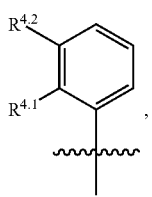

wherein $R^{4.1}$ and $R^{4.2}$ are each independently $R^4$ at a fixed position (e.g., non-floating as shown in the formula described herein) and may independently be any $R^4$ substituent. In embodiments, (Ring A)-$(R^4)_{z4}$ is

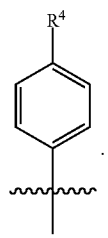

In embodiments, (Ring A)-$(R^4)_{z4}$ is

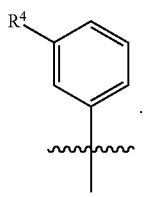

In embodiments, (Ring A)-$(R^4)_{z4}$ is

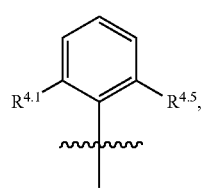

wherein $R^{4.1}$ and $R^{4.5}$ are each independently $R^4$ at a fixed position (e.g., non-floating as shown in the formula described herein) and may independently be any $R^4$ substituent. In embodiments, (Ring A)-$(R^4)_{z4}$ is

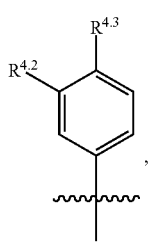

wherein $R^{4.2}$ and $R^{4.3}$ are each independently $R^4$ at a fixed position (e.g., non-floating as shown in the formula described herein) and may independently be any $R^4$ substituent. In embodiments, (Ring A)-$(R^4)_{z4}$ is

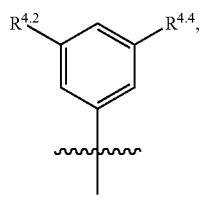

wherein $R^{4.2}$ and $R^{4.4}$ are each independently $R^4$ at a fixed position (e.g., non-floating as shown in the formula described herein) and may independently be any $R^4$ substituent.

In embodiments, (Ring A)-$(R^4)_{z4}$ is

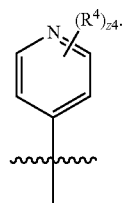

In embodiments, (Ring A)-$(R^4)_{z4}$ is

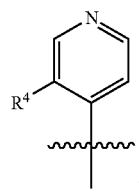

In embodiments, (Ring A)-$(R^4)_{z4}$ is

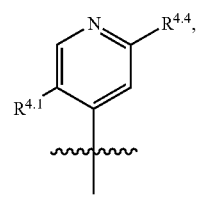

wherein $R^{41}$ and $R^{44}$ are each independently $R^4$ at a fixed position (e.g., non-floating as shown in the formula described herein) and may independently be any $R^4$ substituent. In embodiments, (Ring A)-$(R^4)_{z4}$ is

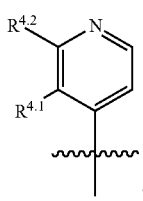

wherein $R^{41}$ and $R^{42}$ are each independently $R^4$ at a fixed position (e.g., non-floating as shown in the formula described herein) and may independently be any $R^4$ substituent.

In embodiments, (Ring A)-$(R^4)_{z4}$ is

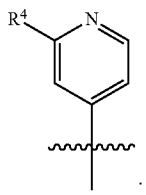

In embodiments, (Ring A)-$(R^4)_{z4}$ is

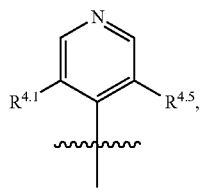

wherein $R^{4.1}$ and $R^{4.5}$ are each independently $R^4$ at a fixed position (e.g., non-floating as shown in the formula described herein) and may independently be any $R^4$ substituent In embodiments, (Ring A)-$(R^4)_{z4}$ is

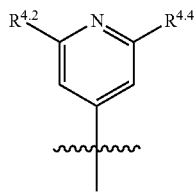

wherein $R^{4.2}$ and $R^{4.4}$ are each independently $R^4$ at a fixed position (e.g., non-floating as shown in the formula described herein) and may independently be any $R^4$ substituent.

In embodiments, (Ring A)-$(R^4)_{z4}$ is

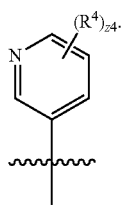

In embodiments, (Ring A)-$(R^4)_{z4}$ is

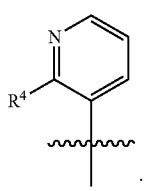

In embodiments, (Ring A)-$(R^4)_{z4}$ is

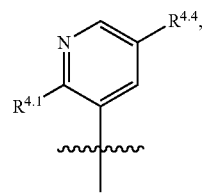

wherein $R^{4.1}$ and $R^{4.4}$ are each independently $R^4$ at a fixed position (e.g., non-floating as shown in the formula described herein) and may independently be any $R^4$ substituent. In embodiments, (Ring A)-$(R^4)_{z4}$ is

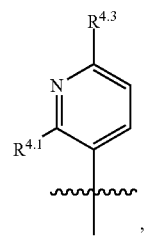

wherein $R^{4.1}$ and $R^{4.3}$ are each independently $R^4$ at a fixed position (e.g., non-floating as shown in the formula described herein) and may independently be any $R^4$ substituent. In embodiments, (Ring A)-$(R^4)_{z4}$ is

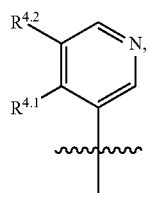

wherein $R^{4.1}$ and $R^{4.2}$ are each independently $R^4$ at a fixed position (e.g., non-floating as shown in the formula described herein) and may independently be any $R^4$ substituent. In embodiments, (Ring A)-$(R^4)_{z4}$ is

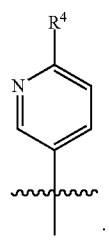

In embodiments, (Ring A)-$(R^4)_{z4}$ is

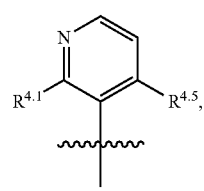

wherein $R^{4.1}$ and $R^{4.5}$ are each independently $R^4$ at a fixed position (e.g., non-floating as shown in the formula described herein) and may independently be any $R^4$ substituent. In embodiments, (Ring A)-$(R^4)_{z4}$ is

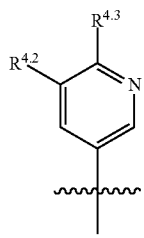

wherein $R^{4.2}$ and $R^{4.3}$ are each independently $R^4$ at a fixed position (e.g., non-floating as shown in the formula described herein) and may independently be any $R^4$ substituent.

In embodiments, (Ring A)-$(R^4)_{z4}$ is

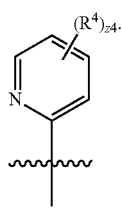

In embodiments, (Ring A)-$(R^4)_{z4}$ is

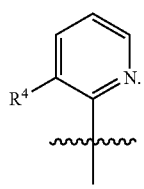

In embodiments, (Ring A)-$(R^4)_{z4}$ is

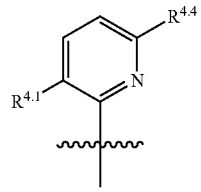

wherein $R^{4.1}$ and $R^{4.4}$ are each independently $R^4$ at a fixed position (e.g., non-floating as shown in the formula described herein) and may independently be any $R^4$ substituent. In embodiments, (Ring A)-$(R^4)_{z4}$ is

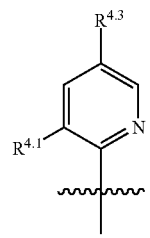

wherein $R^{4.1}$ and $R^{4.3}$ are each independently $R^4$ at a fixed position (e.g., non-floating as shown in the formula described herein) and may independently be any $R^4$ substituent.

In embodiments, (Ring A)-$(R^4)_{z4}$ is

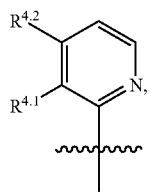

wherein $R^{4.1}$ and $R^{4.2}$ are each independently $R^4$ at a fixed position (e.g., non-floating as shown in the formula described herein) and may independently be any $R^4$ substituent. In embodiments, (Ring A)-$(R^4)_{z4}$ is

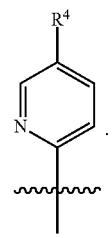

In embodiments, (Ring A)-$(R^4)_{z4}$ is

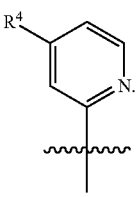

In embodiments, (Ring A)-$(R^4)_{z4}$ is

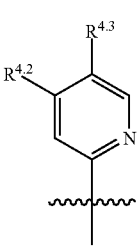

wherein $R^{4.2}$ and $R^{4.3}$ are each independently $R^4$ at a fixed position (e.g., non-floating as shown in the formula described herein) and may independently be any $R^4$ substituent. In embodiments, (Ring A)-$(R^4)_{z4}$ is

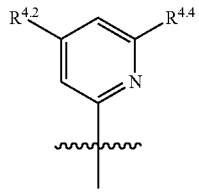

wherein $R^{4.2}$ and $R^{4.4}$ are each independently $R^4$ at a fixed position (e.g., non-floating as shown in the formula described herein) and may independently be any $R^4$ substituent.

In embodiments, (Ring A)-$(R^4)_{z4}$ is

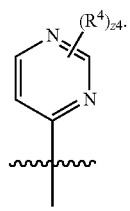

In embodiments, (Ring A)-$(R^4)_{z4}$ is

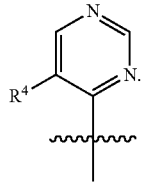

In embodiments, (Ring A)-$(R^4)_{z4}$ is

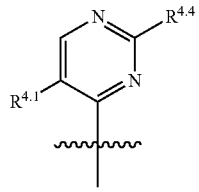

wherein $R^{4.1}$ and $R^{4.4}$ are each independently $R^4$ at a fixed position (e.g., non-floating as shown in the formula described herein) and may independently be any $R^4$ substituent. In embodiments, (Ring A)-$(R^4)_{z4}$ is

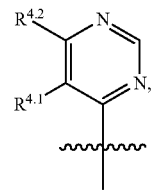

wherein $R^{4.1}$ and $R^{4.2}$ are each independently $R^4$ at a fixed position (e.g., non-floating as shown in the formula described herein) and may independently be any $R^4$ substituent. In embodiments, (Ring A)-$(R^4)_{z4}$ is

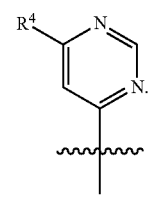

In embodiments, (Ring A)-$(R^4)_{z4}$ is

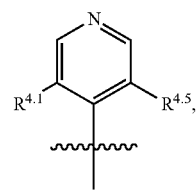

wherein $R^{4.1}$ and $R^{4.5}$ are each independently $R^4$ at a fixed position (e.g., non-floating as shown in the formula described herein) and may independently be any $R^4$ substituent. In embodiments, (Ring A)-$(R^4)_{z4}$ is

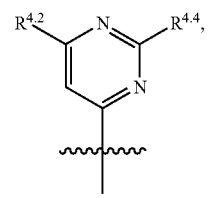

wherein $R^{4.2}$ and $R^{4.4}$ are each independently $R^4$ at a fixed position (e.g., non-floating as shown in the formula described herein) and may independently be any $R^4$ substituent.

In embodiments, $R^4$ is independently hydrogen. In embodiments, $R^4$ is independently halogen. In embodiments, $R^4$ is independently —$CX^4_3$. In embodiments, $R^4$ is independently —$CHX^4_2$. In embodiments, $R^4$ is independently —$CH_{2X4}$. In embodiments, $R^4$ is independently —$OCX^4_3$. In embodiments, $R^4$ is independently —$OCH_2X^4$. In embodiments, $R^4$ is independently —$OCHX^4_2$. In embodiments, $R^4$ is independently —CN. In embodiments, $R^4$ is independently —$SO_{n4}R^{4D}$. In embodiments, $R^4$ is independently —$SO_{v4}NR^{4A}R^{4B}$. In embodiments, $R^4$ is independently —NHC(O)N$R^{4A}R^{4B}$. In embodiments, $R^4$ is independently —N(O)$_{m4}$. In embodiments, $R^4$ is independently —N$R^{4A}R^{4B}$. In embodiments, $R^4$ is independently —C(O)$R^{4C}$. In embodiments, $R^4$ is independently —C(O)—O$R^{4C}$. In embodiments, $R^4$ is independently —C(O)N$R^{4A}R^{4B}$. In embodiments, $R^4$ is independently —O$R^{4D}$. In embodiments, $R^4$ is independently —N$R^{4A}$SO$_2R^{4D}$. In embodiments, $R^4$ is independently —N$R^{4A}$C(O)$R_{4C}$. In embodiments, $R^4$ is independently —N$R^{4A}$C(O)O$R^{4C}$. In embodiments, $R^4$ is independently —N$R^{4A}$O$R^{4C}$. In embodiments, $R^4$ is independently —OH. In embodiments, $R^4$ is independently —NH$_2$. In embodiments, $R^4$ is independently —COOH. In embodiments, $R^4$ is independently —CONH$_2$. In embodiments, $R^4$ is independently —NO$_2$. In embodiments, $R^4$ is independently —SH. In embodiments, $R^4$ is independently halogen, unsubstituted $C_1$-$C_3$ alkyl, or unsubstituted 2 to 4 membered heteroalkyl. In embodiments, $R^4$ is independently halogen, unsubstituted methyl, or —OCH$_3$. In embodiments, $R^4$ is independently —Br. In embodiments, $R^4$ is independently —Cl. In embodiments, $R^4$ is independently —F. In embodiments, $R^4$ is independently —OCH$_3$. In embodiments, $R^4$ is independently —CH$_3$. In embodiments, $R^4$ is independently —CF$_3$.

In embodiments, $R^4$ is independently substituted or unsubstituted alkyl. In embodiments, $R^4$ is independently substituted or unsubstituted heteroalkyl. In embodiments, $R^4$ is independently substituted or unsubstituted cycloalkyl. In embodiments, $R^4$ is independently, substituted or unsubstituted heterocycloalkyl. In embodiments, $R^4$ is independently substituted or unsubstituted aryl. In embodiments, $R^4$ is independently substituted or unsubstituted heteroaryl. In embodiments, $R^4$ is independently substituted alkyl. In embodiments, $R^4$ is independently substituted heteroalkyl. In embodiments, $R^4$ is independently substituted cycloalkyl. In embodiments, $R^4$ is independently, substituted heterocycloalkyl. In embodiments, $R^4$ is independently substituted aryl. In embodiments, $R^4$ is independently substituted heteroaryl. In embodiments, $R^4$ is independently unsubstituted alkyl. In embodiments, $R^4$ is independently unsubstituted heteroalkyl. In embodiments, $R^4$ is independently unsubstituted cycloalkyl. In embodiments, $R^4$ is independently, unsubstituted heterocycloalkyl. In embodiments, $R^4$ is independently unsubstituted aryl. In embodiments, $R^4$ is independently unsubstituted heteroaryl. In embodiments, $R^4$ is independently substituted or unsubstituted $C_1$-$C_5$ alkyl. In embodiments, $R^4$ is independently substituted or unsubstituted 2 to 8 membered heteroalkyl. In embodiments, $R^4$ is independently substituted or unsubstituted $C_3$-$C_8$ cycloalkyl. In embodiments, $R^4$ is independently, substituted or unsubstituted 3 to 8 membered heterocycloalkyl. In embodiments, $R^4$ is independently substituted or unsubstituted $C_6$-$C_{10}$ aryl. In embodiments, $R^4$ is independently substituted or unsubstituted 5 to 10 membered heteroaryl. In embodiments, $R^4$ is independently substituted $C_1$-$C_8$alkyl. In embodiments, $R^4$ is independently substituted 2 to 8 membered heteroalkyl. In embodiments, $R^4$ is independently substituted $C_3$-$C_8$ cycloalkyl. In embodiments, $R^4$ is independently, substituted 3 to 8 membered heterocycloalkyl. In embodiments, $R^4$ is independently substituted $C_6$-$C_{10}$ aryl. In embodiments, $R^4$ is independently substituted 5 to 10 membered heteroaryl. In embodiments, $R^4$ is independently unsubstituted $C_1$-$C_8$ alkyl. In embodiments, $R^4$ is independently unsubstituted 2 to 8 membered heteroalkyl. In embodiments, $R^4$ is independently unsubstituted $C_3$-$C_5$ cycloalkyl. In embodiments, $R^4$ is independently, unsubstituted 3 to 8 membered heterocycloalkyl. In embodiments, $R^4$ is independently unsubstituted $C_6$-$C_{10}$ aryl. In embodiments, $R^4$ is independently unsubstituted 5 to 10 membered heteroaryl. In embodiments, $R^4$ is independently substituted or unsubstituted $C_1$-$C_4$ alkyl. In embodiments, $R^4$ is independently substituted or unsubstituted 2 to 4 membered heteroalkyl. In embodiments, $R^4$ is independently substituted or unsubstituted $C_3$-$C_6$ cycloalkyl. In embodiments, $R^4$ is independently, substituted or unsubstituted 3 to 6 membered heterocycloalkyl. In embodiments, $R^4$ is independently substituted or unsubstituted phenyl. In embodiments, $R^4$ is independently substituted or unsubstituted 5 to 6 membered heteroaryl. In embodiments, $R^4$ is independently substituted $C_1$-$C_4$ alkyl. In embodiments, $R^4$ is independently substituted 2 to 4 membered heteroalkyl. In embodiments, $R^4$ is independently substituted $C_3$-$C_6$ cycloalkyl. In embodiments, $R^4$ is independently, substituted 3 to 6 membered heterocycloalkyl. In embodiments, $R^4$ is independently substituted phenyl. In embodiments, $R^4$ is independently substituted 5 to 6 membered heteroaryl. In embodiments, $R^4$ is independently unsubstituted $C_1$-$C_4$ alkyl. In embodiments, $R^4$ is independently unsubstituted 2 to 4 membered heteroalkyl. In embodiments, $R^4$ is independently unsubstituted $C_3$-$C_6$ cycloalkyl. In embodiments, $R^4$ is independently unsubstituted 3 to 6 membered heterocycloalkyl. In embodiments, $R^4$ is independently unsubstituted phenyl. In embodiments, $R^4$ is independently unsubstituted 5 to 6 membered heteroaryl.

In embodiments, two adjacent $R^4$ substituents may be joined to form a substituted or unsubstituted cycloalkyl, substituted or unsubstituted heterocycloalkyl, substituted or unsubstituted aryl, or substituted or unsubstituted heteroaryl.

In embodiments, two adjacent $R^4$ substituents may be joined to form a substituted or unsubstituted cycloalkyl. In embodiments, two adjacent $R^4$ substituents may be joined to form a substituted or unsubstituted heterocycloalkyl. In embodiments, two adjacent $R^4$ substituents may be joined to form a substituted or unsubstituted aryl. In embodiments, two adjacent $R^4$ substituents may be joined to form a substituted or unsubstituted heteroaryl. In embodiments, two adjacent $R^4$ substituents may be joined to form a substituted cycloalkyl. In embodiments, two adjacent $R^4$ substituents may be joined to form a substituted heterocycloalkyl. In embodiments, two adjacent $R^4$ substituents may be joined to form a substituted aryl. In embodiments, two adjacent $R^4$ substituents may be joined to form a substituted heteroaryl. In embodiments, two adjacent $R^4$ substituents may be joined to form an unsubstituted cycloalkyl. In embodiments, two adjacent $R^4$ substituents may be joined to form an unsubstituted heterocycloalkyl. In embodiments, two adjacent $R^4$ substituents may be joined to form an unsubstituted aryl. In embodiments, two adjacent $R^4$ substituents may be joined to form an unsubstituted heteroaryl.

In embodiments, two adjacent $R^4$ substituents may be joined to form a substituted or unsubstituted $C_3$-$C_8$ cycloalkyl. In embodiments, two adjacent $R^4$ substituents may be joined to form a substituted or unsubstituted 3 to 8 membered heterocycloalkyl. In embodiments, two adjacent $R^4$ substituents may be joined to form a substituted or unsubstituted $C_6$-$C_{10}$ aryl. In embodiments, two adjacent $R^4$ substituents may be joined to form a substituted or unsubstituted 5 to 10 membered heteroaryl. In embodiments, two adjacent $R^4$ substituents may be joined to form a substituted $C_3$-$C_8$ cycloalkyl. In embodiments, two adjacent $R^4$ substituents may be joined to form a substituted 3 to 8 membered heterocycloalkyl. In embodiments, two adjacent $R^4$ substituents may be joined to form a substituted $C_6$-$C_{10}$ aryl. In embodiments, two adjacent $R^4$ substituents may be joined to form a substituted 5 to 10 membered heteroaryl. In embodiments, two adjacent $R^4$ substituents may be joined to form an unsubstituted $C_3$-$C_5$ cycloalkyl. In embodiments, two adjacent $R^4$ substituents may be joined to form an unsubstituted 3 to 8 membered heterocycloalkyl. In embodiments, two adjacent $R^4$ substituents may be joined to form an unsubstituted $C_6$-$C_{10}$ aryl. In embodiments, two adjacent $R^4$ substituents may be joined to form an unsubstituted 5 to 10 membered heteroaryl.

In embodiments, two adjacent $R^4$ substituents may be joined to form a substituted or unsubstituted $C_3$-$C_6$ cycloalkyl. In embodiments, two adjacent $R^4$ substituents may be joined to form a substituted or unsubstituted 3 to 6 membered heterocycloalkyl. In embodiments, two adjacent $R^4$ substituents may be joined to form a substituted or unsubstituted phenyl. In embodiments, two adjacent $R^4$ substituents may be joined to form a substituted or unsubstituted 5 to 6 membered heteroaryl. In embodiments, two adjacent $R^4$ substituents may be joined to form a substituted $C_3$-$C_6$ cycloalkyl. In embodiments, two adjacent $R^4$ substituents may be joined to form a substituted 3 to 6 membered heterocycloalkyl. In embodiments, two adjacent $R^4$ substituents may be joined to form a substituted phenyl. In embodiments, two adjacent $R^4$ substituents may be joined to form a substituted 5 to 6 membered heteroaryl. In embodiments, two adjacent $R^4$ substituents may be joined to form an unsubstituted $C_3$-$C_6$ cycloalkyl. In embodiments, two adjacent $R^4$ substituents may be joined to form an unsubstituted 3 to 6 membered heterocycloalkyl. In embodiments, two adjacent $R^4$ substituents may be joined to form an unsubstituted phenyl. In embodiments, two adjacent $R^4$ substituents may be joined to form an unsubstituted 5 to 6 membered heteroaryl.

In embodiments, $R^{4A}$ is independently hydrogen. In embodiments, $R^{4A}$ is independently —$CX^{4A}_3$. In embodiments, $R^{4A}$ is independently —$CHX^{4A}_2$. In embodiments, $R^{4A}$ is independently —$CH_2X^{4A}$. In embodiments, $R^{4A}$ is independently —CN. In embodiments, $R^{4A}$ is independently —COOH. In embodiments, $R^{4A}$ is independently —$CONH_2$. In embodiments, $R^{4A}$ is independently substituted or unsubstituted alkyl. In embodiments, $R^{4A}$ is independently substituted or unsubstituted heteroalkyl. In embodiments, $R^{4A}$ is independently substituted or unsubstituted cycloalkyl. In embodiments, $R^{4A}$ is independently, substituted or unsubstituted heterocycloalkyl. In embodiments, $R^{4A}$ is independently substituted or unsubstituted aryl. In embodiments, $R^{4A}$ is independently substituted or unsubstituted heteroaryl. In embodiments, $R^{4A}$ is independently substituted alkyl. In embodiments, $R^{4A}$ is independently substituted heteroalkyl. In embodiments, $R^{4A}$ is independently substituted cycloalkyl. In embodiments, $R^{4A}$ is independently, substituted heterocycloalkyl. In embodiments, $R^{4A}$ is independently substituted aryl. In embodiments, $R^{4A}$ is independently substituted heteroaryl. In embodiments, $R^{4A}$ is independently unsubstituted alkyl. In embodiments, $R^{4A}$ is independently unsubstituted heteroalkyl. In embodiments, $R^{4A}$ is independently unsubstituted cycloalkyl. In embodiments, $R^{4A}$ is independently, unsubstituted heterocycloalkyl. In embodiments, $R^{4A}$ is independently unsubstituted aryl. In embodiments, $R^{4A}$ is independently unsubstituted heteroaryl. In embodiments, $R^{4A}$ is independently substituted or unsubstituted $C_1$-$C_8$ alkyl. In embodiments, $R^{4A}$ is independently substituted or unsubstituted 2 to 8 membered heteroalkyl. In embodiments, $R^{4A}$ is independently substituted or unsubstituted $C_3$-$C_8$ cycloalkyl. In embodiments, $R^{4A}$ is independently substituted or unsubstituted 3 to 8 membered heterocycloalkyl. In embodiments, $R^{4A}$ is independently substituted or unsubstituted $C_6$-$C_{10}$ aryl. In embodiments, $R^{4A}$ is independently substituted or unsubstituted 5 to 10 membered heteroaryl. In embodiments, $R^{4A}$ is independently substituted $C_1$-$C_8$ alkyl. In embodiments, $R^{4A}$ is independently substituted 2 to 8 membered heteroalkyl. In embodiments, $R^{4A}$ is independently substituted $C_3$-$C_8$ cycloalkyl. In embodiments, $R^{4A}$ is independently, substituted 3 to 8 membered heterocycloalkyl. In embodiments, $R^{4A}$ is independently substituted $C_6$-$C_{10}$ aryl. In embodiments, $R^{4A}$ is independently substituted 5 to 10 membered heteroaryl. In embodiments, $R^{4A}$ is independently unsubstituted $C_1$-$C_8$ alkyl. In embodiments, $R^{4A}$ is independently unsubstituted 2 to 8 membered heteroalkyl. In embodiments, $R^{4A}$ is independently unsubstituted $C_3$-$C_5$ cycloalkyl. In embodiments, $R^{4A}$ is independently, unsubstituted 3 to 8 membered heterocycloalkyl. In embodiments, $R^{4A}$ is independently unsubstituted $C_6$-$C_{10}$ aryl. In embodiments, $R^{4A}$ is independently unsubstituted 5 to 10 membered heteroaryl. In embodiments, $R^{4A}$ is independently substituted or unsubstituted $C_1$-$C_4$ alkyl. In embodiments, $R^{4A}$ is independently substituted or unsubstituted 2 to 4 membered heteroalkyl. In embodiments, $R^{4A}$ is independently substituted or unsubstituted $C_3$-$C_6$ cycloalkyl. In embodiments, $R^{4A}$ is independently, substituted or unsubstituted 3 to 6 membered heterocycloalkyl. In embodiments, $R^{4A}$ is independently substituted or unsubstituted phenyl. In embodiments, $R^{4A}$ is independently substituted or unsubstituted 5 to 6 membered heteroaryl. In embodiments, $R^{4A}$ is independently substituted $C_1$-$C_4$ alkyl. In embodiments, $R^{4A}$ is independently substituted 2 to 4 membered heteroalkyl. In embodiments, $R^{4A}$ is independently substituted $C_3$-$C_6$ cycloalkyl. In embodiments, $R^{4A}$ is independently, substituted 3 to 6 membered heterocycloalkyl. In embodiments, $R^{4A}$ is independently substituted phenyl. In embodiments, $R^{4A}$ is independently substituted 5 to 6 membered heteroaryl. In embodiments, $R^{4A}$ is independently unsubstituted $C_1$-$C_4$ alkyl. In embodiments, $R^{4A}$ is independently unsubstituted 2 to 4 membered heteroalkyl. In embodiments, $R^{4A}$ is independently unsubstituted $C_3$-$C_6$ cycloalkyl. In embodiments, $R^{4A}$ is independently unsubstituted 3 to 6 membered heterocycloalkyl. In embodiments, $R^{4A}$ is independently unsubstituted phenyl. In embodiments, $R^{4A}$ is independently unsubstituted 5 to 6 membered heteroaryl. In embodiments, $R^{4A}$ is independently unsubstituted methyl. In embodiments, $R^{4A}$ is independently unsubstituted ethyl. In embodiments, $R^{4A}$ is independently unsubstituted propyl. In embodiments, $R^{4A}$ is independently unsubstituted isopropyl. In embodiments, $R^{4A}$ is independently unsubstituted tert-butyl.

In embodiments, $R^{4B}$ is independently hydrogen. In embodiments, $R^{4B}$ is independently —$CX^{4B3}$. In embodiments, $R^{4B}$ is independently —$CHX^{4B2}$. In embodiments, $R^{4B}$ is independently —$CH_2X^{4B}$. In embodiments, $R^{4B}$ is independently —CN. In embodiments, $R^{4B}$ is independently —COOH. In embodiments, $R^{4B}$ is independently —$CONH_2$. In embodiments, $R^{4B}$ is independently substituted or unsubstituted alkyl. In embodiments, $R^{4B}$ is independently substituted or unsubstituted heteroalkyl. In embodiments, $R^{4B}$ is independently substituted or unsubstituted cycloalkyl. In embodiments, $R^{4B}$ is independently, substituted or unsubstituted heterocycloalkyl. In embodiments, $R^{4B}$ is independently substituted or unsubstituted aryl. In embodiments, $R^{4B}$ is independently substituted or unsubstituted heteroaryl. In embodiments, $R^{4B}$ is independently substituted alkyl. In embodiments, $R^{4B}$ is independently substituted heteroalkyl. In embodiments, $R^{4B}$ is independently substituted cycloalkyl. In embodiments, $R^{4B}$ is independently, substituted heterocycloalkyl. In embodiments, $R^{4B}$ is independently substituted aryl. In embodiments, $R^{4B}$ is independently substituted heteroaryl. In embodiments, $R^{4B}$ is independently unsubstituted alkyl. In embodiments, $R^{4B}$ is independently unsubstituted heteroalkyl. In embodiments, $R^{4B}$ is independently unsubstituted cycloalkyl. In embodiments, $R^{4B}$ is independently, unsubstituted heterocycloalkyl. In embodiments, $R^{4B}$ is independently unsubstituted aryl. In embodiments, $R^{4B}$ is independently unsubstituted heteroaryl. In embodiments, $R^{4B}$ is independently substituted or unsubstituted $C_1$-$C_8$ alkyl. In embodiments, $R^{4B}$ is independently substituted or unsubstituted 2 to 8 membered heteroalkyl. In embodiments, $R^{4B}$ is independently substituted or unsubstituted $C_3$—C cycloalkyl. In embodiments, $R^{4B}$ is independently, substituted or unsubstituted 3 to 8 membered heterocycloalkyl. In embodiments, $R^{4B}$ is independently substituted or unsubstituted $C_6$-$C_{10}$ aryl. In embodiments, $R^{4B}$ is independently substituted or unsubstituted 5 to 10 membered heteroaryl. In embodiments, $R^{4B}$ is independently substituted $C_1$-$C_8$ alkyl. In embodiments, $R^{4B}$ is independently substituted 2 to 8 membered heteroalkyl. In embodiments, $R^{4B}$ is independently substituted $C_3$—C cycloalkyl. In embodiments, $R^{4B}$ is independently, substituted 3 to 8 membered heterocycloalkyl. In embodiments, $R^{4B}$ is independently substituted $C_6$-$C_{10}$ aryl. In embodiments, $R^{4B}$ is independently substituted 5 to 10 membered heteroaryl. In embodiments, $R^{4B}$ is independently unsubstituted $C_1$-$C_8$ alkyl. In embodiments, $R^{4B}$ is independently unsubstituted 2 to 8 membered heteroalkyl. In embodiments, $R^{4B}$ is independently unsubstituted $C_3$-$C_8$ cycloalkyl. In embodiments, $R^{4B}$ is independently, unsubstituted 3 to 8 membered heterocycloalkyl. In embodiments, $R^{4B}$ is independently unsubstituted $C_6$-$C_{10}$ aryl. In embodiments, $R^{4B}$ is independently unsubstituted 5 to 10 membered heteroaryl. In embodiments, $R^{4B}$ is independently substituted or unsubstituted $C_1$-$C_4$ alkyl. In embodiments, $R^{4B}$ is independently substituted or unsubstituted 2 to 4 membered heteroalkyl. In embodiments, $R^{4B}$ is independently substituted or unsubstituted $C_3$-$C_6$ cycloalkyl. In embodiments, $R^{4B}$ is independently, substituted or unsubstituted 3 to 6 membered heterocycloalkyl. In embodiments, $R^{4B}$ is independently substituted or unsubstituted phenyl. In embodiments, $R^{4B}$ is independently substituted or unsubstituted 5 to 6 membered heteroaryl. In embodiments, $R^{4B}$ is independently substituted $C_1$-$C_4$ alkyl. In embodiments, $R^{4B}$ is independently substituted 2 to 4 membered heteroalkyl. In embodiments, $R^{4B}$ is independently substituted $C_3$-$C_6$ cycloalkyl. In embodiments, $R^{4B}$ is independently, substituted 3 to 6 membered heterocycloalkyl. In embodiments, $R^{4B}$ is independently substituted phenyl. In embodiments, $R^{4B}$ is independently substituted 5 to 6 membered heteroaryl. In embodiments, $R^{4B}$ is independently unsubstituted $C_1$-$C_4$ alkyl. In embodiments, $R^{4B}$ is independently unsubstituted 2 to 4 membered heteroalkyl. In embodiments, $R^{4B}$ is independently unsubstituted $C_3$-$C_6$ cycloalkyl. In embodiments, $R^{4B}$ is independently unsubstituted 3 to 6 membered heterocycloalkyl. In embodiments, $R^{4B}$ is independently unsubstituted phenyl. In embodiments, $R^{4B}$ is independently unsubstituted 5 to 6 membered heteroaryl. In embodiments, $R^{4B}$ is independently unsubstituted methyl. In embodiments, $R^{4B}$ is independently unsubstituted ethyl. In embodiments, $R^{4B}$ is independently unsubstituted propyl. In embodiments, $R^{4B}$ is independently unsubstituted isopropyl. In embodiments, $R^{4B}$ is independently unsubstituted tert-butyl.

In embodiments, $R^{4A}$ and $R^{4B}$ substituents bonded to the same nitrogen atom may be joined to form a substituted or unsubstituted heterocycloalkyl. In embodiments, $R^{4A}$ and $R^{4B}$ substituents bonded to the same nitrogen atom may be joined to form a substituted or unsubstituted heteroaryl. In embodiments, $R^{4A}$ and $R^{4B}$ substituents bonded to the same nitrogen atom may be joined to form a substituted heterocycloalkyl. In embodiments, $R^{4A}$ and $R^{4B}$ substituents bonded to the same nitrogen atom may be joined to form a substituted heteroaryl. In embodiments, $R^{4A}$ and $R^{4B}$ substituents bonded to the same nitrogen atom may be joined to form a unsubstituted heterocycloalkyl. In embodiments, $R^{4A}$ and $R^{4B}$ substituents bonded to the same nitrogen atom may be joined to form a unsubstituted heteroaryl. In embodiments, $R^{4A}$ and $R^{4B}$ substituents bonded to the same nitrogen atom may be joined to form a substituted or unsubstituted 3 to 8 membered heterocycloalkyl. In embodiments, $R^{4A}$ and $R^{4B}$ substituents bonded to the same nitrogen atom may be joined to form a substituted or unsubstituted 5 to 10 membered heteroaryl. In embodiments, $R^{4A}$ and $R^{4B}$ substituents bonded to the same nitrogen atom may be joined to form a substituted 3 to 8 membered heterocycloalkyl. In embodiments, $R^{4A}$ and $R^{4B}$ substituents bonded to the same nitrogen atom may be joined to form a substituted 5 to 10 membered heteroaryl. In embodiments, $R^{4A}$ and $R^{4B}$ substituents bonded to the same nitrogen atom may be joined to form a unsubstituted 3 to 8 membered heterocycloalkyl. In embodiments, $R^{4A}$ and $R^{4B}$ substituents bonded to the same nitrogen atom may be joined to form a unsubstituted 5 to 10 membered heteroaryl. In embodiments, $R^{4A}$ and $R^{4B}$ substituents bonded to the same nitrogen atom may be joined to form a substituted or unsubstituted 3 to 6 membered heterocycloalkyl. In embodiments, $R^{4A}$ and $R^{4B}$ substituents bonded to the same nitrogen atom may be joined to form a substituted or unsubstituted 5 to 6 membered heteroaryl. In embodiments, $R^{4A}$ and $R^{4B}$ substituents bonded to the same nitrogen atom may be joined to form a substituted 3 to 6 membered heterocycloalkyl. In embodiments, $R^{4A}$ and $R^{4B}$ substituents bonded to the same nitrogen atom may be joined to form a substituted 5 to 6 membered heteroaryl. In embodiments, $R^{4A}$ and $R^{4B}$ substituents bonded to the same nitrogen atom may be joined to form a unsubstituted 3 to 6 membered heterocycloalkyl. In embodiments, $R^{4A}$ and $R^{4B}$ substituents bonded to the same nitrogen atom may be joined to form a unsubstituted 5 to 6 membered heteroaryl.

In embodiments, $R^{4C}$ is independently hydrogen. In embodiments, $R^{4C}$ is independently —$CX^{4C3}$. In embodiments, $R^{4C}$ is independently —$CHX^{4C2}$. In embodiments, $R^{4C}$ is independently —$CH_2X^{4C}$. In embodiments, $R^{4C}$ is independently —CN. In embodiments, $R^{4C}$ is independently —COOH. In embodiments, $R^{4C}$ is independently —$CONH_2$. In embodiments, $R^{4C}$ is independently substituted or unsubstituted alkyl. In embodiments, $R^{4C}$ is independently substituted or unsubstituted heteroalkyl. In embodiments, $R^{4C}$ is independently substituted or unsubstituted cycloalkyl. In embodiments, $R^{4C}$ is independently, substituted or unsubstituted heterocycloalkyl. In embodiments, $R^{4C}$ is independently substituted or unsubstituted aryl. In embodiments, $R^{4C}$ is independently substituted or unsubstituted heteroaryl. In embodiments, $R^{4C}$ is independently substituted alkyl. In embodiments, $R^{4C}$ is independently substituted heteroalkyl. In embodiments, $R^{4C}$ is independently substituted cycloalkyl. In embodiments, $R^{4C}$ is independently, substituted heterocycloalkyl. In embodiments, $R^{4C}$ is independently substituted aryl. In embodiments, $R^{4C}$ is independently substituted heteroaryl. In embodiments, $R^{4C}$ is independently unsubstituted alkyl. In embodiments, $R^{4C}$ is independently unsubstituted heteroalkyl. In embodiments, $R^{4C}$ is independently unsubstituted cycloalkyl. In embodiments, $R^{4C}$ is independently, unsubstituted heterocycloalkyl. In embodiments, $R^{4C}$ is independently unsubstituted aryl. In embodiments, $R^{4C}$ is independently unsubstituted heteroaryl. In embodiments, $R^{4C}$ is independently substituted or unsubstituted $C_1$-$C_8$ alkyl. In embodiments, $R^{4C}$ is independently substituted or unsubstituted 2 to 8 membered heteroalkyl. In embodiments, $R^{4C}$ is independently substituted or unsubstituted $C_3$-$C_8$ cycloalkyl. In embodiments, $R^{4C}$ is independently, substituted or unsubstituted 3 to 8 membered heterocycloalkyl. In embodiments, $R^{4C}$ is independently substituted or unsubstituted $C_6$-$C_{10}$ aryl. In embodiments, $R^{4C}$ is independently substituted or unsubstituted 5 to 10 membered heteroaryl. In embodiments, $R^{4C}$ is independently substituted $C_1$-$C_8$ alkyl. In embodiments, $R^{4C}$ is independently substituted 2 to 8 membered heteroalkyl. In embodiments, $R^{4C}$ is independently substituted $C_3$-$C_5$ cycloalkyl. In embodiments, $R^{4C}$ is independently, substituted 3 to 8 membered heterocycloalkyl. In embodiments, $R^{4C}$ is independently substituted $C_6$-$C_{10}$ aryl. In embodiments, $R^{4C}$ is independently substituted 5 to 10 membered heteroaryl. In embodiments, $R^{4C}$ is independently unsubstituted $C_1$-$C_8$ alkyl. In embodiments, $R^{4C}$ is independently unsubstituted 2 to 8 membered heteroalkyl. In embodiments, $R^{4C}$ is independently unsubstituted $C_3$-$C_8$ cycloalkyl. In embodiments, $R^{4C}$ is independently, unsubstituted 3 to 8 membered heterocycloalkyl. In embodiments, $R^{4C}$ is independently unsubstituted $C_6$-$C_{10}$ aryl. In embodiments, $R^{4C}$ is independently unsubstituted 5 to 10 membered heteroaryl. In embodiments, $R^{4C}$ is independently substituted or unsubstituted $C_1$-$C_4$ alkyl. In embodiments, $R^{4C}$ is independently substituted or unsubstituted 2 to 4 membered heteroalkyl. In embodiments, $R^{4C}$ is independently substituted or unsubstituted $C_3$-$C_6$ cycloalkyl. In embodiments, $R^{4C}$ is independently, substituted or unsubstituted 3 to 6 membered heterocycloalkyl. In embodiments, $R^{4C}$ is independently substituted or unsubstituted phenyl. In embodiments, $R^{4C}$ is independently substituted or unsubstituted 5 to 6 membered heteroaryl. In embodiments, $R^{4C}$ is independently substituted $C_1$-$C_4$ alkyl. In embodiments, $R^{4C}$ is independently substituted 2 to 4 membered heteroalkyl. In embodiments, $R^{4C}$ is independently substituted $C_3$-$C_6$ cycloalkyl. In embodiments, $R^{4C}$ is independently, substituted 3 to 6 membered heterocycloalkyl. In embodiments, $R^{4C}$ is independently substituted phenyl. In embodiments, $R^{4C}$ is independently substituted 5 to 6 membered heteroaryl. In embodiments, $R^{4C}$ is independently unsubstituted $C_1$-$C_4$ alkyl. In embodiments, $R^{4C}$ is independently unsubstituted 2 to 4 membered heteroalkyl. In embodiments, $R^{4C}$ is independently unsubstituted $C_3$-$C_6$ cycloalkyl. In embodiments, $R^{4C}$ is independently unsubstituted 3 to 6 membered heterocycloalkyl. In embodiments, $R^{4C}$ is independently unsubstituted phenyl. In embodiments, $R^{4C}$ is independently unsubstituted 5 to 6 membered heteroaryl. In embodiments, $R^{4C}$ is independently unsubstituted methyl. In embodiments, $R^{4C}$ is independently unsubstituted ethyl. In embodiments, $R^{4C}$ is independently unsubstituted propyl. In embodiments, $R^{4C}$ is independently unsubstituted isopropyl. In embodiments, $R^{4C}$ is independently unsubstituted tert-butyl.

In embodiments, $R^{4D}$ is independently hydrogen. In embodiments, $R^{4D}$ is independently —$CX^{4D}_3$. In embodiments, $R^{4D}$ is independently —$CHX^{4D}_2$. In embodiments, $R^{4D}$ is independently —$CH_2X^{4D}$. In embodiments, $R^{4D}$ is independently —CN. In embodiments, $R^{4D}$ is independently —COOH. In embodiments, $R^{4D}$ is independently —$CONH_2$. In embodiments, $R^{4D}$ is independently substituted or unsubstituted alkyl. In embodiments, $R^{4D}$ is independently substituted or unsubstituted heteroalkyl. In embodiments, $R^{4D}$ is independently substituted or unsubstituted cycloalkyl. In embodiments, $R^{4D}$ is independently, substituted or unsubstituted heterocycloalkyl. In embodiments, $R^{4D}$ is independently substituted or unsubstituted aryl. In embodiments, $R^{4D}$ is independently substituted or unsubstituted heteroaryl. In embodiments, $R^{4D}$ is independently substituted alkyl. In embodiments, $R^{4D}$ is independently substituted heteroalkyl. In embodiments, $R^{4D}$ is independently substituted cycloalkyl. In embodiments, $R^{4D}$ is independently, substituted heterocycloalkyl. In embodiments, $R^{4D}$ is independently substituted aryl. In embodiments, $R^{4D}$ is independently substituted heteroaryl. In embodiments, $R^{4D}$ is independently unsubstituted alkyl. In embodiments, $R^{4D}$ is independently unsubstituted heteroalkyl. In embodiments, $R^{4D}$ is independently unsubstituted cycloalkyl. In embodiments, $R^{4D}$ is independently, unsubstituted heterocycloalkyl. In embodiments, $R^{4D}$ is independently unsubstituted aryl. In embodiments, $R^{4D}$ is independently unsubstituted heteroaryl. In embodiments, $R^{4D}$ is independently substituted or unsubstituted $C_1$-$C_8$ alkyl. In embodiments, $R^{4D}$ is independently substituted or unsubstituted 2 to 8 membered heteroalkyl. In embodiments, $R^{4D}$ is independently substituted or unsubstituted $C_3$-$C_8$ cycloalkyl. In embodiments, $R^{4D}$ is independently, substituted or unsubstituted 3 to 8 membered heterocycloalkyl. In embodiments, $R^{4D}$ is independently substituted or unsubstituted $C_6$-$C_{10}$ aryl. In embodiments, $R^{4D}$ is independently substituted or unsubstituted 5 to 10 membered heteroaryl. In embodiments, $R^{4D}$ is independently substituted $C_1$-$C_8$ alkyl. In embodiments, $R^{4D}$ is independently substituted 2 to 8 membered heteroalkyl. In embodiments, $R^{4D}$ is independently substituted $C_3$-$C_8$ cycloalkyl. In embodiments, $R^{4D}$ is independently, substituted 3 to 8 membered heterocycloalkyl. In embodiments, $R^{4D}$ is independently substituted $C_6$-$C_{10}$ aryl. In embodiments, $R^{4D}$ is independently substituted 5 to 10 membered heteroaryl. In embodiments, $R^{4D}$ is independently unsubstituted $C_1$-$C_8$ alkyl. In embodiments, $R^{4D}$ is independently unsubstituted 2 to 8 membered heteroalkyl. In embodiments, $R^{4D}$ is independently unsubstituted $C_3$-$C_8$ cycloalkyl. In embodiments, $R^{4D}$ is independently, unsubstituted 3 to 8 membered heterocycloalkyl. In embodiments, $R^{4D}$ is independently unsubstituted $C_6$-$C_{10}$ aryl. In embodiments, $R^{4D}$ is independently unsubstituted 5 to 10 membered heteroaryl. In embodiments, $R^{4D}$ is independently substituted or unsubstituted $C_1$-$C_4$ alkyl. In embodiments, $R^{4D}$ is independently substituted or unsubstituted 2 to 4 membered heteroalkyl. In embodiments, $R^{4D}$ is independently substituted or unsubstituted $C_3$-$C_6$ cycloalkyl. In embodiments, $R^{4D}$ is independently, substituted or unsubstituted 3 to 6 membered heterocycloalkyl. In embodiments, $R^{4D}$ is independently substituted or unsubstituted phenyl. In embodiments, $R^{4D}$ is independently substituted or unsubstituted 5 to 6 membered heteroaryl. In embodiments, $R^{4D}$ is independently substituted $C_1$-$C_4$ alkyl. In embodiments, $R^{4D}$ is independently substituted 2 to 4 membered heteroalkyl. In embodiments, $R^{4D}$ is independently substituted $C_3$-$C_6$ cycloalkyl. In embodiments, $R^{4D}$ is independently, substituted 3 to 6 membered heterocycloalkyl. In embodiments, $R^{4D}$ is independently substituted phenyl. In embodiments, $R^{4D}$ is independently substituted 5 to 6 membered heteroaryl. In embodiments, $R^{4D}$ is independently unsubstituted $C_1$-$C_4$ alkyl. In embodiments, $R^{4D}$ is independently unsubstituted 2 to 4 membered heteroalkyl. In embodiments, $R^{4D}$ is independently unsubstituted $C_3$-$C_6$ cycloalkyl. In embodiments, $R^{4D}$ is independently unsubstituted 3 to 6 membered heterocycloalkyl. In embodiments, $R^{4D}$ is independently unsubstituted phenyl. In embodiments, $R^{4D}$ is independently unsubstituted 5 to 6 membered heteroaryl. In embodiments, $R^{4D}$ is independently unsubstituted methyl. In embodiments, $R^{4D}$ is independently unsubstituted ethyl. In embodiments, $R^{4D}$ is independently unsubstituted propyl. In embodiments, $R^{4D}$ is independently unsubstituted isopropyl. In embodiments, $R^{4D}$ is independently unsubstituted tert-butyl.

In embodiments, $R^4$ is independently hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)OR^{4C}$, $-C(O)NR^{4A}R^{4B}$, $-OR^{4D}$, $NR^{4A}SO_2R^{4D}$, $-NR^{4A}C(O)R^{4C}$, $-NR^{4A}C(O)OR^{4C}$, $-NR^{4A}OR^{4C}$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In embodiments, $R^4$ is independently halogen, $-CX^4_3$, $-CHX^4_2$, $-CH_2X^4$, $-OCH_2X^4$, $-OCX^4_3$, $-OCHX^4_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^4_3$, $-OCHX^4_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In embodiments, $R^4$ is independently halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^4_3$, $-OCHX^4_2$, $R^{29}$-substituted or unsubstituted $C_1$-$C_8$ alkyl, $R^{29}$-substituted or unsubstituted 2 to 8 membered heteroalkyl, $R^{29}$-substituted or unsubstituted $C_3$-$C_8$ cycloalkyl, $R^{29}$-substituted or unsubstituted 3 to 8 membered heterocycloalkyl, $R^{29}$-substituted or unsubstituted phenyl, or $R^{29}$-substituted or unsubstituted 5 to 6 membered heteroaryl. $X^4$ is $-F$, $-Cl$, $-Br$, or $-I$. In embodiments, $R^4$ is independently hydrogen. In embodiments, $R^4$ is independently unsubstituted methyl. In embodiments, $R^4$ is independently unsubstituted ethyl. In embodiments, $R^4$ is independently halogen. In embodiments, $R^4$ is independently $-Cl$. In embodiments, $R^4$ is independently $-Br$. In embodiments, $R^4$ is independently $-F$. In embodiments, $R^4$ is independently $-OCH_3$. In embodiments, $R^4$ is independently unsubstituted methyl. In embodiments, $R^4$ is independently $-CF_3$.

In embodiments, two adjacent $R^4$ substituents may be joined to form an $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl.

In embodiments, two adjacent $R^4$ substituents may be joined to form an $R^{29}$-substituted or unsubstituted cycloalkyl. In embodiments, two adjacent $R^4$ substituents may be joined to form an $R^{29}$-substituted or unsubstituted heterocycloalkyl. In embodiments, two adjacent $R^4$ substituents may be joined to form an $R^{29}$-substituted or unsubstituted aryl. In embodiments, two adjacent $R^4$ substituents may be joined to form an $R^{29}$-substituted or unsubstituted heteroaryl. In embodiments, two adjacent $R^4$ substituents may be joined to form an $R^{29}$-substituted cycloalkyl. In embodiments, two adjacent $R^4$ substituents may be joined to form an $R^{29}$-substituted heterocycloalkyl. In embodiments, two adjacent $R^4$ substituents may be joined to form an $R^{29}$-substituted aryl. In embodiments, two adjacent $R^4$ substituents may be joined to form an $R^{29}$-substituted heteroaryl.

In embodiments, two adjacent $R^4$ substituents may be joined to form an $R^{29}$-substituted or unsubstituted $C_3$-$C_8$ cycloalkyl. In embodiments, two adjacent $R^4$ substituents may be joined to form an $R^{29}$-substituted or unsubstituted 3 to 8 membered heterocycloalkyl. In embodiments, two adjacent $R^4$ substituents may be joined to form an $R^{29}$-substituted or unsubstituted $C_6$-$C_{10}$ aryl. In embodiments, two adjacent $R^4$ substituents may be joined to form an $R^{29}$-substituted or unsubstituted 5 to 10 membered heteroaryl. In embodiments, two adjacent $R^4$ substituents may be joined to form an $R^{29}$-substituted $C3$-$C_8$ cycloalkyl. In embodiments, two adjacent $R^4$ substituents may be joined to form an $R^{29}$-substituted 3 to 8 membered heterocycloalkyl. In embodiments, two adjacent $R^4$ substituents may be joined to form an $R^{29}$-substituted $C_6$-$C_{10}$ aryl. In embodiments, two adjacent $R^4$ substituents may be joined to form an $R^{29}$-substituted 5 to 10 membered heteroaryl.

In embodiments, two adjacent $R^4$ substituents may be joined to form an $R^{29}$-substituted or unsubstituted $C_3$-$C_6$ cycloalkyl. In embodiments, two adjacent $R^4$ substituents may be joined to form an $R^{29}$-substituted or unsubstituted 3 to 6 membered heterocycloalkyl. In embodiments, two adjacent $R^4$ substituents may be joined to form an $R^{29}$-substituted or unsubstituted phenyl. In embodiments, two adjacent $R^4$ substituents may be joined to form an $R^{29}$-substituted or unsubstituted 5 to 6 membered heteroaryl. In embodiments, two adjacent $R^4$ substituents may be joined to form an $R^{29}$-substituted $C_3$-$C_6$ cycloalkyl. In embodiments, two adjacent $R^4$ substituents may be joined to form an $R^{29}$-substituted 3 to 6 membered heterocycloalkyl. In embodiments, two adjacent $R^4$ substituents may be joined to form an $R^{29}$-substituted phenyl. In embodiments, two adjacent $R^4$ substituents may be joined to form an $R^{29}$-substituted 5 to 6 membered heteroaryl.

$R^{29}$ is independently oxo, halogen, $-CX^{29}_3$, $-CHX^{29}_2$, $-CH_2X^{29}$, $-OCH_2X^{29}$, $-OCX^{29}_3$, $-OCHX^{29}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $R^{30}$-substituted or unsubstituted alkyl, $R^{30}$-substituted or unsubstituted heteroalkyl, $R^{30}$ substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl. In embodiments, $R^{29}$ is independently oxo, halogen, $-CX^{29}_3$, $-CHX^{29}_2$, $-CH_2X^{29}$, $-OCH_2X^{29}$, $-OCX^{29}_3$, $-OCHX^{29}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $R^{30}$-substituted or unsubstituted $C_1$-$C_8$ alkyl, $R^{30}$-substituted or unsubstituted 2 to 8 membered heteroalkyl, $R^{30}$-substituted or unsubstituted $C_3$-$C_8$ cycloalkyl, $R^{30}$-substituted or unsubstituted 3 to 8 membered heterocycloalkyl, $R^{30}$-substituted or unsubstituted phenyl, or $R^{30}$-substituted or unsubstituted 5 to 6 membered heteroaryl. $X^{29}$ is $-F$, $-Cl$, $-Br$, or $-I$.

$R^{30}$ is independently oxo, halogen, $-CX^{30}_3$, $-CHX^{30}_2$, $-CH_2X^{30}$, $-OCH_2X^{30}$, $-OCX^{30}_3$, $-OCHX^{30}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $R^{31}$-substituted or unsubstituted alkyl, $R^{31}$-substituted or unsubstituted heteroalkyl, $R^{31}$ substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl. In embodiments, $R^{30}$ is independently oxo, halogen, $-CX^{30}_3$, $-CHX^{30}_2$, $-CH_2X^{30}$, $-OCH_2X^{30}$, $-OCX^{30}_3$, $-OCHX^{30}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, —NHSO$_2$H, —NHC(O)H, —NHC(O)OH, —NHOH, R$^{31}$-substituted or unsubstituted C$_1$-C$_8$ alkyl, R$^{31}$-substituted or unsubstituted 2 to 8 membered heteroalkyl, R$^{31}$-substituted or unsubstituted C$_3$-C$_8$ cycloalkyl, R$^{31}$-substituted or unsubstituted 3 to 8 membered heterocycloalkyl, R$^{31}$-substituted or unsubstituted phenyl, or R$^{31}$ substituted or unsubstituted 5 to 6 membered heteroaryl. X$^{30}$ is —F, —Cl, —Br, or —I.

In embodiments, R$^{4A}$ is independently hydrogen, —CX$^{4A}_3$, —CN, —COOH, —CONH$_2$, —CHX$^{4A}_2$, —CH$_2$X$^{4A}$, R$^{29A}$-substituted or unsubstituted alkyl, R$^{29A}$-substituted or unsubstituted heteroalkyl, R$^{29A}$-substituted or unsubstituted cycloalkyl, R$^{29A}$-substituted or unsubstituted heterocycloalkyl, R$^{29A}$-substituted or unsubstituted aryl, or R$^{29A}$-substituted or unsubstituted heteroaryl. In embodiments, R$^{4A}$ is independently hydrogen, —CX$^{4A}_3$, —CN, —COOH, —CONH$_2$, —CHX$^{4A}_2$, —CH$_2$X$^{4A}$, R$^{29A}$-substituted or unsubstituted C$_1$-C$_8$ alkyl, R$^{29A}$-substituted or unsubstituted 2 to 8 membered heteroalkyl, R$^{29A}$-substituted or unsubstituted C$_3$-C$_8$ cycloalkyl, R$^{29A}$-substituted or unsubstituted 3 to 8 membered heterocycloalkyl, R$^{29A}$-substituted or unsubstituted phenyl, or R$^{29A}$-substituted or unsubstituted 5 to 6 membered heteroaryl. X$^{4A}$ is —F, —Cl, —Br, or —I. In embodiments, R$^{4A}$ is independently hydrogen. In embodiments, R$^{4A}$ is independently unsubstituted methyl. In embodiments, R$^{4A}$ is independently unsubstituted ethyl.

In embodiments, R$^{4A}$ and R$^{4B}$ substituents bonded to the same nitrogen atom may optionally be joined to form a R$^{29A}$-substituted or unsubstituted heterocycloalkyl or R$^{29A}$ substituted or unsubstituted heteroaryl. In embodiments, R$^{4A}$ and R$^{4B}$ substituents bonded to the same nitrogen atom may optionally be joined to form a R$^{29A}$-substituted or unsubstituted 3 to 6 membered heterocycloalkyl or R$^{29A}$-substituted or unsubstituted 5 to 6 membered heteroaryl.

R$^{29A}$ is independently oxo, halogen, —CX$^{29A}_3$, —CHX$^{29A}_2$, —CH$_2$X$^{29A}$, —OCH$_2$X$^{29A}$, —OCX$^{29A}_3$, —OCHX$^{29A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, R$^{30A}$-substituted or unsubstituted alkyl, R$^{30A}$-substituted or unsubstituted heteroalkyl, R$^{30A}$-substituted or unsubstituted cycloalkyl, R$^{30A}$-substituted or unsubstituted heterocycloalkyl, R$^{30A}$-substituted or unsubstituted aryl, or R$^{30A}$-substituted or unsubstituted heteroaryl. In embodiments, R$^{29A}$ is independently oxo, halogen, —CX$^{29A}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{29A}_3$, —OCHX$^{29A}_2$, R$^{30A}$-substituted or unsubstituted C$_1$-C$_8$ alkyl, R$^{30A}$-substituted or unsubstituted 2 to 8 membered heteroalkyl, R$^{30A}$-substituted or unsubstituted C$_3$-C$_8$ cycloalkyl, R$^{30A}$-substituted or unsubstituted 3 to 8 membered heterocycloalkyl, R$^{30A}$-substituted or unsubstituted phenyl, or R$^{30A}$-substituted or unsubstituted 5 to 6 membered heteroaryl. X$^{29A}$ is —F, —Cl, —Br, or —I.

R$^{30A}$ is independently oxo, halogen, —CX$^{30A}_3$, —CHX$^{30A}_2$, —CH$_2$X$^{30A}$, —OCH$_2$X$^{30A}$, —OCX$^{30A}_3$, —OCHX$^{30A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{30A}_3$, —OCHX$^{30A}_2$, R$^{31A}$-substituted or unsubstituted alkyl, R$^{31A}$-substituted or unsubstituted heteroalkyl, R$^{31A}$-substituted or unsubstituted cycloalkyl, R$^{31A}$-substituted or unsubstituted heterocycloalkyl, R$^{31A}$-substituted or unsubstituted aryl, or R$^{31A}$-substituted or unsubstituted heteroaryl. In embodiments, R$^{30A}$ is independently oxo, halogen, —CX$^{30A}_3$, —CN, —OH, —NH$_2$, —COOH, —CONH$_2$, —NO$_2$, —SH, —SO, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{30A}_3$, —OCHX$^{30A}_2$, R$^{31A}$-substituted or unsubstituted C$_1$-C$_8$ alkyl, R$^{31A}$-substituted or unsubstituted 2 to 8 membered heteroalkyl, R$^{31A}$-substituted or unsubstituted C$_3$-C$_8$ cycloalkyl, R$^{31A}$-substituted or unsubstituted 3 to 8 membered heterocycloalkyl, R$^{31A}$-substituted or unsubstituted phenyl, or R$^{31A}$-substituted or unsubstituted 5 to 6 membered heteroaryl. X$^{30A}$ is —F, —Cl, —Br, or —I.

In embodiments, R$^{4B}$ is independently hydrogen, —CX$^{29B}_3$, —CHX$^{29B}_2$, —CH$_2$X$^{29B}$, —OCH$_2$X$^{29B}$, —OCX$^{29B}_3$, —OCHX$^{29B}_2$, —CN, —COOH, —CONH$_2$, —CHX$^{4B2}$, —CH$_2$X$^{4B}$, R$^{29B}$-substituted or unsubstituted alkyl, R$^{29B}$-substituted or unsubstituted heteroalkyl, R$^{29B}$-substituted or unsubstituted cycloalkyl, R$^{29B}$-substituted or unsubstituted heterocycloalkyl, R$^{29B}$-substituted or unsubstituted aryl, or R$^{29B}$-substituted or unsubstituted heteroaryl. In embodiments, R$^{4B}$ is independently hydrogen, —CX$^{4B3}$, —CN, —COOH, —CONH$_2$, —CHX$^{4B2}$, —CH$_2$X$^{4B}$, R$^{29B}$-substituted or unsubstituted C$_1$-C$_8$ alkyl, R$^{29B}$-substituted or unsubstituted 2 to 8 membered heteroalkyl, R$^{29B}$-substituted or unsubstituted C$_3$-C$_8$ cycloalkyl, R$^{29B}$-substituted or unsubstituted 3 to 8 membered heterocycloalkyl, R$^{29B}$-substituted or unsubstituted phenyl, or R$^{29B}$-substituted or unsubstituted 5 to 6 membered heteroaryl. X$^{4B}$ is —F, —Cl, —Br, or —I. In embodiments, R$^{4B}$ is independently hydrogen. In embodiments, R$^{4B}$ is independently unsubstituted methyl. In embodiments, R$^{4B}$ is independently unsubstituted ethyl.

In embodiments, R$^{4A}$ and R$^{4B}$ substituents bonded to the same nitrogen atom may optionally be joined to form a R$^{29B}$-substituted or unsubstituted heterocycloalkyl or R$^{29B}$ substituted or unsubstituted heteroaryl. In embodiments, R$^{4A}$ and R$^{4B}$ substituents bonded to the same nitrogen atom may optionally be joined to form a R$^{29B}$-substituted or unsubstituted 3 to 6 membered heterocycloalkyl or R$^{29B}$-substituted or unsubstituted 5 to 6 membered heteroaryl.

R$^{29B}$ is independently oxo, halogen, —CX$^{29}_3$, —CHX$^{29B}_2$, —CH$_2$X$^{29B}$, —OCH$_2$X$^{29B}$, —OCX$^{29B}_3$, —OCHX$^{29B2}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, R$^{30B}$-substituted or unsubstituted alkyl, R$^{30B}$-substituted or unsubstituted heteroalkyl, R$^{30B}$-substituted or unsubstituted cycloalkyl, R$^{30B}$-substituted or unsubstituted heterocycloalkyl, R$^{30B}$-substituted or unsubstituted aryl, or R$^{30B}$-substituted or unsubstituted heteroaryl. In embodiments, R$^{29B}$ is independently oxo, halogen, —CX$^{29}_3$, —CHX$^{29B}_2$, —CH$_2$X$^{29B}$, —OCH$_2$X$^{29B}$, —OCX$^{29B}_3$, —OCHX$^{29B}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, R$^{30B}$-substituted or unsubstituted C$_1$-C$_8$ alkyl, R$^{30B}$-substituted or unsubstituted 2 to 8 membered heteroalkyl, R$^{30B}$-substituted or unsubstituted C$_3$-C$_8$ cycloalkyl, R$^{30B}$-substituted or unsubstituted 3 to 8 membered heterocycloalkyl, R$^{30B}$-substituted or unsubstituted phenyl, or R$^{30B}$-substituted or unsubstituted 5 to 6 membered heteroaryl. X$^{29B}$ is —F, —Cl, —Br, or —I.

R$^{30B}$ is independently oxo, halogen, —CX$^{30B}_3$, —CHX$^{30B}_2$, —CH$_2$X$^{30B}$, —OCH$_2$X$^{30B}$, —OCX$^{30B}_3$, —OCHX$^{30B}_2$, —CN, —OH, —NH$_2$, —COOH, —CONH$_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{31B}$-substituted or unsubstituted alkyl, $R^{31B}$-substituted or unsubstituted heteroalkyl, $R^{31B}$-substituted or unsubstituted cycloalkyl, $R^{31B}$-substituted or unsubstituted heterocycloalkyl, $R^{31B}$-substituted or unsubstituted aryl, or $R^{31B}$-substituted or unsubstituted heteroaryl. In embodiments, $R^{30B}$ is independently oxo, halogen, —$CX^{30B}_3$, —$CHX^{30B}_2$, —$CH_2X^{30B}$, —$OCH_2X^{30B}$, —$OCX^{30B}_3$, —$OCHX^{30B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{31B}$-substituted or unsubstituted $C_1$-$C_8$ alkyl, $R^{31B}$-substituted or unsubstituted 2 to 8 membered heteroalkyl, $R^{31B}$-substituted or unsubstituted $C_3$-$C_8$ cycloalkyl, $R^{31B}$-substituted or unsubstituted 3 to 8 membered heterocycloalkyl, $R^{31B}$-substituted or unsubstituted phenyl, or $R^{31B}$-substituted or unsubstituted 5 to 6 membered heteroaryl. $X^{30B}$ is —F, —Cl, —Br, or —I.

In embodiments, $R^{4C}$ is independently hydrogen, —$CX^{4C}_3$, —CN, —COOH, —$CONH_2$, —$CHX^{4C}_2$, —$CH_2X^{4C}$, $R^{29C}$-substituted or unsubstituted alkyl, $R^{29C}$-substituted or unsubstituted heteroalkyl, $R^{29C}$-substituted or unsubstituted cycloalkyl, $R^{29C}$-substituted or unsubstituted heterocycloalkyl, $R^{29C}$-substituted or unsubstituted aryl, or $R^{29C}$-substituted or unsubstituted heteroaryl. In embodiments, $R^{4C}$ is independently hydrogen, —$CX^{4C}_3$, —CN, —COOH, —$CONH_2$, —$CHX^{4C}_2$, —$CH_2X^{4C}$, $R^{29C}$-substituted or unsubstituted $C_1$-$C_8$ alkyl, $R^{29C}$-substituted or unsubstituted 2 to 8 membered heteroalkyl, $R^{29C}$-substituted or unsubstituted $C_3$-$C_8$ cycloalkyl, $R^{29C}$-substituted or unsubstituted 3 to 8 membered heterocycloalkyl, $R^{29C}$-substituted or unsubstituted phenyl, or $R^{29C}$-substituted or unsubstituted 5 to 6 membered heteroaryl. $X^{4c}$ is —F, —Cl, —Br, or —I. In embodiments, $R^{4C}$ is independently hydrogen. In embodiments, $R^{4C}$ is independently unsubstituted methyl. In embodiments, $R^{4C}$ is independently unsubstituted ethyl.

$R^{29C}$ is independently oxo, halogen, —$CX^{29C}_3$, —$CHX^{29C}_2$, —$CH_2X^{29}C$, —$OCH_2X^{29}C$, —$OCX^{29C}_3$, —$OCHX^{29C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{30C}$-substituted or unsubstituted alkyl, $R^{30C}$-substituted or unsubstituted heteroalkyl, $R^{30C}$-substituted or unsubstituted cycloalkyl, $R^{30C}$-substituted or unsubstituted heterocycloalkyl, $R^{30C}$-substituted or unsubstituted aryl, or $R^{30C}$-substituted or unsubstituted heteroaryl. In embodiments, $R^{29C}$ is independently oxo, halogen, —$CX^{29C}_3$, —$CHX^{29C}_2$, —$CH_2X^{29C}$, —$OCH_2X^{29C}$, —$OCX^{29C}_3$, —$OCHX^{29C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{29C}_3$, —$OCHX^{29C}_2$, $R^{30C}$-substituted or unsubstituted $C_1$-$C_8$ alkyl, $R^{30C}$-substituted or unsubstituted 2 to 8 membered heteroalkyl, $R^{30C}$-substituted or unsubstituted $C_3$-$C_8$ cycloalkyl, $R^{30C}$-substituted or unsubstituted 3 to 8 membered heterocycloalkyl, $R^{30C}$-substituted or unsubstituted phenyl, or $R^{30C}$-substituted or unsubstituted 5 to 6 membered heteroaryl. $X^{29C}$ is —F, —Cl, —Br, or —I.

$R^{30C}$ is independently oxo, halogen, —$CX^{30C}_3$, —$CHX^{30C}_2$, —$CH_2X^{30C}$, —$OCH_2X^{30C}$, —$OCX^{30C}_3$, —$OCHX^{30C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{31C}$-substituted or unsubstituted alkyl, $R^{31C}$-substituted or unsubstituted heteroalkyl, $R^{30C}$-substituted or unsubstituted cycloalkyl, $R^{31C}$-substituted or unsubstituted heterocycloalkyl, $R^{31C}$-substituted or unsubstituted aryl, or $R^{31C}$-substituted or unsubstituted heteroaryl. In embodiments, $R^{30C}$ is independently oxo, halogen, —$CX^{30C}_3$, —$CHX^{30C}_2$, —$CH_2X^{30C}$, —$OCH_2X^{30C}$, —$OCX^{30C}_3$, —$OCHX^{30C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{31C}$-substituted or unsubstituted $C_1$-$C_8$ alkyl, $R^{31C}$-substituted or unsubstituted 2 to 8 membered heteroalkyl, $R^{31C}$-substituted or unsubstituted $C_3$-$C_8$ cycloalkyl, $R^{31C}$-substituted or unsubstituted 3 to 8 membered heterocycloalkyl, $R^{31C}$-substituted or unsubstituted phenyl, or $R^{31C}$-substituted or unsubstituted 5 to 6 membered heteroaryl. $X^{30C}$ is —F, —Cl, —Br, or —I.

In embodiments, $R^{4D}$ is independently hydrogen, —$CX^{4D}_3$, —CN, —COOH, —$CONH_2$, —$CHX^{4D}_2$, —$CH_2X^{4D}$, $R^{29D}$-substituted or unsubstituted alkyl, $R^{29D}$-substituted or unsubstituted heteroalkyl, $R^{29D}$-substituted or unsubstituted cycloalkyl, $R^{29D}$-substituted or unsubstituted heterocycloalkyl, $R^{29D}$-substituted or unsubstituted aryl, or $R^{29D}$-substituted or unsubstituted heteroaryl. In embodiments, $R^{4D}$ is independently hydrogen, —$CX^{4D}_3$, —CN, —COOH, —$CONH_2$, —$CHX^{4D}_2$, —$CH_2X^{4D}$, $R^{29D}$-substituted or unsubstituted $C_1$-$C_8$ alkyl, $R^{29D}$-substituted or unsubstituted 2 to 8 membered heteroalkyl, $R^{29D}$-substituted or unsubstituted $C_3$-$C_8$ cycloalkyl, $R^{29D}$-substituted or unsubstituted 3 to 8 membered heterocycloalkyl, $R^{29D}$-substituted or unsubstituted phenyl, or $R^{29D}$-substituted or unsubstituted 5 to 6 membered heteroaryl. $X^{4D}$ is —F, —Cl, —Br, or —I. In embodiments, $R^{4D}$ is independently hydrogen. In embodiments, $R^{4D}$ is independently unsubstituted methyl. In embodiments, $R^{4D}$ is independently unsubstituted ethyl.

$R^{29D}$ is independently oxo, halogen, —$CX^{29D}_3$, —$CHX^{29D}_2$, —$CH_2X^{29D}$, —$OCH_2X^{29D}$, —$OCX^{29D}_3$, —$OCHX^{29D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{30D}$-substituted or unsubstituted alkyl, $R^{30D}$-substituted or unsubstituted heteroalkyl, $R^{30D}$-substituted or unsubstituted cycloalkyl, $R^{30D}$-substituted or unsubstituted heterocycloalkyl, $R^{30D}$-substituted or unsubstituted aryl, or $R^{30D}$-substituted or unsubstituted heteroaryl. In embodiments, $R^{29D}$ is independently oxo, halogen, —$CX^{29D}_3$, —$CHX^{29D}_2$, —$CH_2X^{29D}$, —$OCH_2X^{29D}$, —$OCX^{29D}_3$, —$OCHX^{29D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{30D}$-substituted or unsubstituted $C_1$-$C_8$ alkyl, $R^{30D}$-substituted or unsubstituted 2 to 8 membered heteroalkyl, $R^{30D}$-substituted or unsubstituted $C_3$-$C_8$ cycloalkyl, $R^{30D}$-substituted or unsubstituted 3 to 8 membered heterocycloalkyl, $R^{30D}$-substituted or unsubstituted phenyl, or $R^{30D}$-substituted or unsubstituted 5 to 6 membered heteroaryl. $X^{29D}$ is —F, —Cl, —Br, or —I.

$R^{30D}$ is independently oxo, halogen, —$CX^{30D}_3$, —$CHX^{30D}_2$, —$CH_2X^{30D}$, —$OCH_2X^{30D}$, —$OCX^{3D3}_3$, —$OCHX^{30D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{31D}$-substituted or unsubstituted alkyl, $R^{31D}$-substituted or unsubstituted heteroalkyl, $R^{31D}$-substituted or unsubstituted cycloalkyl, $R^{31D}$-substituted or unsubstituted heterocycloalkyl, $R^{31D}$-substituted or unsubstituted aryl, or $R^{31D}$-substituted or unsubstituted heteroaryl. In embodiments, $R^{30D}$ is independently oxo, halogen, —$CX^{30D}{}_3$, —$CHX^{30D}{}_2$, —$CH_2X^{30D}$, —$OCH_2X^{30D}$, —$OCX^{30D}{}_3$, —$OCHX^{30D}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{31D}$-substituted or unsubstituted $C_1$-$C_8$ alkyl, $R^{31D}$-substituted or unsubstituted 2 to 8 membered heteroalkyl, $R^{31D}$-substituted or unsubstituted $C_3$-$C_8$ cycloalkyl, $R^{31D}$-substituted or unsubstituted 3 to 8 membered heterocycloalkyl, $R^{31D}$-substituted or unsubstituted phenyl, or $R^{31D}$-substituted or unsubstituted 5 to 6 membered heteroaryl. $X^{30D}$ is —F, —Cl, —Br, or —I.

$R^{31}$, $R^{31A}$, $R^{31B}R_3$, $R^{31C}$, and $R^{31D}$ are independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{31}$, $R^{31A}$, $R^{31B}$, $R^{31C}$, and $R^{31D}$ are independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{31}$, $R^{31A}$, $R^{31B}$, $R^{31C}$, and $R^{31D}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{31}$, $R^{31A}$, $R^{31B}$, $R^{31C}$, and $R^{31D}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted $C_1$-$C_5$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $R^4$ is independently —F, —Cl, —Br, —I, —CN, —$NH_2$, —OH, —SH, —$COCH_3$, —COOH, —$COOCH_3$, —$CX^4{}_3$, —$CHX^4{}_2$, —$CH_2X^4$, —$OCX^4{}_3$, —$OCHX^4{}_2$, —$OCH_2X^4{}_2$, —$SCX^4{}_3$, —$SCH_2X^4{}_2$, —$SCH_2X^4$, —$CH_3$, —$CH_2CH_3$, —$OCH_3$, —$OCH_2CH_3$, —$NHCH_3$, —$N(CH_3)_2$, —$NHCH_2CH_3$, —$N(CH_3)(CH_2CH_3)$, —$N(CH_2CH_3)_2$, —$SCH_3$, or —$SCH_2CH_3$. In embodiments, $R^4$ is independently —F. In embodiments, $R^4$ is independently —Cl. In embodiments, $R^4$ is independently —Br. In embodiments, $R^4$ is independently —I. In embodiments, $R^4$ is independently —CN. In embodiments, $R^4$ is independently —$NH_2$. In embodiments, $R^4$ is independently —OH. In embodiments, $R^4$ is independently —SH. In embodiments, $R^4$ is independently —$COCH_3$. In embodiments, $R^4$ is independently —COOH. In embodiments, $R^4$ is independently —$COOCH_3$. In embodiments, $R^4$ is independently —$CX^4{}_3$. In embodiments, $R^4$ is independently —$CHX^4{}_2$. In embodiments, $R^4$ is independently —$CH_2X^4$. In embodiments, $R^4$ is independently —$OCX^4{}_3$. In embodiments, $R^4$ is independently —$OCHX^4{}_2$. In embodiments, $R^4$ is independently —$OCH_2X^4$. In embodiments, $R^4$ is independently —$SCX^4{}_3$. In embodiments, $R^4$ is independently —$SCHX^4{}_2$. In embodiments, $R^4$ is independently —$SCH_2X^4$. In embodiments, $R^4$ is independently —$CH_3$. In embodiments, $R^4$ is independently —$CH_2CH_3$. In embodiments, $R^4$ is independently —$OCH_3$. In embodiments, $R^4$ is independently —$OCH_2CH_3$. In embodiments, $R^4$ is independently —$NHCH_3$. In embodiments, $R^4$ is independently —$N(CH_3)_2$. In embodiments, $R^4$ is independently —$NHCH_2CH_3$. In embodiments, $R^4$ is independently —$N(CH_3)(CH_2CH_3)$. In embodiments, $R^4$ is independently —$N(CH_2CH_3)_2$. In embodiments, $R^4$ is independently —$SCH_3$. In embodiments, $R^4$ is independently —$SCH_2CH_3$. In embodiments, $X^4$ is independently —F. In embodiments, $X^4$ is independently —Cl. In embodiments, $X^4$ is independently —Br. In embodiments, $X^4$ is independently —I.

In embodiments, $R^4$ is independently —OPh. In embodiments, $R^4$ is independently tert-butyl. In embodiments, $R^4$ is independently —$OCH_2Ph$. In embodiments, $R^4$ is independently —$OCH_2CH_3$. In embodiments, $R^4$ is independently —$OCH(CH_3)_2$. In embodiments, $R^4$ is independently —$OCH_2CH_2CH_3$. In embodiments, $R^4$ is independently —$OCH_2CH(CH_3)_2$. In embodiments, $R^4$ is independently —$OCH_2CH_2CH_2CH_3$. In embodiments, $R^4$ is independently —$OCH_2CHCH_2$. In embodiments, $R^4$ is independently —$OCH_2CH_2Ph$. In embodiments, $R^4$ is independently —$OCH_2CH_2CH_3$. In embodiments, $R^4$ is independently -Ph. In embodiments, $R^4$ is independently —$CH_2Ph$. In embodiments, $R^4$ is independently —$CH_2CH_2Ph$. In embodiments, $R^4$ is independently —$CH_2CH_2CH_2CH_3$. In embodiments, $R^4$ is independently —$CH_2CH_2CH_2CH_2CH_3$. In embodiments, $R^4$ is independently —$CH_2CH(CH_3)_2$. In embodiments, $R^4$ is independently —$CH_2CH_2CH(CH_3)_2$.

$R^{4.1}$ is $R^4$ at a fixed position (e.g., non-floating as shown in the formula described herein) and may independently be any $R^4$ substituent. $R^{41A}$ is $R^{4A}$ at a fixed position (e.g., non-floating as shown in the formula described herein) and may independently be any $R^{4A}$ substituent. $R^{41B}$ is $R^{4B}$ at a fixed position (e.g., non-floating as shown in the formula described herein) and may independently be any $R^{4B}$ substituent. $R^{4.1c}$ is $R^{4C}$ at a fixed position (e.g., non-floating as shown in the formula described herein) and may independently be any $R^{4C}$ substituent. $R^{41D}$ is $R^{4D}$ at a fixed position (e.g., non-floating as shown in the formula described herein) and may independently be any $R^{4D}$ substituent. The symbol n4.1 is n4 at a fixed position (e.g., non-floating as shown in the formula described herein) and may independently be any n4 substituent. The symbol m4.1 is m4 at a fixed position (e.g., non-floating as shown in the formula described herein) and may independently be any m4 substituent. The symbol v4.1 is v4 at a fixed position (e.g., non-floating as shown in the formula described herein) and may independently be any v4 substituent. In embodiments, $R^{4.1}$ is independently —F, —Cl, —Br, —I, —CN, —NH$_2$, —OH, —SH, —COCH$_3$, —COOH, —COOCH$_3$, —CX$^{4.1}_3$, —CHX$^{4.1}_2$, —CH$_2$X$^{4.1}$, —OCX$^{4.1}_3$, —OCHX$^{4.1}_2$, —OCH$_2$X$^{4.1}$, —SCX$^{4.1}_3$, —SCHX$^{4.1}_2$, —SCH$_2$X$^{4.1}$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$C H$_3$. In embodiments, $R^{4.1}$ is independently-F. In embodiments, $R^{4.1}$ is independently —Cl. In embodiments, $R^{4.1}$ is independently —Br. In embodiments, $R^{4.1}$ is independently —I. In embodiments, $R^{4.1}$ is independently —CN. In embodiments, $R^{4.1}$ is independently —NH$_2$. In embodiments, $R^{4.1}$ is independently —OH. In embodiments, $R^{4.1}$ is independently —SH. In embodiments, $R^{4.1}$ is independently —COCH$_3$. In embodiments, $R^{4.1}$ is independently —COOH. In embodiments, $R^{4.1}$ is independently —COOCH$_3$. In embodiments, $R^{4.1}$ is independently —CX$^{4.1}_3$. In embodiments, $R^{4.1}$ is independently —CHX$^{4.12}$. In embodiments, $R^{4.1}$ is independently —CH$_2$X$^{4.1}$. In embodiments, $R^{4.1}$ is independently —OCX$^{4.1}_3$. In embodiments, $R^{4.1}$ is independently —OCHX$^{4.1}_2$. In embodiments, $R^{4.1}$ is independently —OCH$_2$X$^{4.1}$. In embodiments, $R^{4.1}$ is independently —SCX$^{4.13}$. In embodiments, $R^{4.1}$ is independently —SCHX$^{4.1}_2$. In embodiments, $R^{4.1}$ is independently —SCH$_2$X$^{4.1}$. In embodiments, $R^{4.1}$ is independently —CH$_3$. In embodiments, $R^{4.1}$ is independently —CH$_2$CH$_3$. In embodiments, $R^{4.1}$ is independently —OCH$_3$. In embodiments, $R^{4.1}$ is independently —OCH$_2$CH$_3$. In embodiments, $R^{4.1}$ is independently —NHCH$_3$. In embodiments, $R^{4.1}$ is independently —N(CH$_3$)$_2$. In embodiments, $R^{4.1}$ is independently —NHCH$_2$CH$_3$. In embodiments, $R^{4.1}$ is independently —N(CH$_3$)(CH$_2$CH$_3$). In embodiments, $R^{4.1}$ is independently —N(CH$_2$CH$_3$)$_2$. In embodiments, $R^{4.1}$ is independently —SCH$_3$. In embodiments, $R^{4.1}$ is independently —SCH$_2$CH$_3$. In embodiments, $X^{4.1}$ is independently-F. In embodiments, $X^{4.1}$ is independently —Cl. In embodiments, $X^{4.1}$ is independently —Br. In embodiments, $X^{4.1}$ is independently —I. In embodiments, $R^{4.1}$ is independently —OPh. In embodiments, $R^{4.1}$ is independently tert-butyl. In embodiments, $R^{4.1}$ is independently —OCH$_2$Ph. In embodiments, $R^{4.1}$ is independently —OCH$_2$CH$_3$. In embodiments, $R^{4.1}$ is independently —OCH(CH$_3$)$_2$. In embodiments, $R^{4.1}$ is independently —OCH$_2$CH$_2$CH$_3$. In embodiments, $R^{4.1}$ is independently —OCH$_2$CH(CH$_3$)$_2$. In embodiments, $R^{4.1}$ is independently —OCH$_2$CH$_2$CH$_2$CH$_3$. In embodiments, $R^{4.1}$ is independently —OCH$_2$CHCH$_2$. In embodiments, $R^{4.1}$ is independently —OCH$_2$CH$_2$Ph. In embodiments, $R^{4.1}$ is independently —OCH$_2$CH$_2$CH$_3$. In embodiments, $R^{4.1}$ is independently -Ph. In embodiments, $R^{4.1}$ is independently —CH$_2$Ph. In embodiments, $R^{4.1}$ is independently —CH$_2$CH$_2$Ph. In embodiments, $R^{4.1}$ is independently —CH$_2$CH$_2$CH$_2$CH$_3$. In embodiments, $R^{4.1}$ is independently —CH$_2$CH$_2$CH$_2$CH$_2$CH$_3$. In embodiments, $R^{4.1}$ is independently —CH$_2$CH(CH$_3$)$_2$. In embodiments, $R^{4.1}$ is independently —CH$_2$CH$_2$CH(CH$_3$)$_2$. In embodiments, $R^{4.1}$ is independently hydrogen. In embodiments, $R^{4.1}$ is independently halogen. In embodiments, $R^{4.1}$ is independently —CX$^{4.1}_3$. In embodiments, $R^{4.1}$ is independently —CHX$^4$12. In embodiments, $R^{4.1}$ is independently —CH$^2$X$^{4.1}$. In embodiments, $R^{4.1}$ is independently —OCX$^{4.1}_3$. In embodiments, $R^{4.1}$ is independently —OCH$_2$X$^{4.1}$. In embodiments, $R^{4.1}$ is independently —OCHX$^{4.1}_2$. In embodiments, $R^{4.1}$ is independently —CN. In embodiments, $R^{4.1}$ is independently —OH. In embodiments, $R^{4.1}$ is independently —NH$_2$. In embodiments, $R^{4.1}$ is independently —COOH. In embodiments, $R^{4.1}$ is independently —CONH$_2$. In embodiments, $R^{4.1}$ is independently —NO$_2$. In embodiments, $R^{4.1}$ is independently —SH. In embodiments, $R^{4.1}$ is independently —SO$_{n4.1}$R$^{4.1D}$. In embodiments, $R^{4.1}$ is independently —SO$_{v4.1}$NR$^{4.1A}$R$^{4.1B}$. In embodiments, $R^{4.1}$ is independently —NHC(O)NR$^{4.1A}$R$^{4.1B}$. In embodiments, $R^{4.1}$ is independently —N(O)$_{m4.1}$. In embodiments, $R^{4.1}$ is independently —NR$^{4.1A}$R$^{4.1B}$. In embodiments, $R^{4.1}$ is independently —C(O)R$^{4C}$. In embodiments, $R^{4.1}$ is independently —C(O)—OR$^{4.1}$. In embodiments, $R^{4.1}$ is independently —C(O)NR$^{4.1A}$R$^{4.1B}$. In embodiments, $R^{4.1}$ is independently —OR$^{4.1D}$. In embodiments, $R^{4.1}$ is independently —NR$^{4.1A}$SO$_2$R$^{4.1D}$. In embodiments, $R^{4.1}$ is independently —NR$^{4.1A}$C(O)R$^{4.1C}$. In embodiments, $R^{4.1}$ is independently —NR$^{4.1A}$C(O)OR$^{4.1C}$. In embodiments, $R^{4.1}$ is independently —NR$^{4.1A}$OR$^{4.1C}$. In embodiments, $R^{4.1}$ is independently —SO$_{n4}$R$^{4D}$. In embodiments, $R^{4.1}$ is independently —SO$_{v4}$NR$^{4A}$R$^{4B}$. In embodiments, $R^{4.1}$ is independently —NHC(O)NR$^{4A}$R$^{4B}$. In embodiments, $R^{4.1}$ is independently —N(O)$_{m4}$. In embodiments, $R^{4.1}$ is independently —NR$^{4A}$R$^{4B}$ In embodiments, $R^{4.1}$ is independently —C(O)R$^{4C}$. In embodiments, $R^{4.1}$ is independently —C(O)—OR$^{4C}$. In embodiments, $R^{4.1}$ is independently —C(O)NR$^{4A}$R$^{4B}$. In embodiments, $R^{4.1}$ is independently —OR$^{4D}$. In embodiments, $R^{4.1}$ is independently —NR$^{4A}$SO$_2$R$^{4D}$. In embodiments, $R^{4.1}$ is independently —NR$^{4A}$C(O)R$^{4C}$. In embodiments, $R^{4.1}$ is independently —NR$^{4A}$C(O)OR$^{4C}$. In embodiments, $R^{4.1}$ is independently —NR$^{4A}$OR$^{4C}$.

$R^{4.2}$ is $R^4$ at a fixed position (e.g., non-floating as shown in the formula described herein) and may independently be any $R^4$ substituent. $R^{4.2A}$ is $R^{4A}$ at a fixed position (e.g., non-floating as shown in the formula described herein) and may independently be any $R^{4A}$ substituent. $R^{4.2B}$ is $R^{4B}$ at a fixed position (e.g., non-floating as shown in the formula described herein) and may independently be any $R^{4B}$ substituent. $R^{4.2C}$ is $R^{4C}$ at a fixed position (e.g., non-floating as shown in the formula described herein) and may independently be any $R^{4C}$ substituent. $R^{4.2D}$ is $R^{4D}$ at a fixed position (e.g., non-floating as shown in the formula described herein) and may independently be any $R^{4D}$ substituent. The symbol n4.2 is n4 at a fixed position (e.g., non-floating as shown in the formula described herein) and may independently be any n4 substituent. The symbol m4.2 is m4 at a fixed position (e.g., non-floating as shown in the formula described herein) and may independently be any m4 substituent. The symbol v4.2 is v4 at a fixed position (e.g., non-floating as shown in the formula described herein) and may independently be any v4 substituent.

In embodiments, $R^{4.2}$ is independently —F, —Cl, —Br, —I, —CN, —NH$_2$, —OH, —SH, —COCH$_3$, —COOH, —COOCH$_3$, —CX$^{4.2}_3$, —CHX$^{4.2}_2$, —CH$_2$X$^{4.2}$, —OCX$^{4.2}_3$, —OCHX$^{4.2}_2$, —OCH$_2$X$^{4.2}$, —SCX$^{4.2}_3$, —SCHX$^{4.2}_2$, —SCH$_2$X$^{4.2}$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$C H$_3$. In embodiments, $R^{4.2}$ is independently-F. In embodiments, $R^{4.2}$ is independently —Cl. In embodiments, $R^{4.2}$ is independently —Br. In embodiments, $R^{4.2}$ is independently —I. In embodiments, $R^{4.2}$ is independently —CN. In embodiments, $R^{4.2}$ is independently —NH$_2$. In embodiments, $R^{4.2}$ is independently —OH. In embodiments, $R^{4.2}$ is independently —SH. In embodiments, $R^{4.2}$ is independently —COCH$_3$. In embodiments, $R^{4.2}$ is independently —COOH. In embodiments, $R^{4.2}$ is independently —COOCH$_3$. In embodiments, $R^{4.2}$ is independently —CX$^{4.2}_3$. In embodiments, $R^{4.2}$ is independently —CHX$^{4.2}_2$. In embodiments, $R^{4.2}$ is independently —CH$_2$X$^{4.2}$. In embodiments, $R^{4.2}$ is independently —OCX$^{4.2}$$_3$. In embodiments, R$^{4.2}$ is independently —OCHX$^{4.2}$$_2$. In embodiments, R$^{4.2}$ is independently —OCH$_2$X$^{4.2}$. In embodiments, R$^{4.2}$ is independently —SCX$^{4.2}$$_3$. In embodiments, R$^{4.2}$ is independently —SCHX$^{4.2}$$_2$. In embodiments, R$^{4.2}$ is independently —SCH$_2$X$^{4.2}$. In embodiments, R$^{4.2}$ is independently —CH$_3$. In embodiments, R$^{4.2}$ is independently —CH$_2$CH$_3$. In embodiments, R$^{4.2}$ is independently —OCH$_3$. In embodiments, R$^{4.2}$ is independently —OCH$_2$CH$_3$. In embodiments, R$^{4.2}$ is independently —NHCH$_3$. In embodiments, R$^{4.2}$ is independently —N(CH$_3$)$_2$. In embodiments, R$^{4.2}$ is independently —NHCH$_2$CH$_3$. In embodiments, R$^{4.2}$ is independently —N(CH$_3$)(CH$_2$CH$_3$). In embodiments, R$^{4.2}$ is independently —N(CH$_2$CH$_3$)$_2$. In embodiments, R$^{4.2}$ is independently —SCH$_3$. In embodiments, R$^{4.2}$ is independently —SCH$_2$CH$_3$. In embodiments, X$^{4.2}$ is independently-F. In embodiments, X$^{4.2}$ is independently —Cl. In embodiments, X$^{4.2}$ is independently —Br. In embodiments, X$^{4.2}$ is independently —I. In embodiments, R$^{4.2}$ is independently —OPh. In embodiments, R$^{4.2}$ is independently tert-butyl. In embodiments, R$^{4.2}$ is independently —OCH$_2$Ph. In embodiments, R$^{4.2}$ is independently —OCH$_2$CH$_3$. In embodiments, R$^{4.2}$ is independently —OCH(CH$_3$)$_2$. In embodiments, R$^{4.2}$ is independently —OCH$_2$CH$_2$CH$_3$. In embodiments, R$^{4.2}$ is independently —OCH$_2$CH(CH$_3$)$_2$. In embodiments, R$^{4.2}$ is independently —OCH$_2$CH$_2$CH$_2$CH$_3$. In embodiments, R$^{4.2}$ is independently —OCH$_2$CHCH$_2$. In embodiments, R$^{4.2}$ is independently —OCH$_2$CH$_2$Ph. In embodiments, R$^{4.2}$ is independently —OCH$_2$CH$_2$CH$_3$. In embodiments, R$^{4.2}$ is independently -Ph. In embodiments, R$^{4.2}$ is independently —CH$_2$Ph. In embodiments, R$^{4.2}$ is independently —CH$_2$CH$_2$Ph. In embodiments, R$^{4.2}$ is independently —CH$_2$CH$_2$CH$_2$CH$_3$. In embodiments, R$^{4.2}$ is independently —CH$_2$CH$_2$CH$_2$CH$_2$CH$_3$. In embodiments, R$^{4.2}$ is independently —CH$_2$CH(CH$_3$)$_2$. In embodiments, R$^{4.2}$ is independently —CH$_2$CH$_2$CH(CH$_3$)$_2$. In embodiments, R$^{4.2}$ is independently hydrogen. In embodiments, R$^{4.2}$ is independently halogen. In embodiments, R$^{4.2}$ is independently —CX$^{4.2}$$_3$. In embodiments, R$^{4.2}$ is independently —CHX$^{4.2}$$_2$. In embodiments, R$^{4.2}$ is independently —CH$_2$X$^{4.2}$. In embodiments, R$^{4.2}$ is independently —OCX$^{4.2}$$_3$. In embodiments, R$^{4.2}$ is independently —OCH$_2$X$^{4.2}$. In embodiments, R$^{4.2}$ is independently —OCHX$^{4.2}$$_2$. In embodiments, R$^{4.2}$ is independently —CN. In embodiments, R$^{4.2}$ is independently —SO$_{n4.2}$R$^{4.2D}$. In embodiments, R$^{4.2}$ is independently —SO$_{v4}$0.2NR$^{4.2A}$R$^{4.2B}$ In embodiments, R$^{4.2}$ is independently —NHC(O)NR$^{4.2A}$R$^{4.2B}$. In embodiments, R$^{4.2}$ is independently —N(O)$_{m4}$0.2. In embodiments, R$^{4.2}$ is independently —NR$^{4.2A}$R$^{4.2B}$. In embodiments, R$^{4.2}$ is independently —C(O)R$^{4.2C}$. In embodiments, R$^{4.2}$ is independently —C(O)—OR$^{4.2C}$ In embodiments, R$^{4.2}$ is independently —C(O)NR$^{4.2A}$R$^{4.2B}$. In embodiments, R$^{4.2}$ is independently —OR$^{4.2D}$. In embodiments, R$^{4.2}$ is independently —NR$^{4.2A}$SO$_2$R$^{4.2D}$ In embodiments, R$^{4.2}$ is independently —NR$^{4.2A}$C(O)R$^{4.2C}$. In embodiments, R$^{4.2}$ is independently —NR$^{4.2A}$C(O)OR$^{4.2C}$. In embodiments, R$^{4.2}$ is independently —NR$^{4.2A}$OR$^{4.2C}$. In embodiments, R$^{4.2}$ is independently —OH. In embodiments, R$^{4.2}$ is independently —NH$_2$. In embodiments, R$^{4.2}$ is independently —COOH. In embodiments, R$^{4.2}$ is independently —CONH$_2$. In embodiments, R$^{4.2}$ is independently —NO$_2$. In embodiments, R$^{4.2}$ is independently —SH. In embodiments, R$^{4.2}$ is independently —SO$_{n4}$R$^{4D}$. In embodiments, R$^{4.2}$ is independently —SO$_{v4}$NR$^{4A}$R$^{4B}$. In embodiments, R$^{4.2}$ is independently —NHC(O)NR$^{4A}$R$^{4B}$. In embodiments, R$^{4.2}$ is independently —N(O)$_{m4}$. In embodiments, R$^{4.2}$ is independently —NR$^{4A}$R$^{4B}$In embodiments, R$^{4.2}$ is independently —C(O) R$^{4C}$. In embodiments, R$^{4.2}$ is independently —C(O)—OR$^{4C}$. In embodiments, R$^{4.2}$ is independently —C(O) NR$^{4A}$R$^{4B}$. In embodiments, R$^{4.2}$ is independently —OR$^{4D}$. In embodiments, R$^{4.2}$ is independently —NR$^{4A}$SO$_2$R$^{4D}$. In embodiments, R$^{4.2}$ is independently —NR$^{4A}$C(O)R$^{4C}$. In embodiments, R$^{4.2}$ is independently —NR$^{4A}$C(O)OR$^{4C}$. In embodiments, R$^{4.2}$ is independently —NR$^{4A}$OR$^{4C}$.

R$^{4.3}$ is R$^4$ at a fixed position (e.g., non-floating as shown in the formula described herein) and may independently be any R$^4$ substituent. R$^{4.3A}$ is R$^{4A}$ at a fixed position (e.g., non-floating as shown in the formula described herein) and may independently be any R$^{4A}$ substituent. R$^{4.3B}$ is R$^{4B}$ at a fixed position (e.g., non-floating as shown in the formula described herein) and may independently be any R$^{4B}$ substituent. R$^{4.3C}$ is R$^{4C}$ at a fixed position (e.g., non-floating as shown in the formula described herein) and may independently be any R$^{4C}$ substituent. R$^{4.3D}$ is R$^{4D}$ at a fixed position (e.g., non-floating as shown in the formula described herein) and may independently be any R$^{4D}$ substituent. The symbol n4.3 is n4 at a fixed position (e.g., non-floating as shown in the formula described herein) and may independently be any n4 substituent. The symbol m4.3 is m4 at a fixed position (e.g., non-floating as shown in the formula described herein) and may independently be any m4 substituent. The symbol v4.3 is v4 at a fixed position (e.g., non-floating as shown in the formula described herein) and may independently be any v4 substituent.

In embodiments, R$^{4.3}$ is independently —F, —Cl, —Br, —I, —CN, —NH$_2$, —OH, —SH, —COCH$_3$, —COOH, —COOCH$_3$, —CX$^{4.3}$$_3$, —CHX$^{4.3}$$_2$, —CH$_2$X$^{4.3}$, —OCX$^{4.3}$$_3$, —OCHX$^{4.3}$$_2$, —OCH$_2$X$^{4.3}$, —SCX$^{4.3}$$_3$, —SCHX$^{4.3}$$_2$, —SCH$_2$X$^{4.3}$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$CH$_3$. In embodiments, R$^{4.3}$ is independently-F. In embodiments, R$^{4.3}$ is independently —Cl. In embodiments, R$^{4.3}$ is independently —Br. In embodiments, R$^{4.3}$ is independently —I. In embodiments, R$^{4.3}$ is independently —CN. In embodiments, R$^{4.3}$ is independently —NH$_2$. In embodiments, R$^{4.3}$ is independently —OH. In embodiments, R$^{4.3}$ is independently —SH. In embodiments, R$^{4.3}$ is independently —COCH$_3$. In embodiments, R$^{4.3}$ is independently —COOH. In embodiments, R$^{4.3}$ is independently —COOCH$_3$. In embodiments, R$^{4.3}$ is independently —CX$^{4.3}$$_3$. In embodiments, R$^{4.3}$ is independently —CHX$^{4.3}$$_2$. In embodiments, R$^{4.3}$ is independently —CH$_2$X$^{4.3}$. In embodiments, R$^{4.3}$ is independently —OCX$^{4.3}$$_3$. In embodiments, R$^{4.3}$ is independently —OCHX$^{4.3}$$_2$. In embodiments, R$^{4.3}$ is independently —OCH$_2$X$^{4.3}$. In embodiments, R$^{4.3}$ is independently —SCX$^{4.3}$$_3$. In embodiments, R$^{4.3}$ is independently —SCHX$^{4.3}$$_2$. In embodiments, R$^{4.3}$ is independently —SCH$_2$X$^{4.3}$. In embodiments, R$^{4.3}$ is independently —CH$_3$. In embodiments, R$^{4.3}$ is independently —CH$_2$CH$_3$. In embodiments, R$^{4.3}$ is independently —OCH$_3$. In embodiments, R$^{4.3}$ is independently —OCH$_2$CH$_3$. In embodiments, R$^{4.3}$ is independently —NHCH$_3$. In embodiments, R$^{4.3}$ is independently —N(CH$_3$)$_2$. In embodiments, R$^{4.3}$ is independently —NHCH$_2$CH$_3$. In embodiments, R$^{4.3}$ is independently —N(CH$_3$)(CH$_2$CH$_3$). In embodiments, R$^{4.3}$ is independently —N(CH$_2$CH$_3$)$_2$. In embodiments, R$^{4.3}$ is independently —SCH$_3$. In embodiments, R$^{4.3}$ is independently —SCH$_2$CH$_3$. In embodiments, X$^4$$_3$ is independently-F. In embodiments, X$^4$$_3$ is independently —Cl. In embodiments, X$^4$$_3$ is independently —Br. In embodiments, X$^4$$_3$ is independently —I. In embodiments, R$^{4.3}$ is independently —OPh. In embodiments, R$^{4.3}$ is independently tert-butyl. In embodiments, $R^{4.3}$ is independently —OCH$_2$Ph. In embodiments, $R^{4.3}$ is independently —OCH$_2$CH$_3$. In embodiments, $R^{4.3}$ is independently —OCH(CH$_3$)$_2$. In embodiments, $R^{4.3}$ is independently —OCH$_2$CH$_2$CH$_3$. In embodiments, $R^{4.3}$ is independently —OCH$_2$CH(CH$_3$)$_2$. In embodiments, $R^{4.3}$ is independently —OCH$_2$CH$_2$CH$_2$CH$_3$. In embodiments, $R^{4.3}$ is independently —OCH$_2$CHCH$_2$. In embodiments, $R^{43}$ is independently —OCH$_2$CH$_2$Ph. In embodiments, $R^{43}$ is independently —OCH$_2$CH$_2$CH$_3$. In embodiments, $R^{43}$ is independently -Ph. In embodiments, $R^{43}$ is independently —CH$_2$Ph. In embodiments, $R^{43}$ is independently —CH$_2$CH$_2$Ph. In embodiments, $R^{43}$ is independently —CH$_2$CH$_2$CH$_2$CH$_3$. In embodiments, $R^{43}$ is independently —CH$_2$CH$_2$CH$_2$CH$_2$CH$_3$. In embodiments, $R^{43}$ is independently —CH$_2$CH(CH$_3$)$_2$. In embodiments, $R^{43}$ is independently —CH$_2$CH$_2$CH(CH$_3$)$_2$. In embodiments, $R^{43}$ is independently hydrogen. In embodiments, $R^{43}$ is independently halogen. In embodiments, $R^{43}$ is independently —CX$^{4.3}$$_3$. In embodiments, $R^{43}$ is independently —CHX$^{4.3}$$_2$. In embodiments, $R^{43}$ is independently —CH$_2$X$^{4.3}$. In embodiments, $R^{43}$ is independently —OCX$^{4.3}$$_3$. In embodiments, $R^{43}$ is independently —OCH$_2$X$^{4.3}$. In embodiments, $R^{43}$ is independently —OCHX$^{4.3}$$_2$. In embodiments, $R^{43}$ is independently —CN. In embodiments, $R^{4.3}$ is independently —SO$_{n4.3}$R$^{4.3D}$. In embodiments, $R^{4.3}$ is independently —SO$_{v4.3}$NR$^{43A}$R$^{43B}$. In embodiments, $R^{4.3}$ is independently —NHC(O)NR$^{4.3A}$R$^{4.3B}$. In embodiments, $R^{4.3}$ is independently —N(O)$_{m4.3}$. In embodiments, $R^{4.3}$ is independently —NR$^{4.3A}$R$^{4.3B}$. In embodiments, $R^{4.3}$ is independently —C(O)R$^{4.3C}$. In embodiments, $R^{4.3}$ is independently —C(O)—OR$^{4.3C}$. In embodiments, $R^{4.3}$ is independently —C(O)NR$^{4.3A}$R$^{4.3B}$. In embodiments, $R^{4.3}$ is independently —OR$^{4.3D}$. In embodiments, $R^{4.3}$ is independently —NR$^{4.3A}$SO$_2$R$^{4.3D}$. In embodiments, $R^{4.3}$ is independently —NR$^{4.3A}$C(O)R$^{4.3}$c. In embodiments, $R^{4.3}$ is independently —NR$^{4.3A}$C(O)OR$^{4.3C}$. In embodiments, $R^{4.3}$ is independently —NR$^{4.3A}$OR$^{4.3C}$. In embodiments, $R^{4.3}$ is independently —OH. In embodiments, $R^{4.3}$ is independently —NH$_2$. In embodiments, $R^{4.3}$ is independently —COOH. In embodiments, $R^{4.3}$ is independently —CONH$_2$. In embodiments, $R^{4.3}$ is independently —NO$_2$. In embodiments, $R^{4.3}$ is independently —SH. In embodiments, $R^{4.3}$ is independently —SO$_{n4}$R$^{4D}$. In embodiments, $R^{4.3}$ is independently —SO$_{v4}$NR$^{4A}$R$^{4B}$. In embodiments, $R^{4.3}$ is independently —NHC(O)NR$^{4A}$R$^{4B}$. In embodiments, $R^{4.3}$ is independently —N(O)$_{m4}$. In embodiments, $R^{4.3}$ is independently —NR$^{4A}$R$^{4B}$ In embodiments, $R^{4.3}$ is independently —C(O)R$^{4C}$. In embodiments, $R^{4.3}$ is independently —C(O)—OR$^{4C}$. In embodiments, $R^{4.3}$ is independently —C(O)NR$^{4A}$R$^{4B}$. In embodiments, $R^{4.3}$ is independently —OR$^{4D}$. In embodiments, $R^{4.3}$ is independently —NR$^{4A}$SO$_2$R$^{4D}$. In embodiments, $R^{4.3}$ is independently —NR$^{4A}$C(O)R$^{4C}$. In embodiments, $R^{4.3}$ is independently —NR$^{4A}$C(O)OR$^{4C}$. In embodiments, $R^{4.3}$ is independently —NR$^{4A}$OR$^{4C}$.

$R^{4.4}$ is $R^4$ at a fixed position (e.g., non-floating as shown in the formula described herein) and may independently be any $R^4$ substituent. $R^{4.4A}$ is $R^{4A}$ at a fixed position (e.g., non-floating as shown in the formula described herein) and may independently be any $R^{4A}$ substituent. $R^{4.4B}$ is $R^{4B}$ at a fixed position (e.g., non-floating as shown in the formula described herein) and may independently be any $R^{4B}$ substituent. $R^{4.4C}$ is $R^{4C}$ at a fixed position (e.g., non-floating as shown in the formula described herein) and may independently be any $R^{4C}$ substituent. $R^{4.4D}$ is $R^{4D}$ at a fixed position (e.g., non-floating as shown in the formula described herein) and may independently be any $R^{4D}$ substituent. The symbol n4.4 is n4 at a fixed position (e.g., non-floating as shown in the formula described herein) and may independently be any n4 substituent. The symbol m4.4 is m4 at a fixed position (e.g., non-floating as shown in the formula described herein) and may independently be any m4 substituent. The symbol v4.4 is v4 at a fixed position (e.g., non-floating as shown in the formula described herein) and may independently be any v4 substituent.

In embodiments, $R^{4.4}$ is independently —F, —Cl, —Br, —I, —CN, —NH$_2$, —OH, —SH, —COCH$_3$, —COOH, —COOCH$_3$, —CX$^{4.4}$$_3$, —CHX$^{4.4}$$_2$, —CH$_2$X$^{4.4}$, —OCX$^{4.4}$$_3$, —OCHX$^{4.4}$$_2$, —OCH$_2$X$^{4.4}$, —SCX$^{4.4}$$_3$, —SCHX$^{4.4}$$_2$, —SCH$_2$X$^{4.4}$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$CH$_3$. In embodiments, $R^{4.4}$ is independently -F. In embodiments, $R^{4.4}$ is independently —Cl. In embodiments, $R^{4.4}$ is independently —Br. In embodiments, $R^{4.4}$ is independently —I. In embodiments, $R^{4.4}$ is independently —CN. In embodiments, $R^{4.4}$ is independently —NH$_2$. In embodiments, $R^{4.4}$ is independently —OH. In embodiments, $R^{4.4}$ is independently —SH. In embodiments, $R^{4.4}$ is independently —COCH$_3$. In embodiments, $R^{4.4}$ is independently —COOH. In embodiments, $R^{4.4}$ is independently —COOCH$_3$. In embodiments, $R^{4.4}$ is independently —CX$^{4.4}$$_3$. In embodiments, $R^{4.4}$ is independently —CHX$^{4.4}$$_2$. In embodiments, $R^{4.4}$ is independently —CH$_2$X$^{4.4}$. In embodiments, $R^{4.4}$ is independently —OCX$^{4.4}$$_3$. In embodiments, $R^{4.4}$ is independently —OCHX$^{4.4}$$_2$. In embodiments, $R^{4.4}$ is independently —OCH$_2$X$^{4.4}$. In embodiments, $R^{4.4}$ is independently —SCX$^{4.4}$$_3$. In embodiments, $R^{4.4}$ is independently —SCHX$^{4.4}$$_2$. In embodiments, $R^{4.4}$ is independently —SCH$_2$X$^{4.4}$. In embodiments, $R^{4.4}$ is independently —CH$_3$. In embodiments, $R^{4.4}$ is independently —CH$_2$CH$_3$. In embodiments, $R^{4.4}$ is independently —OCH$_3$. In embodiments, $R^{4.4}$ is independently —OCH$_2$CH$_3$. In embodiments, $R^{4.4}$ is independently —NHCH$_3$. In embodiments, $R^{4.4}$ is independently —N(CH$_3$)$_2$. In embodiments, $R^{4.4}$ is independently —NHCH$_2$CH$_3$. In embodiments, $R^{4.4}$ is independently —N(CH$_3$)(CH$_2$CH$_3$). In embodiments, $R^{4.4}$ is independently —N(CH$_2$CH$_3$)$_2$. In embodiments, $R^{4.4}$ is independently —SCH$_3$. In embodiments, $R^{4.4}$ is independently —SCH$_2$CH$_3$. In embodiments, $X^{4.4}$ is independently-F. In embodiments, $X^{4.4}$ is independently —Cl. In embodiments, $X^{4.4}$ is independently —Br. In embodiments, $X^{4.4}$ is independently —I. In embodiments, $R^{4.4}$ is independently —OPh. In embodiments, $R^{4.4}$ is independently tert-butyl. In embodiments, $R^{4.4}$ is independently —OCH$_2$Ph. In embodiments, $R^{4.4}$ is independently —OCH$_2$CH$_3$. In embodiments, $R^{4.4}$ is independently —OCH(CH$_3$)$_2$. In embodiments, $R^{4.4}$ is independently —OCH$_2$CH$_2$CH$_3$. In embodiments, $R^{4.4}$ is independently —OCH$_2$CH(CH$_3$)$_2$. In embodiments, $R^{4.4}$ is independently —OCH$_2$CH$_2$CH$_2$CH$_3$. In embodiments, $R^{4.4}$ is independently —OCH$_2$CHCH$_2$. In embodiments, $R^{4.4}$ is independently —OCH$_2$CH$_2$Ph. In embodiments, $R^{4.4}$ is independently —OCH$_2$CH$_2$CH$_3$. In embodiments, $R^{4.4}$ is independently -Ph. In embodiments, $R^{4.4}$ is independently —CH$_2$Ph. In embodiments, $R^{4.4}$ is independently —CH$_2$CH$_2$Ph. In embodiments, $R^{4.4}$ is independently —CH$_2$CH$_2$CH$_2$CH$_3$. In embodiments, $R^{4.4}$ is independently —CH$_2$CH$_2$CH$_2$CH$_2$CH$_3$. In embodiments, $R^{4.4}$ is independently —CH$_2$CH(CH$_3$)$_2$. In embodiments, $R^{4.4}$ is independently —CH$_2$CH$_2$CH(CH$_3$)$_2$. In embodiments, $R^{4.4}$ is independently hydrogen. In embodiments, $R^{4.4}$ is independently halogen. In embodiments, $R^{4.4}$ is independently —CX$^{4.4}$$_3$. In embodiments, $R^{4.4}$ is independently —CHX$^{4.4}$$_2$. In embodiments, $R^{4.4}$ is independently —CH$_2$X$^{4.4}$. In embodiments, $R^{4.4}$ is independently —OCX$^{4.4}$$_3$. In embodiments, $R^{4.4}$ is independently —OCH$_2$X$^{4.4}$. In embodiments, $R^{4.4}$ is independently —OCHX$^{4.4}$$_2$. In embodiments, $R^{4.4}$ is independently —CN. In embodiments, $R^{4.4}$ is independently —SO$_{n4.4}$R$^{4.4D}$. In embodiments, $R^{4.4}$ is independently —SO$_{v4}$$_{.4}$NR$^{4.4A}$R$^{4.4B}$ In embodiments, $R^{4.4}$ is independently —NHC(O)NR$^{4.4A}$R$^{4.4B}$. In embodiments, $R^{4.4}$ is independently —N(O)$_{m4.4}$. In embodiments, $R^{4.4}$ is independently —NR$^{4.4A}$R$^{4.4B}$. In embodiments, $R^{4.4}$ is independently —C(O)R$^{4.4C}$. In embodiments, $R^{4.4}$ is independently —C(O)—OR$^4$. In embodiments, $R^{4.4}$ is independently —C(O)NR$^{4.4A}$R$^{4.4B}$. In embodiments, $R^{4.4}$ is independently —OR$^{4.4D}$. In embodiments, $R^{4.4}$ is independently —NR$^{4.4A}$SO$_2$R$^{4.4D}$ In embodiments, $R^{4.4}$ is independently —NR$^{4.4A}$C(O)R$^{4.4}$c. In embodiments, $R^{4.4}$ is independently —NR$^{4.4A}$C(O)OR$^{4.4C}$ In embodiments, $R^{4.4}$ is independently —NR$^{4.4A}$OR$^{4.4C}$. In embodiments, $R^{4.4}$ is independently —OH. In embodiments, $R^{4.4}$ is independently —NH$_2$. In embodiments, $R^{4.4}$ is independently —COOH. In embodiments, $R^{4.4}$ is independently —CONH$_2$. In embodiments, $R^{4.4}$ is independently —NO$_2$. In embodiments, $R^{4.4}$ is independently —SH. In embodiments, $R^{4.4}$ is independently —SO$_{n4}$R$^{4D}$. In embodiments, $R^{4.4}$ is independently —SO$_{v4}$NR$^{4A}$R$^{4B}$. In embodiments, $R^{4.4}$ is independently —NHC(O)NR$^{4A}$R$^{4B}$. In embodiments, $R^{4.4}$ is independently —N(O)$_{m4}$. In embodiments, $R^{4.4}$ is independently —NR$^{4A}$R$^{4B}$ In embodiments, $R^{4.4}$ is independently —C(O)R$^{4C}$. In embodiments, $R^{4.4}$ is independently —C(O)—OR$^{4C}$. In embodiments, $R^{4.4}$ is independently —C(O)NR$^{4A}$R$^{4B}$. In embodiments, $R^{4.4}$ is independently —OR$^{4D}$. In embodiments, $R^{4.4}$ is independently —NR$^{4A}$SO$_2$R$^{4D}$. In embodiments, $R^{4.4}$ is independently —NR$^{4A}$C(O)R$^{4C}$. In embodiments, $R^{4.4}$ is independently —NR$^{4A}$C(O)OR$^{4C}$. In embodiments, $R^{4.4}$ is independently —NR$^{4A}$OR$^{4C}$.

$R^{4.5}$ is $R^4$ at a fixed position (e.g., non-floating as shown in the formula described herein) and may independently be any $R^4$ substituent. $R^{4.5A}$ is $R^{4A}$ at a fixed position (e.g., non-floating as shown in the formula described herein) and may independently be any $R^{4A}$ substituent. $R^{4.5B}$ is $R^{4B}$ at a fixed position (e.g., non-floating as shown in the formula described herein) and may independently be any $R^{4B}$ substituent. $R^{4.5C}$ is $R^{4C}$ at a fixed position (e.g., non-floating as shown in the formula described herein) and may independently be any $R^{4C}$ substituent. $R^{4.5D}$ is $R^{4D}$ at a fixed position (e.g., non-floating as shown in the formula described herein) and may independently be any $R^{4D}$ substituent. The symbol n4.5 is n4 at a fixed position (e.g., non-floating as shown in the formula described herein) and may independently be any n4 substituent. The symbol m4.5 is m4 at a fixed position (e.g., non-floating as shown in the formula described herein) and may independently be any m4 substituent. The symbol v4.5 is v4 at a fixed position (e.g., non-floating as shown in the formula described herein) and may independently be any v4 substituent.

In embodiments, $R^{4.5}$ is independently —F, —Cl, —Br, —I, —CN, —NH$_2$, —OH, —SH, —COCH$_3$, —COOH, —COOCH$_3$, —CX$^{4.5}$$_3$, —CHX$^{4.5}$$_2$, —CH$_2$X$^{4.5}$, —OCX$^{4.5}$$_3$, —OCHX$^{4.5}$$_2$, —OCH$_2$X$^{4.5}$, —SCX$^{4.5}$$_3$, —SCHX$^{4.5}$$_2$, —SCH$_2$X$^{4.5}$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$CH$_3$. In embodiments, $R^{4.5}$ is independently-F. In embodiments, $R^{4.5}$ is independently —Cl. In embodiments, $R^{4.5}$ is independently —Br. In embodiments, $R^{4.5}$ is independently —I. In embodiments, $R^{4.5}$ is independently —CN. In embodiments, $R^{4.5}$ is independently —NH$_2$. In embodiments, $R^{4.5}$ is independently —OH. In embodiments, $R^{4.5}$ is independently —SH. In embodiments, $R^{4.5}$ is independently —COCH$_3$. In embodiments, $R^{4.5}$ is independently —COOH. In embodiments, $R^{4.5}$ is independently —COOCH$_3$. In embodiments, $R^{4.5}$ is independently —CX$^{4.5}$$_3$. In embodiments, $R^{4.5}$ is independently —CHX$^{4.5}$$_2$. In embodiments, $R^{4.5}$ is independently —CH$_2$X$^{4.5}$. In embodiments, $R^{4.5}$ is independently —OCX$^{4.5}$$_3$. In embodiments, $R^{4.5}$ is independently —OCHX$^{4.5}$$_2$. In embodiments, $R^{4.5}$ is independently —OCH$_2$X$^{4.5}$. In embodiments, $R^{4.5}$ is independently —SCX$^{4.5}$$_3$. In embodiments, $R^{4.5}$ is independently —SCHX$^{4.5}$$_2$. In embodiments, $R^{4.5}$ is independently —SCH$_2$X$^{4.5}$. In embodiments, $R^{4.5}$ is independently —CH$_3$. In embodiments, $R^{4.5}$ is independently —CH$_2$CH$_3$. In embodiments, $R^{4.5}$ is independently —OCH$_3$. In embodiments, $R^{4.5}$ is independently —OCH$_2$CH$_3$. In embodiments, $R^{4.5}$ is independently —NHCH$_3$. In embodiments, $R^{4.5}$ is independently —N(CH$_3$)$_2$. In embodiments, $R^{4.5}$ is independently —NHCH$_2$CH$_3$. In embodiments, $R^{4.5}$ is independently —N(CH$_3$)(CH$_2$CH$_3$). In embodiments, $R^{4.5}$ is independently —N(CH$_2$CH$_3$)$_2$. In embodiments, $R^{4.5}$ is independently —SCH$_3$. In embodiments, $R^{4.5}$ is independently —SCH$_2$CH$_3$. In embodiments, $X^{4.5}$ is independently-F. In embodiments, $X^{4.5}$ is independently —Cl. In embodiments, $X^{4.5}$ is independently —Br. In embodiments, $X^{4.5}$ is independently —I. In embodiments, $R^{4.5}$ is independently —OPh. In embodiments, $R^{4.5}$ is independently tert-butyl. In embodiments, $R^{4.5}$ is independently —OCH$_2$Ph. In embodiments, $R^{4.5}$ is independently —OCH$_2$CH$_3$. In embodiments, $R^{4.5}$ is independently —OCH(CH$_3$)$_2$. In embodiments, $R^{4.5}$ is independently —OCH$_2$CH$_2$CH$_3$. In embodiments, $R^{4.5}$ is independently —OCH$_2$CH(CH$_3$)$_2$. In embodiments, $R^{4.5}$ is independently —OCH$_2$CH$_2$CH$_2$CH$_3$. In embodiments, $R^{4.5}$ is independently —OCH$_2$CHCH$_2$. In embodiments, $R^{4.5}$ is independently —OCH$_2$CH$_2$Ph. In embodiments, $R^{4.5}$ is independently —OCH$_2$CH$_2$CH$_3$. In embodiments, $R^{4.5}$ is independently -Ph. In embodiments, $R^{4.5}$ is independently —CH$_2$Ph. In embodiments, $R^{4.5}$ is independently —CH$_2$CH$_2$Ph. In embodiments, $R^{4.5}$ is independently —CH$_2$CH$_2$CH$_2$CH$_3$. In embodiments, $R^{4.5}$ is independently —CH$_2$CH$_2$CH$_2$CH$_2$CH$_3$. In embodiments, $R^{4.5}$ is independently —CH$_2$CH(CH$_3$)$_2$. In embodiments, $R^{4.5}$ is independently —CH$_2$CH$_2$CH(CH$_3$)$_2$. In embodiments, $R^{4.5}$ is independently hydrogen. In embodiments, $R^{4.5}$ is independently halogen. In embodiments, $R^{4.5}$ is independently —CX$^{4.5}$$_3$. In embodiments, $R^{4.5}$ is independently —CHX$^{4.5}$$_2$. In embodiments, $R^{4.5}$ is independently —CH$_2$X$^{4.5}$. In embodiments, $R^{4.5}$ is independently —OCX$^{4.5}$$_3$. In embodiments, $R^{4.5}$ is independently —OCH$_2$X$^{4.5}$. In embodiments, $R^{4.5}$ is independently —OCHX$^{4.5}$$_2$. In embodiments, $R^{4.5}$ is independently —CN. In embodiments, $R^{4.5}$ is independently —SO$_{n4.5}$R$^{4.5D}$. In embodiments, $R^{4.5}$ is independently —SO$_{v4.5}$NR$^{4.5A}$R$^{4.5B}$. In embodiments, $R^{4.5}$ is independently —NHC(O)NR$^{4.5A}$R$^{4.5B}$. In embodiments, $R^{4.5}$ is independently —N(O)$_{m4.5}$. In embodiments, $R^{4.5}$ is independently —NR$^{4.5A}$R$^{4.5B}$. In embodiments, $R^{4.5}$ is independently —C(O)R$^{4.5C}$. In embodiments, $R^{4.5}$ is independently —C(O)—OR$^{4.5C}$. In embodiments, $R^{4.5}$ is independently —C(O)NR$^{4.5A}$R$^{4.5B}$. In embodiments, $R^{4.5}$ is independently —OR$^{4.5D}$. In embodiments, $R^{4.5}$ is independently —NR$^{4.5A}$SO$_2$R$^{4.5D}$ In embodiments, $R^{4.5}$ is independently —NR$^{4.5A}$C(O)R$^{4.5}$c. In embodiments, $R^{4.5}$ is independently —NR$^{4.5A}$C(O)OR$^{4.5}$. In embodiments, $R^{4.5}$ is independently —NR$^{4.5A}$OR$^{4.5C}$. In embodiments, $R^{4.5}$ is independently —OH. In embodiments, $R^{4.5}$ is independently —NH$_2$. In embodiments, $R^{4.5}$ is independently —COOH. In embodiments, $R^{4.5}$ is independently —CONH$_2$. In embodiments, $R^{4.5}$ is independently —$NO_2$. In embodiments, $R^{4.5}$ is independently —SH. In embodiments, $R^{4.5}$ is independently —$SO_{n4}R^{4D}$. In embodiments, $R^{4.5}$ is independently —$SO_{v4}NR^{4A}R^{4B}$. In embodiments, $R^{4.5}$ is independently —$NHC(O)NR^{4A}R^{4B}$. In embodiments, $R^{4.5}$ is independently —$N(O)_{m4}$. In embodiments, $R^{4.5}$ is independently —$NR^{4A}R^{4B}$ In embodiments, $R^{4.5}$ is independently —$C(O)R^{4C}$. In embodiments, $R^{4.5}$ is independently —$C(O)$—$OR^{4C}$. In embodiments, $R^{4.5}$ is independently —$C(O)NR^{4A}R^{4B}$. In embodiments, $R^{4.5}$ is independently —$OR^{4D}$. In embodiments, $R^{4.5}$ is independently —$NR^{4A}SO_2R^{4D}$. In embodiments, $R^{4.5}$ is independently —$NR^{4A}C(O)R^{4C}$. In embodiments, $R^{4.5}$ is independently —$NR^{4A}C(O)OR^{4C}$. In embodiments, $R^{4.5}$ is independently —$NR^{4A}OR^{4C}$.

In embodiments, z4 is 5. In embodiments, z4 is 4. In embodiments, z4 is 3. In embodiments, z4 is 2. In embodiments, z4 is 1. In embodiments, z4 is 0.

In embodiments, Ring B is 3 to 7 membered heterocycloalkyl. In embodiments, Ring B is 3 to 6 membered heterocycloalkyl. In embodiments, Ring B is aziridinyl, azirinyl, diaziridinyl, diazirinyl, oxaziridinyl, azetidinyl, azetyl, diazetidinyl, diazetyl, pyrrolidinyl, pyrazolidinyl, oxazolidinyl, isoxazolidinyl, thiazolidinyl, isothiazolidinyl, furazanyl, dithiazolyl, piperidinyl, piperazinyl, morpholinyl, or thiomorpholinyl. In embodiments, Ring B is a 6 membered heterocycloalkyl. In embodiments, Ring B is piperidinyl or piperazinyl. In embodiments, Ring B is 5 to 10 membered heteroaryl. In embodiments, Ring B is benzofuranyl, isobenzofuranyl, indolyl, isoindolyl, benzothienyl, benzo[c]thienyl, benzimidazolyl, azaindolyl, benzoisoxazolyl, pyrrolopyridinyl, purinyl, indazolyl, benzoxazolyl, benzisoxazolyl, benzothiazolyl, quinolinyl, isoquinolinyl, quinoxalinyl, quinazolinyl, cinnolinyl, or phthalazinyl. In embodiments, Ring B is furanyl, pyrrolyl, thienyl, imidazolyl, pyrazolyl, oxazolyl, isoxazolyl, thiazolyl, isothiazolyl, triazolyl, oxadiazolyl, thiadiazolyl, tetrazolyl, pyridinyl, pyrazinyl, pyrimidinyl, pyridazinyl, or triazinyl. In embodiments, Ring B is a 6 membered heteroaryl. In embodiments, Ring B is pyridinyl, pyrazinyl, pyrimidinyl, or pyridazinyl.

In embodiments, Ring B is 3 to 7 membered heterocycloalkyl or 5 to 10 membered heteroaryl.

In embodiments, Ring B is heterocycloalkyl. In embodiments, Ring B is 3 to 7 membered heterocycloalkyl. In embodiments, Ring B is 3 to 6 membered heterocycloalkyl. In embodiments, Ring B is 3 to 5 membered heterocycloalkyl. In embodiments, Ring B is 5 to 6 membered heterocycloalkyl. In embodiments, Ring B is 3 membered heterocycloalkyl. In embodiments, Ring B is 4 membered heterocycloalkyl. In embodiments, Ring B is 5 membered heterocycloalkyl. In embodiments, Ring B is 6 membered heterocycloalkyl. In embodiments, Ring B is 7 membered heterocycloalkyl.

In embodiments, Ring B is heteroaryl. In embodiments, Ring B is 5 to 10 membered heteroaryl. In embodiments, Ring B is 5 to 9 membered heteroaryl. In embodiments, Ring B is 5 to 6 membered heteroaryl. In embodiments, Ring B is 5 membered heteroaryl. In embodiments, Ring B is 6 membered heteroaryl. In embodiments, Ring B is 9 membered heteroaryl. In embodiments, Ring B is 10 membered heteroaryl.

In embodiments, Ring B is aziridinyl. In embodiments, Ring B is azirinyl. In embodiments, Ring B is diaziridinyl. In embodiments, Ring B is diazirinyl. In embodiments, Ring B is oxaziridinyl. In embodiments, Ring B is azetidinyl. In embodiments, Ring B is azetyl. In embodiments, Ring B is diazetidinyl. In embodiments, Ring B is diazetyl. In embodiments, Ring B is pyrrolidinyl. In embodiments, Ring B is pyrazolidinyl. In embodiments, Ring B is oxazolidinyl. In embodiments, Ring B is isoxazolidinyl. In embodiments, Ring B is thiazolidinyl. In embodiments, Ring B is isothiazolidinyl. In embodiments, Ring B is furazanyl. In embodiments, Ring B is dithiazolyl. In embodiments, Ring B is piperidinyl. In embodiments, Ring B is piperazinyl. In embodiments, Ring B is morpholinyl. In embodiments, Ring B is thiomorpholinyl.

In embodiments, Ring B is piperidinyl. In embodiments, Ring B is piperazinyl. In embodiments, Ring B is benzofuranyl. In embodiments, Ring B is isobenzofuranyl. In embodiments, Ring B is indolyl. In embodiments, Ring B is isoindolyl. In embodiments, Ring B is benzothienyl. In embodiments, Ring B is benzo[c]thienyl. In embodiments, Ring B is benzimidazolyl. In embodiments, Ring B is azaindolyl. In embodiments, Ring B is benzoisoxazolyl. In embodiments, Ring B is pyrrolopyridinyl. In embodiments, Ring B is purinyl. In embodiments, Ring B is indazolyl. In embodiments, Ring B is benzoxazolyl. In embodiments, Ring B is benzisoxazolyl. In embodiments, Ring B is benzothiazolyl. In embodiments, Ring B is quinolinyl. In embodiments, Ring B is isoquinolinyl. In embodiments, Ring B is quinoxalinyl. In embodiments, Ring B is quinazolinyl. In embodiments, Ring B is cinnolinyl. In embodiments, Ring B is phthalazinyl. In embodiments, Ring B is furanyl. In embodiments, Ring B is pyrrolyl. In embodiments, Ring B is thienyl. In embodiments, Ring B is imidazolyl. In embodiments, Ring B is pyrazolyl. In embodiments, Ring B is oxazolyl. In embodiments, Ring B is isoxazolyl. In embodiments, Ring B is thiazolyl. In embodiments, Ring B is isothiazolyl. In embodiments, Ring B is triazolyl. In embodiments, Ring B is oxadiazolyl. In embodiments, Ring B is thiadiazolyl. In embodiments, Ring B is tetrazolyl. In embodiments, Ring B is pyridinyl. In embodiments, Ring B is pyrazinyl. In embodiments, Ring B is pyrimidinyl. In embodiments, Ring B is pyridazinyl. In embodiments, Ring B is triazinyl. In embodiments, Ring B is 6 membered heteroaryl. In embodiments, Ring B is pyridinyl. In embodiments, Ring B is pyrazinyl. In embodiments, Ring B is pyrimidinyl. In embodiments, Ring B is pyridazinyl.

In embodiments, Ring B is $C_3$-$C_8$ cycloalkyl. In embodiments, Ring B is substituted or unsubstituted cycloalkyl (e.g., $C_3$-$C_8$ cycloalkyl, $C_3$-$C_6$ cycloalkyl, or $C_5$-$C_6$ cycloalkyl). In embodiments, Ring B is substituted cycloalkyl (e.g., $C_3$-$C_8$ cycloalkyl, $C_3$-$C_6$ cycloalkyl, or $C_5$-$C_6$ cycloalkyl). In embodiments, Ring B is an unsubstituted cycloalkyl (e.g., $C_3$-$C_8$ cycloalkyl, $C_3$-$C_6$ cycloalkyl, or $C_5$-$C_6$ cycloalkyl). In embodiments, Ring B is substituted or unsubstituted cyclooctanyl, substituted or unsubstituted cycloheptanyl, substituted or unsubstituted cyclohexanyl, or substituted or unsubstituted cyclopentanyl. In embodiments, Ring B is unsubstituted cyclooctanyl, unsubstituted cycloheptanyl, unsubstituted cyclohexanyl, or unsubstituted cyclopentanyl. In embodiments, Ring B is substituted or unsubstituted cycloheptanyl. In embodiments, Ring B is substituted or unsubstituted cyclohexanyl. In embodiments, Ring B is substituted or unsubstituted cyclopentanyl. In embodiments, Ring B is unsubstituted cycloheptanyl. In embodiments, Ring B is unsubstituted cyclohexanyl. In embodiments, Ring B is unsubstituted cyclopentanyl. In embodiments, Ring B is unsubstituted cyclopropyl.

In embodiments, $R^5$ is independently hydrogen. In embodiments, $R^5$ is independently halogen. In embodiments, $R^5$ is independently —$CX^5_3$. In embodiments, $R^5$ is independently —$CHX^5_2$. In embodiments, $R^5$ is independently —$CH_2X^5$. In embodiments, $R^5$ is independently —OCX$^5_3$. In embodiments, R$^5$ is independently —OCH$_2$X$^5$. In embodiments, R$^5$ is independently —OCHX$^5_2$. In embodiments, R$^5$ is independently —CN. In embodiments, R$^5$ is independently —SO$_{n5}$R$^{5D}$. In embodiments, R$^5$ is independently —SO$_{v5}$NR$^{5A}$R$^{5B}$. In embodiments, R$^5$ is independently —NHC(O)NR$^{5A}$R$^{5B}$. In embodiments, R$^5$ is independently —N(O)$_{m5}$. In embodiments, R$^5$ is independently —NR$^{5A}$R$^{5B}$. In embodiments, R$^5$ is independently —C(O)R$^{5C}$ In embodiments, R$^5$ is independently —C(O)—OR$^{5C}$. In embodiments, R$^5$ is independently —C(O)NR$^{5A}$R$^{5B}$. In embodiments, R$^5$ is independently —OR$^{5D}$. In embodiments, R$^5$ is independently —NR$^{5A}$SO$_2$R$^{5D}$. In embodiments, R$^5$ is independently —NR$^{5A}$C(O)R$^{SC}$. In embodiments, R$^5$ is independently —NR$^A$C(O)OR$^{SC}$. In embodiments, R$^5$ is independently —NR$^{5A}$OR$^{5C}$. In embodiments, R$^5$ is independently —OH. In embodiments, R$^5$ is independently —NH$_2$. In embodiments, R$^5$ is independently —COOH. In embodiments, R$^5$ is independently —CONH$_2$. In embodiments, R$^5$ is independently —NO$_2$. In embodiments, R$^5$ is independently —SH. In embodiments, R$^5$ is independently halogen, unsubstituted C$_1$-C$_3$ alkyl, or unsubstituted 2 to 4 membered heteroalkyl. In embodiments, R$^5$ is independently halogen, unsubstituted methyl, or —OCH$_3$. In embodiments, R$^5$ is Br. In embodiments, R$^5$ is Cl. In embodiments, R$^5$ is F. In embodiments, R$^5$ is —OCH$_3$. In embodiments, R$^5$ is —CH$_3$. In embodiments, R$^5$ is —CF$_3$.

In embodiments, R$^5$ is independently substituted or unsubstituted alkyl. In embodiments, R$^5$ is independently substituted or unsubstituted heteroalkyl. In embodiments, R$^5$ is independently substituted or unsubstituted cycloalkyl. In embodiments, R$^5$ is independently, substituted or unsubstituted heterocycloalkyl. In embodiments, R$^5$ is independently substituted or unsubstituted aryl. In embodiments, R$^5$ is independently substituted or unsubstituted heteroaryl. In embodiments, R$^5$ is independently substituted alkyl. In embodiments, R$^5$ is independently substituted heteroalkyl. In embodiments, R$^5$ is independently substituted cycloalkyl. In embodiments, R$^5$ is independently, substituted heterocycloalkyl. In embodiments, R$^5$ is independently substituted aryl. In embodiments, R$^5$ is independently substituted heteroaryl. In embodiments, R$^5$ is independently unsubstituted alkyl. In embodiments, R$^5$ is independently unsubstituted heteroalkyl. In embodiments, R$^5$ is independently unsubstituted cycloalkyl. In embodiments, R$^5$ is independently, unsubstituted heterocycloalkyl. In embodiments, R$^5$ is independently unsubstituted aryl. In embodiments, R$^5$ is independently unsubstituted heteroaryl. In embodiments, R$^5$ is independently substituted or unsubstituted C$_1$-C$_8$ alkyl. In embodiments, R$^5$ is independently substituted or unsubstituted 2 to 8 membered heteroalkyl. In embodiments, R$^5$ is independently substituted or unsubstituted C$_3$-C$_8$ cycloalkyl. In embodiments, R$^5$ is independently, substituted or unsubstituted 3 to 8 membered heterocycloalkyl. In embodiments, R$^5$ is independently substituted or unsubstituted C$_6$-C$_{10}$ aryl. In embodiments, R$^5$ is independently substituted or unsubstituted 5 to 10 membered heteroaryl. In embodiments, R$^5$ is independently substituted C$_1$-C$_8$ alkyl. In embodiments, R$^5$ is independently substituted 2 to 8 membered heteroalkyl. In embodiments, R$^5$ is independently substituted C$_3$-C$_8$ cycloalkyl. In embodiments, R$^5$ is independently, substituted 3 to 8 membered heterocycloalkyl. In embodiments, R$^5$ is independently substituted C$_6$-C$_{10}$ aryl. In embodiments, R$^5$ is independently substituted 5 to 10 membered heteroaryl. In embodiments, R$^5$ is independently unsubstituted C$_1$-C$_5$ alkyl. In embodiments, R$^5$ is independently unsubstituted 2 to 8 membered heteroalkyl. In embodiments, R$^5$ is independently unsubstituted C$_3$-C$_8$ cycloalkyl. In embodiments, R$^5$ is independently, unsubstituted 3 to 8 membered heterocycloalkyl. In embodiments, R$^5$ is independently unsubstituted C$_6$-C$_{10}$ aryl. In embodiments, R$^5$ is independently unsubstituted 5 to 10 membered heteroaryl. In embodiments, R$^5$ is independently substituted or unsubstituted C$_1$-C$_4$ alkyl. In embodiments, R$^5$ is independently substituted or unsubstituted 2 to 4 membered heteroalkyl. In embodiments, R$^5$ is independently substituted or unsubstituted C$_3$-C$_6$ cycloalkyl. In embodiments, R$^5$ is independently, substituted or unsubstituted 3 to 6 membered heterocycloalkyl. In embodiments, R$^5$ is independently substituted or unsubstituted phenyl. In embodiments, R$^5$ is independently substituted or unsubstituted 5 to 6 membered heteroaryl. In embodiments, R$^5$ is independently substituted C$_1$-C$_4$ alkyl. In embodiments, R$^5$ is independently substituted 2 to 4 membered heteroalkyl. In embodiments, R$^5$ is independently substituted C$_3$-C$_6$ cycloalkyl. In embodiments, R$^5$ is independently, substituted 3 to 6 membered heterocycloalkyl. In embodiments, R$^5$ is independently substituted phenyl. In embodiments, R$^5$ is independently substituted 5 to 6 membered heteroaryl. In embodiments, R$^5$ is independently unsubstituted C$_1$-C$_4$ alkyl. In embodiments, R$^5$ is independently unsubstituted 2 to 4 membered heteroalkyl. In embodiments, R$^5$ is independently unsubstituted C$_3$-C$_6$ cycloalkyl. In embodiments, R$^5$ is independently unsubstituted 3 to 6 membered heterocycloalkyl. In embodiments, R$^5$ is independently unsubstituted phenyl. In embodiments, R$^5$ is independently unsubstituted 5 to 6 membered heteroaryl.

In embodiments, two adjacent R$^5$ substituents may be joined to form a substituted or unsubstituted cycloalkyl, substituted or unsubstituted heterocycloalkyl, substituted or unsubstituted aryl, or substituted or unsubstituted heteroaryl.

In embodiments, two adjacent R$^5$ substituents may be joined to form a substituted or unsubstituted cycloalkyl. In embodiments, two adjacent R$^5$ substituents may be joined to form a substituted or unsubstituted heterocycloalkyl. In embodiments, two adjacent R$^5$ substituents may be joined to form a substituted or unsubstituted aryl. In embodiments, two adjacent R$^5$ substituents may be joined to form a substituted or unsubstituted heteroaryl. In embodiments, two adjacent R$^5$ substituents may be joined to form a substituted cycloalkyl. In embodiments, two adjacent R$^5$ substituents may be joined to form a substituted heterocycloalkyl. In embodiments, two adjacent R$^5$ substituents may be joined to form a substituted aryl. In embodiments, two adjacent R$^5$ substituents may be joined to form a substituted heteroaryl. In embodiments, two adjacent R$^5$ substituents may be joined to form an unsubstituted cycloalkyl. In embodiments, two adjacent R$^5$ substituents may be joined to form an unsubstituted heterocycloalkyl. In embodiments, two adjacent R$^5$ substituents may be joined to form an unsubstituted aryl. In embodiments, two adjacent R$^5$ substituents may be joined to form an unsubstituted heteroaryl.

In embodiments, two adjacent R$^5$ substituents may be joined to form a substituted or unsubstituted C$_3$-C$_8$ cycloalkyl. In embodiments, two adjacent R$^5$ substituents may be joined to form a substituted or unsubstituted 3 to 8 membered heterocycloalkyl. In embodiments, two adjacent R$^5$ substituents may be joined to form a substituted or unsubstituted C$_6$-C$_{10}$ aryl. In embodiments, two adjacent R$^5$ substituents may be joined to form a substituted or unsubstituted 5 to 10 membered heteroaryl. In embodiments, two adjacent R$^5$ substituents may be joined to form a substituted C$_3$-C$_8$ cycloalkyl. In embodiments, two adjacent R$^5$ substituents may be joined to form a substituted 3 to 8 membered heterocycloalkyl. In embodiments, two adjacent R$^5$ substituents may be joined to form a substituted $C_6$-$C_{10}$ aryl. In embodiments, two adjacent $R^5$ substituents may be joined to form a substituted 5 to 10 membered heteroaryl. In embodiments, two adjacent $R^5$ substituents may be joined to form an unsubstituted $C_3$-$C_8$ cycloalkyl. In embodiments, two adjacent $R^5$ substituents may be joined to form an unsubstituted 3 to 8 membered heterocycloalkyl. In embodiments, two adjacent $R^5$ substituents may be joined to form an unsubstituted $C_6$-$C_{10}$ aryl. In embodiments, two adjacent $R^5$ substituents may be joined to form an unsubstituted 5 to 10 membered heteroaryl.

In embodiments, two adjacent $R^5$ substituents may be joined to form a substituted or unsubstituted $C_3$-$C_6$ cycloalkyl. In embodiments, two adjacent $R^5$ substituents may be joined to form a substituted or unsubstituted 3 to 6 membered heterocycloalkyl. In embodiments, two adjacent $R^5$ substituents may be joined to form a substituted or unsubstituted phenyl. In embodiments, two adjacent $R^5$ substituents may be joined to form a substituted or unsubstituted 5 to 6 membered heteroaryl. In embodiments, two adjacent $R^5$ substituents may be joined to form a substituted $C_3$-$C_6$ cycloalkyl. In embodiments, two adjacent $R^5$ substituents may be joined to form a substituted 3 to 6 membered heterocycloalkyl. In embodiments, two adjacent $R^5$ substituents may be joined to form a substituted phenyl. In embodiments, two adjacent $R^5$ substituents may be joined to form a substituted 5 to 6 membered heteroaryl. In embodiments, two adjacent $R^5$ substituents may be joined to form an unsubstituted $C_3$-$C_6$ cycloalkyl. In embodiments, two adjacent $R^5$ substituents may be joined to form an unsubstituted 3 to 6 membered heterocycloalkyl. In embodiments, two adjacent $R^5$ substituents may be joined to form an unsubstituted phenyl. In embodiments, two adjacent $R^5$ substituents may be joined to form an unsubstituted 5 to 6 membered heteroaryl.

In embodiments, -$L^2$-(Ring B)-$(R^5)_{z5}$ is

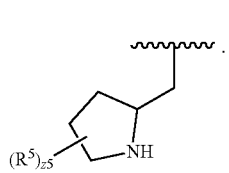

In embodiments, -$L^2$-(Ring B)—$(R^5)_{z5}$ is

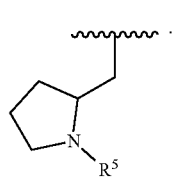

In embodiments, -$L^2$-(Ring B)-$(R^5)_{z5}$ is

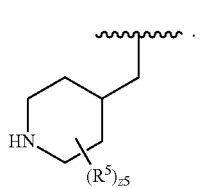

In embodiments, -$L^2$-(Ring B)-$(R^5)_{z5}$ is

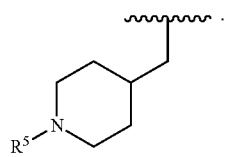

In embodiments, -$L^2$-(Ring B)-$(R^5)_{z5}$ is

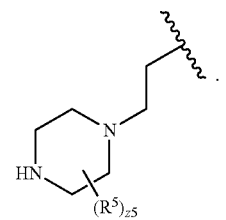

In embodiments, -$L^2$-(Ring B)-$(R^5)_{z5}$ is

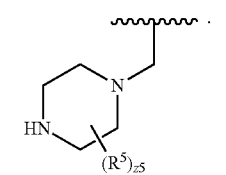

In embodiments, -$L^2$n (Ring B)-$(R^5)_{z5}$ is

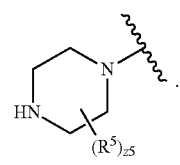

In embodiments, -$L^2$-(Ring B)-$(R^5)_{z5}$ is

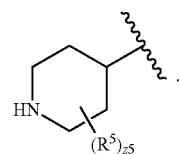

In embodiments, -$L^2$-(Ring B)-$(R^5)_{z5}$ is

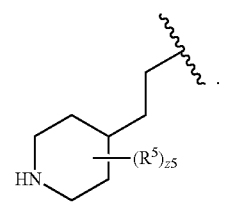

In embodiments, -L²-(Ring B)-(R⁵)₅_z is
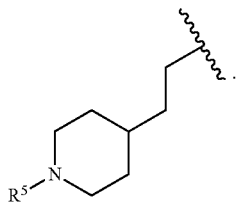
In embodiments, -L²-(Ring B)-(R⁵)_z5 is
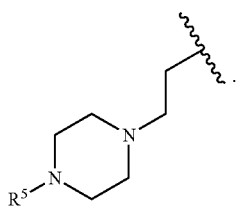
In embodiments, -L²-(Ring B)-(R⁵)_z5 is
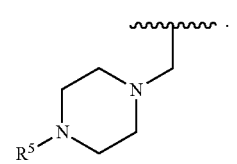
In embodiments, -L²-(Ring B)-(R⁵)_z5 is
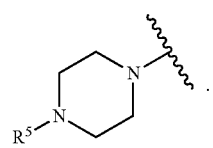
In embodiments, -L²-(Ring B)-(R⁵)_z5 is
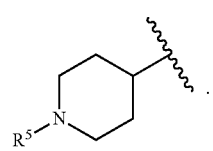
In embodiments, -L²-(Ring B)-(R⁵)_z5 is
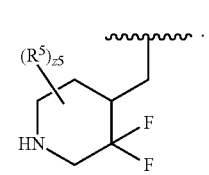
In embodiments, -L²-(Ring B)-(R⁵)_z5 is
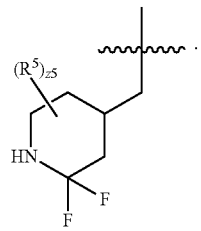
In embodiments, -L²-(Ring B)-(R⁵)_z5 is
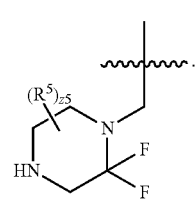
In embodiments, -L²-(Ring B)-(R⁵)_z5 is
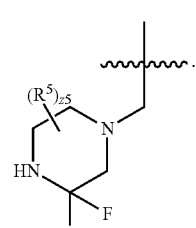
In embodiments, -L²-(Ring B)-(R⁵)_z5 is
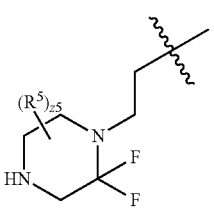
In embodiments, -L²-(Ring B)-(R⁵)_z5 is
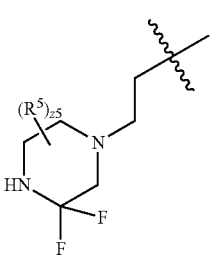

In embodiments, -L²-(Ring B)-(R⁵)_{z5} is
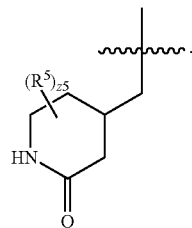
In embodiments, L²-(Ring B) is
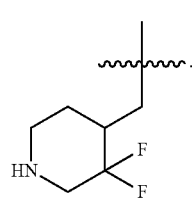
In embodiments, L²-(Ring B) is
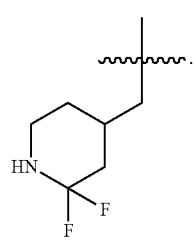 [SMILES: *CC1CCNC(F)(F)C1]
In embodiments, L²-(Ring B) is
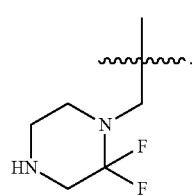 [SMILES: *CN1CCNCC1(F)F]
In embodiments, L²-(Ring B) is
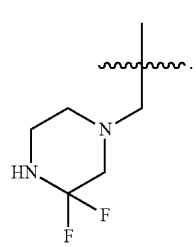 [SMILES: *CN1CCNC(F)(F)C1]
In embodiments, L²-(Ring B) is
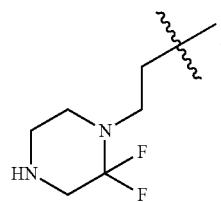
In embodiments, L²-(Ring B) is
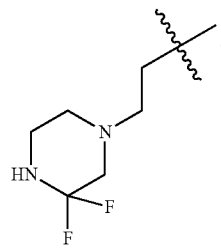
In embodiments, L²-(Ring B) is
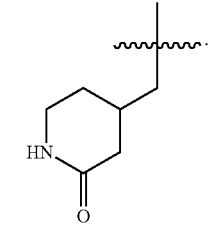
In embodiments, L²-(Ring B) is
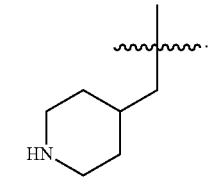
In embodiments, L²-(Ring B) is
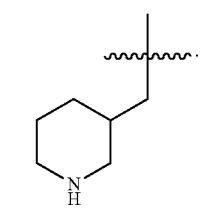 [SMILES: *CC1CCCNC1]

In embodiments, L²-(Ring B) is
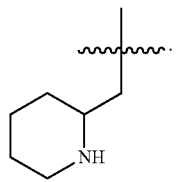 [SMILES: *CC1CCCCN1]
In embodiments, L²-(Ring B) is
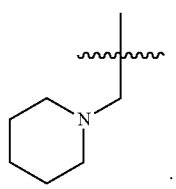 [SMILES: *CN1CCCCC1]
In embodiments, L²-(Ring B) is
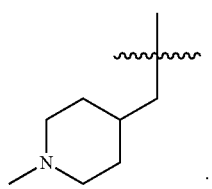 [SMILES: *CC1CCN(C)CC1]
In embodiments, L²-(Ring B) is
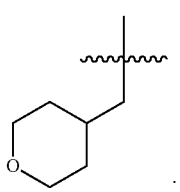 [SMILES: *CC1CCOCC1]
In embodiments, L²-(Ring B) is
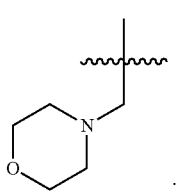
In embodiments, L²-(Ring B) is
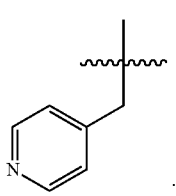
In embodiments, L²-(Ring B) is
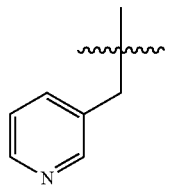
In embodiments, L²-(Ring B) is
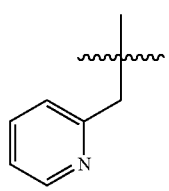
In embodiments, L²-(Ring B) is
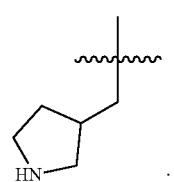 [SMILES: *CC1CCNC1]
In embodiments, L²-(Ring B) is
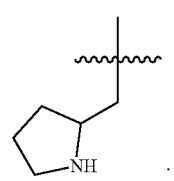 [SMILES: *CC1CCCN1]
In embodiments, L²-(Ring B) is
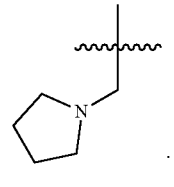 [SMILES: *CN1CCCC1]
In embodiments, L²-(Ring B) is
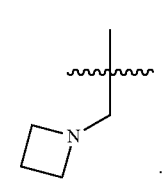

In embodiments, L²-(Ring B) is

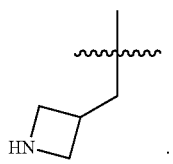

In embodiments, L²-(Ring B) is

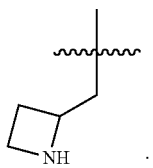

In embodiments, L²-(Ring B) is

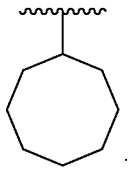 [SMILES: *C1CCCCCCC1]

In embodiments, L²-(Ring B) is

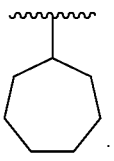 [SMILES: *C1CCCCCC1]

In embodiments, L²-(Ring B) is

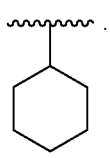 [SMILES: *C1CCCCC1]

In embodiments, L²-(Ring B) is

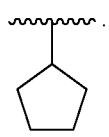

In embodiments, L²-(Ring B) is

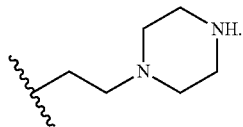

In embodiments, L²-(Ring B) is

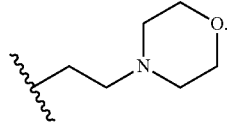 [SMILES: *CCN1CCOCC1]

In embodiments, -L²-(Ring B)-(R⁵)$_{z5}$ is

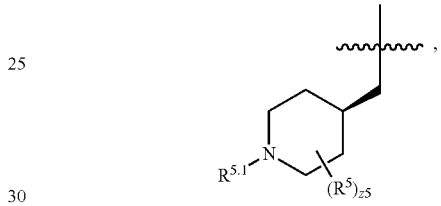

wherein $R^5$ and z5 are as described herein. $R^{5.1}$ is $R^5$ at a fixed position (e.g., non-floating as shown in the formula described herein) and may independently be any $R^5$ substituent. In embodiments, $R^5$ is —OH, F, COOH, or —C(O)NR$^{5A}$R$^{5B}$. In embodiments, $R^{5.1}$ is hydrogen, —C(O)NR$^{5A}$R$^{5B}$, —C(N)N$^{5A}$R$^{5B}$, substituted or unsubstituted alkyl, substituted or unsubstituted cycloalkyl (e.g., cyclopropyl), —C(O)-(substituted or unsubstituted alkyl), —C(O)-(substituted or unsubstituted cyclopropyl), —C(N)-(substituted or unsubstituted alkyl), or —C(N)-(substituted or unsubstituted cyclopropyl).

In embodiments, -L²-(Ring B)-(R⁵)$_{z5}$ is

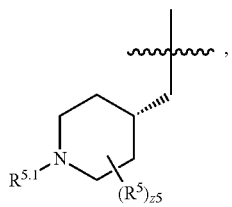

wherein $R^5$ and z5 are as described herein. $R^{5.1}$ is $R^5$ at a fixed position (e.g., non-floating as shown in the formula described herein) and may independently be any $R^5$ substituent. In embodiments, $R^5$ is —OH, F, COOH, or —C(O)NR$^{5A}$R$^{5B}$. In embodiments, $R^{5.1}$ is hydrogen, —C(O)NR$^{5A}$R$^{5B}$, C(N)N$^{5A}$R$^{5B}$ substituted or unsubstituted alkyl, substituted or unsubstituted cycloalkyl (e.g., cyclopropyl), —C(O)-(substituted or unsubstituted alkyl), —C(O)-(substituted or unsubstituted cyclopropyl), —C(N)-(substituted or unsubstituted alkyl), or —C(N)-(substituted or unsubstituted cyclopropyl).

In embodiments, -L²-(Ring B)-(R⁵)$_{z5}$ is

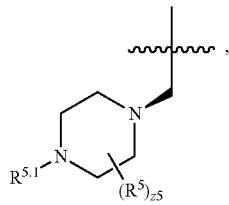

wherein R⁵ and z5 are as described herein. R$^{5.1}$ is R⁵ at a fixed position (e.g., non-floating as shown in the formula described herein) and may independently be any R⁵ substituent. In embodiments, R⁵ is —OH, F, COOH, or —C(O)NR$^{5A}$R$^{5B}$. In embodiments, R$^{5.1}$ is hydrogen, —C(O)NR$^{5A}$R$^{5B}$, —C(N)NR$^{5A}$R$^{5B}$, substituted or unsubstituted alkyl, substituted or unsubstituted cycloalkyl (e.g., cyclopropyl), —C(O)-(substituted or unsubstituted alkyl), —C(O)-(substituted or unsubstituted cyclopropyl), —C(N)-(substituted or unsubstituted alkyl), or —C(N)-(substituted or unsubstituted cyclopropyl).

In embodiments, -L²-(Ring B)-(R⁵)$_{z5}$ is

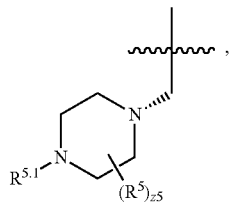

wherein R⁵ and z5 are as described herein. R$^{5.1}$ is R⁵ at a fixed position (e.g., non-floating as shown in the formula described herein) and may independently be any R⁵ substituent. In embodiments, R⁵ is —OH, F, COOH, or —C(O)NR$^{5A}$R$^{5B}$. In embodiments, R$^{5.1}$ is hydrogen, —C(O)NR$^{5A}$R$^{5B}$, —C(N)NR$^{5A}$R$^{5B}$, substituted or unsubstituted alkyl, substituted or unsubstituted cycloalkyl (e.g., cyclopropyl), —C(O)-(substituted or unsubstituted alkyl), —C(O)-(substituted or unsubstituted cyclopropyl), —C(N)-(substituted or unsubstituted alkyl), or —C(N)-(substituted or unsubstituted cyclopropyl).

In embodiments, R⁵ is independently oxo. In embodiments, R⁵ is independently halogen. In embodiments, R⁵ is independently —F. In embodiments, R⁵ is independently —Cl. In embodiments, R⁵ is independently —COOH. In embodiments, R⁵ is independently —C(O)NR$^{5A}$R$^{5B}$.

In embodiments, R$^{5.1}$ is hydrogen. In embodiments, R$^{5.1}$ is substituted or unsubstituted alkyl. In embodiments, R$^{5.1}$ is independently substituted or unsubstituted alkyl. In embodiments, R$^{5.1}$ is R$^{32}$-substituted or unsubstituted alkyl (e.g., C₁-C₈ alkyl, C₁-C₆ alkyl, or C₁-C₄ alkyl). In embodiments, R$^{5.1}$ is R$^{32}$-substituted alkyl (e.g., C₁-C₈ alkyl, C₁-C₆ alkyl, or C₁-C₄ alkyl). In embodiments, R$^{5.1}$ is an unsubstituted alkyl (e.g., C₁-C₈ alkyl, C₁-C₆ alkyl, or C₁-C₄ alkyl). In embodiments, R$^{5.1}$ is independently substituted or unsubstituted cycloalkyl. In embodiments, R$^{5.1}$ is R$^{32}$-substituted or unsubstituted cycloalkyl (e.g., C₃-C₈ cycloalkyl, C₃-C₆ cycloalkyl, or C₅-C₆ cycloalkyl). In embodiments, R$^{5.1}$ is R$^{32}$-substituted cycloalkyl (e.g., C₃-C₈ cycloalkyl, C₃-C₆ cycloalkyl, or C₅-C₆ cycloalkyl). In embodiments, R$^{5.1}$ is an unsubstituted cycloalkyl (e.g., C₃-C₈ cycloalkyl, C₃-C₆ cycloalkyl, or C₅-C₆ cycloalkyl). In embodiments, R$^{5.1}$ is unsubstituted cyclopropyl.

In embodiments, R$^{5.1}$ is R$^{32}$-substituted cyclopropyl. In embodiments, R$^{5.1}$ is —C(O)NH₂. In embodiments, R$^{5.1}$ is —C(O)NR$^{5A}$R$^{5B}$,

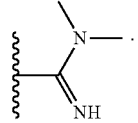

In embodiments, R$^{5.1}$ is

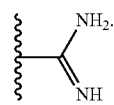

In embodiments, R$^{5.1}$ is

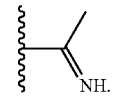

In embodiments, R$^{5.1}$ is

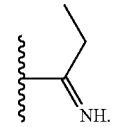

In embodiments, R$^{5.1}$ is

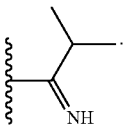

In embodiments, R$^{5.1}$ is

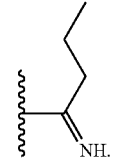

In embodiments, $R^{5.1}$ is

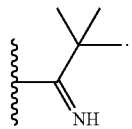

In embodiments, $R^{5.1}$ is —C(N)-(substituted or unsubstituted alkyl). In embodiments, $R^{5.1}$ is —C(N)-(substituted or unsubstituted $C_1$-$C_8$ alkyl). In embodiments, $R^{5.1}$ is —C(N)-(substituted or unsubstituted $C_1$-$C_6$ alkyl). In embodiments, $R^{5.1}$ is —C(N)-(substituted or unsubstituted $C_1$-$C_4$ alkyl). In embodiments, $R^{5.1}$ is —C(N)—($R^{32}$-substituted or unsubstituted alkyl). In embodiments, $R^{5.1}$ is —C(N)-(unsubstituted alkyl). In embodiments, $R^{5.1}$ is —C(N)—($R^{32}$-substituted alkyl).

In embodiments, $R^{5.1}$ is —C(N)-(substituted or unsubstituted cycloalkyl). In embodiments, $R^{5.1}$ is —C(N)-(substituted or unsubstituted $C_3$-$C_8$ cycloalkyl). In embodiments, $R^{5.1}$ is —C(N)-(substituted or unsubstituted $C_3$-$C_6$ cycloalkyl). In embodiments, $R^{5.1}$ is —C(N)-(substituted or unsubstituted $C_5$-$C_6$ cycloalkyl). In embodiments, $R^{5.1}$ is —C(N)—($R^{32}$-substituted or unsubstituted cycloalkyl). In embodiments, $R^{5.1}$ is —C(N)-(unsubstituted cycloalkyl). In embodiments, $R^{5.1}$ is —C(N)—($R^{32}$-substituted cycloalkyl).

In embodiments, $R^{5.1}$ is —C(O)-(substituted or unsubstituted alkyl). In embodiments, $R^{5.1}$ is —C(O)-(substituted or unsubstituted $C_1$-$C_8$ alkyl). In embodiments, $R^{5.1}$ is —C(O)-(substituted or unsubstituted $C_1$-$C_6$ alkyl). In embodiments, $R^{5.1}$ is —C(O)-(substituted or unsubstituted $C_1$-$C_4$ alkyl). In embodiments, $R^{5.1}$ is —C(O)—($R^{32}$-substituted or unsubstituted alkyl). In embodiments, $R^{5.1}$ is —C(O)-(unsubstituted alkyl). In embodiments, $R^{5.1}$ is —C(O)—($R^{32}$-substituted alkyl).

In embodiments, $R^{5.1}$ is —C(O)-(substituted or unsubstituted cycloalkyl). In embodiments, $R^{5.1}$ is —C(O)-(substituted or unsubstituted $C_3$-$C_8$ cycloalkyl). In embodiments, $R^{5.1}$ is —C(O)-(substituted or unsubstituted $C_3$-$C_6$ cycloalkyl). In embodiments, $R^{5.1}$ is —C(O)-(substituted or unsubstituted $C_5$-$C_6$ cycloalkyl). In embodiments, $R^{5.1}$ is —C(O)—($R^{32}$-substituted or unsubstituted cycloalkyl). In embodiments, $R^{5.1}$ is —C(O)-(unsubstituted cycloalkyl). In embodiments, $R^{5.1}$ is —C(O)—($R^{32}$-substituted cycloalkyl).

In embodiments, z4 and z5 are independently an integer from 0 to 2. In embodiments z4 is 0. In embodiments z4 is 1. In embodiments z4 is 2. In embodiments z5 is 0. In embodiments z5 is 1. In embodiments z5 is 2.

In embodiments, $L^2$-(Ring B) is

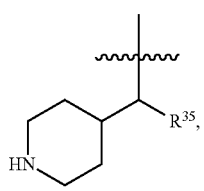

wherein $R^{35}$ is as described herein. In embodiments, $L^2$-(Ring B) is

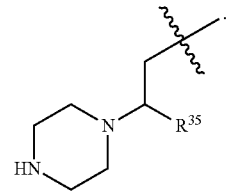

In embodiments, $L^2$-(Ring B) is

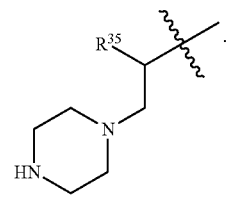

In embodiments, $L^2$-(Ring B) is

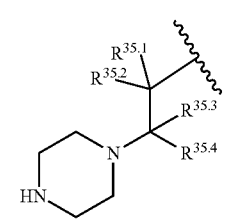

wherein $R^{35.1}$, $R^{35.2}$, $R^{35.3}$, and $R^{35.4}$ is $R^{35}$ at a fixed position (e.g., non-floating as shown in the formula described herein) and may independently be any $R^{35}$ substituent. In embodiments, $L^2$-(Ring B) is

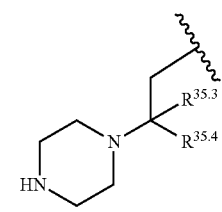

wherein $R^{35.3}$ and $R^{35.4}$ is $R^{35}$ at a fixed position (e.g., non-floating as shown in the formula described herein) and may independently be any $R^{35}$ substituent. In embodiments, $L^2$-(Ring B) is

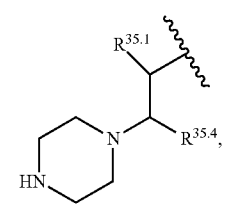

wherein $R^{35.1}$ and $R^{35.4}$ is $R^{35}$ at a fixed position (e.g., non-floating as shown in the formula described herein) and may independently be any $R^{35}$ substituent. In embodiments, $R^{35.1}$ is halogen. In embodiments, $R^{35.1}$ is F.

In embodiments, L²-(Ring B) is

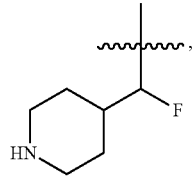

wherein R³⁵ is as described herein. In embodiments, L²-(Ring B) is

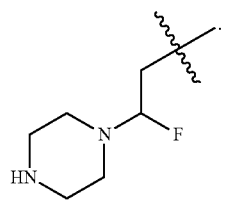 [SMILES: *CC(F)N1CCNCC1]

In embodiments, L²-(Ring B) is

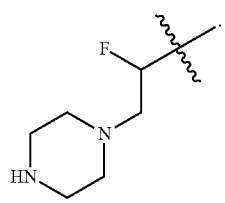

In embodiments, L²-(Ring B) is

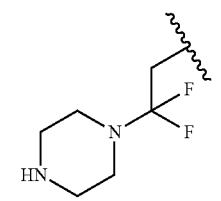 [SMILES: *CC(F)(F)N1CCNCC1]

wherein $R^{35.1}$, $R^{35.2}$, $R^{35.3}$, and $R^{35.4}$ is $R^{35}$ at a fixed position (e.g., non-floating as shown in the formula described herein) and may independently be any $R^{35}$ substituent. In embodiments, L²-(Ring B) is

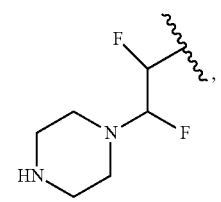

wherein $R^{35.1}$ and $R^{35.4}$ is $R^{35}$ at a fixed position (e.g., non-floating as shown in the formula described herein) and may independently be any $R^{35}$ substituent. In embodiments, $R^{35.1}$ is halogen. In embodiments, $R^{35.1}$ is F. In embodiments, L²-(Ring B) is

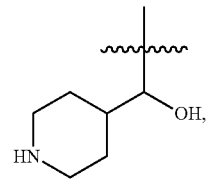

wherein $R^{35}$ is as described herein. In embodiments, L²-(Ring B) is

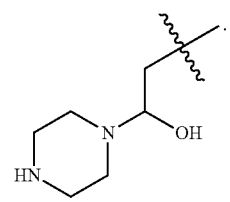

In embodiments, L-(Ring B) is

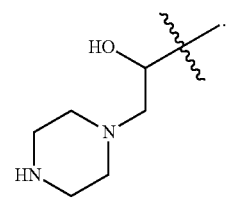 [SMILES: *C(O)CN1CCNCC1]

In embodiments, $R^{5A}$ is independently hydrogen. In embodiments, $R^{5A}$ is independently $-CX^{5A}_3$. In embodiments, $R^{5A}$ is independently $-CHX^{5A}_2$. In embodiments, $R^{5A}$ is independently $-CH_2X^{5A}$. In embodiments, $R^{5A}$ is independently $-CN$. In embodiments, $R^{5A}$ is independently $-COOH$. In embodiments, $R^{5A}$ is independently $-CONH_2$. In embodiments, $R^{5A}$ is independently substituted or unsubstituted alkyl. In embodiments, $R^{5A}$ is independently substituted or unsubstituted heteroalkyl. In embodiments, $R^{5A}$ is independently substituted or unsubstituted cycloalkyl. In embodiments, $R^{5A}$ is independently, substituted or unsubstituted heterocycloalkyl. In embodiments, $R^{5A}$ is independently substituted or unsubstituted aryl. In embodiments, $R^{5A}$ is independently substituted or unsubstituted heteroaryl. In embodiments, $R^{5A}$ is independently substituted alkyl. In embodiments, $R^{5A}$ is independently substituted heteroalkyl. In embodiments, $R^{5A}$ is independently substituted cycloalkyl. In embodiments, $R^{5A}$ is independently, substituted heterocycloalkyl. In embodiments, $R^{5A}$ is independently substituted aryl. In embodiments, $R^{5A}$ is independently substituted heteroaryl. In embodiments, $R^{5A}$ is independently unsubstituted alkyl. In embodiments, $R^{5A}$ is independently unsubstituted heteroalkyl. In embodiments, $R^{5A}$ is independently unsubstituted cycloalkyl. In embodiments, $R^{5A}$ is independently, unsubstituted heterocycloalkyl. In embodiments, $R^{5A}$ is independently unsubstituted aryl. In embodiments, $R^{5A}$ is independently unsubstituted heteroaryl. In embodiments, $R^{5A}$ is independently substituted or unsubstituted $C_1$-$C_8$ alkyl. In embodiments, $R^{5A}$ is independently substituted or unsubstituted 2 to 8 membered heteroalkyl. In embodiments, $R^{5A}$ is independently substituted or unsubstituted $C_3$-$C_8$ cycloalkyl. In embodiments, $R^{5A}$ is independently, substituted or unsubstituted 3 to 8 membered heterocycloalkyl. In embodiments, $R^{5A}$ is independently substituted or unsubstituted $C_6$-$C_{10}$ aryl. In embodiments, $R^{5A}$ is independently substituted or unsubstituted 5 to 10 membered heteroaryl. In embodiments, $R^{5A}$ is independently substituted $C_1$-$C_8$ alkyl. In embodiments, $R^{5A}$ is independently substituted 2 to 8 membered heteroalkyl. In embodiments, $R^{5A}$ is independently substituted $C_3$-$C_8$ cycloalkyl. In embodiments, $R^{5A}$ is independently, substituted 3 to 8 membered heterocycloalkyl. In embodiments, $R^{5A}$ is independently substituted $C_6$-$C_{10}$ aryl. In embodiments, $R^{5A}$ is independently substituted 5 to 10 membered heteroaryl. In embodiments, $R^{5A}$ is independently unsubstituted $C_1$-$C_8$ alkyl. In embodiments, $R^{5A}$ is independently unsubstituted 2 to 8 membered heteroalkyl. In embodiments, $R^{5A}$ is independently unsubstituted $C_3$-$C_8$ cycloalkyl. In embodiments, $R^{5A}$ is independently, unsubstituted 3 to 8 membered heterocycloalkyl. In embodiments, $R^{5A}$ is independently unsubstituted $C_6$-$C_{10}$ aryl. In embodiments, $R^{5A}$ is independently unsubstituted 5 to 10 membered heteroaryl. In embodiments, $R^{5A}$ is independently substituted or unsubstituted $C_1$-$C_4$ alkyl. In embodiments, $R^{5A}$ is independently substituted or unsubstituted 2 to 4 membered heteroalkyl. In embodiments, $R^{5A}$ is independently substituted or unsubstituted $C_3$-$C_6$ cycloalkyl. In embodiments, $R^{5A}$ is independently, substituted or unsubstituted 3 to 6 membered heterocycloalkyl. In embodiments, $R^{5A}$ is independently substituted or unsubstituted phenyl. In embodiments, $R^{5A}$ is independently substituted or unsubstituted 5 to 6 membered heteroaryl. In embodiments, $R^{5A}$ is independently substituted $C_1$-$C_4$ alkyl. In embodiments, $R^{5A}$ is independently substituted 2 to 4 membered heteroalkyl. In embodiments, $R^{5A}$ is independently substituted $C_3$-$C_6$ cycloalkyl. In embodiments, $R^{5A}$ is independently, substituted 3 to 6 membered heterocycloalkyl. In embodiments, $R^{5A}$ is independently substituted phenyl. In embodiments, $R^{5A}$ is independently substituted 5 to 6 membered heteroaryl. In embodiments, $R^{5A}$ is independently unsubstituted $C_1$-$C_4$ alkyl. In embodiments, $R^{5A}$ is independently unsubstituted 2 to 4 membered heteroalkyl. In embodiments, $R^{5A}$ is independently unsubstituted $C_3$-$C_6$ cycloalkyl. In embodiments, $R^{5A}$ is independently unsubstituted 3 to 6 membered heterocycloalkyl. In embodiments, $R^{5A}$ is independently unsubstituted phenyl. In embodiments, $R^{5A}$ is independently unsubstituted 5 to 6 membered heteroaryl. In embodiments, $R^{5A}$ is independently unsubstituted methyl. In embodiments, $R^{5A}$ is independently unsubstituted ethyl. In embodiments, $R^{5A}$ is independently unsubstituted propyl. In embodiments, $R^{5A}$ is independently unsubstituted isopropyl. In embodiments, $R^{5A}$ is independently unsubstituted tert-butyl.

In embodiments, $R^{5B}$ is independently hydrogen. In embodiments, $R^{5B}$ is independently —$CX^{5B}_3$. In embodiments, $R^{5B}$ is independently —$CHX^{5B}_2$. In embodiments, $R^{5B}$ is independently —$CH_2X^{5B}$. In embodiments, $R^{5B}$ is independently —CN. In embodiments, $R^{5B}$ is independently —COOH. In embodiments, $R^{5B}$ is independently —$CONH_2$. In embodiments, $R^{5B}$ is independently substituted or unsubstituted alkyl. In embodiments, $R^{5B}$ is independently substituted or unsubstituted heteroalkyl. In embodiments, $R^{5B}$ is independently substituted or unsubstituted cycloalkyl. In embodiments, $R^{5B}$ is independently, substituted or unsubstituted heterocycloalkyl. In embodiments, $R^{5B}$ is independently substituted or unsubstituted aryl. In embodiments, $R^{5B}$ is independently substituted or unsubstituted heteroaryl. In embodiments, $R^{5B}$ is independently substituted alkyl. In embodiments, $R^{5B}$ is independently substituted heteroalkyl. In embodiments, $R^{5B}$ is independently substituted cycloalkyl. In embodiments, $R^{5B}$ is independently, substituted heterocycloalkyl. In embodiments, $R^{5B}$ is independently substituted aryl. In embodiments, $R^{5B}$ is independently substituted heteroaryl. In embodiments, $R^{5B}$ is independently unsubstituted alkyl. In embodiments, $R^{5B}$ is independently unsubstituted heteroalkyl. In embodiments, $R^{5B}$ is independently unsubstituted cycloalkyl. In embodiments, $R^{5B}$ is independently, unsubstituted heterocycloalkyl. In embodiments, $R^{5B}$ is independently unsubstituted aryl. In embodiments, $R^{5B}$ is independently unsubstituted heteroaryl. In embodiments, $R^{5B}$ is independently substituted or unsubstituted $C_1$-$C_8$ alkyl. In embodiments, $R^{5B}$ is independently substituted or unsubstituted 2 to 8 membered heteroalkyl. In embodiments, $R^{5B}$ is independently substituted or unsubstituted $C_3$-$C_8$ cycloalkyl. In embodiments, $R^{5B}$ is independently, substituted or unsubstituted 3 to 8 membered heterocycloalkyl. In embodiments, $R^{5B}$ is independently substituted or unsubstituted $C_6$-$C_{10}$ aryl. In embodiments, $R^{5B}$ is independently substituted or unsubstituted 5 to 10 membered heteroaryl. In embodiments, $R^{5B}$ is independently substituted $C_1$-$C_8$ alkyl. In embodiments, $R^{5B}$ is independently substituted 2 to 8 membered heteroalkyl. In embodiments, $R^{5B}$ is independently substituted $C_3$-$C_8$ cycloalkyl. In embodiments, $R^{5B}$ is independently, substituted 3 to 8 membered heterocycloalkyl. In embodiments, $R^{5B}$ is independently substituted $C_6$-$C_{10}$ aryl. In embodiments, $R^{5B}$ is independently substituted 5 to 10 membered heteroaryl. In embodiments, $R^{5B}$ is independently unsubstituted $C_1$-$C_8$ alkyl. In embodiments, $R^{5B}$ is independently unsubstituted 2 to 8 membered heteroalkyl. In embodiments, $R^{5B}$ is independently unsubstituted $C_3$-$C_8$ cycloalkyl. In embodiments, $R^{5B}$ is independently, unsubstituted 3 to 8 membered heterocycloalkyl. In embodiments, $R^{5B}$ is independently unsubstituted $C_6$-$C_{10}$ aryl. In embodiments, $R^{5B}$ is independently unsubstituted 5 to 10 membered heteroaryl. In embodiments, $R^{5B}$ is independently substituted or unsubstituted $C_1$-$C_4$ alkyl. In embodiments, $R^{5B}$ is independently substituted or unsubstituted 2 to 4 membered heteroalkyl. In embodiments, $R^{5B}$ is independently substituted or unsubstituted $C_3$-$C_6$ cycloalkyl. In embodiments, $R^{5B}$ is independently, substituted or unsubstituted 3 to 6 membered heterocycloalkyl. In embodiments, $R^{5B}$ is independently substituted or unsubstituted phenyl. In embodiments, $R^{5B}$ is independently substituted or unsubstituted 5 to 6 membered heteroaryl. In embodiments, $R^{5B}$ is independently substituted $C_1$-$C_4$ alkyl. In embodiments, $R^{5B}$ is independently substituted 2 to 4 membered heteroalkyl. In embodiments, $R^{5B}$ is independently substituted $C_3$-$C_6$ cycloalkyl. In embodiments, $R^{5B}$ is independently, substituted 3 to 6 membered heterocycloalkyl. In embodiments, $R^{5B}$ is independently substituted phenyl. In embodiments, $R^{5B}$ is independently substituted 5 to 6 membered heteroaryl. In embodiments, $R^{5B}$ is independently unsubstituted $C_1$-$C_4$ alkyl. In embodiments, $R^{5B}$ is independently unsubstituted 2 to 4 membered heteroalkyl. In embodiments, $R^{5B}$ is independently unsubstituted $C_3$-$C_6$ cycloalkyl. In embodiments, $R^{5B}$ is independently unsubstituted 3 to 6 membered heterocycloalkyl. In embodiments, $R^{5B}$ is independently unsubstituted phenyl. In embodiments, $R^{5B}$ is independently unsubstituted 5 to 6 membered heteroaryl. In embodiments, $R^{5B}$ is independently unsubstituted methyl. In embodiments, $R^{5B}$ is independently unsubstituted ethyl. In embodiments, $R^{5B}$ is independently unsubstituted propyl. In embodiments, $R^{5B}$ is independently unsubstituted isopropyl. In embodiments, $R^{5B}$ is independently unsubstituted tert-butyl.

In embodiments, $R^{5A}$ and $R^{5B}$ substituents bonded to the same nitrogen atom may be joined to form a substituted or unsubstituted heterocycloalkyl. In embodiments, $R^{5A}$ and $R^{5B}$ substituents bonded to the same nitrogen atom may be joined to form a substituted or unsubstituted heteroaryl. In embodiments, $R^{5A}$ and $R^{5B}$ substituents bonded to the same nitrogen atom may be joined to form a substituted heterocycloalkyl. In embodiments, $R^{5A}$ and $R^{5B}$ substituents bonded to the same nitrogen atom may be joined to form a substituted heteroaryl. In embodiments, $R^{5A}$ and $R^{5B}$ substituents bonded to the same nitrogen atom may be joined to form a unsubstituted heterocycloalkyl. In embodiments, $R^{5A}$ and $R^{5B}$ substituents bonded to the same nitrogen atom may be joined to form a unsubstituted heteroaryl. In embodiments, $R^{5A}$ and $R^{5B}$ substituents bonded to the same nitrogen atom may be joined to form a substituted or unsubstituted 3 to 8 membered heterocycloalkyl. In embodiments, $R^{5A}$ and $R^{5B}$ substituents bonded to the same nitrogen atom may be joined to form a substituted or unsubstituted 5 to 10 membered heteroaryl. In embodiments, $R^{5A}$ and $R^{5B}$ substituents bonded to the same nitrogen atom may be joined to form a substituted 3 to 8 membered heterocycloalkyl. In embodiments, $R^{5A}$ and $R^{5B}$ substituents bonded to the same nitrogen atom may be joined to form a substituted 5 to 10 membered heteroaryl. In embodiments, $R^{5A}$ and $R^{5B}$ substituents bonded to the same nitrogen atom may be joined to form a unsubstituted 3 to 8 membered heterocycloalkyl. In embodiments, $R^{5A}$ and $R^{5B}$ substituents bonded to the same nitrogen atom may be joined to form a unsubstituted 5 to 10 membered heteroaryl. In embodiments, $R^{5A}$ and $R^{5B}$ substituents bonded to the same nitrogen atom may be joined to form a substituted or unsubstituted 3 to 6 membered heterocycloalkyl. In embodiments, $R^{5A}$ and $R^{5B}$ substituents bonded to the same nitrogen atom may be joined to form a substituted or unsubstituted 5 to 6 membered heteroaryl. In embodiments, $R^{5A}$ and $R^{5B}$ substituents bonded to the same nitrogen atom may be joined to form a substituted 3 to 6 membered heterocycloalkyl. In embodiments, $R^{5A}$ and $R^{5B}$ substituents bonded to the same nitrogen atom may be joined to form a substituted 5 to 6 membered heteroaryl. In embodiments, $R^{5A}$ and $R^{5B}$ substituents bonded to the same nitrogen atom may be joined to form a unsubstituted 3 to 6 membered heterocycloalkyl. In embodiments, $R^{5A}$ and $R^{5B}$ substituents bonded to the same nitrogen atom may be joined to form a unsubstituted 5 to 6 membered heteroaryl.

In embodiments, $R^{5C}$ is independently hydrogen. In embodiments, $R^{5C}$ is independently —$CX^{5C}_3$. In embodiments, $R^{5C}$ is independently —$CHX^{5C}_2$. In embodiments, $R^{5C}$ is independently —$CH_2X^{5C}$. In embodiments, $R^{5C}$ is independently —CN. In embodiments, $R^{5C}$ is independently —COOH. In embodiments, $R^{5C}$ is independently —$CONH_2$. In embodiments, $R^{5C}$ is independently substituted or unsubstituted alkyl. In embodiments, $R^{5C}$ is independently substituted or unsubstituted heteroalkyl. In embodiments, $R^{5C}$ is independently substituted or unsubstituted cycloalkyl. In embodiments, $R^{5C}$ is independently, substituted or unsubstituted heterocycloalkyl. In embodiments, $R^{5C}$ is independently substituted or unsubstituted aryl. In embodiments, $R^{5C}$ is independently substituted or unsubstituted heteroaryl. In embodiments, $R^{5C}$ is independently substituted alkyl. In embodiments, $R^{5C}$ is independently substituted heteroalkyl. In embodiments, $R^{5C}$ is independently substituted cycloalkyl. In embodiments, $R^{5C}$ is independently, substituted heterocycloalkyl. In embodiments, $R^{5C}$ is independently substituted aryl. In embodiments, $R^{5C}$ is independently substituted heteroaryl. In embodiments, $R^{5C}$ is independently unsubstituted alkyl. In embodiments, $R^{5C}$ is independently unsubstituted heteroalkyl. In embodiments, $R^{5C}$ is independently unsubstituted cycloalkyl. In embodiments, $R^{5C}$ is independently, unsubstituted heterocycloalkyl. In embodiments, $R^{5C}$ is independently unsubstituted aryl. In embodiments, $R^{5C}$ is independently unsubstituted heteroaryl. In embodiments, $R^{5C}$ is independently substituted or unsubstituted $C_1$-$C_8$ alkyl. In embodiments, $R^{5C}$ is independently substituted or unsubstituted 2 to 8 membered heteroalkyl. In embodiments, $R^{5C}$ is independently substituted or unsubstituted $C_3$-$C_8$ cycloalkyl. In embodiments, $R^{5C}$ is independently, substituted or unsubstituted 3 to 8 membered heterocycloalkyl. In embodiments, $R^{5C}$ is independently substituted or unsubstituted $C_6$-$C_{10}$ aryl. In embodiments, $R^{5C}$ is independently substituted or unsubstituted 5 to 10 membered heteroaryl. In embodiments, $R^{5C}$ is independently substituted $C_1$-$C_8$ alkyl. In embodiments, $R^{5C}$ is independently substituted 2 to 8 membered heteroalkyl. In embodiments, $R^{5C}$ is independently substituted $C_3$-$C_8$ cycloalkyl. In embodiments, $R^{5C}$ is independently, substituted 3 to 8 membered heterocycloalkyl. In embodiments, $R^{5C}$ is independently substituted $C_6$-$C_{10}$ aryl. In embodiments, $R^{5C}$ is independently substituted 5 to 10 membered heteroaryl. In embodiments, $R^{5C}$ is independently unsubstituted $C_1$-$C_8$ alkyl. In embodiments, $R^{5C}$ is independently unsubstituted 2 to 8 membered heteroalkyl. In embodiments, $R^{5C}$ is independently unsubstituted $C_3$-$C_8$ cycloalkyl. In embodiments, $R^{5C}$ is independently, unsubstituted 3 to 8 membered heterocycloalkyl. In embodiments, $R^{5C}$ is independently unsubstituted $C_6$-$C_{10}$ aryl. In embodiments, $R^{5C}$ is independently unsubstituted 5 to 10 membered heteroaryl. In embodiments, $R^{5C}$ is independently substituted or unsubstituted $C_1$-$C_4$ alkyl. In embodiments, $R^{5C}$ is independently substituted or unsubstituted 2 to 4 membered heteroalkyl. In embodiments, $R^{5C}$ is independently substituted or unsubstituted $C_3$-$C_6$ cycloalkyl. In embodiments, $R^{5C}$ is independently, substituted or unsubstituted 3 to 6 membered heterocycloalkyl. In embodiments, $R^{5C}$ is independently substituted or unsubstituted phenyl. In embodiments, $R^{5C}$ is independently substituted or unsubstituted 5 to 6 membered heteroaryl. In embodiments, $R^{5C}$ is independently substituted $C_1$-$C_4$ alkyl. In embodiments, $R^{5C}$ is independently substituted 2 to 4 membered heteroalkyl. In embodiments, $R^{5C}$ is independently substituted $C_3$-$C_6$ cycloalkyl. In embodiments, $R^{5C}$ is independently, substituted 3 to 6 membered heterocycloalkyl. In embodiments, $R^{5C}$ is independently substituted phenyl. In embodiments, $R^{5C}$ is independently substituted 5 to 6 membered heteroaryl. In embodiments, $R^{5C}$ is independently unsubstituted $C_1$-$C_4$ alkyl. In embodiments, $R^{5C}$ is independently unsubstituted 2 to 4 membered heteroalkyl. In embodiments, $R^{5C}$ is independently unsubstituted $C_3$-$C_6$ cycloalkyl. In embodiments, $R^{5C}$ is independently unsubstituted 3 to 6 membered heterocycloalkyl. In embodiments, $R^{5C}$ is independently unsubstituted phenyl. In embodiments, $R^{5C}$ is independently unsubstituted 5 to 6 membered heteroaryl. In embodiments, $R^{5C}$ is independently unsubstituted methyl. In embodiments, $R^{5C}$ is independently unsubstituted ethyl. In embodiments, $R^{5C}$ is independently unsubstituted propyl. In embodiments, $R^{5C}$ is independently unsubstituted isopropyl. In embodiments, $R^{5C}$ is independently unsubstituted tert-butyl.

In embodiments, $R^{5D}$ is independently hydrogen. In embodiments, $R^{5D}$ is independently —$CX^{5D}_3$. In embodiments, $R^{5D}$ is independently —$CHX^{5D}_2$. In embodiments, $R^{5D}$ is independently —$CH_2X^{5D}$. In embodiments, $R^{5D}$ is independently —CN. In embodiments, $R^{5D}$ is independently —COOH. In embodiments, $R^{5D}$ is independently —$CONH_2$. In embodiments, $R^{5D}$ is independently substituted or unsubstituted alkyl. In embodiments, $R^{5D}$ is independently substituted or unsubstituted heteroalkyl. In embodiments, $R^{5D}$ is independently substituted or unsubstituted cycloalkyl. In embodiments, $R^{5D}$ is independently, substituted or unsubstituted heterocycloalkyl. In embodiments, $R^{5D}$ is independently substituted or unsubstituted aryl. In embodiments, $R^{5D}$ is independently substituted or unsubstituted heteroaryl. In embodiments, $R^{5D}$ is independently substituted alkyl. In embodiments, $R^{5D}$ is independently substituted heteroalkyl. In embodiments, $R^{5D}$ is independently substituted cycloalkyl. In embodiments, $R^{5D}$ is independently, substituted heterocycloalkyl. In embodiments, $R^{5D}$ is independently substituted aryl. In embodiments, $R^{5D}$ is independently substituted heteroaryl. In embodiments, $R^{5D}$ is independently unsubstituted alkyl. In embodiments, $R^{5D}$ is independently unsubstituted heteroalkyl. In embodiments, $R^{5D}$ is independently unsubstituted cycloalkyl. In embodiments, $R^{5D}$ is independently, unsubstituted heterocycloalkyl. In embodiments, $R^{5D}$ is independently unsubstituted aryl. In embodiments, $R^{5D}$ is independently unsubstituted heteroaryl. In embodiments, $R^{5D}$ is independently substituted or unsubstituted $C_1$-$C_8$ alkyl. In embodiments, $R^{5D}$ is independently substituted or unsubstituted 2 to 8 membered heteroalkyl. In embodiments, $R^{5D}$ is independently substituted or unsubstituted $C_3$-$C_8$ cycloalkyl. In embodiments, $R^{5D}$ is independently, substituted or unsubstituted 3 to 8 membered heterocycloalkyl. In embodiments, $R^{5D}$ is independently substituted or unsubstituted $C_6$-$C_{10}$ aryl. In embodiments, $R^{5D}$ is independently substituted or unsubstituted 5 to 10 membered heteroaryl. In embodiments, $R^{5D}$ is independently substituted $C_1$-$C_8$ alkyl. In embodiments, $R^{5D}$ is independently substituted 2 to 8 membered heteroalkyl. In embodiments, $R^{5D}$ is independently substituted $C_3$-$C_8$ cycloalkyl. In embodiments, $R^{5D}$ is independently, substituted 3 to 8 membered heterocycloalkyl. In embodiments, $R^{5D}$ is independently substituted $C_6$-$C_{10}$ aryl. In embodiments, $R^{5D}$ is independently substituted 5 to 10 membered heteroaryl. In embodiments, $R^{5D}$ is independently unsubstituted $C_1$-$C_8$ alkyl. In embodiments, $R^{5D}$ is independently unsubstituted 2 to 8 membered heteroalkyl. In embodiments, $R^{5D}$ is independently unsubstituted $C_3$-$C_8$ cycloalkyl. In embodiments, $R^{5D}$ is independently, unsubstituted 3 to 8 membered heterocycloalkyl. In embodiments, $R^{5D}$ is independently unsubstituted $C_6$-$C_{10}$ aryl. In embodiments, $R^{5D}$ is independently unsubstituted 5 to 10 membered heteroaryl. In embodiments, $R^{5D}$ is independently substituted or unsubstituted $C_1$-$C_4$ alkyl. In embodiments, $R^{5D}$ is independently substituted or unsubstituted 2 to 4 membered heteroalkyl. In embodiments, $R^{5D}$ is independently substituted or unsubstituted $C_3$-$C_6$ cycloalkyl. In embodiments, $R^{5D}$ is independently, substituted or unsubstituted 3 to 6 membered heterocycloalkyl. In embodiments, $R^{5D}$ is independently substituted or unsubstituted phenyl. In embodiments, $R^{5D}$ is independently substituted or unsubstituted 5 to 6 membered heteroaryl. In embodiments, $R^{5D}$ is independently substituted $C_1$-$C_4$ alkyl. In embodiments, $R^{5D}$ is independently substituted 2 to 4 membered heteroalkyl. In embodiments, $R^{5D}$ is independently substituted $C_3$-$C_6$ cycloalkyl. In embodiments, $R^{5D}$ is independently, substituted 3 to 6 membered heterocycloalkyl. In embodiments, $R^{5D}$ is independently substituted phenyl. In embodiments, $R^{5D}$ is independently substituted 5 to 6 membered heteroaryl. In embodiments, $R^{5D}$ is independently unsubstituted $C_1$-$C_4$ alkyl. In embodiments, $R^{5D}$ is independently unsubstituted 2 to 4 membered heteroalkyl. In embodiments, $R^{5D}$ is independently unsubstituted $C_3$-$C_6$ cycloalkyl. In embodiments, $R^{5D}$ is independently unsubstituted 3 to 6 membered heterocycloalkyl. In embodiments, $R^{5D}$ is independently unsubstituted phenyl. In embodiments, $R^{5D}$ is independently unsubstituted 5 to 6 membered heteroaryl. In embodiments, $R^{5D}$ is independently unsubstituted methyl. In embodiments, $R^{5D}$ is independently unsubstituted ethyl. In embodiments, $R^{5D}$ is independently unsubstituted propyl. In embodiments, $R^{5D}$ is independently unsubstituted isopropyl. In embodiments, $R^{5D}$ is independently unsubstituted tert-butyl.

In embodiments, $R^5$ is independently hydrogen, halogen, —$CX^5_3$, —$CHX^5_2$, —$CH_2X^5$, —$OCX^5_3$, —$OCH_2X^5$, —$OCHX^5_2$, —CN, —$SO_{n5}R^{5D}$, —$SO_{v5}NR^{5A}R^{5B}$, —NHC(O)$NR^{5A}R^{5B}$, —N(O)$_{m5}$, —$NR^{5A}R^{5B}$, —C(O)$R^{5C}$, —C(O)$OR^{5C}$, —C(O)$NR^{5A}R^{5B}$, —$OR^{5D}$, $NR^{5A}SO_2R^{5D}$, —$NR^{5A}C(O)R^{5C}$, —$NR^{5A}C(O)OR^{5C}$, —$NR^{5A}OR^{5C}$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In embodiments, $R^5$ is independently halogen, —$CX^5_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^5_3$, —$OCHX^5_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In embodiments, $R^5$ is independently halogen, —$CX^5_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^5_3$, —$OCHX^5_2$, $R^{32}$-substituted or unsubstituted $C_1$-$C_8$ alkyl, $R^{32}$-substituted or unsubstituted 2 to 8 membered heteroalkyl, $R^{32}$-substituted or unsubstituted $C_3$-$C_8$ cycloalkyl, $R^{32}$-substituted or unsubstituted 3 to 8 membered heterocycloalkyl, $R^{32}$-substituted or unsubstituted phenyl, or $R^{32}$-substituted or unsubstituted 5 to 6 membered heteroaryl. $X^5$ is —F, —Cl, —Br, or —I. In embodiments, $R^5$ is independently hydrogen. In embodiments, $R^5$ is independently unsubstituted methyl. In embodiments, $R^5$ is independently unsubstituted ethyl.

In embodiments, $R^5$ is —$CX^5_3$, —$CHX^5_2$, —$CH_2X^5$, —$OCH_2X^5$, —$OCX^5_3$, or —$OCHX^5_2$. In embodiments, $R^5$ is —$CF_3$, —$CHF_2$, —$CH_2F$, —$OCH_2F$, —$OCF_3$, or —$OCHF_2$. In embodiments, $R^5$ is unsubstituted cyclopropyl. In embodiments, $R^5$ is unsubstituted methyl. In embodiments, $R^5$ is —$CF_3$. In embodiments, $R^5$ is —$CHF_2$. In embodiments, $R^5$ is —$CH_2F$. In embodiments, $R^5$ is —$OCH_2F$. In embodiments, $R^5$ is —$OCF_3$. In embodiments, $R^5$ is —$OCHF_2$.

In embodiments, two adjacent $R^5$ substituents may be joined to form an $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

In embodiments, two adjacent $R^5$ substituents may be joined to form an $R^{32}$-substituted or unsubstituted cycloalkyl. In embodiments, two adjacent $R^5$ substituents may be joined to form an $R^{32}$-substituted or unsubstituted heterocycloalkyl. In embodiments, two adjacent $R^5$ substituents may be joined to form an $R^{32}$-substituted or unsubstituted aryl. In embodiments, two adjacent $R^5$ substituents may be joined to form an $R^{32}$-substituted or unsubstituted heteroaryl. In embodiments, two adjacent $R^5$ substituents may be joined to form an $R^{32}$-substituted cycloalkyl. In embodiments, two adjacent $R^5$ substituents may be joined to form an $R^{32}$-substituted heterocycloalkyl. In embodiments, two adjacent $R^5$ substituents may be joined to form an $R^{32}$- substituted aryl. In embodiments, two adjacent $R^5$ substituents may be joined to form an $R^{32}$-substituted heteroaryl.

In embodiments, two adjacent $R^5$ substituents may be joined to form an $R^{32}$-substituted or unsubstituted $C_3$-$C_8$ cycloalkyl. In embodiments, two adjacent $R^5$ substituents may be joined to form an $R^{32}$-substituted or unsubstituted 3 to 8 membered heterocycloalkyl. In embodiments, two adjacent $R^5$ substituents may be joined to form an $R^{32}$-substituted or unsubstituted $C_6$-$C_{10}$ aryl. In embodiments, two adjacent $R^5$ substituents may be joined to form an $R^{32}$-substituted or unsubstituted 5 to 10 membered heteroaryl. In embodiments, two adjacent $R^5$ substituents may be joined to form an $R^{32}$-substituted $C_3$-$C_8$ cycloalkyl. In embodiments, two adjacent $R^5$ substituents may be joined to form an $R^{32}$-substituted 3 to 8 membered heterocycloalkyl. In embodiments, two adjacent $R^5$ substituents may be joined to form an $R^{32}$-substituted $C_6$-$C_{10}$ aryl. In embodiments, two adjacent $R^5$ substituents may be joined to form an $R^{32}$-substituted 5 to 10 membered heteroaryl.

In embodiments, two adjacent $R^5$ substituents may be joined to form an $R^{32}$-substituted or unsubstituted $C_3$-$C_6$ cycloalkyl. In embodiments, two adjacent $R^5$ substituents may be joined to form an $R^{32}$-substituted or unsubstituted 3 to 6 membered heterocycloalkyl. In embodiments, two adjacent $R^5$ substituents may be joined to form an $R^{32}$-substituted or unsubstituted phenyl. In embodiments, two adjacent $R^5$ substituents may be joined to form an $R^{32}$-substituted or unsubstituted 5 to 6 membered heteroaryl. In embodiments, two adjacent $R^5$ substituents may be joined to form an $R^{32}$-substituted $C_3$-$C_6$ cycloalkyl. In embodiments, two adjacent $R^5$ substituents may be joined to form an $R^{32}$-substituted 3 to 6 membered heterocycloalkyl. In embodiments, two adjacent $R^5$ substituents may be joined to form an $R^{32}$-substituted phenyl. In embodiments, two adjacent $R^5$ substituents may be joined to form an $R^{32}$-substituted 5 to 6 membered heteroaryl.

$R^{32}$ is independently oxo, halogen, —$CX^{32}_3$, —$CHX^{32}_2$, —$CH_2X^{32}$, —$OCH_2X^{32}$, —$OCX^{32}_3$, —$OCHX^{32}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl. In embodiments, $R^{32}$ is independently oxo, halogen, —$CX^{32}_3$, —$CHX^{32}_2$, —$CH_2X^{32}$, —$OCH_2X^{32}$, —$OCX^{32}_3$, —$OCHX^{32}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, $R^{33}$-substituted or unsubstituted $C_1$-$C_8$ alkyl, $R^{33}$-substituted or unsubstituted 2 to 8 membered heteroalkyl, $R^{33}$-substituted or unsubstituted $C_3$-$C_8$ cycloalkyl, $R^{33}$-substituted or unsubstituted 3 to 8 membered heterocycloalkyl, $R^{33}$-substituted or unsubstituted phenyl, or $R^{33}$-substituted or unsubstituted 5 to 6 membered heteroaryl. $X^{32}$ is —F, —Cl, —Br, or —I.

$R^{33}$ is independently oxo, halogen, —$CX^{33}_3$, —$CHX^{33}_2$, —$CH_2X^{33}$, —$OCH_2X^{33}$, —$OCX^{33}_3$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl. In embodiments, $R^{33}$ is independently oxo, halogen, —$CX^{33}_3$, —$CHX^{33}_2$, —$CH_2X^{33}$, —$OCH_2X^{33}$, —$OCX^{33}_3$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, $R^{34}$-substituted or unsubstituted $C_1$-$C_8$ alkyl, $R^{34}$-substituted or unsubstituted 2 to 8 membered heteroalkyl, $R^{34}$-substituted or unsubstituted $C_3$-$C_8$ cycloalkyl, $R^{34}$-substituted or unsubstituted 3 to 8 membered heterocycloalkyl, $R^{34}$-substituted or unsubstituted phenyl, or $R^{34}$-substituted or unsubstituted 5 to 6 membered heteroaryl. $X^{33}$ is —F, —Cl, —Br, or —I.

In embodiments, $R^{5A}$ is independently hydrogen, —$CX^{5A}_3$, —CN, —COOH, —$CONH_2$, —$CHX^{5A2}$, —$CH_2X^{5A}$, $R^{32A}$-substituted or unsubstituted alkyl, $R^{32A}$-substituted or unsubstituted heteroalkyl, $R^{32A}$-substituted or unsubstituted cycloalkyl, $R^{32A}$-substituted or unsubstituted heterocycloalkyl, $R^{32A}$-substituted or unsubstituted aryl, or $R^{32A}$-substituted or unsubstituted heteroaryl. In embodiments, $R^{5A}$ is independently hydrogen, —$CX^{5A}_3$, —CN, —COOH, —$CONH_2$, —$CHX^{5A2}$, —$CH_2X^{5A}$, $R^{32A}$-substituted or unsubstituted $C_1$-$C_8$ alkyl, $R^{32A}$-substituted or unsubstituted 2 to 8 membered heteroalkyl, $R^{32A}$-substituted or unsubstituted $C_3$-$C_8$ cycloalkyl, $R^{32A}$-substituted or unsubstituted 3 to 8 membered heterocycloalkyl, $R^{32A}$-substituted or unsubstituted phenyl, or $R^{32A}$-substituted or unsubstituted 5 to 6 membered heteroaryl. $X^{5A}$ is —F, —Cl, —Br, or —I. In embodiments, $R^{5A}$ is independently hydrogen. In embodiments, $R^{5A}$ is independently unsubstituted methyl. In embodiments, $R^{5A}$ is independently unsubstituted ethyl.

In embodiments, $R^{5A}$ and $R^{5B}$ substituents bonded to the same nitrogen atom may optionally be joined to form a $R^{32A}$-substituted or unsubstituted heterocycloalkyl or $R^{32A}$ substituted or unsubstituted heteroaryl. In embodiments, $R^{5A}$ and $R^{5B}$ substituents bonded to the same nitrogen atom may optionally be joined to form a $R^{32A}$-substituted or unsubstituted 3 to 6 membered heterocycloalkyl or $R^{32A}$-substituted or unsubstituted 5 to 6 membered heteroaryl.

$R^{32A}$ is independently oxo, halogen, —$CX^{32A}_3$, —$CHX^{32A}_2$, —$CH_2X^{32A}$, —$OCH_2X^{32A}$, —$OCX^{32A}_3$, —$OCHX^{32A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, $R^{33A}$-substituted or unsubstituted alkyl, $R^{33A}$-substituted or unsubstituted heteroalkyl, $R^{33A}$-substituted or unsubstituted cycloalkyl, $R^{33A}$-substituted or unsubstituted heterocycloalkyl, $R^{33A}$-substituted or unsubstituted aryl, or $R^{33A}$-substituted or unsubstituted heteroaryl. In embodiments, $R^{32A}$ is independently oxo, halogen, —$CX^{32A}_3$, —$CHX^{32A}_2$, —$CH_2X^{32A}$, —$OCH_2X^{32A}$, —$OCX^{32A}_3$, —$OCHX^{32A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, $R^{33A}$-substituted or unsubstituted $C_1$-$C_8$ alkyl, $R^{33A}$-substituted or unsubstituted 2 to 8 membered heteroalkyl, $R^{33A}$-substituted or unsubstituted $C_3$-$C_8$ cycloalkyl, $R^{33A}$-substituted or unsubstituted 3 to 8 membered heterocycloalkyl, $R^{33A}$-substituted or unsubstituted phenyl, or $R^{33A}$-substituted or unsubstituted 5 to 6 membered heteroaryl. $X^{32A}$ is —F, —Cl, —Br, or —I.

$R^{33A}$ is independently oxo, halogen, —$CX^{33A}_3$, —$CHX^{33A}_2$, —$CH_2X^{33A}$, —$OCH_2X^{33A}$, —$OCX^{33A}_3$, —$OCHX^{33A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, $R^{34A}$-substituted or unsubstituted alkyl, $R^{34A}$-substituted or unsubstituted heteroalkyl, $R^{34A}$-substituted or unsubstituted cycloalkyl, $R^{34A}$-substituted or unsubstituted heterocycloalkyl, $R^{34A}$-substituted or unsubstituted aryl, or $R^{34A}$-substituted or unsubstituted heteroaryl. In embodiments, $R^{33A}$ is independently oxo, halogen, —$CX^{33A}_3$, —$CHX^{33A}_2$, —$CH_2X^{33A}$, —$OCH_2X^{33A}$, —$OCX^{33A}_3$, —$OCHX^{33A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCX^{33A3}$, —$OCHX^{33A}_2$, $R^{34A}$-substituted or unsubstituted $C_1$-$C_8$ alkyl, $R^{34A}$-substituted or unsubstituted 2 to 8 membered heteroalkyl, $R^{34A}$-substituted or unsubstituted $C_3$-$C_8$ cycloalkyl, $R^{34A}$-substituted or unsubstituted 3 to 8 membered heterocycloalkyl, $R^{34A}$-substituted or unsubstituted phenyl, or $R^{34A}$-substituted or unsubstituted 5 to 6 membered heteroaryl. $X^{33A}$ is —F, —Cl, —Br, or —I.

In embodiments, $R^{5B}$ is independently hydrogen, —$CX^{5B3}$, —CN, —COOH, —$CONH_2$, —$CHX^{B2}$, —$CH_2X^{5B}$, $R^{32B}$-substituted or unsubstituted alkyl, $R^{32B}$-substituted or unsubstituted heteroalkyl, $R^{32B}$-substituted or unsubstituted cycloalkyl, $R^{32B}$-substituted or unsubstituted heterocycloalkyl, $R^{32B}$-substituted or unsubstituted aryl, or $R^{32B}$-substituted or unsubstituted heteroaryl. In embodiments, $R^{5B}$ is independently hydrogen, —$CX^{5B3}$, —CN, —COOH, —$CONH_2$, —$CHX^{5B2}$, —$CH_2X^{5B}$, $R^{32B}$-substituted or unsubstituted $C_1$-$C_8$ alkyl, $R^{32B}$-substituted or unsubstituted 2 to 8 membered heteroalkyl, $R^{32B}$-substituted or unsubstituted $C_3$-$C_8$ cycloalkyl, $R^{32B}$-substituted or unsubstituted 3 to 8 membered heterocycloalkyl, $R^{32B}$-substituted or unsubstituted phenyl, or $R^{32B}$-substituted or unsubstituted 5 to 6 membered heteroaryl. $X^{5B}$ is —F, —Cl, —Br, or —I. In embodiments, $R^{5B}$ is independently hydrogen. In embodiments, $R^{5B}$ is independently unsubstituted methyl. In embodiments, $R^{5B}$ is independently unsubstituted ethyl.

In embodiments, $R^{5A}$ and $R^{5B}$ substituents bonded to the same nitrogen atom may optionally be joined to form a $R^{32B}$-substituted or unsubstituted heterocycloalkyl or $R^{32B}$ substituted or unsubstituted heteroaryl. In embodiments, $R^{5A}$ and $R^{5B}$ substituents bonded to the same nitrogen atom may optionally be joined to form a $R^{32B}$-substituted or unsubstituted 3 to 6 membered heterocycloalkyl or $R^{32B}$-substituted or unsubstituted 5 to 6 membered heteroaryl.

$R^{32B}$ is independently oxo, halogen, —$CX^{32B}_3$, —$CHX^{32B}_2$, —$CH_2X^{32B}$, —$OCH_2X^{32B}$, —$OCX^{32B}3$, —$OCHX^{32B}_2$, —CN, —OH, —$NH_2$, —C OOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, $R^{33B}$-substituted or unsubstituted alkyl, $R^{33B}$-substituted or unsubstituted heteroalkyl, $R^{33B}$-substituted or unsubstituted cycloalkyl, $R^{33B}$-substituted or unsubstituted heterocycloalkyl, $R^{33B}$-substituted or unsubstituted aryl, or $R^{33B}$-substituted or unsubstituted heteroaryl. In embodiments, $R^{32B}$ is independently oxo, halogen, —$CX^{32B}_3$, —$CHX^{32}B_2$, —$CH_2X^{32B}$, —$OCH_2X^{32B}$, —$OCX^{32B}3$, —$OCHX^{32B}_2$, —CN, —OH, —$NH_2$, —C OOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, $R^{33B}$-substituted or unsubstituted $C_1$-$C_8$ alkyl, $R^{33B}$-substituted or unsubstituted 2 to 8 membered heteroalkyl, $R^{33B}$-substituted or unsubstituted $C_3$-$C_8$ cycloalkyl, $R^{33B}$-substituted or unsubstituted 3 to 8 membered heterocycloalkyl, $R^{33B}$-substituted or unsubstituted phenyl, or $R^{33B}$-substituted or unsubstituted 5 to 6 membered heteroaryl. $X^{32B}$ is —F, —Cl, —Br, or —I.

$R^{33B}$ is independently oxo, halogen, —$CX^{33B}_3$, —$CHX^{33B}_2$, —$CH_2X^{33}B$, —$OCH_2X^{33B}$, —$OCX^{33B}_3$, —$OCHX^{33B}_2$, —CN, —OH, —$NH_2$, —C OOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, $R^{34B}$-substituted or unsubstituted alkyl, $R^{34B}$-substituted or unsubstituted heteroalkyl, $R^{34B}$-substituted or unsubstituted cycloalkyl, $R^{34B}$-substituted or unsubstituted heterocycloalkyl, $R^{34B}$-substituted or unsubstituted aryl, or $R^{34B}$-substituted or unsubstituted heteroaryl. In embodiments, $R^{33B}$ is independently oxo, halogen, —$CX^{33B}_3$, —$CHX^{33B}_2$, —$CH_2X^{33B}$, —$OCH_2X^{33B}$, —$OCX^{33B}_3$, —$OCHX^{33B}_2$, —CN, —OH, —$NH_2$, —C OOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, $R^{34B}$-substituted or unsubstituted $C_1$-$C_8$ alkyl, $R^{34B}$-substituted or unsubstituted 2 to 8 membered heteroalkyl, $R^{34B}$-substituted or unsubstituted $C_3$-$C_8$ cycloalkyl, $R^{34B}$-substituted or unsubstituted 3 to 8 membered heterocycloalkyl, $R^{34B}$-substituted or unsubstituted phenyl, or $R^{34B}$-substituted or unsubstituted 5 to 6 membered heteroaryl. $X^{33B}$ is —F, —Cl, —Br, or —I.

In embodiments, $R^{5C}$ is independently hydrogen, —$CX^{5C}_3$, —CN, —COOH, —$CONH_2$, —$CHX^{5C}_2$, —$CH_2X^5c$, $R^{32C}$-substituted or unsubstituted alkyl, $R^{32C}$-substituted or unsubstituted heteroalkyl, $R^{32C}$-substituted or unsubstituted cycloalkyl, $R^{32C}$-substituted or unsubstituted heterocycloalkyl, $R^{32C}$-substituted or unsubstituted aryl, or $R^{32C}$-substituted or unsubstituted heteroaryl. In embodiments, $R^{5C}$ is independently hydrogen, —$CX^{5C3}$, —CN, —COOH, —$CONH_2$, —$CHX^{5C}_2$, —$CH_2X^5c$, $R^{32C}$-substituted or unsubstituted $C_1$-$C_8$ alkyl, $R^{32C}$-substituted or unsubstituted 2 to 8 membered heteroalkyl, $R^{32C}$-substituted or unsubstituted $C_3$-$C_8$ cycloalkyl, $R^{32C}$-substituted or unsubstituted 3 to 8 membered heterocycloalkyl, $R^{32C}$-substituted or unsubstituted phenyl, or $R^{32C}$-substituted or unsubstituted 5 to 6 membered heteroaryl. $X^{5C}$ is —F, —Cl, —Br, or —I. In embodiments, $R^{5C}$ is independently hydrogen. In embodiments, $R^{5C}$ is independently unsubstituted methyl. In embodiments, $R^{5C}$ is independently unsubstituted ethyl.

$R^{32C}$ is independently oxo, halogen, —$CX^{32C}_3$, —$CHX^{32C}_2$, —$CH_2X^{32C}$, —$OCH_2X^{32C}$, —$OCX^{32C}_3$, —$OCHX^{32C}_2$, —CN, —OH, —$NH_2$, —C OOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, $R^{33C}$-substituted or unsubstituted alkyl, $R^{33C}$-substituted or unsubstituted heteroalkyl, $R^{33C}$-substituted or unsubstituted cycloalkyl, $R^{33C}$-substituted or unsubstituted heterocycloalkyl, $R^{33C}$-substituted or unsubstituted aryl, or $R^{33C}$-substituted or unsubstituted heteroaryl. In embodiments, $R^{32C}$ is independently oxo, halogen, —$CX^{32C}_3$, —$CHX^{32C}_2$, —$CH_2X^{32C}$, —$OCH_2X^{32C}$, —$OCX^{32C}_3$, —$OCHX^{32C}_2$, —CN, —OH, —$NH_2$, —C OOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, $R^{33C}$-substituted or unsubstituted $C_1$-$C_8$ alkyl, $R^{33C}$-substituted or unsubstituted 2 to 8 membered heteroalkyl, $R^{33C}$-substituted or unsubstituted $C_3$-$C_8$ cycloalkyl, $R^{33C}$-substituted or unsubstituted 3 to 8 membered heterocycloalkyl, $R^{33C}$-substituted or unsubstituted phenyl, or $R^{33C}$-substituted or unsubstituted 5 to 6 membered heteroaryl. $X^{32C}$ is —F, —Cl, —Br, or —I.

$R^{33C}$ is independently oxo, halogen, —$CX^{33C}_3$, —$CHX^{33C}_2$, —$CH_2X^{33C}$, —$OCH_2X^{33C}$, —$OCX^{33C}_3$, —$OCHX^{33C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{34C}$-substituted or unsubstituted alkyl, $R^{34C}$-substituted or unsubstituted heteroalkyl, $R^{34C}$-substituted or unsubstituted cycloalkyl, $R^{34}$-substituted or unsubstituted heterocycloalkyl, $R^{34C}$-substituted or unsubstituted aryl, or $R^{34}$-substituted or unsubstituted heteroaryl. In embodiments, $R^{33C}$ is independently oxo, halogen, —$CX^{33C}_3$, —$CHX^{33C}_2$, —$CH_2X^{33C}$, —$OCH_2X^{33C}$, —$OCX^{33C}_3$, —$OCHX^{33C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{34C}$-substituted or unsubstituted $C_1$-$C_8$ alkyl, $R^{34C}$-substituted or unsubstituted 2 to 8 membered heteroalkyl, $R^{34C}$-substituted or unsubstituted $C_3$-$C_8$ cycloalkyl, $R^{34C}$-substituted or unsubstituted 3 to 8 membered heterocycloalkyl, $R^{34C}$-substituted or unsubstituted phenyl, or $R^{34C}$-substituted or unsubstituted 5 to 6 membered heteroaryl. $X^{33C}$ is —F, —Cl, —Br, or —I.

In embodiments, $R^{5D}$ is independently hydrogen, —$CX^{5D}_3$, —CN, —COOH, —$CONH_2$, —$CHX^{5D}_2$, —$CH_2X^{5D}$, $R^{32D}$-substituted or unsubstituted alkyl, $R^{32D}$-substituted or unsubstituted heteroalkyl, $R^{32D}$-substituted or unsubstituted cycloalkyl, $R^{32D}$-substituted or unsubstituted heterocycloalkyl, $R^{32D}$-substituted or unsubstituted aryl, or $R^{32D}$-substituted or unsubstituted heteroaryl. In embodiments, $R^{5D}$ is independently hydrogen, —$CX^{5D3}$, —CN, —COOH, —$CONH_2$, —$CHX^{5D}_2$, —$CH_2X^{5D}$, $R^{32D}$-substituted or unsubstituted $C_1$-$C_8$ alkyl, $R^{32D}$-substituted or unsubstituted 2 to 8 membered heteroalkyl, $R^{32D}$-substituted or unsubstituted $C_3$-$C_8$ cycloalkyl, $R^{32D}$-substituted or unsubstituted 3 to 8 membered heterocycloalkyl, $R^{32D}$-substituted or unsubstituted phenyl, or $R^{32D}$-substituted or unsubstituted 5 to 6 membered heteroaryl. $X^{5D}$ is —F, —Cl, —Br, or —I. In embodiments, $R^{5D}$ is independently hydrogen. In embodiments, $R^{5D}$ is independently unsubstituted methyl. In embodiments, $R^{5D}$ is independently unsubstituted ethyl.

$R^{32D}$ is independently oxo, halogen, —$CX^{32D}_3$, —$CHX^{32D}_2$, —$CH_2X^{32D}$, —$OCH_2X^{32D}$, —$OCX^{32D}_3$, —$OCHX^{32D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{33D}$-substituted or unsubstituted alkyl, $R^{33D}$-substituted or unsubstituted heteroalkyl, $R^{33D}$-substituted or unsubstituted cycloalkyl, $R^{33D}$-substituted or unsubstituted heterocycloalkyl, $R^{33D}$-substituted or unsubstituted aryl, or $R^{33D}$-substituted or unsubstituted heteroaryl. In embodiments, $R^{32D}$ is independently oxo, halogen, —$CX^{32D}_3$, —$CHX^{32D}_2$, —$CH_2X^{32D}$, —$OCH_2X^{32D}$, —$OCX^{32D}_3$, —$OCHX^{32D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, $R^{33D}$-substituted or unsubstituted $C_1$—$C_8$ alkyl, $R^{33D}$-substituted or unsubstituted 2 to 8 membered heteroalkyl, $R^{33D}$-substituted or unsubstituted $C_3$-$C_8$ cycloalkyl, $R^{33D}$-substituted or unsubstituted 3 to 8 membered heterocycloalkyl, $R^{33D}$-substituted or unsubstituted phenyl, or $R^{33D}$-substituted or unsubstituted 5 to 6 membered heteroaryl. $X^{32D}$ is —F, —Cl, —Br, or —I.

$R^{33D}$ is independently oxo, halogen, —$CX^{33D3}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC (O)H, —NHC(O)OH, —NHOH, —$OCX^{33D3}$, —$OCHX^{33D2}$, $R^{34D}$-substituted or unsubstituted alkyl, $R^{34D}$-substituted or unsubstituted heteroalkyl, $R^{34D}$-substituted or unsubstituted cycloalkyl, $R^{34D}$-substituted or unsubstituted heterocycloalkyl, $R^{34D}$-substituted or unsubstituted aryl, or $R^{34D}$-substituted or unsubstituted heteroaryl. In embodiments, $R^{33D}$ is independently oxo, halogen, —$CX^{33D3}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{33D}_3$, —$OCHX^{32}$, $R^{34D}$-substituted or unsubstituted $C_1$-$C_8$ alkyl, $R^{34D}$-substituted or unsubstituted 2 to 8 membered heteroalkyl, $R^{34D}$-substituted or unsubstituted $C_3$-$C_8$ cycloalkyl, $R^{34D}$-substituted or unsubstituted 3 to 8 membered heterocycloalkyl, $R^{34D}$-substituted or unsubstituted phenyl, or $R^{34D}$-substituted or unsubstituted 5 to 6 membered heteroaryl. $X^{33D}$ is —F, —Cl, —Br, or —I.

$R^{34}$, $R^{34A}$, $R^{34B}$, $R^{34C}$, and $R^{34D}$ are independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{34}$, $R^{34A}$, $R^{34B}$, $R^{34C}$, and $R^{34D}$ are independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{34}$, $R^{34A}$, $R^{34B}$, $R^{34C}$, and $R^{34D}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{34}$, $R^{34A}$, $R^{34B}$, $R^{34C}$, and $R^{34D}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, R⁵ is independently —F, —Cl, —Br, —I, —CN, —NH₂, —OH, —SH, —COCH₃, —COOH, —COOCH₃, —CX⁵₃, —CHX⁵₂, —CH₂X⁵, —OCX⁵₃, —OCHX⁵₂, —OCH₂X⁵, —SCX⁵₃, —SCHX⁵₂, —SCH₂X⁵, —CH₃, —CH₂CH₃, —OCH₃, —OCH₂CH₃, —NHCH₃, —N(CH₃)₂, —NHCH₂CH₃, —N(CH₃)(CH₂CH₃), —N(CH₂CH₃)₂, —SCH₃, or —SCH₂CH₃. In embodiments, R⁵ is independently —F. In embodiments, R⁵ is independently —Cl. In embodiments, R⁵ is independently —Br. In embodiments, R⁵ is independently —I. In embodiments, R⁵ is independently —CN. In embodiments, R⁵ is independently —NH₂. In embodiments, R⁵ is independently —OH. In embodiments, R⁵ is independently —SH. In embodiments, R⁵ is independently —COCH₃. In embodiments, R⁵ is independently —COOH. In embodiments, R⁵ is independently —COOCH₃. In embodiments, R⁵ is independently —CX⁵₃. In embodiments, R⁵ is independently —CHX⁵₂. In embodiments, R⁵ is independently —CH₂X⁵. In embodiments, R⁵ is independently —OCX⁵₃. In embodiments, R⁵ is independently —OCHX⁵₂. In embodiments, R⁵ is independently —OCH₂X⁵. In embodiments, R⁵ is independently —SCX⁵₃. In embodiments, R⁵ is independently —SCHX⁵₂. In embodiments, R⁵ is independently —SCH₂X⁵. In embodiments, R⁵ is independently —CH₃. In embodiments, R⁵ is independently —CH₂CH₃. In embodiments, R⁵ is independently —OCH₃. In embodiments, R⁵ is independently —OCH₂CH₃. In embodiments, R⁵ is independently —NHCH₃. In embodiments, R⁵ is independently —N(CH₃)₂. In embodiments, R⁵ is independently —NHCH₂CH₃. In embodiments, R⁵ is independently —N(CH₃)(CH₂CH₃). In embodiments, R⁵ is independently —N(CH₂CH₃)₂. In embodiments, R⁵ is independently —SCH₃. In embodiments, R⁵ is independently —SCH₂CH₃.

In embodiments, z5 is 5. In embodiments, z5 is 4. In embodiments, z5 is 3. In embodiments, z5 is 2. In embodiments, z5 is 1. In embodiments, z5 is 0.

In embodiments, n4 is 0. In embodiments, n4 is 1. In embodiments, n4 is 2. In embodiments, n4 is 3. In embodiments, n4 is 4. In embodiments, n5 is 0. In embodiments, n5 is 1. In embodiments, n5 is 2. In embodiments, n5 is 3. In embodiments, n5 is 4.

In embodiments, m4 is 1. In embodiments, m4 is 2. In embodiments, m5 is 1. In embodiments, m5 is 2.

In embodiments, v4 is 1. In embodiments, v4 is 2. In embodiments, v5 is 1. In embodiments, v5 is 2.

In embodiments, the compound has the formula:

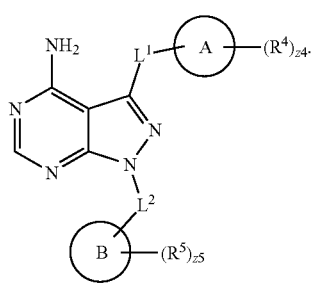

L¹, L², R⁴, R⁵, Ring A, Ring B, z4, and z5 are as described herein.

In embodiments, the compound has the formula:

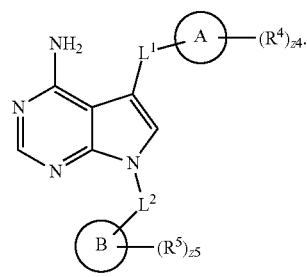

L¹, L², R⁴, R⁵, Ring A, Ring B, z4, and z5 are as described herein.

In embodiments, the compound has the formula:

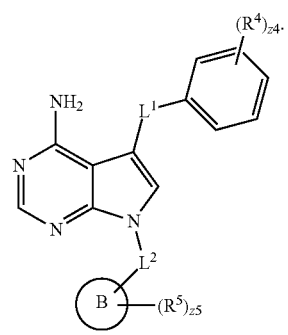

L¹, L², R⁴, R⁵, Ring B, z4, and z5 are as described herein.

In embodiments, the compound has the formula:

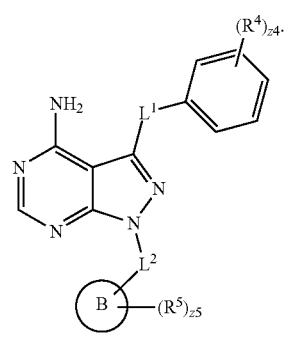

L¹, L², R⁴, R⁵, Ring B, z4, and z5 are as described herein.

In embodiments, the compound has the formula:

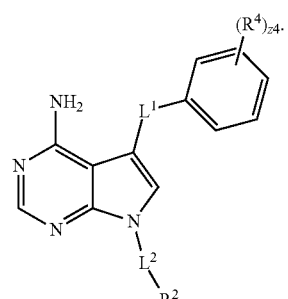

L¹, L², R⁴, R², and z4 are as described herein.

In embodiments, the compound has the formula:

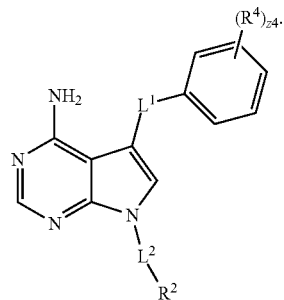

L¹, L², R⁴, R², and z4 are as described herein.

In embodiments, the compound has the formula:

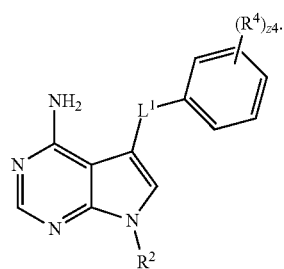

L¹, R² and z4 are as described herein.

In embodiments, the compound has the formula:

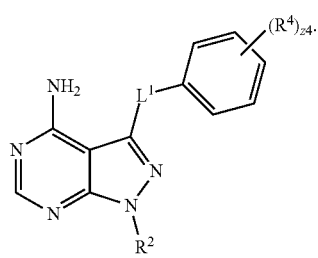

L¹, R², and z4 are as described herein.

In embodiments, the compound has the formula:

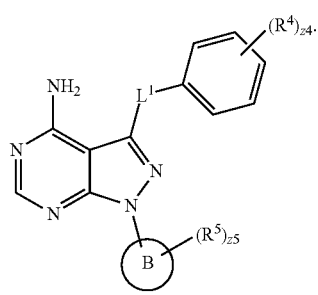

L¹, Ring B, z5, and z4 are as described herein. In embodiments, Ring B is substituted or unsubstituted cyclooctanyl, substituted or unsubstituted cycloheptanyl, substituted or unsubstituted cyclohexanyl, or substituted or unsubstituted cyclopentanyl.

In embodiments, the compound has the formula:

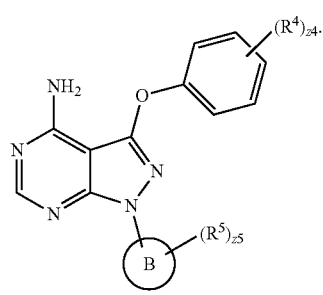

L¹, Ring B, z5, and z4 are as described herein. In embodiments, Ring B is substituted or unsubstituted cyclooctanyl, substituted or unsubstituted cycloheptanyl, substituted or unsubstituted cyclohexanyl, or substituted or unsubstituted cyclopentanyl.

In embodiments, the compound has the formula:

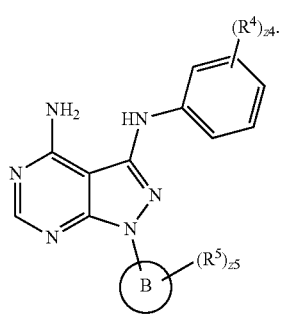

L¹, Ring B, z5, and z4 are as described herein. In embodiments, Ring B is substituted or unsubstituted cyclooctanyl, substituted or unsubstituted cycloheptanyl, substituted or unsubstituted cyclohexanyl, or substituted or unsubstituted cyclopentanyl.

In embodiments, the compound has the formula:

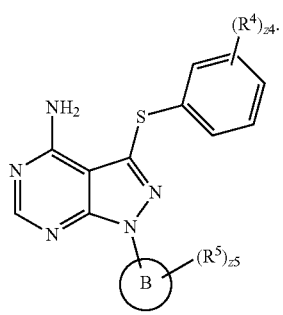

L¹, Ring B, z5, and z4 are as described herein. In embodiments, Ring B is substituted or unsubstituted cyclooctanyl, substituted or unsubstituted cycloheptanyl, substituted or unsubstituted cyclohexanyl, or substituted or unsubstituted cyclopentanyl.

In embodiments, the compound has the formula:

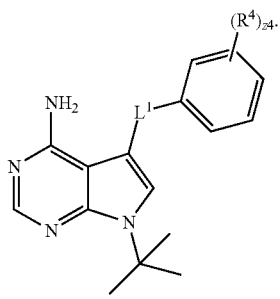

$L^1$, $L^2$, $R^4$, $R^2$, and z4 are as described herein.

In embodiments, the compound has the formula:

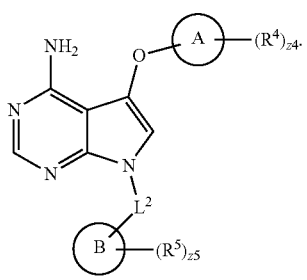

$L^1$, $L^2$, $R^4$, $R^5$, Ring A, Ring B, z4, and z5 are as described herein.

In embodiments, the compound has the formula:

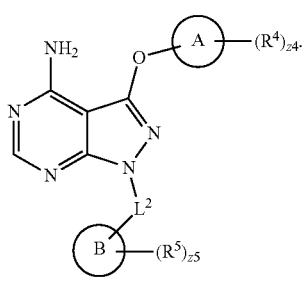

$L^1$, $L^2$, $R^4$, $R^5$, Ring A, Ring B, z4, and z5 are as described herein.

In embodiments, the compound has the formula:

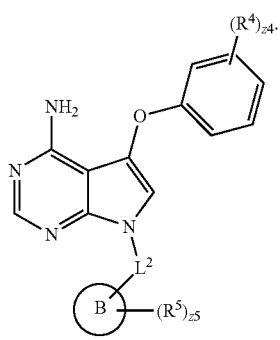

$L^1$, $L^2$, $R^4$, $R^5$, Ring B, z4, and z5 are as described herein.

In embodiments, the compound has the formula:

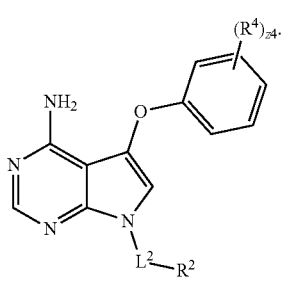

$L^1$, $L^2$, $R^4$, $R^2$, and z4 are as described herein.

In embodiments, the compound has the formula:

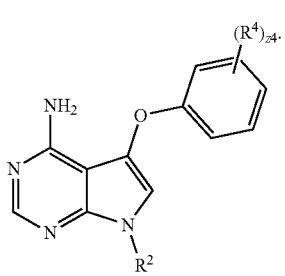

$L^1$, $L^2$, $R^4$, $R^2$, and z4 are as described herein.

In embodiments, the compound has the formula:

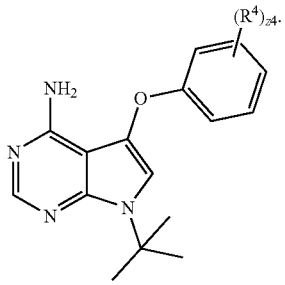

$L^1$, $L^2$, $R^4$, $R^2$, and z4 are as described herein.

In embodiments, the compound has the formula:

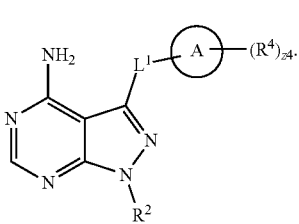

$L^1$, $R^2$, $R^4$, Ring A, and z4 are as described herein.

In embodiments, the compound has the formula:

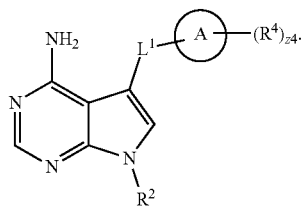

In embodiments, the compound has the formula:

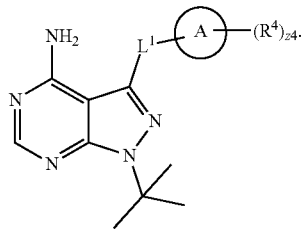

L¹, R⁴, Ring A, and z4 are as described herein.

In embodiments, the compound has the formula:

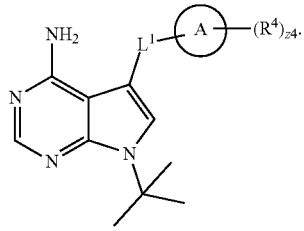

L¹, R⁴, Ring A, and z4 are as described herein.

In embodiments, the compound has the formula:

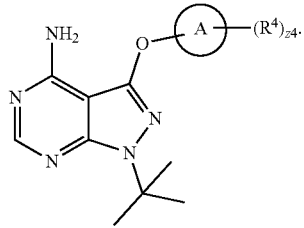

L¹, R⁴, Ring A, and z4 are as described herein.

In embodiments, the compound has the formula:

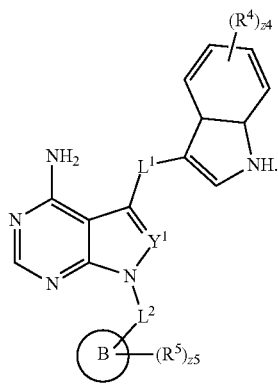

L¹, L², R⁴, R⁵, Ring B, z4, z5, and Y¹ are as described herein.

In embodiments, the compound has the formula:

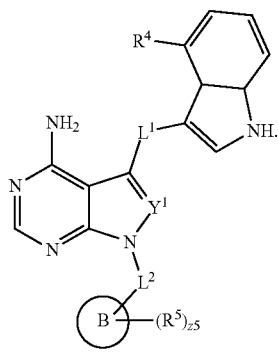

L¹, L², R⁴, R⁵, Ring B, z5, and Y¹ are as described herein.

In embodiments, the compound has the formula:

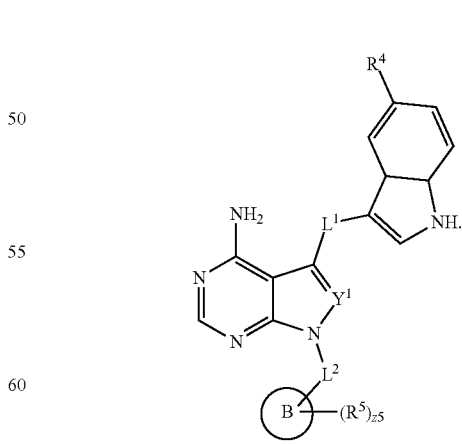

L¹, L², R⁴, R⁵, Ring B, z5, and Y¹ are as described herein.

In embodiments, the compound has the formula:

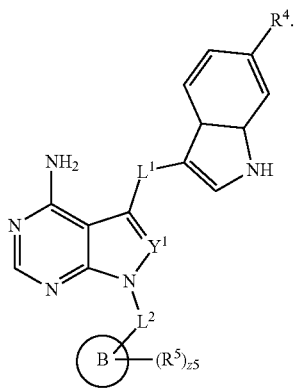

$L^1$, $L^2$, $R^4$, $R^5$, Ring B, z5, and $Y^1$ are as described herein.

In embodiments, the compound has the formula:

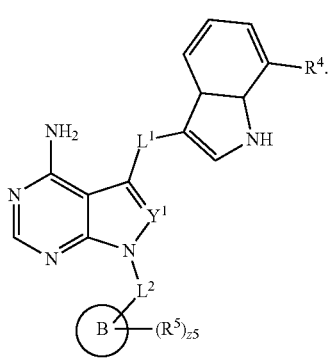

$L^1$, $L^2$, $R^4$, $R^5$, Ring B, z5, and $Y^1$ are as described herein.

In embodiments, the compound has the formula:

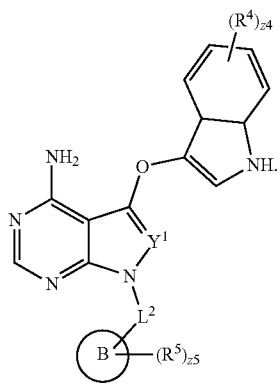

$L^2$, $R^4$, $R^5$, Ring B, z4, z5, and $Y^1$ are as described herein.

In embodiments, the compound has the formula:

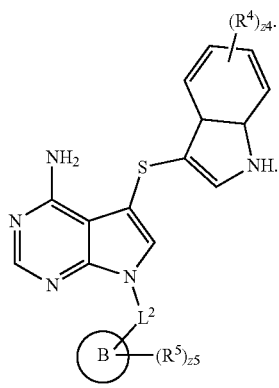

$L^2$, $R^4$, $R^5$, Ring B, z4, z5, and $Y^1$ are as described herein.

In embodiments, the compound has the formula:

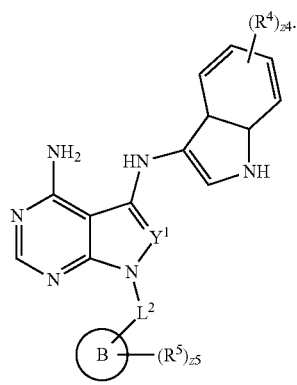

$L^2$, $R^4$, $R^5$, Ring B, z4, z5, and $Y^1$ are as described herein.

In embodiments, the compound has the formula:

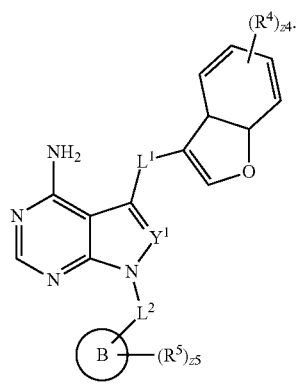

$L^1$, $L^2$, $R^4$, $R^5$, Ring B, z4, z5, and $Y^1$ are as described herein.

In embodiments, the compound has the formula:

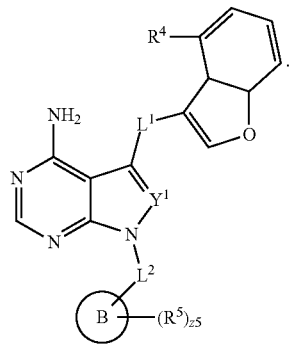

L¹, L², R⁴, R⁵, Ring B, z5, and Y¹ are as described herein.

In embodiments, the compound has the formula:

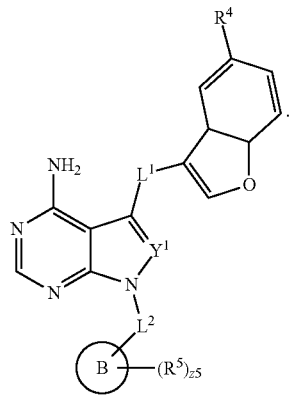

L¹, L², R⁴, R⁵, Ring B, z5, and Y¹ are as described herein.

In embodiments, the compound has the formula:

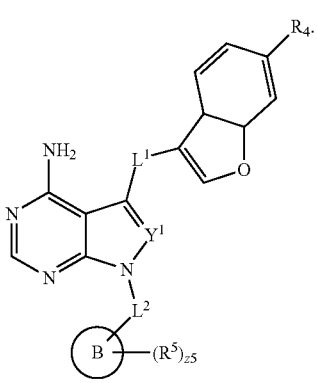

L¹, L², R⁴, R⁵, Ring B, z5, and Y¹ are as described herein.

In embodiments, the compound has the formula:

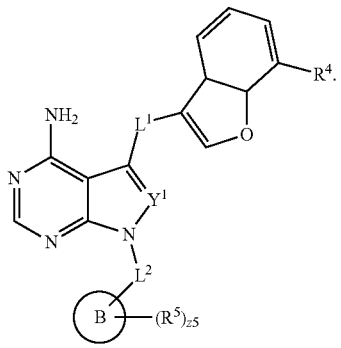

L¹, L², R⁴, R⁵, Ring B, z5, and Y¹ are as described herein.

In embodiments, the compound has the formula:

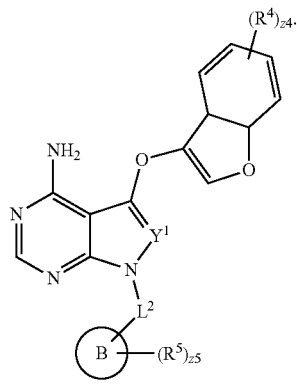

L², R⁴, R⁵, Ring B, z4, z5, and Y¹ are as described herein.

In embodiments, the compound has the formula:

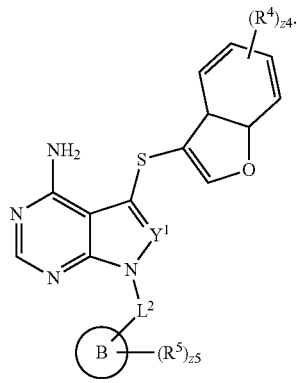

L², R⁴, R⁵, Ring B, z4, z5, and Y¹ are as described herein.

In embodiments, the compound has the formula:

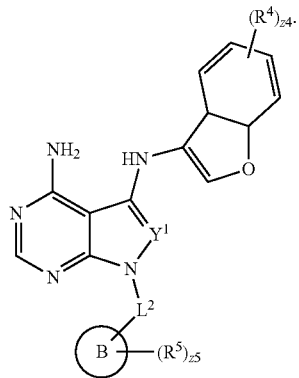

$L^2$, $R^4$, $R^5$, Ring B, z4, z5, and $Y^1$ are as described herein.

In embodiments, the compound has the formula:

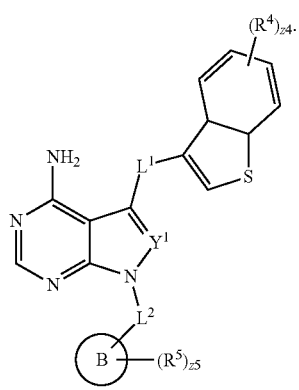

$L^1$, $L^2$, $R^4$, $R^5$, Ring B, z4, z5, and $Y^1$ are as described herein.

In embodiments, the compound has the formula:

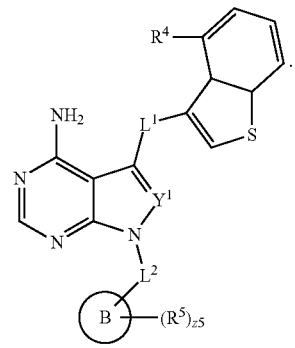

$L^1$, $L^2$, $R^4$, $R^5$, Ring B, z5, and $Y^1$ are as described herein.

In embodiments, the compound has the formula

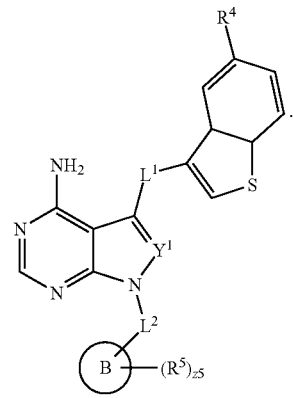

$L^1$, $L^2$, $R^4$, $R^5$, Ring B, z5, and $Y^1$ are as described herein.

In embodiments, the compound has the formula:

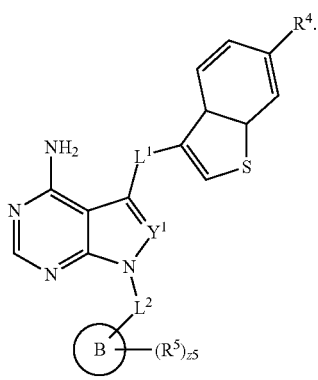

$L^1$, $L^2$, $R^4$, $R^5$, Ring B, z5, and $Y^1$ are as described herein.

In embodiments, the compound has the formula:

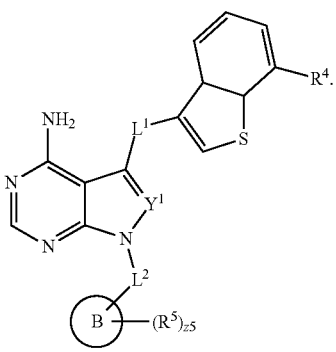

$L^1$, $L^2$, $R^4$, $R^5$, Ring B, z5, and $Y^1$ are as described herein.

In embodiments, the compound has the formula:

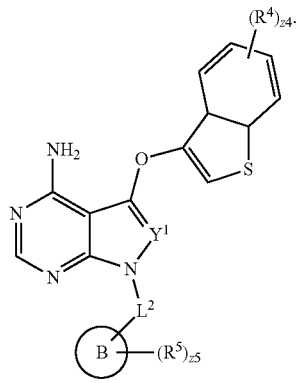

$L^2$, $R^4$, $R^5$, Ring B, z4, z5, and $Y^1$ are as described herein.

In embodiments, the compound has the formula:

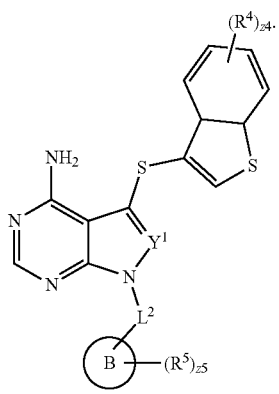

$L^2$, $R^4$, $R^5$, Ring B, z4, z5, and $Y^1$ are as described herein.

In embodiments, the compound has the formula:

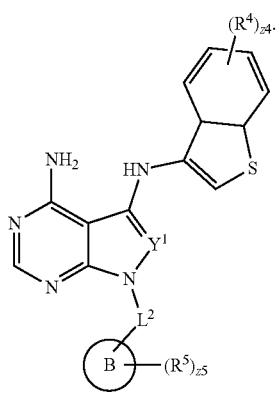

$L^2$, $R^4$, $R^5$, Ring B, z4, z5, and $Y^1$ are as described herein.

In embodiments, the compound has the formula:

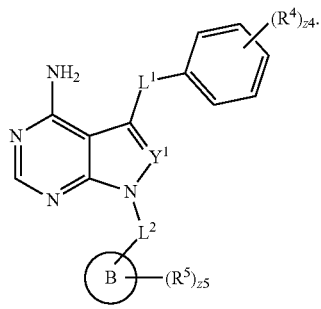

$L^1$, $L^2$, $R^4$, $R^5$, Ring B, z4, z5, and $Y^1$ are as described herein.

In embodiments, the compound has the formula:

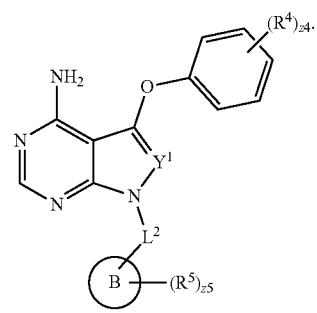

$L^2$, $R^4$, $R^5$, Ring B, z4, z5, and $Y^1$ are as described herein.

In embodiments, the compound has the formula

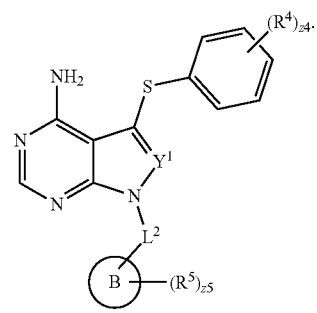

$L^2$, $R^4$, $R^5$, Ring B, z4, z5, and $Y^1$ are as described herein.

In embodiments, the compound has the formula:

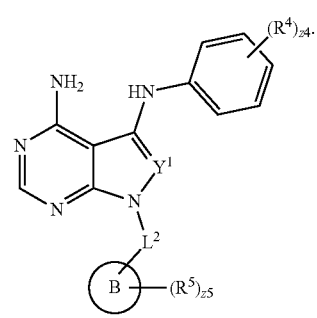

$L^2$, $R^4$, $R^5$, Ring B, z4, z5, and $Y^1$ are as described herein.

In embodiments, the compound has the formula:

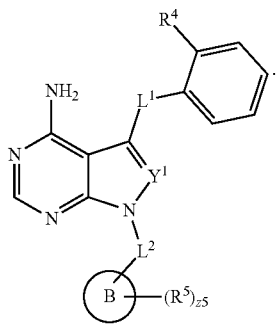

$L^1$, $L^2$, $R^4$, $R^5$, Ring B, z5, and $Y^1$ are as described herein.

In embodiments, the compound has the formula:

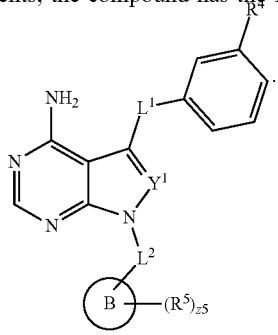

$L^1$, $L^2$, $R^4$, $R^5$, Ring B, z5, and $Y^1$ are as described herein.

In embodiments, the compound has the formula:

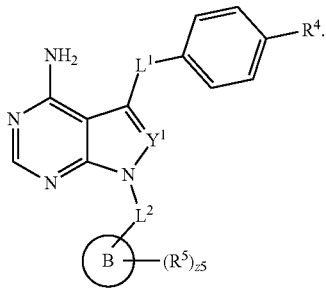

$L^1$, $L^2$, $R^4$, $R^5$, Ring B, z5, and $Y^1$ are as described herein.

In embodiments, the compound has the formula:

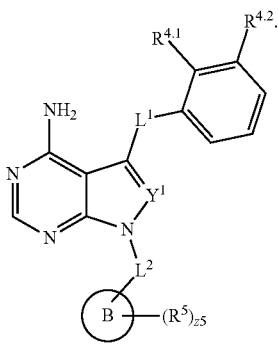

$L^1$, $L^2$, $R^{4.1}$, $R^{4.2}$, $R^5$, Ring B, z5, and $Y^1$ are as described herein.

In embodiments, the compound has the formula:

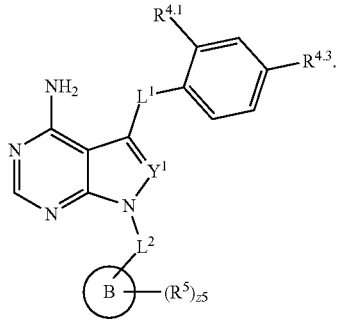

$L^1$, $L^2$, $R^{4.1}$, $R^{4.3}$, $R^5$, Ring B, z5, and $Y^1$ are as described herein.

In embodiments, the compound has the formula:

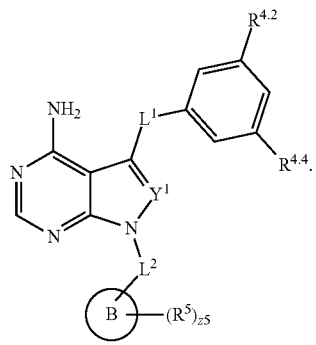

$L^1$, $L^2$, $R^{4.2}$, $R^{4.4}$, $R^5$, Ring B, z5, and $Y^1$ are as described herein.

In embodiments, the compound has the formula:

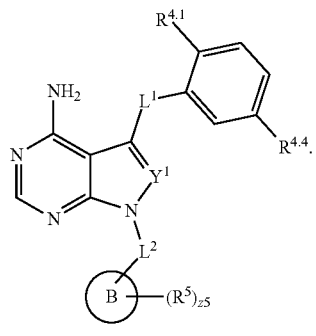

$L^1$, $L^2$, $R^{4.1}$, $R^{4.4}$, $R^5$, Ring B, z5, and $Y^1$ are as described herein.

In embodiments, the compound has the formula:

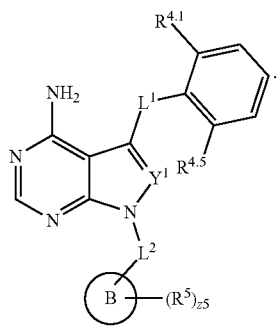

$L^1$, $L^2$, $R^{4.1}$, $R^{4.5}$, $R^5$, Ring B, z5, and $Y^1$ are as described herein.

In embodiments, the compound has the formula:

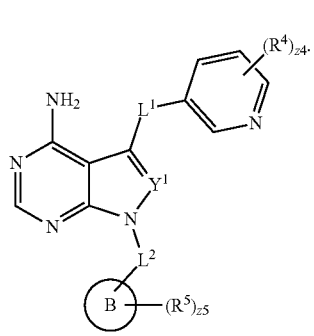

$L^1$, $L^2$, $R^4$, $R^5$, Ring B, z4, z5, and $Y^1$ are as described herein.

In embodiments, the compound has the formula:

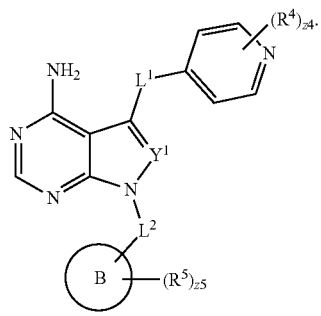

$L^1$, $L^2$, $R^4$, $R^5$, Ring B, z4, z5, and $Y^1$ are as described herein.

In embodiments, the compound has the formula:

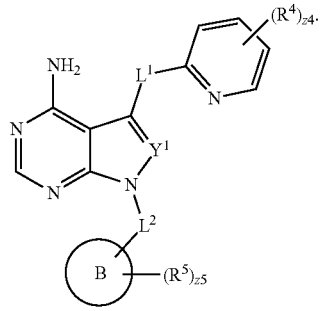

$L^1$, $L^2$, $R^4$, $R^5$, Ring B, z4, z5, and $Y^1$ are as described herein.

In embodiments, the compound has the formula:

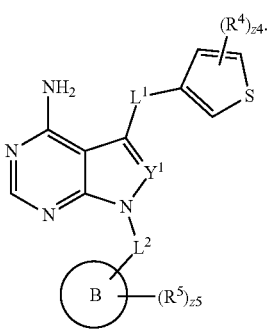

$L^1$, $L^2$, $R^4$, $R^5$, Ring B, z4, z5, and $Y^1$ are as described herein.

In embodiments, the compound has the formula:

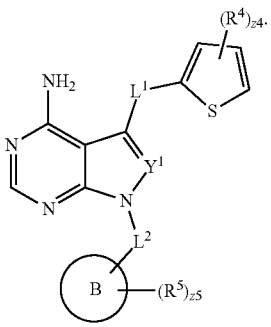

$L^1$, $L^2$, $R^4$, $R^5$, Ring B, z4, z5, and $Y^1$ are as described herein.

In embodiments, the compound has the formula:

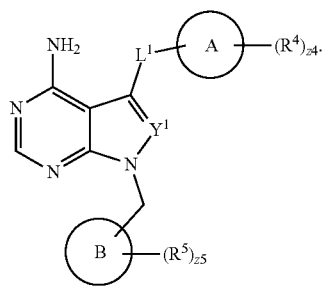

$L^1$, $R^4$, $R^5$, Ring B, z4, z5, and $Y^1$ are as described herein.

In embodiments, the compound has the formula:

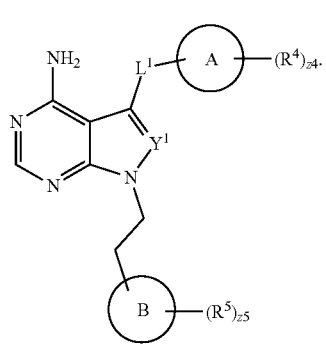

$L^1$, $R^4$, $R^5$, Ring B, z4, z5, and $Y^1$ are as described herein.

In embodiments, the compound has the formula:

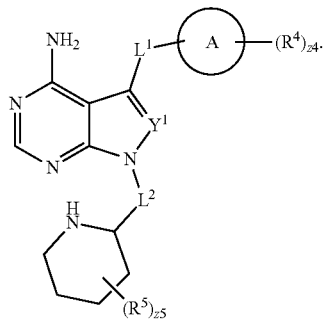

$L^1$, $L^2$, $R^4$, $R^5$, Ring A, z4, z5, and $Y^1$ are as described herein.

In embodiments, the compound has the formula:

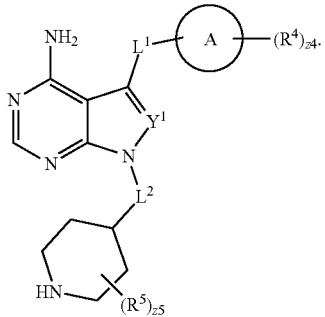

$L^1$, $L^2$, $R^4$, $R^5$, Ring A, z4, z5, and $Y^1$ are as described herein.

In embodiments, the compound has the formula:

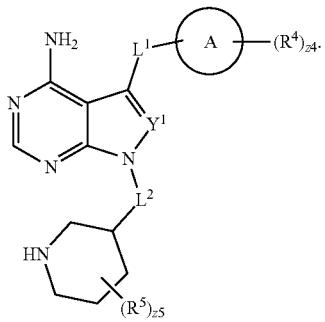

$L^1$, $L^2$, $R^4$, $R^5$, Ring A, z4, z5, and $Y^1$ are as described herein.

In embodiments, the compound has the formula:

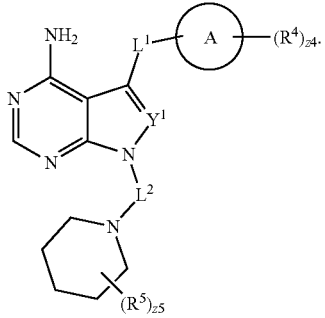

$L^1$, $L^2$, $R^4$, $R^5$, Ring A, z4, z5, and $Y^1$ are as described herein.

In embodiments, the compound has the formula:

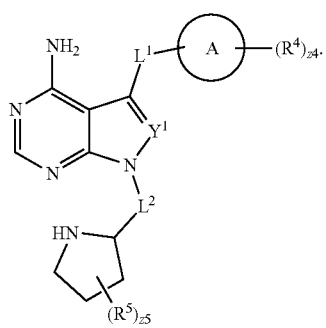

$L^1$, $L^2$, $R^4$, $R^5$, Ring A, z4, z5, and $Y^1$ are as described herein.

In embodiments, the compound has the formula:

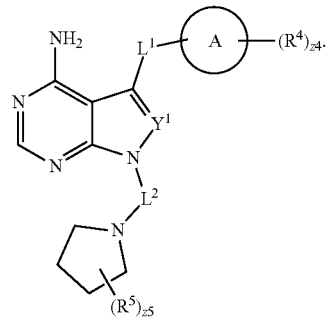

$L^1$, $L^2$, $R^4$, $R^5$, Ring A, z4, z5, and $Y^1$ are as described herein.

In embodiments, the compound has the formula:

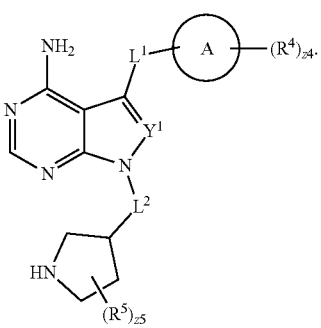

$L^1$, $L^2$, $R^4$, $R^5$, Ring A, z4, z5, and $Y^1$ are as described herein.

In embodiments, the compound has the formula:

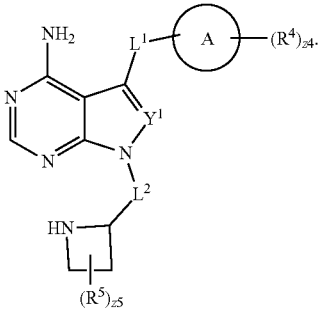

$L^1$, $L^2$, $R^4$, $R^5$, Ring A, z4, z5, and $Y^1$ are as described herein.

In embodiments, the compound has the formula:

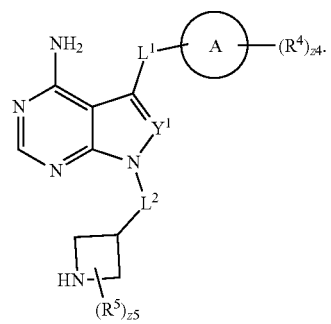

$L^1$, $L^2$, $R^4$, $R^5$, Ring A, z4, z5, and $Y^1$ are as described herein.

In embodiments, the compound has the formula:

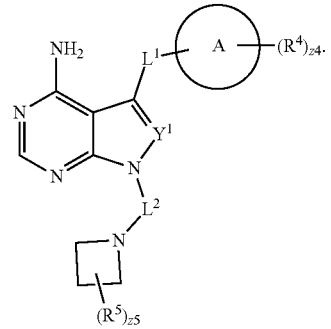

$L^1$, $L^2$, $R^4$, $R^5$, Ring A, z4, z5, and $Y^1$ are as described herein.

In embodiments, the compound has the formula:

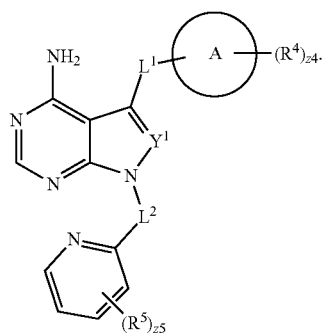

$L^1$, $L^2$, $R^4$, $R^5$, Ring A, z4, z5, and $Y^1$ are as described herein.

In embodiments, the compound has the formula:

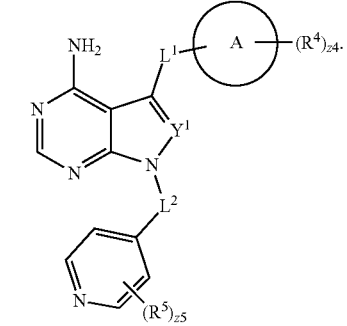

$L^1$, $L^2$, $R^4$, $R^5$, Ring A, z4, z5, and $Y^1$ are as described herein.

In embodiments, the compound has the formula:

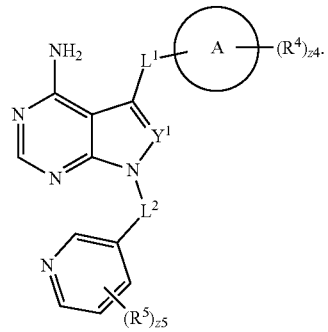

$L^1$, $L^2$, $R^4$, $R^5$, Ring A, z4, z5, and $Y^1$ are as described herein.

In embodiments, the compound has the formula:

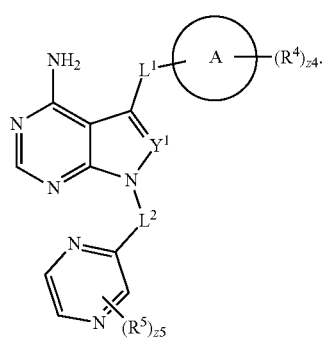

$L^1$, $L^2$, $R^4$, $R^5$, Ring A, z4, z5, and $Y^1$ are as described herein.

In embodiments, the compound has the formula:

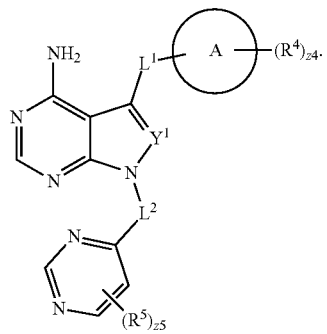

$L^1$, $L^2$, $R^4$, $R^5$, Ring A, z4, z5, and $Y^1$ are as described herein.

In embodiments, the compound has the formula:

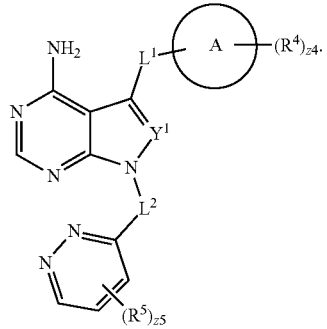

$L^1$, $L^2$, $R^4$, $R^5$, Ring A, z4, z5, and $Y^1$ are as described herein.

In embodiments, the compound has the formula:

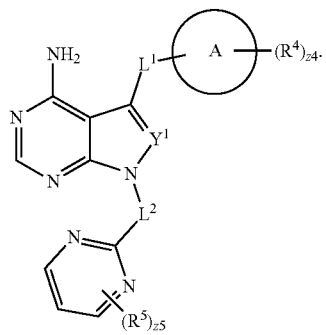

$L^1$, $L^2$, $R^4$, $R^5$, Ring A, z4, z5, and $Y^1$ are as described herein.

In embodiments, the compound has the formula:

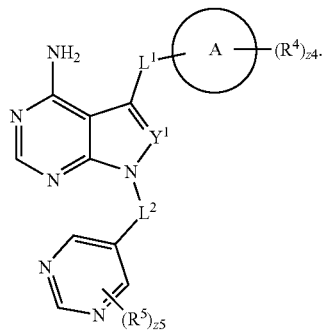

$L^1$, $L^2$, $R^4$, $R^5$, Ring A, z4, z5, and $Y^1$ are as described herein.

In embodiments, the compound has the formula:

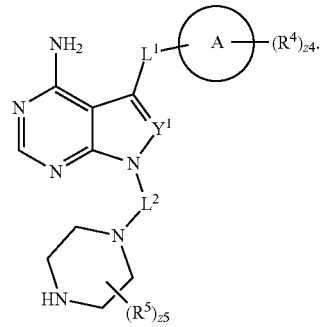

$L^1$, $L^2$, $R^4$, $R^5$, Ring A, z4, z5, and $Y^1$ are as described herein.

In embodiments, the compound has the formula:

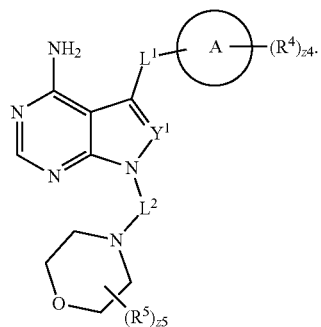

$L^1$, $L^2$, $R^4$, $R^5$, Ring A, z4, z5, and $Y^1$ are as described herein.

In embodiments, the compound has the formula:

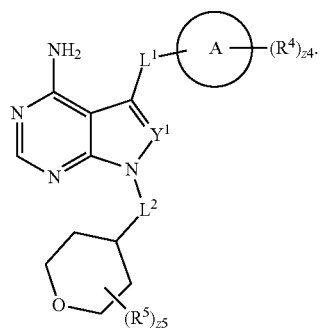

$L^1$, $L^2$, $R^4$, $R^5$, Ring A, z4, z5, and $Y^1$ are as described herein.

In embodiments, the compound has the formula:

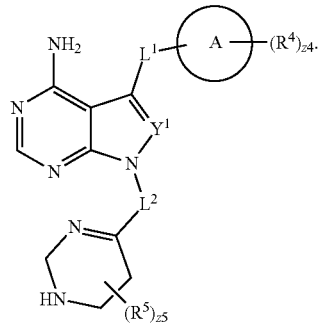

$L^1$, $L^2$, $R^4$, $R^5$, Ring A, z4, z5, and $Y^1$ are as described herein.

In embodiments, the compound has the formula:

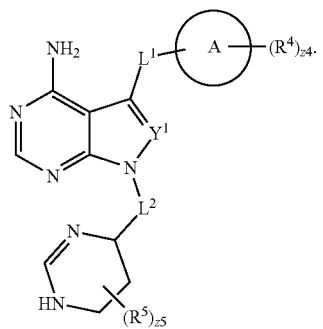

$L^1$, $L^2$, $R^4$, $R^5$, Ring A, z4, z5, and $Y^1$ are as described herein.

In embodiments, the compound has the formula:

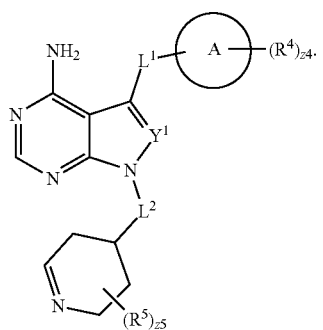

$L^1$, $L^2$, $R^4$, $R^5$, Ring A, z4, z5, and $Y^1$ are as described herein.

In embodiments, the compound has the formula:

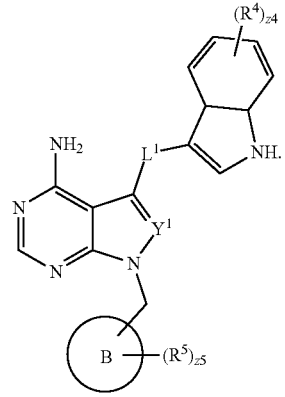

$L^1$, $R^4$, $R^5$, Ring B, z4, z5, and $Y^1$ are as described herein.

In embodiments, the compound has the formula:

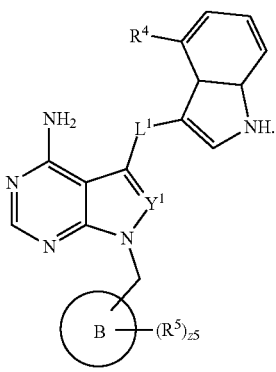

$L^1$, $R^4$, $R^5$, Ring B, z5, and $Y^1$ are as described herein.

In embodiments, the compound has the formula:

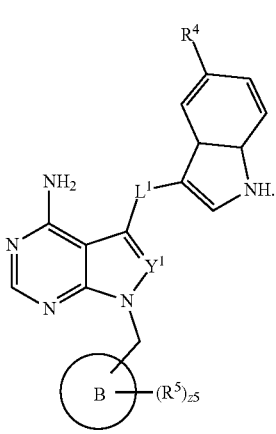

$L^1$, $R^4$, $R^5$, Ring B, z5, and $Y^1$ are as described herein.

In embodiments, the compound has the formula:

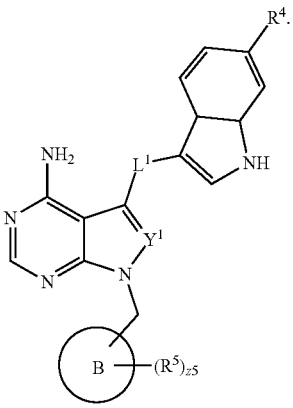

$L^1$, $R^4$, $R^5$, Ring B, z5, and $Y^1$ are as described herein.

In embodiments, the compound has the formula:

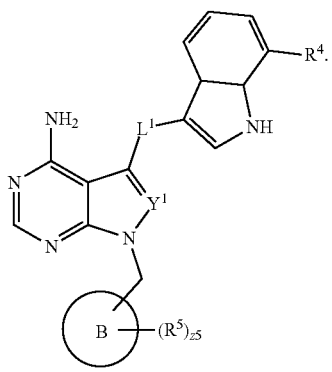

$L^1$, $R^4$, $R^5$, Ring B, z5, and $Y^1$ are as described herein.

In embodiments, the compound has the formula:

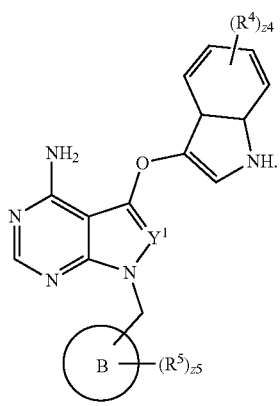

$R^4$, $R^5$, Ring B, z4, z5, and $Y^1$ are as described herein.

In embodiments, the compound has the formula:

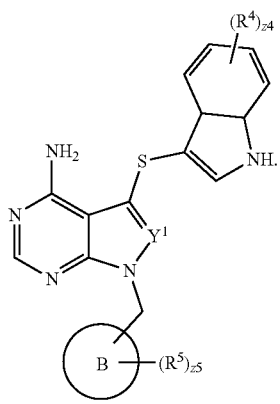

$R^4$, $R^5$, Ring B, z4, z5, and $Y^1$ are as described herein.

In embodiments, the compound has the formula:

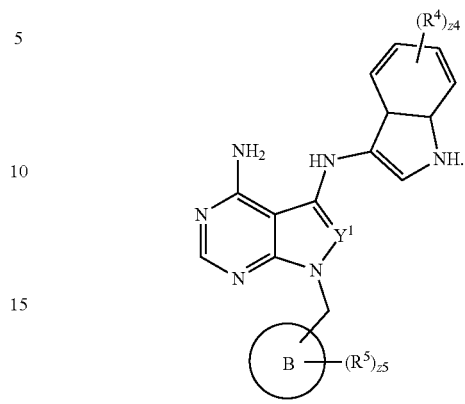

$R^4$, $R^5$, Ring B, z4, z5, and $Y^1$ are as described herein.

In embodiments, the compound has the formula:

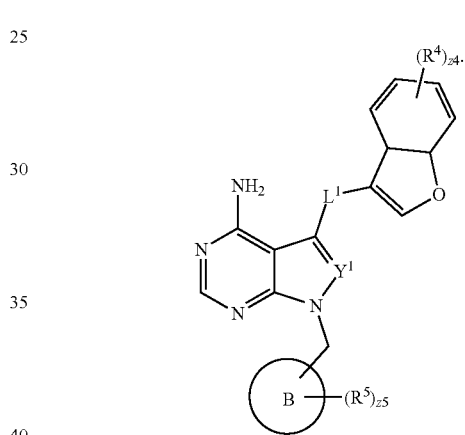

$L^1$, $R^4$, $R^5$, Ring B, z4, z5, and $Y^1$ are as described herein.

In embodiments, the compound has the formula:

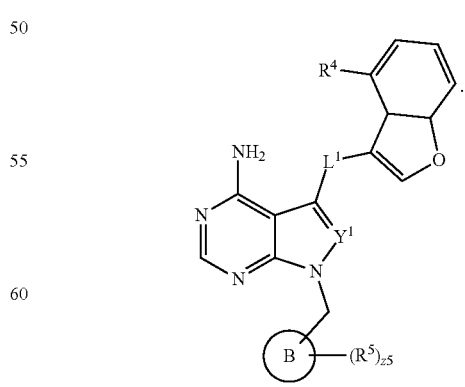

$L^1$, $R^4$, $R^5$, Ring B, z5, and $Y^1$ are as described herein.

In embodiments, the compound has the formula:

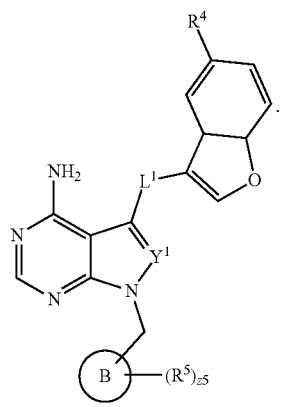

L¹, R⁴, R⁵, Ring B, z5, and Y¹ are as described herein.
In embodiments, the compound has the formula:

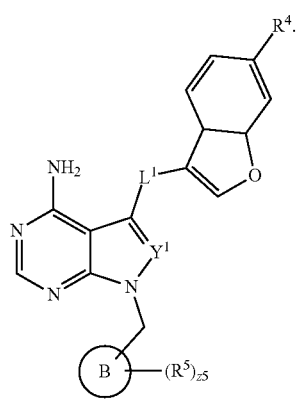

L¹, R⁴, R⁵, Ring B, z5, and Y¹ are as described herein.
In embodiments, the compound has the formula:

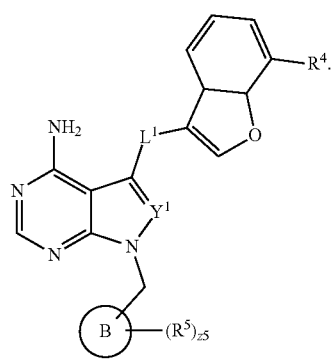

L¹, R⁴, R⁵, Ring B, z5, and Y¹ are as described herein.

In embodiments, the compound has the formula:

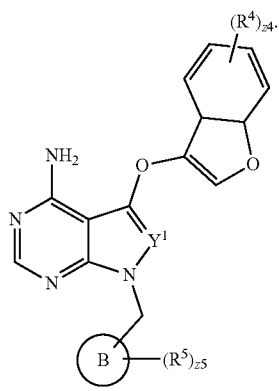

R⁴, R⁵, Ring B, z4, z5, and Y¹ are as described herein.
In embodiments, the compound has the formula:

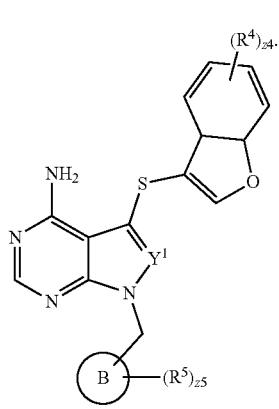

R⁴, R⁵, Ring B, z4, z5, and Y¹ are as described herein.
In embodiments, the compound has the formula:

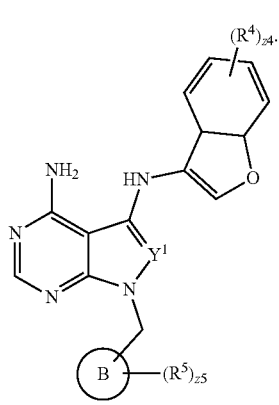

R⁴, R⁵, Ring B, z4, z5, and Y¹ are as described herein.

In embodiments, the compound has the formula:

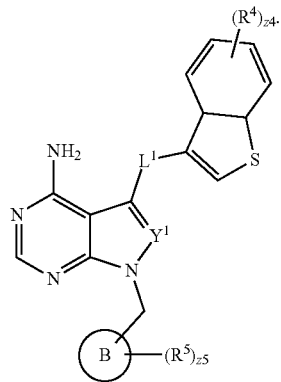

$L^1$, $R^4$, $R^5$, Ring B, z4, z5, and $Y^1$ are as described herein.

In embodiments, the compound has the formula:

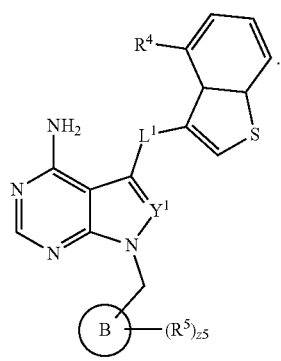

$L^1$, $R^4$, $R^5$, Ring B, z5, and $Y^1$ are as described herein.

In embodiments, the compound has the formula:

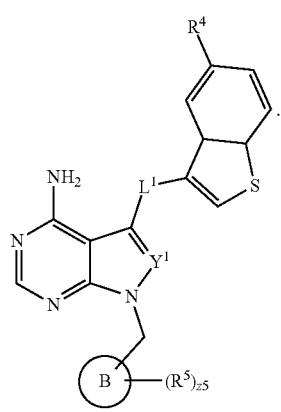

$L^1$, $R^4$, $R^5$, Ring B, z5, and $Y^1$ are as described herein.

In embodiments, the compound has the formula:

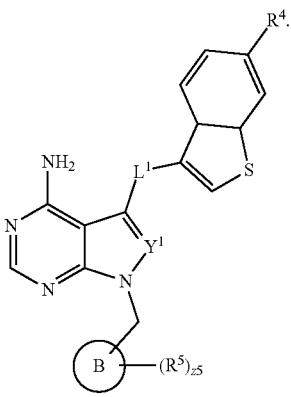

$L^1$, $R^4$, $R^5$, Ring B, z5, and $Y^1$ are as described herein.

In embodiments, the compound has the formula:

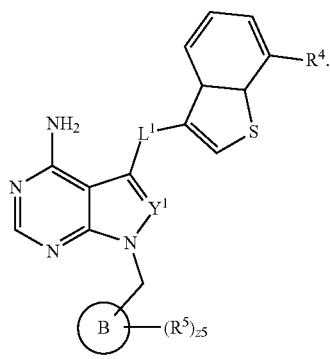

$L^1$, $R^4$, $R^5$, Ring B, z5, and $Y^1$ are as described herein.

In embodiments, the compound has the formula:

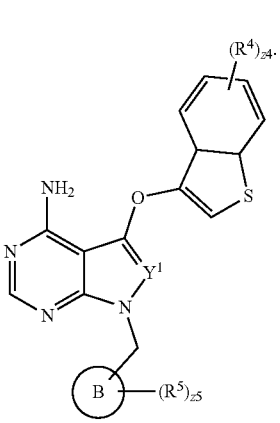

$R^4$, $R^5$, Ring B, z4, z5, and $Y^1$ are as described herein.

In embodiments, the compound has the formula:

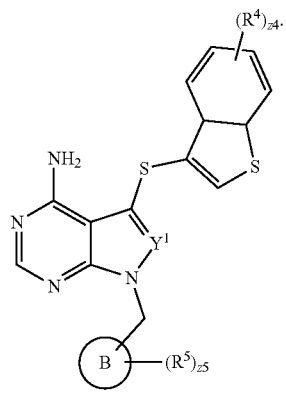

$R^4$, $R^5$, Ring B, z4, z5, and $Y^1$ are as described herein.
In embodiments, the compound has the formula:

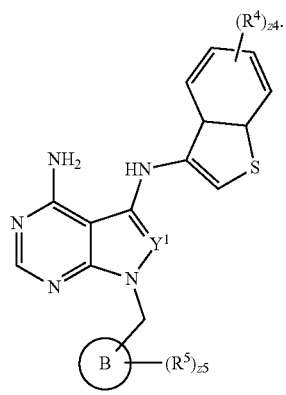

$R^4$, $R^5$, Ring B, z4, z5, and $Y^1$ are as described herein.
In embodiments, the compound has the formula:

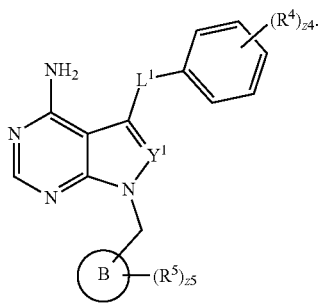

$L^1$, $R^4$, $R^5$, Ring B, z4, z5, and $Y^1$ are as described herein.

In embodiments, the compound has the formula:

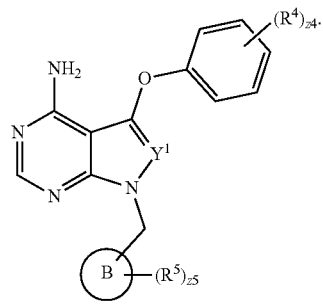

$R^4$, $R^5$, Ring B, z4, z5, and $Y^1$ are as described herein.
In embodiments, the compound has the formula:

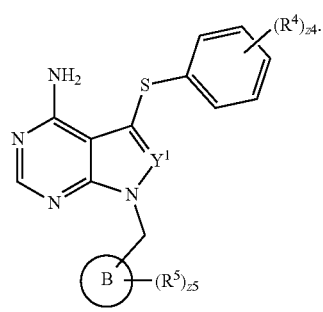

$R^4$, $R^5$, Ring B, z4, z5, and $Y^1$ are as described herein.
In embodiments, the compound has the formula:

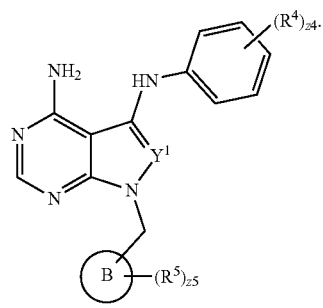

$R^4$, $R^5$, Ring B, z4, z5, and $Y^1$ are as described herein.
In embodiments, the compound has the formula:

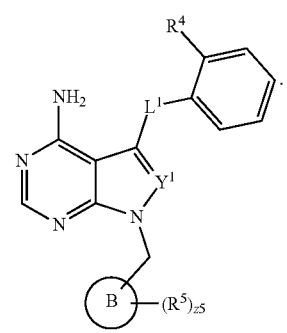

$L^1$, $R^4$, $R^5$, Ring B, z5, and $Y^1$ are as described herein.

In embodiments, the compound has the formula:

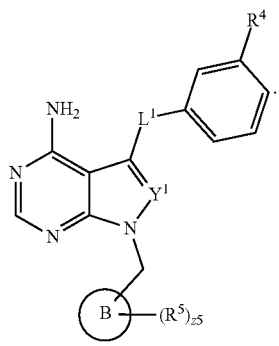

$L^1$, $R^4$, $R^5$, Ring B, z5, and $Y^1$ are as described herein.
In embodiments, the compound has the formula:

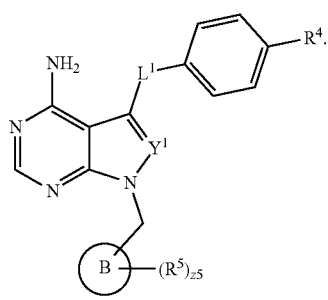

$L^1$, $R^4$, $R^5$, Ring B, z5, and $Y^1$ are as described herein.
In embodiments, the compound has the formula:

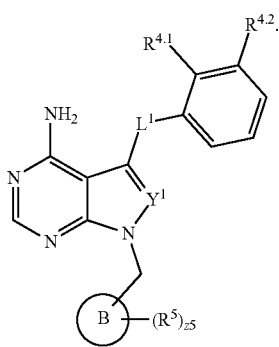

$L^1$, $R^{4.1}$, $R^{4.2}$, $R^5$, Ring B, z5, and $Y^1$ are as described herein.
In embodiments, the compound has the formula:

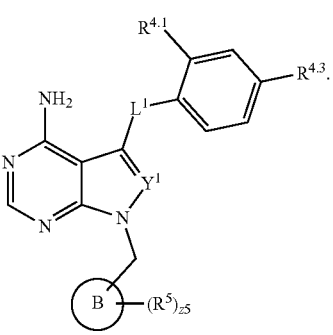

$L^1$, $R^{4.1}$, $R^{4.3}$, $R^5$, Ring B, z5, and $Y^1$ are as described herein.

In embodiments, the compound has the formula:

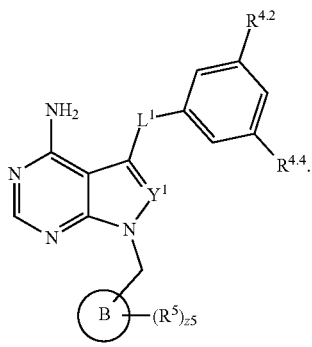

$L^1$, $R^{4.2}$, $R^{4.4}$, $R^5$, Ring B, z5, and $Y^1$ are as described herein.
In embodiments, the compound has the formula:

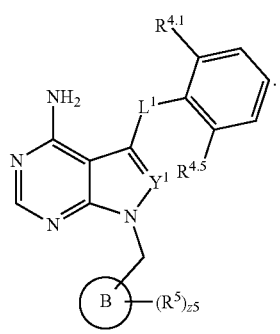

$L^1$, $R^{4.1}$, $R^{4.5}$, $R^5$, Ring B, z5, and $Y^1$ are as described herein.
In embodiments, the compound has the formula:

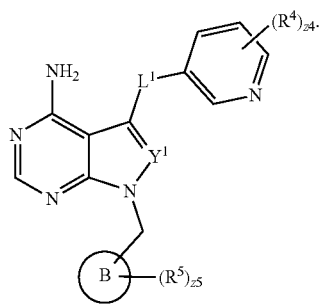

$L^1$, $R^4$, $R^5$, Ring B, z4, z5, and $Y^1$ are as described herein.
In embodiments, the compound has the formula:

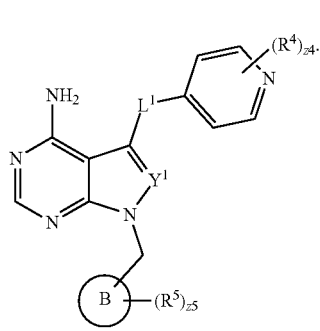

$L^1$, $R^4$, $R^5$, Ring B, z4, z5, and $Y^1$ are as described herein.

In embodiments, the compound has the formula:

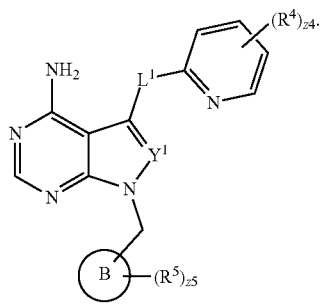

$L^1$, $R^4$, $R^5$, Ring B, z4, z5, and $Y^1$ are as described herein.

In embodiments, the compound has the formula:

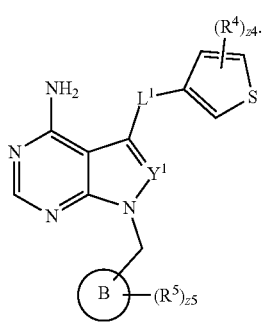

$L^1$, $R^4$, $R^5$, Ring B, z4, z5, and $Y^1$ are as described herein.

In embodiments, the compound has the formula:

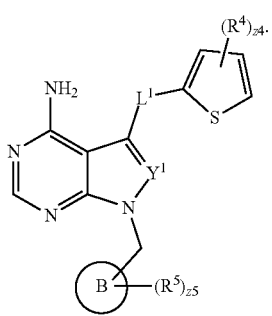

$L^1$, $R^4$, $R^5$, Ring B, z4, z5, and $Y^1$ are as described herein.

In embodiments, the compound has the formula:

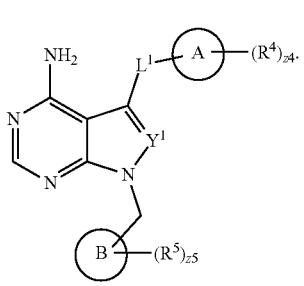

$L^1$, $R^4$, $R^5$, Ring A, Ring B, z4, z5, and $Y^1$ are as described herein.

In embodiments, the compound has the formula:

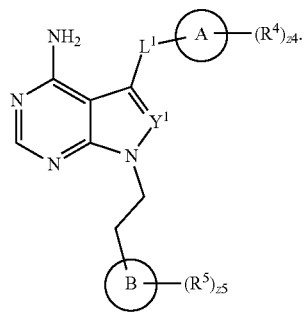

$L^1$, $R^4$, $R^5$, Ring A, Ring B, z4, z5, and $Y^1$ are as described herein.

In embodiments, the compound has the formula:

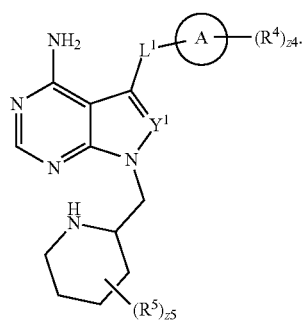

$L^1$, $R^4$, $R^5$, Ring A, z4, z5, and $Y^1$ are as described herein.

In embodiments, the compound has the formula:

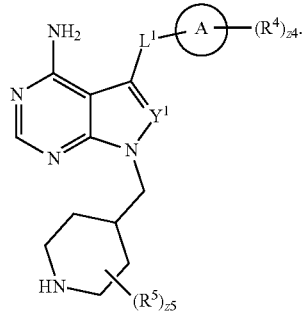

$L^1$, $R^4$, $R^5$, Ring A, z4, z5, and $Y^1$ are as described herein.

In embodiments, the compound has the formula:

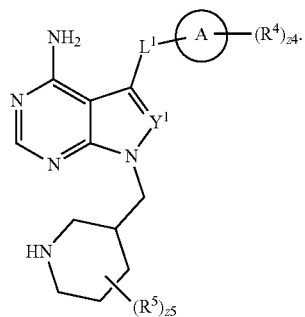

$L^1$, $R^4$, $R^5$, Ring A, z4, z5, and $Y^1$ are as described herein.

In embodiments, the compound has the formula:

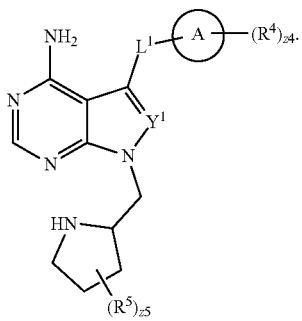

$L^1$, $R^4$, $R^5$, Ring A, z4, z5, and $Y^1$ are as described herein.

In embodiments, the compound has the formula:

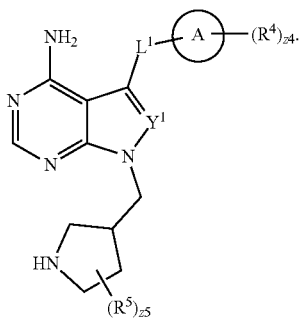

$L^1$, $R^4$, $R^5$, Ring A, z4, z5, and $Y^1$ are as described herein.

In embodiments, the compound has the formula:

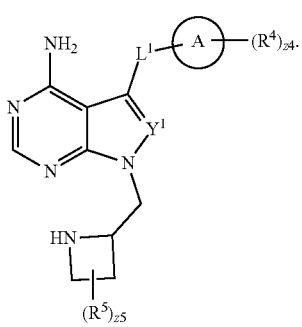

$L^1$, $R^4$, $R^5$, Ring A, z4, z5, and $Y^1$ are as described herein.

In embodiments, the compound has the formula:

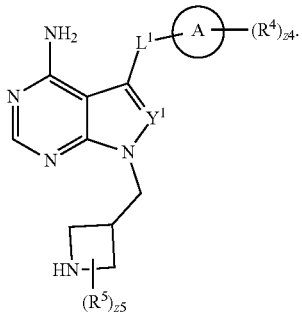

$L^1$, $R^4$, $R^5$, Ring A, z4, z5, and $Y^1$ are as described herein.

In embodiments, the compound has the formula:

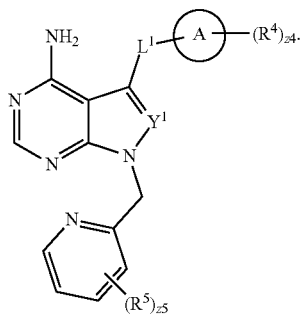

$L^1$, $R^4$, $R^5$, Ring A, z4, z5, and $Y^1$ are as described herein.

In embodiments, the compound has the formula:

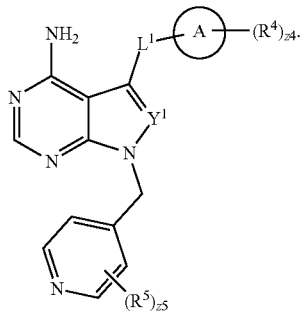

$L^1$, $R^4$, $R^5$, Ring A, z4, z5, and $Y^1$ are as described herein.

In embodiments, the compound has the formula:

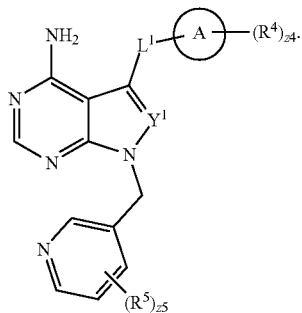

$L^1$, $R^4$, $R^5$, Ring A, z4, z5, and $Y^1$ are as described herein.

205

In embodiments, the compound has the formula:

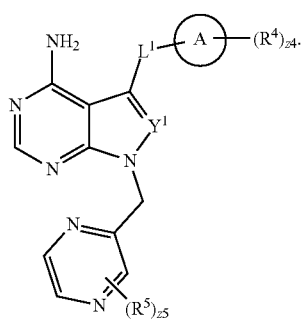

$L^1$, $R^4$, $R^5$, Ring A, z4, z5, and $Y^1$ are as described herein.

In embodiments, the compound has the formula:

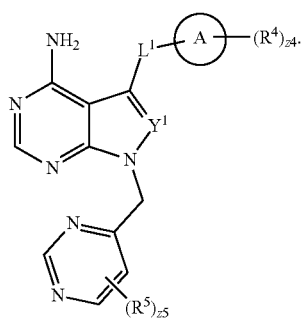

$L^1$, $R^4$, $R^5$, Ring A, z4, z5, and $Y^1$ are as described herein.

In embodiments, the compound has the formula:

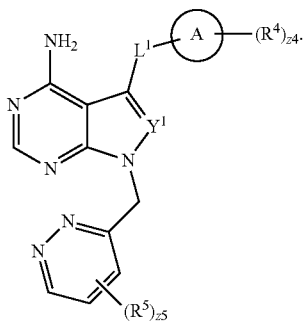

$L^1$, $R^4$, $R^5$, Ring A, z4, z5, and $Y^1$ are as described herein.

206

In embodiments, the compound has the formula:

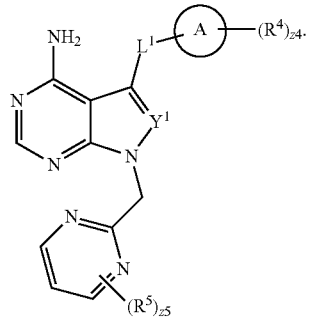

$L^1$, $R^4$, $R^5$, Ring A, z4, z5, and $Y^1$ are as described herein.

In embodiments, the compound has the formula:

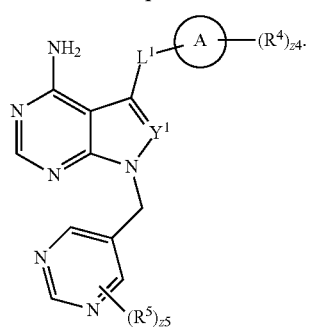

$L^1$, $R^4$, $R^5$, Ring A, z4, z5, and $Y^1$ are as described herein.

In embodiments, the compound has the formula:

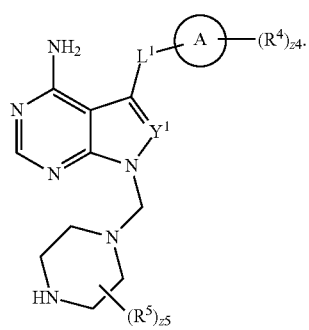

$L^1$, $R^4$, $R^5$, Ring A, z4, z5, and $Y^1$ are as described herein.

In embodiments, the compound has the formula:

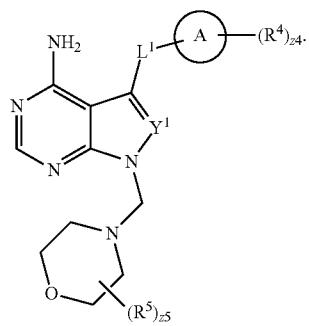

$L^1$, $R^4$, $R^5$, Ring A, z4, z5, and $Y^1$ are as described herein.

In embodiments, the compound has the formula:

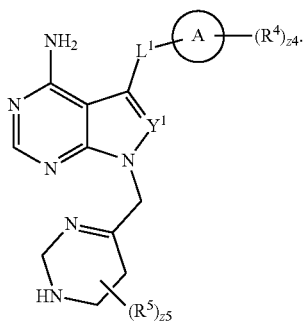

$L^1$, $R^4$, $R^5$, Ring A, z4, z5, and $Y^1$ are as described herein.
In embodiments, the compound has the formula:

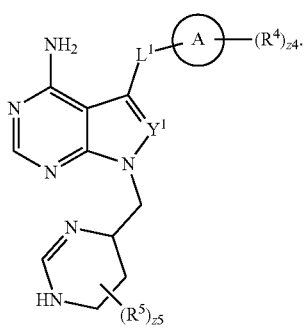

$L^1$, $R^4$, $R^5$, Ring A, z4, z5, and $Y^1$ are as described herein.
In embodiments, the compound has the formula:

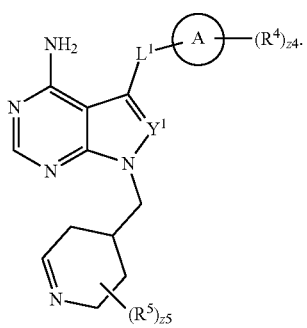

$L^1$, $R^4$, $R^5$, Ring A, z4, z5, and $Y^1$ are as described herein.
In embodiments, the compound has the formula:

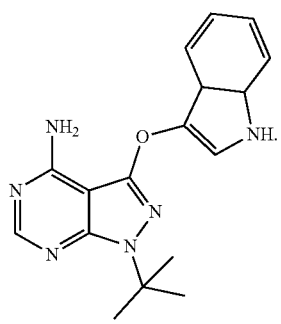

In embodiments, the compound has the formula:

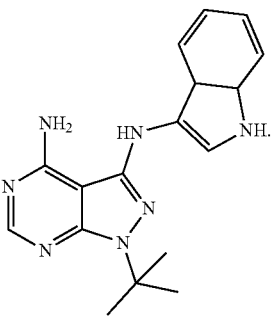 [SMILES: CC(C)(C)n1nc(NC2=CNC3C=CC=CC23)c2c(N)ncnc21]

In embodiments, the compound has the formula:

In embodiments, the compound has the formula:

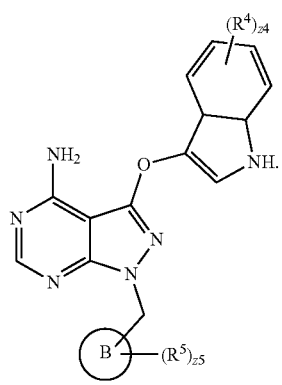

$R^4$, $R^5$, Ring B, z4, and z5 are as described herein. In embodiments, the compound has the formula:

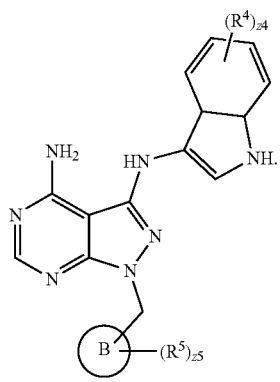

R⁴, R⁵, Ring B, z4, and z5 are as described herein. In embodiments, the compound has the formula:

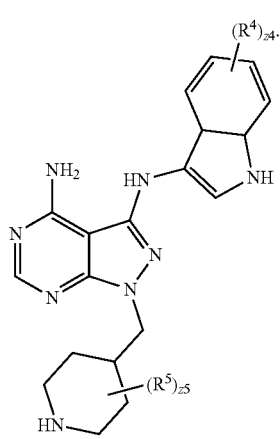

R⁴, R⁵, z4, and z5 are as described herein. In embodiments, the compound has the formula:

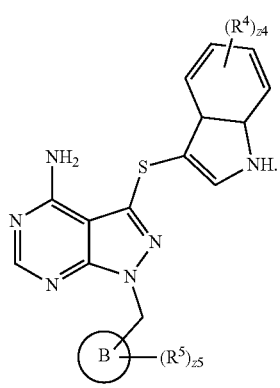

R⁴, R⁵, Ring B, z4, and z5 are as described herein. In embodiments, the compound has the formula:

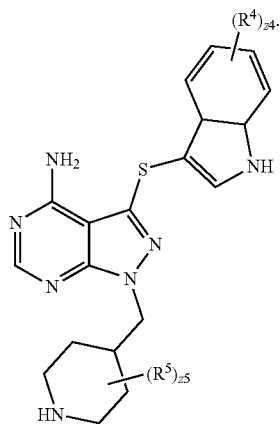

R⁴, R⁵, z4, and z5 are as described herein. In embodiments, the compound has the formula:

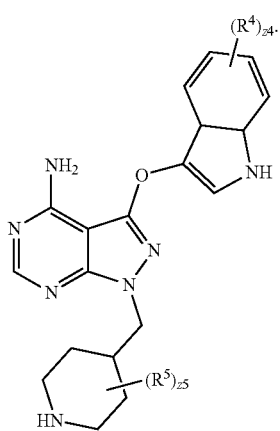

R⁴, R⁵, z4, and z5 are as described herein. In embodiments, the compound has the formula:

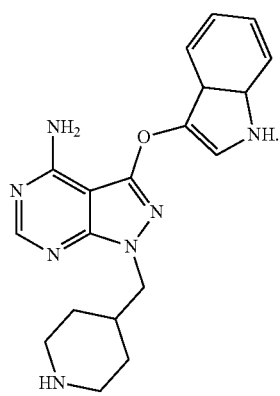 [SMILES: Nc1ncnc2c1c(OC1=CNC3C=CC=CC13)nn2CC1CCNCC1]

In embodiments, the compound has the formula:

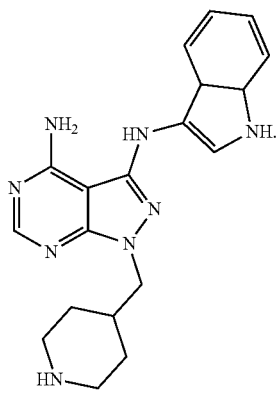

In embodiments, the compound has the formula:

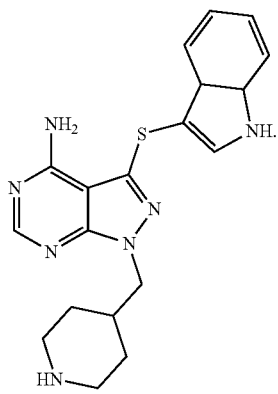

In an aspect is provided a compound having the formula:

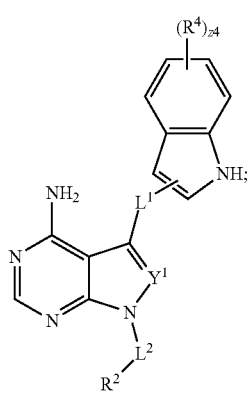 (III)

$Y^1$, $R^2$, $R^3$, $R^4$, $L^2$, z4 are as described herein. $L^1$ is —O—, —S—, —N($R^3$)—, or substituted or unsubstituted $C_1$-$C_3$ alkylene. In embodiments, $L^1$ is substituted or unsubstituted $C_1$-$C_3$ alkylene (e.g., $C_1$-$C_2$ alkylene, $C_2$-$C_3$ alkylene, n-propylene, isopropylene, ethylene, or methylene). In embodiments, $L^1$ is unsubstituted $C_1$-$C_3$ alkylene (e.g., $C_1$-$C_2$ alkylene, $C_2$-$C_3$ alkylene, n-propylene, isopropylene, ethylene, or methylene). In embodiments, $R^2$ is substituted or unsubstituted alkyl. In embodiments, $R^2$ is substituted alkyl. In embodiments, $R^2$ is unsubstituted alkyl. In embodiments, $R^2$ is substituted or unsubstituted $C_1$-$C_8$ alkyl. In embodiments, $R^2$ is substituted $C_1$-$C_8$ alkyl. In embodiments, $R^2$ is unsubstituted $C_1$-$C_8$ alkyl. In embodiments, $R^2$ is substituted or unsubstituted $C_1$-$C_4$ alkyl. In embodiments, $R^2$ is substituted $C_1$-$C_4$ alkyl. In embodiments, $R^2$ is unsubstituted $C_1$-$C_4$ alkyl. In embodiments, $R^2$ is $R^{23}$-substituted or unsubstituted alkyl. In embodiments, $R^2$ is $R^{23}$-substituted or unsubstituted $C_1$-$C_8$ alkyl. In embodiments, $R^2$ is hydrogen. In embodiments, $R^2$ is unsubstituted methyl. In embodiments, $R^2$ is unsubstituted ethyl. In embodiments, $R^2$ is unsubstituted n-propyl. In embodiments, $R^2$ is unsubstituted isopropyl. In embodiments, $R^2$ is unsubstituted n-butyl. In embodiments, $R^2$ is unsubstituted isobutyl. In embodiments, $R^2$ is unsubstituted tert-butyl. In embodiments, $R^2$ is unsubstituted pentyl. In embodiments, the compound of formula (III) is

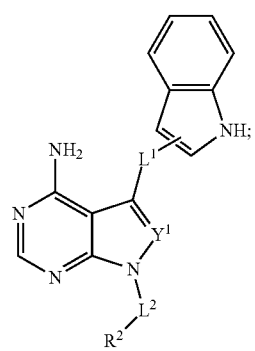

$Y^1$, $R^2$, $L^1$, and $L^2$ are as described herein. In embodiments, the compound of formula (III) is

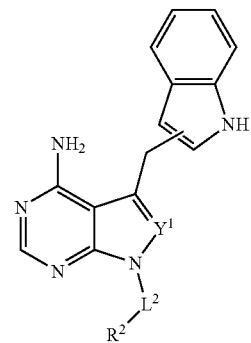

$Y^1$, $R^2$, and $L^2$ are as described herein. In embodiments, the compound of formula (III) is

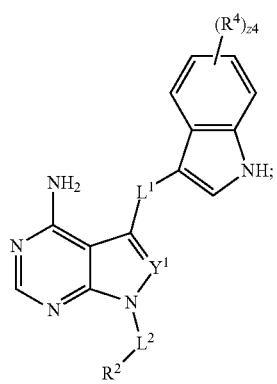

$Y^1$, $R^2$, $R^4$, z4, $L^1$, and $L^2$ are as described herein. In embodiments, the compound of formula (III) is

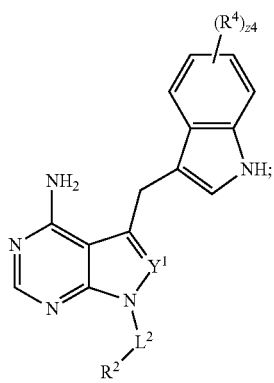

$Y^1$, $R^2$, $R^4$, z4, and $L^2$ are as described herein. In embodiments, the compound of formula (III) is

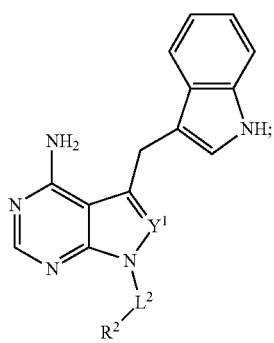

$Y^1$, $R^2$, and $L^2$ are as described herein. In embodiments, the compound of formula (III) is

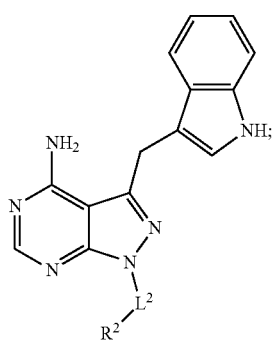

$R^2$ and $L^2$ are as described herein. In embodiments, the compound of formula (III) is

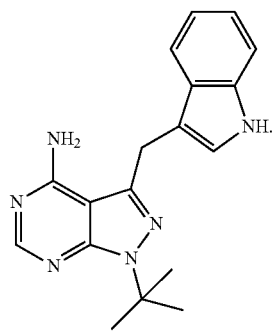 [SMILES: CC(C)(C)n1nc(Cc2c[nH]c3ccccc23)c2c(N)ncnc21]

In embodiments, the compound of formula (III) is

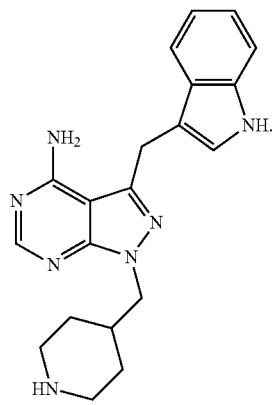 [SMILES: Nc1ncnc2c1c(Cc1c[nH]c3ccccc13)nn2CC1CCNCC1]

In embodiments, the compound has the formula:

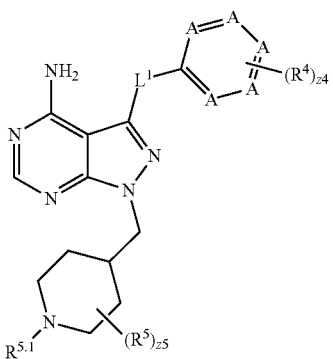

wherein, A is —C($R^4$)= or —N=; $R^4$ is independently substituted or unsubstituted alkyl, substituted or unsubstituted cycloalkyl, halogen, —CF$_3$, —OCH$_3$, —CN, —SO$_2$CH$_3$, —SO$_2$NHR$^{4B}$, —OCF$_3$; $R^5$ is independently oxo, halogen, —COOH, or —C(O)NR$^{5A}$R$^{5B}$; $R^{5.1}$ is hydrogen, substituted or unsubstituted alkyl, substituted or unsubstituted cycloalkyl, —C(O)NR$^{5A}$R$^{5B}$,

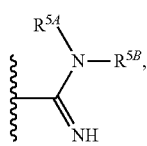

—C(N)-(substituted or unsubstituted alkyl), —C(N)-(substituted or unsubstituted cycloalkyl), —C(O)-(substituted or unsubstituted alkyl), or —C(O)-(substituted or unsubstituted cycloalkyl); z4 and z5 are independently an integer from 0 to 2; and $R^{5A}$ and $R^{5B}$ are independently hydrogen or substituted or unsubstituted alkyl.

In embodiments, the compound has the formula:

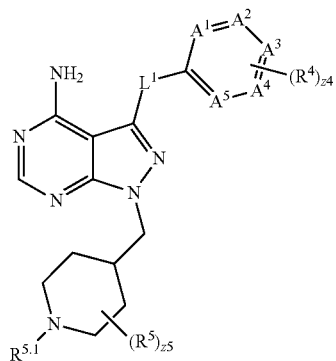

wherein, $A^1$, $A^2$, $A^3$, $A^4$, and $A^5$, are each independently —C($R^4$)= or —N=; and wherein $L^1$, $R^4$, z4, $R^5$, z5, and $R^{5.1}$ are as described herein.

In embodiments, the compound has the formula:

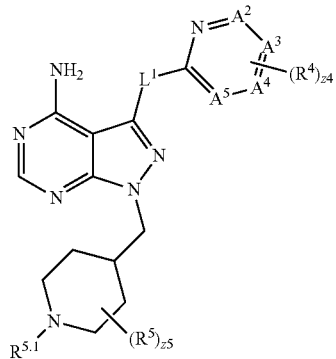

wherein, $A^2$, $A^3$, $A^4$, and $A^5$, are each independently —C($R^4$)= or —N=; and wherein $L^1$, $R^4$, z4, $R^5$, z5, and $R^{5.1}$ are as described herein.

In embodiments, the compound has the formula:

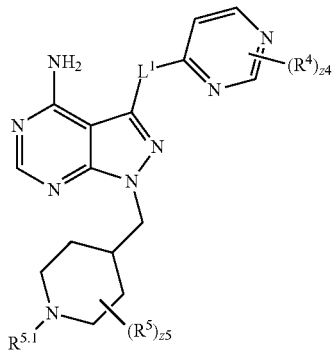

wherein, $A^1$, $A^2$, $A^3$, $A^4$, and $A^5$, are each independently —C($R^4$)= or —N=; and wherein $L^1$, $R^4$, z4, $R^5$, z5, and $R^{5.1}$ are as described herein.

In embodiments, the compound has the formula:

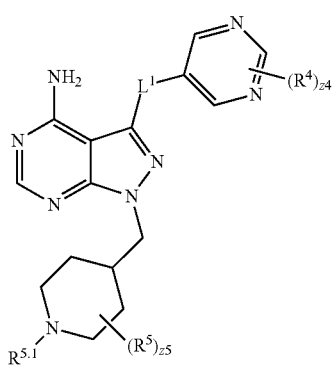

wherein, $A^1$, $A^2$, $A^3$, $A^4$, and $A^5$, are each independently —C($R^4$)= or —N=; and wherein $L^1$, $R^4$, z4, $R^5$, z5, and $R^{5.1}$ are as described herein.

In embodiments, the compound has the formula:

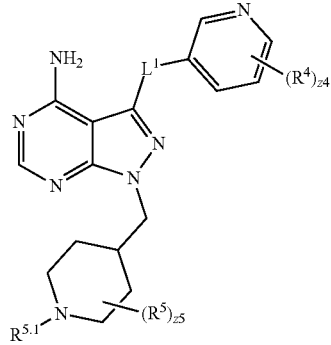

wherein, $A^1$, $A^2$, $A^3$, $A^4$, and $A^5$, are each independently —C($R^4$)= or —N=; and wherein $L^1$, $R^4$, z4, $R^5$, z5, and $R^{5.1}$ are as described herein.

In embodiments, the compound has the formula:

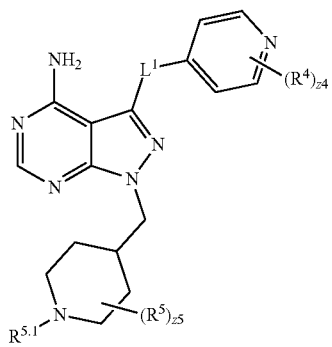

wherein, $A^1$, $A^2$, $A^3$, $A^4$, and $A^5$, are each independently —C($R^4$)═ or —N═; and wherein $L^1$, $R^4$, z4, $R^5$, z5, and $R^{5.1}$ are as described herein.

In embodiments, the compound has the formula:

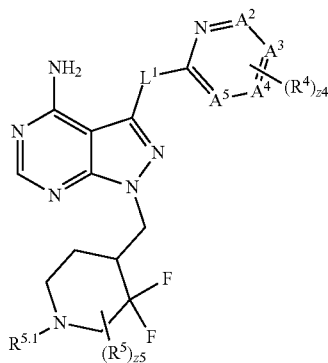

wherein, $A^2$, $A^3$, $A^4$, and $A^5$, are each independently —C($R^4$)═ or —N═; and wherein $L^1$, $R^4$, z4, $R^5$, z5, and $R^{5.1}$ are as described herein.

In embodiments, A is —C($R^4$)═. In embodiments, A is —N═. In embodiments, A is —CH═.

In embodiments, $R^4$ is independently substituted or unsubstituted alkyl. In embodiments, $R^4$ is $R^{29}$-substituted or unsubstituted alkyl (e.g., $C_1$-$C_8$ alkyl, $C_1$-$C_6$ alkyl, or $C_1$-$C_4$ alkyl). In embodiments, $R^4$ is $R^{29}$-substituted alkyl (e.g., $C_1$-$C_8$ alkyl, $C_1$-$C_6$ alkyl, or $C_1$-$C_4$ alkyl). In embodiments, $R^4$ is an unsubstituted alkyl (e.g., $C_1$-$C_8$ alkyl, $C_1$-$C_6$ alkyl, or $C_1$-$C_4$ alkyl). In embodiments, $R^4$ is independently substituted or unsubstituted cycloalkyl. In embodiments, $R^4$ is $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^4$ is $R^{29}$-substituted cycloalkyl (e.g., $C_3$-$C_8$ cycloalkyl, $C_3$-$C_6$ cycloalkyl, or $C_5$-$C_6$ cycloalkyl). In embodiments, $R^4$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^4$ is unsubstituted cyclopropyl. In embodiments, $R^4$ is $R^{29}$-substituted cyclopropyl. In embodiments, $R^4$ is independently halogen. In embodiments, $R^4$ is independently —CF$_3$. In embodiments, $R^4$ is independently —OCH$_3$. In embodiments, $R^4$ is independently —CN. In embodiments, $R^4$ is independently —SO$_2$CH$_3$. In embodiments, $R^4$ is independently —SO$_2$NHR$^{4B}$. In embodiments, $R^4$ is independently —OCF$_3$. In embodiments, $R^4$ is —CX$^4_3$, —CHX$^4_2$, —CH$_2$X$^4$, —OCH$_2$X$^4$, —OCX$^4_3$, or —OCHX$^4_2$. In embodiments, $R^4$ is —CF$_3$, —CHF$_2$, —CH$_2$F, —OCH$_2$F, —OCF$_3$, or —OCHF$_2$. In embodiments, $R^4$ is unsubstituted cyclopropyl. In embodiments, $R^4$ is unsubstituted methyl. In embodiments, $R^4$ is —CF$_3$. In embodiments, $R^4$ is —CHF$_2$. In embodiments, $R^4$ is —CH$_2$F. In embodiments, $R^4$ is —OCH$_2$F. In embodiments, $R^4$ is —OCF$_3$. In embodiments, $R^4$ is —OCHF$_2$.

In embodiments, $R^5$ is independently oxo. In embodiments, $R^5$ is independently halogen. In embodiments, $R^5$ is independently —F. In embodiments, $R^5$ is independently —Cl. In embodiments, $R^5$ is independently —COOH. In embodiments, $R^5$ is independently —C(O)NR$^{5A}$R$^{5B}$.

In embodiments, $R^{5.1}$ is hydrogen. In embodiments, $R^{5.1}$ is substituted or unsubstituted alkyl. In embodiments, $R^{5.1}$ is independently substituted or unsubstituted alkyl. In embodiments, $R^{5.1}$ is $R^{32}$-substituted or unsubstituted alkyl (e.g., $C_1$-$C_8$ alkyl, $C_1$-$C_6$ alkyl, or $C_1$-$C_4$ alkyl). In embodiments, $R^{5.1}$ is $R^{32}$-substituted alkyl (e.g., $C_1$-$C_8$ alkyl, $C_1$-$C_6$ alkyl, or $C_1$-$C_4$ alkyl). In embodiments, $R^{5.1}$ is an unsubstituted alkyl (e.g., $C_1$-$C_8$ alkyl, $C_1$-$C_6$ alkyl, or $C_1$-$C_4$ alkyl).

In embodiments, $R^{5.1}$ is independently substituted or unsubstituted cycloalkyl. In embodiments, $R^{5.1}$ is $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5.1}$ is $R^{32}$-substituted cycloalkyl (e.g., $C_3$-$C_8$ cycloalkyl, $C_3$-$C_6$ cycloalkyl, or $C_5$-$C_6$ cycloalkyl). In embodiments, $R^{5.1}$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5.1}$ is unsubstituted cyclopropyl. In embodiments, $R^{5.1}$ is $R^{32}$-substituted cyclopropyl. In embodiments, $R^{5.1}$ is —C(O)NR$^{5A}$R$^{5B}$. In embodiments, $R^{5.1}$ is

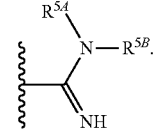

In embodiments, $R^{5.1}$ is

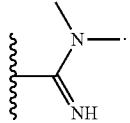

In embodiments, $R^{5.1}$ is

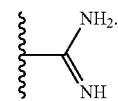

In embodiments, $R^{5.1}$ is

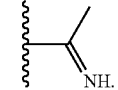

In embodiments, $R^{5.1}$ is

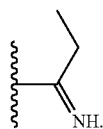

In embodiments, $R^{5.1}$

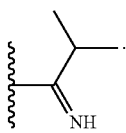 [SMILES: *C(=N)C(C)C]

In embodiments, $R^{5.1}$ is

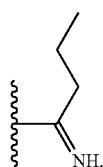 [SMILES: *C(=N)CCC]

In embodiments, $R^{5.1}$ is

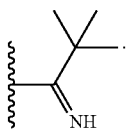 [SMILES: *C(=N)C(C)(C)C]

In embodiments, $R^{5.1}$ is —C(N)-(substituted or unsubstituted alkyl). In embodiments, $R^{5.1}$ is —C(N)—($C_1$-$C_8$ alkyl). In embodiments, $R^{5.1}$ is —C(N)—($C_1$-$C_6$ alkyl). In embodiments, $R^{5.1}$ is —C(N)—($C_1$-$C_4$ alkyl). In embodiments, $R^{5.1}$ is —C(N)—($R^{32}$-substituted or unsubstituted alkyl). In embodiments, $R^{5.1}$ is —C(N)-(unsubstituted alkyl). In embodiments, $R^{51}$ is —C(N)—($R^{32}$-substituted alkyl).

In embodiments, $R^{5.1}$ is —C(N)-(substituted or unsubstituted cycloalkyl). In embodiments, $R^{5.1}$ is —C(N)—($C_3$-$C_8$ cycloalkyl). In embodiments, $R^{5.1}$ is —C(N)—($C_3$-$C_6$ cycloalkyl). In embodiments, $R^{5.1}$ is —C(N)—($C_5$-$C_6$ cycloalkyl). In embodiments, $R^{5.1}$ is —C(N)—($R^{32}$-substituted or unsubstituted cycloalkyl). In embodiments, $R^{5.1}$ is —C(N)-(unsubstituted cycloalkyl). In embodiments, $R^{5.1}$ is —C(N)—($R^{32}$-substituted cycloalkyl).

In embodiments, $R^{5.1}$ is —C(O)-(substituted or unsubstituted alkyl). In embodiments, $R^{5.1}$ is —C(O)-(substituted or unsubstituted $C_1$-$C_8$ alkyl). In embodiments, $R^{5.1}$ is —C(O)-(substituted or unsubstituted $C_1$-$C_6$ alkyl). In embodiments, $R^{5.1}$ is —C(O)-(substituted or unsubstituted $C_1$-$C_4$ alkyl). In embodiments, $R^{5.1}$ is —C(O)—($R^{32}$-substituted or unsubstituted alkyl). In embodiments, $R^{5.1}$ is —C(O)-(unsubstituted alkyl). In embodiments, $R^{5.1}$ is —C(O)—($R^{32}$-substituted alkyl).

In embodiments, $R^{5.1}$ is —C(O)-(substituted or unsubstituted cycloalkyl). In embodiments, $R^{5.1}$ is —C(O)-(substituted or unsubstituted $C_3$-$C_8$ cycloalkyl). In embodiments, $R^{5.1}$ is —C(O)-(substituted or unsubstituted $C_3$-$C_6$ cycloalkyl). In embodiments, $R^{5.1}$ is —C(O)-(substituted or unsubstituted $C_5$-$C_6$ cycloalkyl). In embodiments, $R^{5.1}$ is —C(O)—($R^{32}$-substituted or unsubstituted cycloalkyl). In embodiments, $R^{5.1}$ is —C(O)-(unsubstituted cycloalkyl). In embodiments, $R^{5.1}$ is —C(O)—($R^{32}$-substituted cycloalkyl).

In embodiments, z4 and z5 are independently an integer from 0 to 2. In embodiments z4 is 0. In embodiments z4 is 1. In embodiments z4 is 2. In embodiments z5 is 0. In embodiments z5 is 1. In embodiments z5 is 2.

In embodiments, $R^{5A}$ is hydrogen or substituted or unsubstituted alkyl. In embodiments, $R^{5A}$ is independently substituted or unsubstituted alkyl. In embodiments, $R^{5A}$ is $R^{32A}$-substituted or unsubstituted alkyl (e.g., $C_1$-$C_8$ alkyl, $C_1$-$C_6$ alkyl, or $C_1$-$C_4$ alkyl). In embodiments, $R^{5A}$ is $R^{32A}$-substituted alkyl (e.g., $C_1$-$C_8$ alkyl, $C_1$-$C_6$ alkyl, or $C_1$-$C_4$ alkyl). In embodiments, $R^{5A}$ is an unsubstituted alkyl (e.g., $C_1$-$C_8$ alkyl, $C_1$-$C_6$ alkyl, or $C_1$-$C_4$ alkyl). In embodiments, $R^{5A}$ is hydrogen.

In embodiments, $R^{5B}$ is hydrogen or substituted or unsubstituted alkyl. In embodiments, $R^{5B}$ is independently substituted or unsubstituted alkyl. In embodiments, $R^{5B}$ is $R^{32B}$-substituted or unsubstituted alkyl (e.g., $C_1$-$C_8$ alkyl, $C_1$-$C_6$ alkyl, or $C_1$-$C_4$ alkyl). In embodiments, $R^{5B}$ is $R^{32B}$-substituted alkyl (e.g., $C_1$—C alkyl, $C_1$-$C_6$ alkyl, or $C_1$-$C_4$ alkyl). In embodiments, $R^{5B}$ is an unsubstituted alkyl (e.g., $C_1$-$C_8$ alkyl, $C_1$-$C_6$ alkyl, or $C_1$-$C_4$ alkyl). In embodiments, $R^{5B}$ is hydrogen.

In embodiments, the compound has the formula:

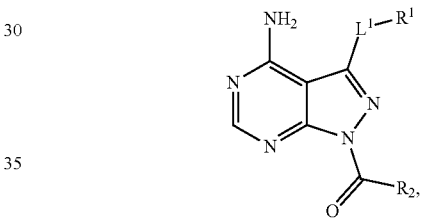

wherein $L^1$, $R^2$, and $R^1$ are as described herein.

In embodiments, the compound has the formula:

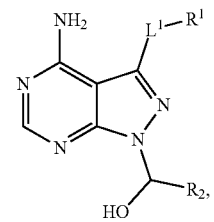

wherein $L^1$, $R^2$, and $R^1$ are as described herein.

In embodiments, the compound has the formula:

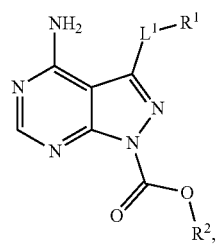

wherein $L^1$, $R^2$, and $R^1$ are as described herein.

In embodiments, the compound has the formula:

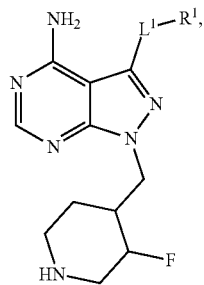

wherein L¹ and R¹ are as described herein. In embodiments, the compound has the formula:

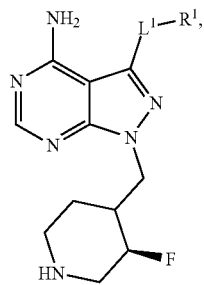

wherein L¹ and R¹ are as described herein. In embodiments, the compound has the formula:

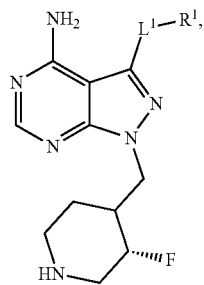

wherein L¹ and R¹ are as described herein.
In embodiments, the compound has the formula:

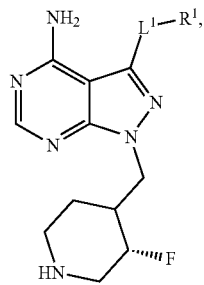

wherein L¹ and R¹ are as described herein.
In embodiments, the compound (e.g., described herein) inhibits TgCDPK1 more potently than other CDPK proteins (e.g., kinases containing intermediate sized gatekeeper residues (e.g., Ser, Thr, or Ala)). In embodiments, the potency of inhibition is measured by IC50 (e.g., in an in vivo assay, in a cell assay, in an in vitro assay). In embodiments, the potency of inhibition is measured by binding affinity (e.g., in an in vivo assay, in a cell assay, in an in vitro assay). In embodiments, the compound inhibits TgCDPK1 at least 1.1, 1.2, 1.3, 1.4, 1.5, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000, or 100000 times more potently than the compound inhibits other CDPK proteins (e.g., kinases containing intermediate sized gatekeeper residues (e.g., Ser, Thr, or Ala)).

In embodiments, the compound (e.g., described herein) inhibits a parasite CDPK1 (e.g., TgCDPK1) more potently than a homologous human protein (e.g., human kinases such as Src kinase). In embodiments, the potency of inhibition is measured by IC50 (e.g., in an in vivo assay, in a cell assay, in an in vitro assay). In embodiments, the potency of inhibition is measured by binding affinity (e.g., in an in vivo assay, in a cell assay, in an in vitro assay). In embodiments, the compound inhibits a parasite CDPK1 (e.g., TgCDPK1) at least 1.1, 1.2, 1.3, 1.4, 1.5, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000, or 100000 times more potently than the compound inhibits a homologous human protein (e.g., human kinases such as Src kinase).

In embodiments, the compound (e.g., described herein) has a half-life of at least 1, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1,000 hours. In embodiments, the compound (e.g., described herein) has a half-life of about 1, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 100000 hours. In embodiments, the compound (e.g., described herein) has a half-life of 1, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1,000 hours. In embodiments, the half-life is a plasma half-life. In embodiments, the half-life is a tissue half-life. In embodiments, the half-life is the half-life in a cell. In embodiments, the half-life is a blood half-life.

In embodiments, the compound (e.g., described herein) inhibits a parasite CDPK1 (e.g., TgCDPK1) with an IC50 (e.g., measured using a standard assay in the art or an assay described herein) of at least 1 µM, relative to the absence of the compound. In embodiments, the compound (e.g., described herein) inhibits a parasite CDPK1 (e.g., TgCDPK1) with an IC50 (e.g., measured using a standard assay in the art or an assay described herein) of at least 0.5 µM, relative to the absence of the compound. In embodiments, the compound (e.g., described herein) inhibits a parasite CDPK1 (e.g., TgCDPK1) with an IC50 (e.g., measured using a standard assay in the art or an assay described herein) of at least 0.2 µM, relative to the absence of the compound. In embodiments, the compound (e.g., described herein) inhibits a parasite CDPK1 (e.g., TgCDPK1) with an IC50 (e.g., measured using a standard assay in the art or an assay described herein) of at least 0.15 µM, relative to the absence of the compound. In embodiments, the compound (e.g., described herein) inhibits a parasite CDPK1 (e.g., TgCDPK1) with an IC50 (e.g., measured using a standard assay in the art or an assay described herein) of at least 0.0 µM, relative to the absence of the compound. In embodiments, the compound (e.g., described herein) inhibits a parasite CDPK1 (e.g., TgCDPK1) with an IC50 (e.g., measured using a standard assay in the art or an assay described herein) of at least 0.02 µM, relative to the absence of the compound. In embodiments, the compound (e.g., described herein) inhibits a parasite CDPK1 (e.g., TgCDPK1) with an IC50 (e.g., measured using a standard assay in the art or an assay described herein) of at least 0.03 µM, relative to the absence of the compound. In embodiments, the compound (e.g., described herein) inhibits a parasite CDPK1 (e.g., TgCDPK1) with an IC50 (e.g., measured using a standard assay in the art or an assay described herein) of at least 0.04 µM, relative to the absence of the compound. In embodiments, the compound (e.g., described herein) inhibits a parasite CDPK1 (e.g., TgCDPK1) with an IC50 (e.g., measured using a standard assay in the art or an assay described herein) of at least 0.05 µM, relative to the absence of the compound.

In embodiments, the compound (e.g., described herein) inhibits a parasite CDPK1 (e.g., TgCDPK1) with an IC50 (e.g., measured using a standard assay in the art or an assay described herein) of about 1 µM. In embodiments, the compound (e.g., described herein) inhibits a parasite CDPK1 (e.g., TgCDPK1) with an IC50 (e.g., measured using a standard assay in the art or an assay described herein) of about 0. µM. In embodiments, the compound (e.g., described herein) inhibits a parasite CDPK1 (e.g., TgCDPK1) with an IC50 (e.g., measured using a standard assay in the art or an assay described herein) of about 0. µM. In embodiments, the compound (e.g., described herein) inhibits a parasite CDPK1 (e.g., TgCDPK1) with an IC50 (e.g., measured using a standard assay in the art or an assay described herein) of about 0.1 µM. In embodiments, the compound (e.g., described herein) inhibits a parasite CDPK1 (e.g., TgCDPK1) with an IC50 (e.g., measured using a standard assay in the art or an assay described herein) of about 0.01M. In embodiments, the compound (e.g., described herein) inhibits a parasite CDPK1 (e.g., TgCDPK1) with an IC50 (e.g., measured using a standard assay in the art or an assay described herein) of about 0.02 µM. In embodiments, the compound (e.g., described herein) inhibits a parasite CDPK1 (e.g., TgCDPK1) with an IC50 (e.g., measured using a standard assay in the art or an assay described herein) of about 0.0 µM. In embodiments, the compound (e.g., described herein) inhibits a parasite CDPK1 (e.g., TgCDPK1) with an IC50 (e.g., measured using a standard assay in the art or an assay described herein) of about 0.04 µM. In embodiments, the compound (e.g., described herein) inhibits a parasite CDPK1 (e.g., TgCDPK1) with an IC50 (e.g., measured using a standard assay in the art or an assay described herein) of about 0.05 µM.

In embodiments, the compound (e.g., described herein) inhibits a parasite CDPK1 (e.g., TgCDPK1) with an IC50 (e.g., measured using a standard assay in the art or an assay described herein) is about 0.001 µM to about 1 µM. In embodiments, the compound (e.g., described herein) inhibits a parasite CDPK1 (e.g., TgCDPK1) with an IC50 (e.g., measured using a standard assay in the art or an assay described herein) is about 0.001 µM to about 0.7 µM. In embodiments, the compound (e.g., described herein) inhibits a parasite CDPK1 (e.g., TgCDPK1) with an IC50 (e.g., measured using a standard assay in the art or an assay described herein) is about 0.002 µM to about 0. µM. In embodiments, the compound (e.g., described herein) inhibits a parasite CDPK1 (e.g., TgCDPK1) with an IC50 (e.g., measured using a standard assay in the art or an assay described herein) is about 0.003 µM to about 0. µM. In embodiments, the compound (e.g., described herein) inhibits a parasite CDPK1 (e.g., TgCDPK1) with an IC50 (e.g., measured using a standard assay in the art or an assay described herein) is about 0.003 µM to about 0. µM. In embodiments, the compound (e.g., described herein) inhibits a parasite CDPK1 (e.g., TgCDPK1) with an IC50 (e.g., measured using a standard assay in the art or an assay described herein) is about 0.003 µM to about 0.2 µM. In embodiments, the compound (e.g., described herein) inhibits a parasite CDPK1 (e.g., TgCDPK1) with an IC50 (e.g., measured using a standard assay in the art or an assay described herein) is about 0.003 µM to about 0. µM. In embodiments, the compound (e.g., described herein) inhibits a parasite CDPK1 (e.g., TgCDPK1) with an IC50 (e.g., measured using a standard assay in the art or an assay described herein) is about 0.007 µM to about 0.2 µM. In embodiments, the compound (e.g., described herein) inhibits a parasite CDPK1 (e.g., TgCDPK1) with an IC50 (e.g., measured using a standard assay in the art or an assay described herein) is about 0.01 µM to about 0.2 µM. In embodiments, the compound (e.g., described herein) inhibits a parasite CDPK1 (e.g., TgCDPK1) with an IC50 (e.g., measured using a standard assay in the art or an assay described herein) is about 0.003 µM to about 0.1 µM. In embodiments, the compound (e.g., described herein) inhibits a parasite CDPK1 (e.g., TgCDPK1) with an IC50 (e.g., measured using a standard assay in the art or an assay described herein) is about 0.003 µM to about 0.10 µM.

In embodiments, the compound is any one of the compounds described herein (e.g., in an aspect, embodiment, claim, figure, table, or example).

In embodiments, the compound described herein may include multiple instances of $R^4$ and/or $R^5$, and/or other variables. In such embodiments, each variable may optional be different and be appropriately labeled to distinguish each group for greater clarity. For example, where each $R^4$ and/or $R^5$, is different, they may be referred to, for example, as $R^{4.1}$, $R^{4.2}$, $R^{4.3}$, $R^{4.4}$, $R^{4.5}$, $R^{5.1}$, $R^{5.2}$, $R^{5.3}$, $R^{5.4}$, $R^{5.5}$, respectively, wherein the definition of $R^4$ is assumed by $R^{4.1}$, $R^{4.2}$, $R^{4.3}$, $R^{4.4}$, $R^{4.5}$ and $R^5$ is assumed by $R^{5.1}$, $R^{5.2}$, $R^{5.3}$, $R^{5.4}$, $R^{5.5}$. The variables used within a definition of $R^4$ and $R^5$ and/or other variables that appear at multiple instances and are different may similarly be appropriately labeled to distinguish each group for greater clarity.

In embodiments, the compound has the formula:

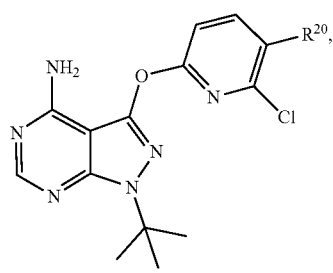

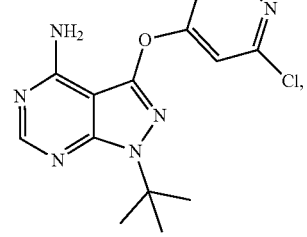

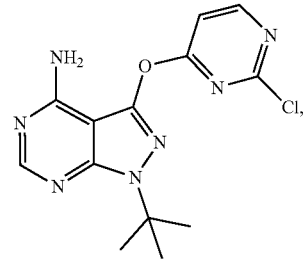

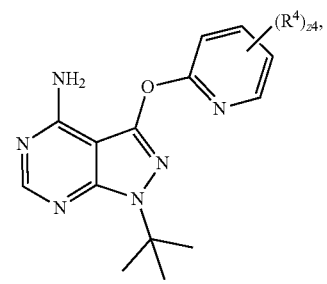

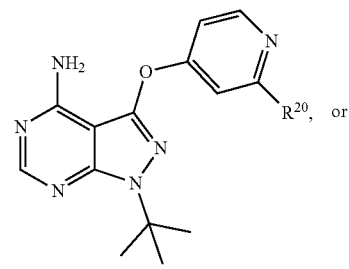

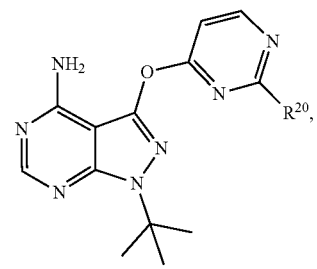

wherein $R^4$, z4, and $R^{20}$ is as described herein. In embodiments, $R^4$ and R20 are independently —OH, —OCH$_3$, —NH$_2$, —NHCH$_3$, unsubstituted heterocycle, or unsubstituted aryl.

In embodiments, the compound has the formula:

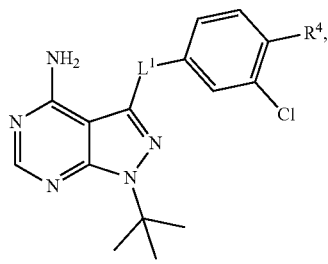

wherein L¹ and R⁴ are as described herein.
In embodiments, the compound has the formula:

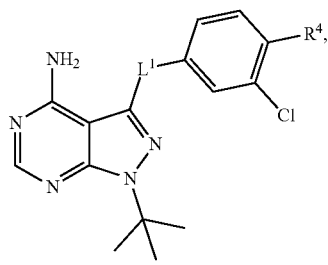

wherein L and R⁴ are as described herein. In embodiments, R⁴ is halogen.
In embodiments, the compound has the formula:

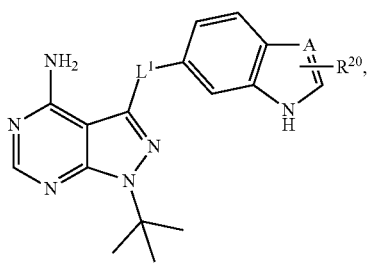

wherein L¹, A, and R²⁰ are as described herein. In embodiments, A is —CH═. In embodiments A is —N═. In embodiments, R²⁰ is unsubstituted $C_1$-$C_3$ alkyl. In embodiments, R²⁰ is unsubstituted methyl.
In embodiments, the compound has the formula:

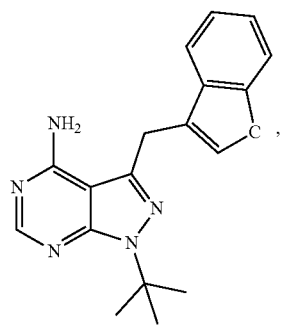

wherein C is S, N, or O.

In embodiments, the compound has the formula:

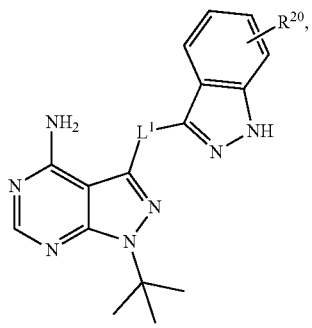

wherein L¹ and R²⁰ are as described herein.
In embodiments, the compound is:

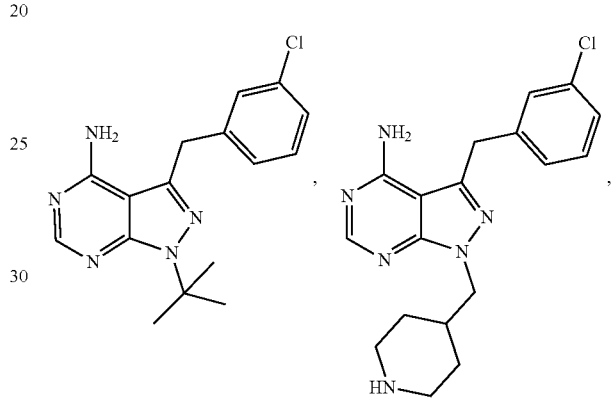

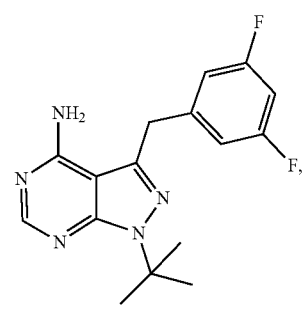

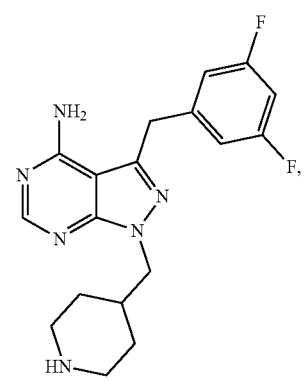 [SMILES: Nc1ncnc2c1c(Cc1cc(F)cc(F)c1)nn2CC1CCNCC1]

229
-continued
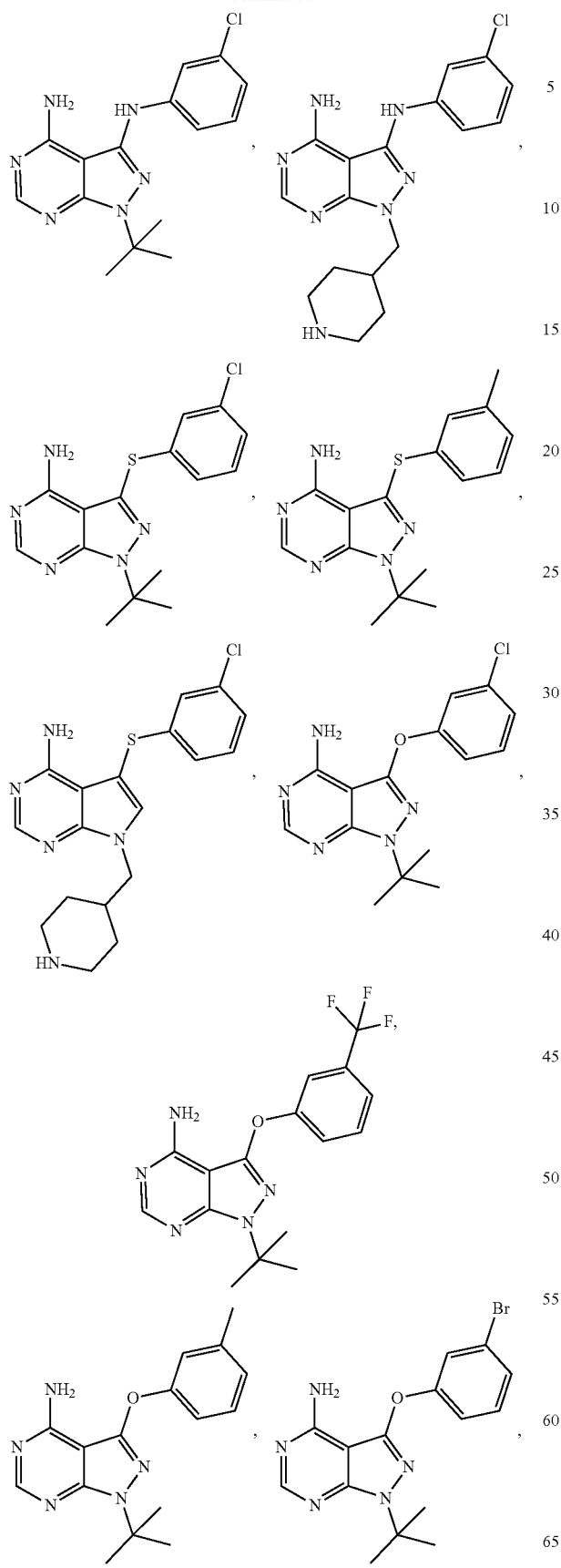
230
-continued
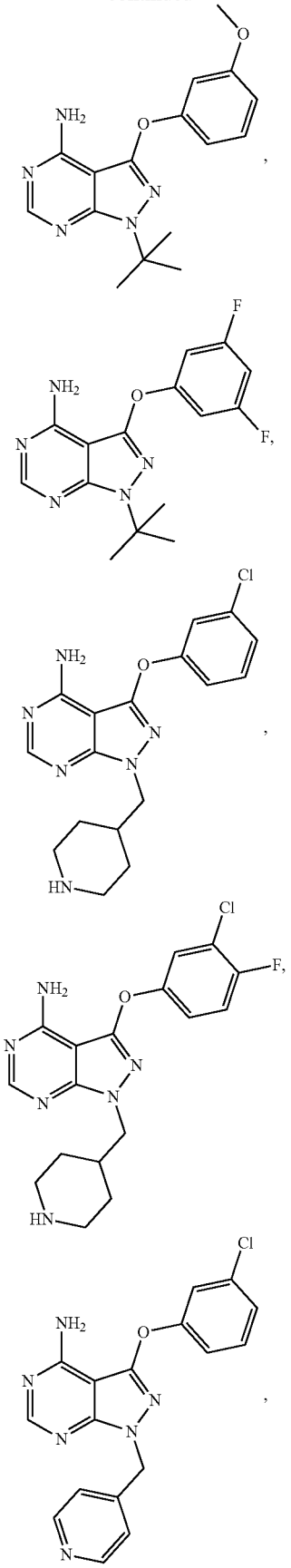

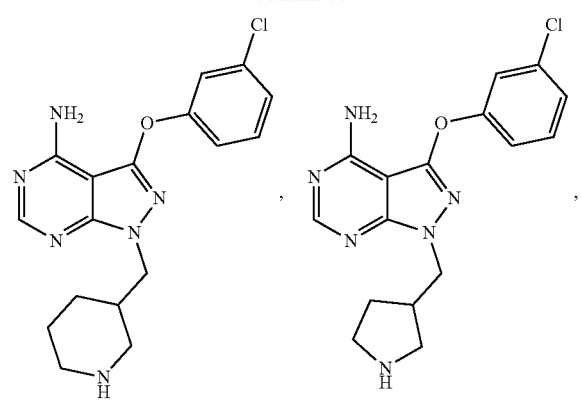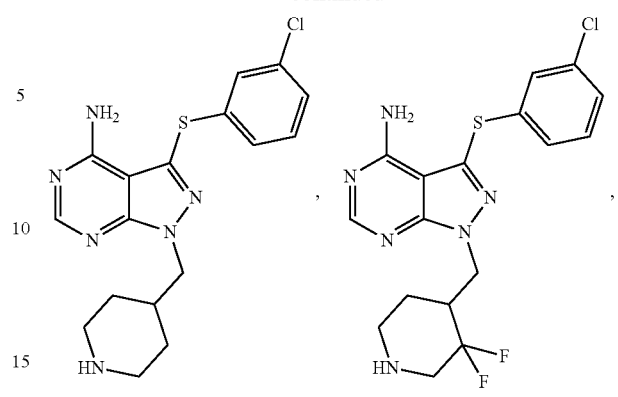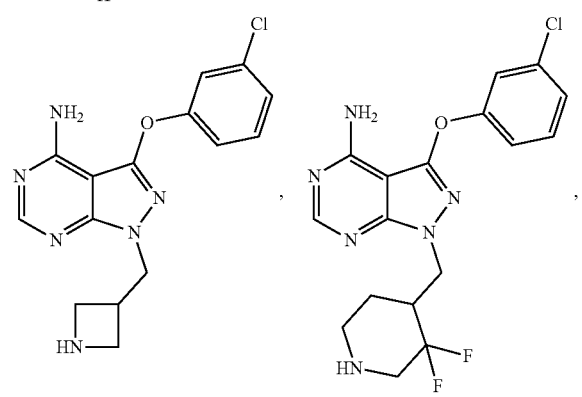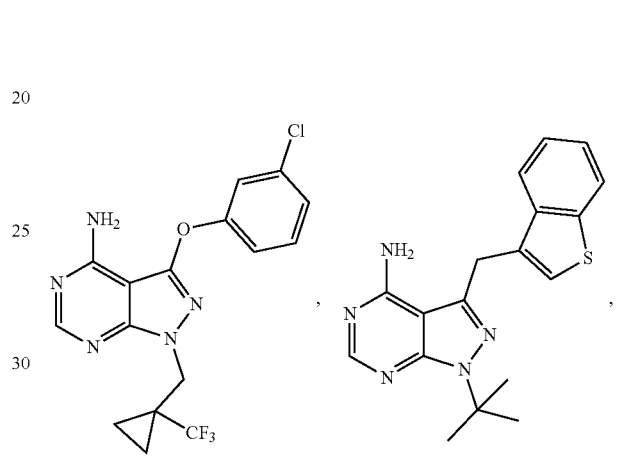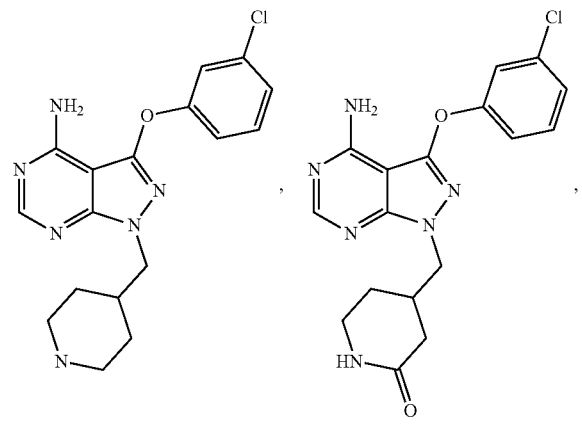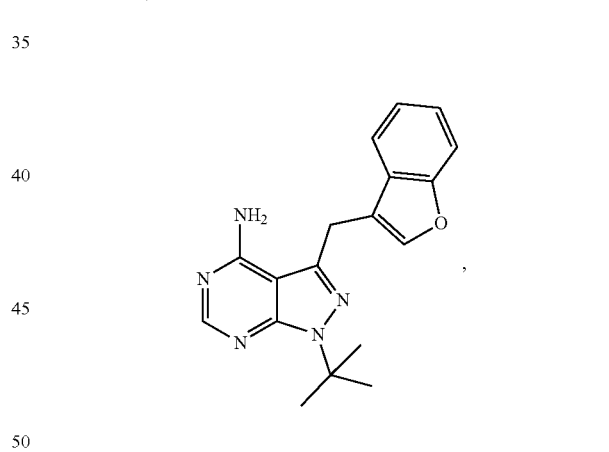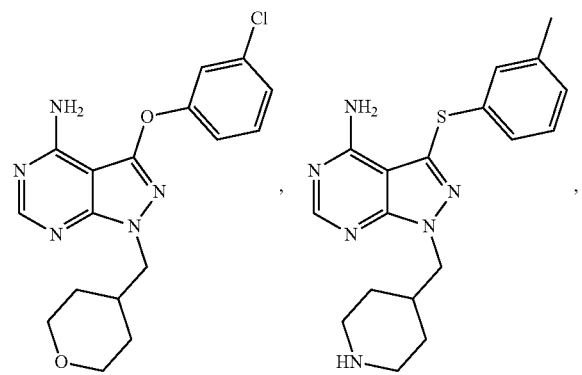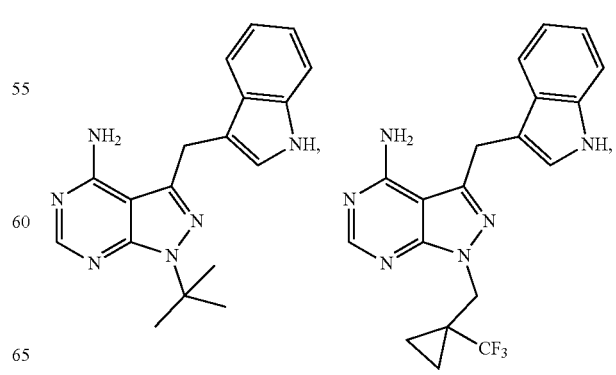

233
-continued
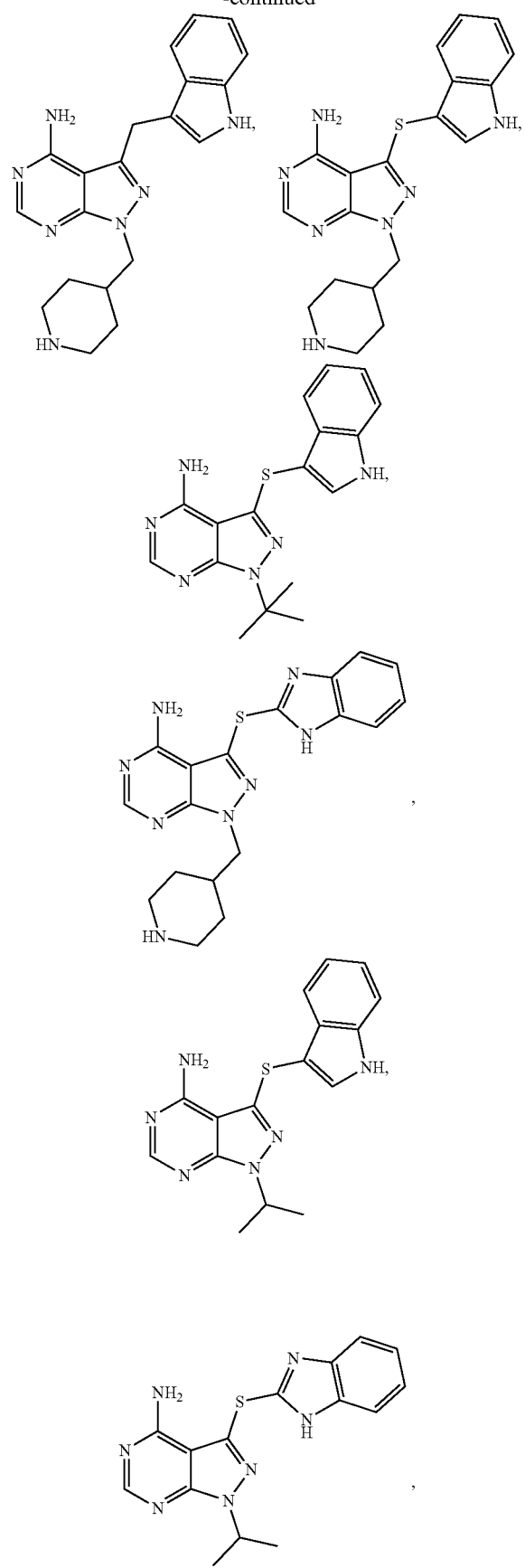
234
-continued
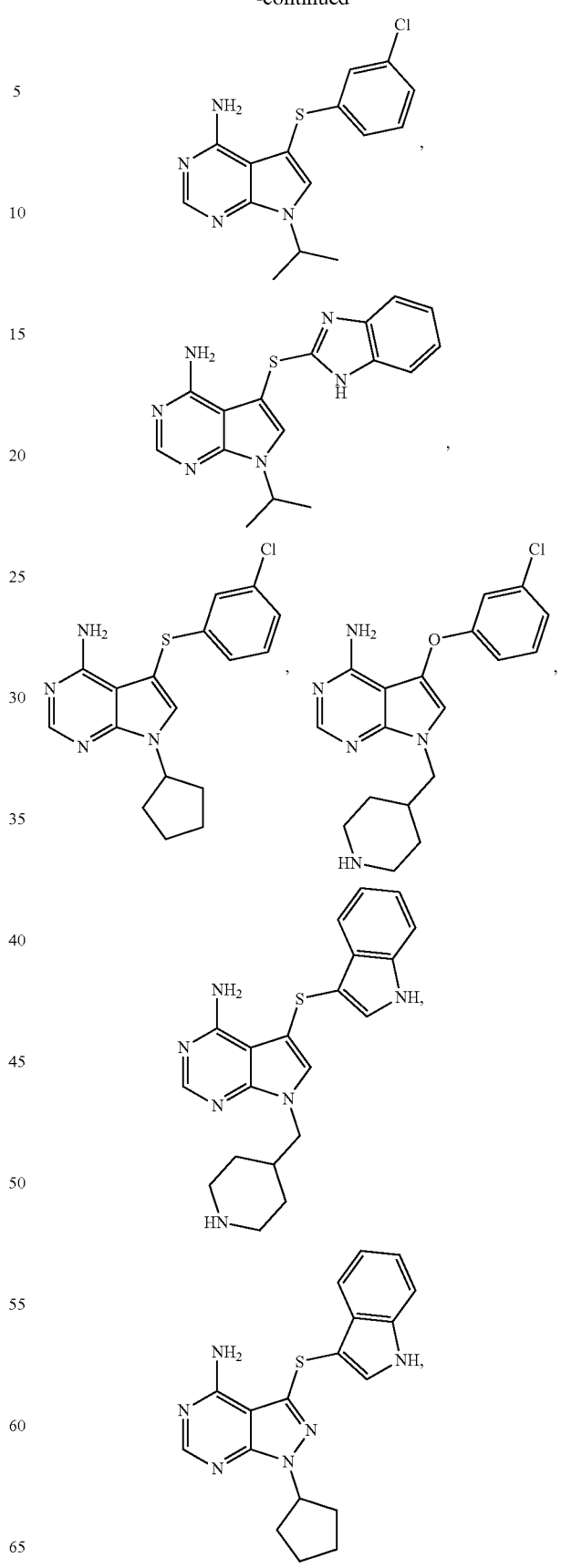

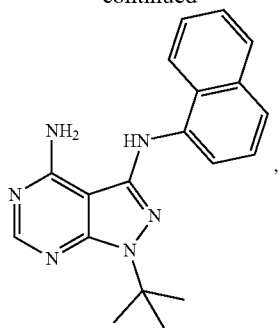
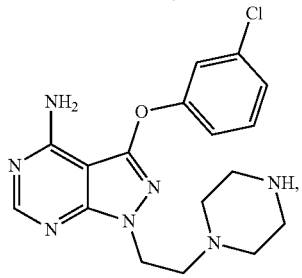
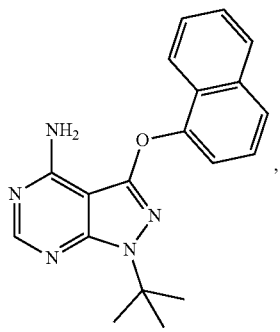
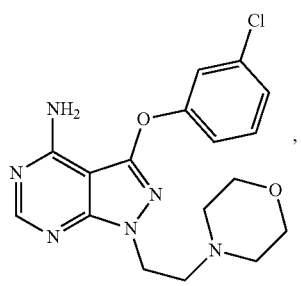
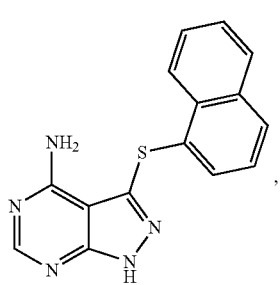
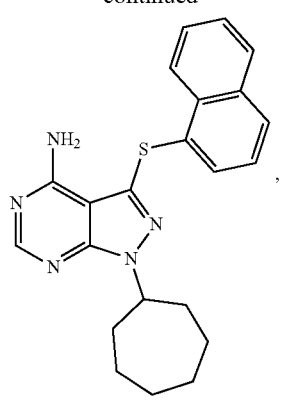
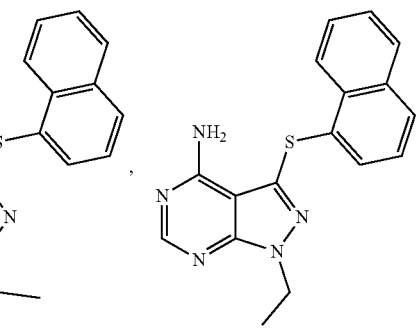
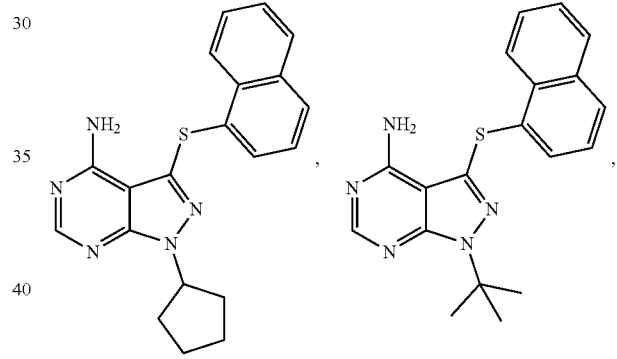
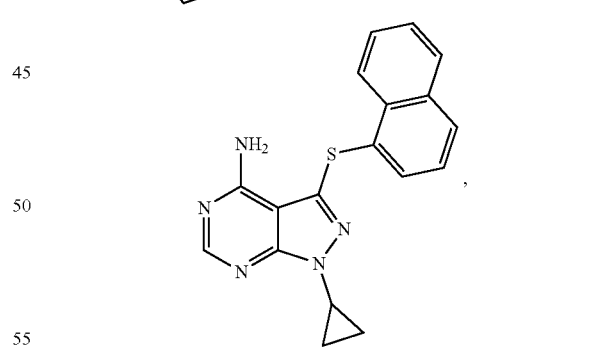
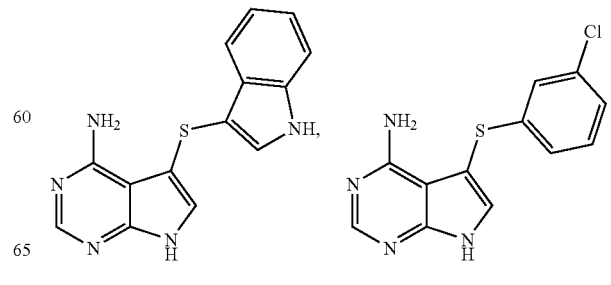

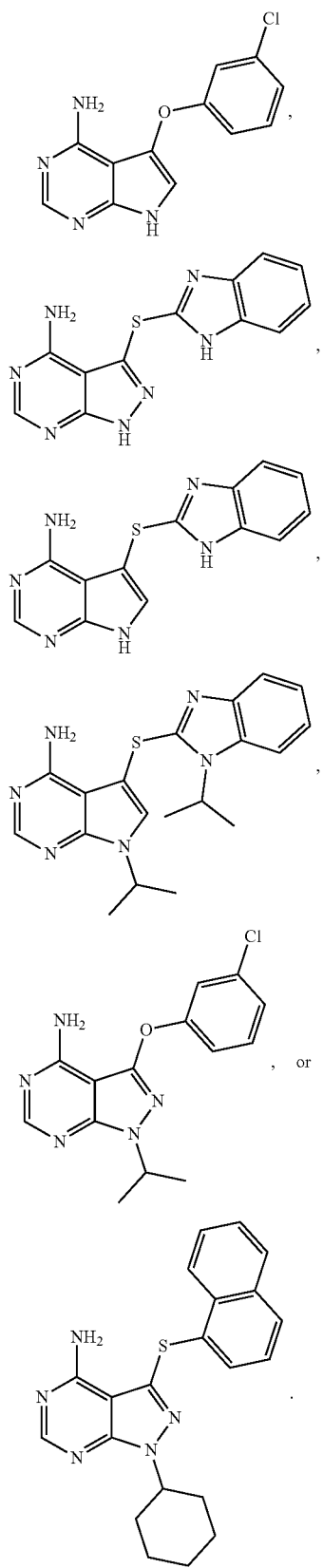
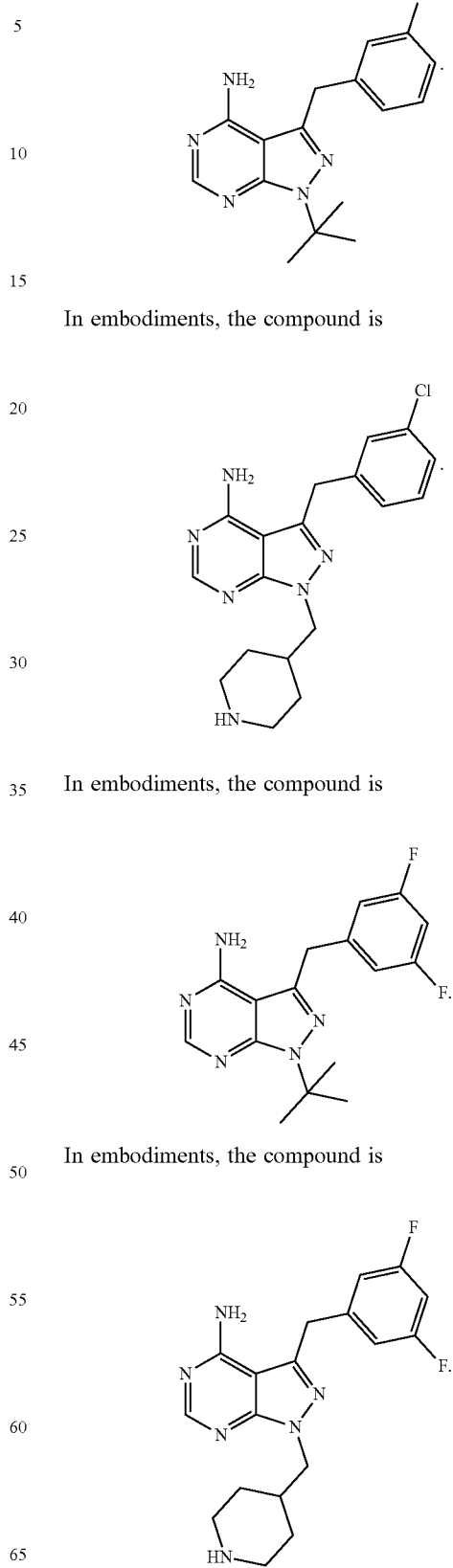
In embodiments, the compound is
In embodiments, the compound is
In embodiments, the compound is
In embodiments, the compound is In embodiments, the compound is
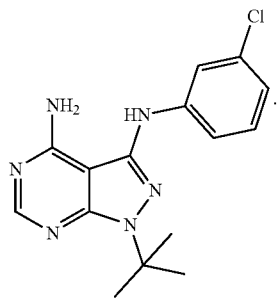
In embodiments, the compound is
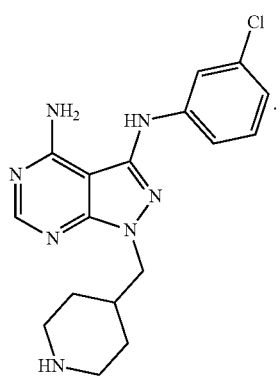
In embodiments, the compound is
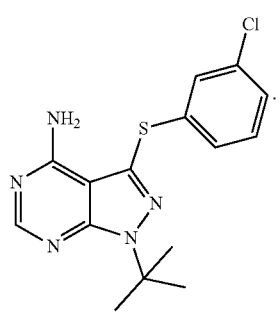 [SMILES: CC(C)(C)n1nc(Sc2cccc(Cl)c2)c2c(N)ncnc21]
In embodiments, the compound is
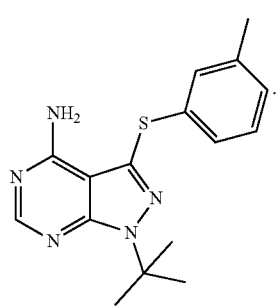
In embodiments, the compound is
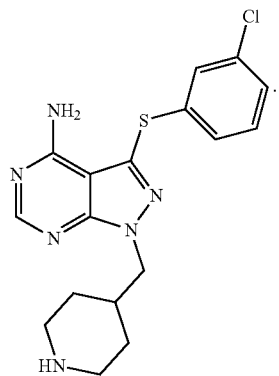
In embodiments, the compound is
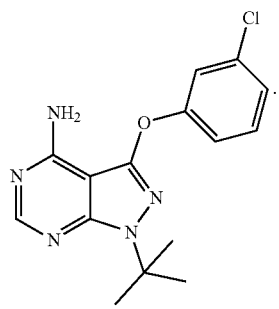 [SMILES: CC(C)(C)n1nc(Oc2cccc(Cl)c2)c2c(N)ncnc21]
In embodiments, the compound is
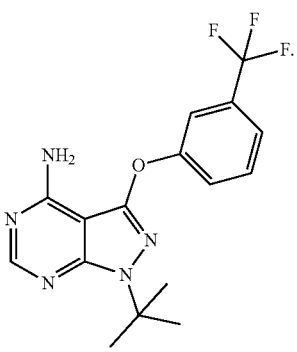 [SMILES: CC(C)(C)n1nc(Oc2cccc(C(F)(F)F)c2)c2c(N)ncnc21]
In embodiments, the compound is
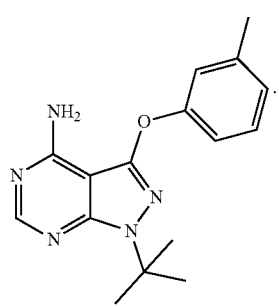

In embodiments, the compound is
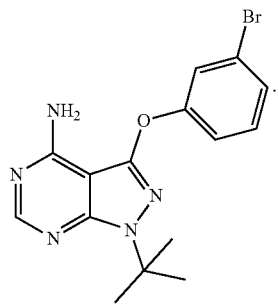
In embodiments, the compound is
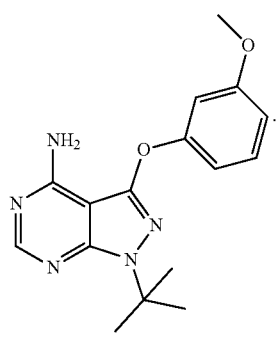 [SMILES: COc1cccc(Oc2nn(C(C)(C)C)c3ncnc(N)c23)c1]
In embodiments, the compound is
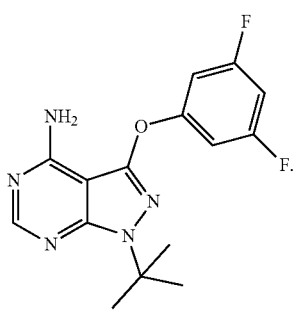
In embodiments, the compound is
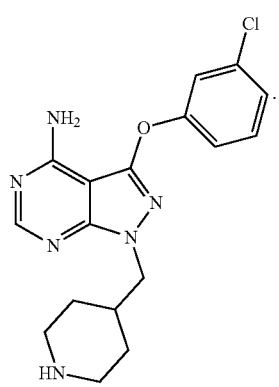 [SMILES: Nc1ncnc2c1c(Oc1cccc(Cl)c1)nn2CC1CCNCC1]
In embodiments, the compound is
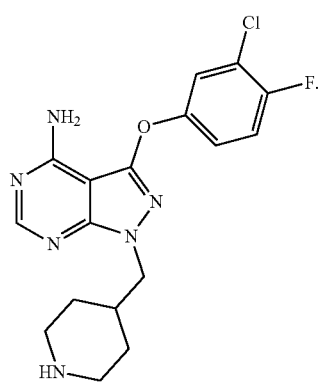 [SMILES: Nc1ncnc2c1c(Oc1ccc(F)c(Cl)c1)nn2CC1CCNCC1]
In embodiments, the compound is
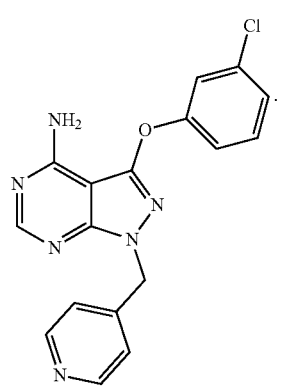 [SMILES: Nc1ncnc2c1c(Oc1cccc(Cl)c1)nn2Cc1ccncc1]
In embodiments, the compound is
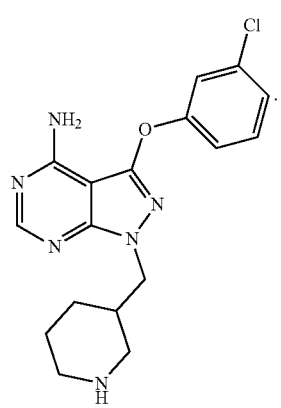 [SMILES: Nc1ncnc2c1c(Oc1cccc(Cl)c1)nn2CC1CCCNC1]

243
In embodiments, the compound is
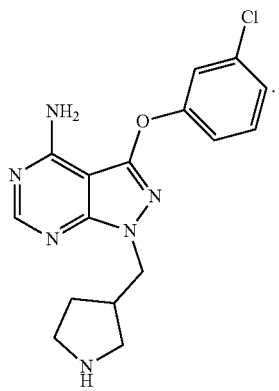 [SMILES: Nc1ncnc2c1c(Oc1cccc(Cl)c1)nn2CC1CCNC1]
In embodiments, the compound is
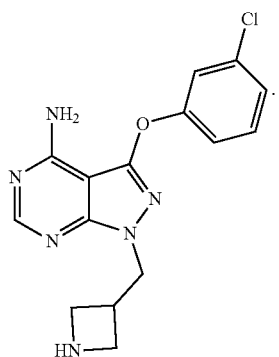 [SMILES: Nc1ncnc2c1c(Oc1cccc(Cl)c1)nn2CC1CNC1]
In embodiments, the compound is
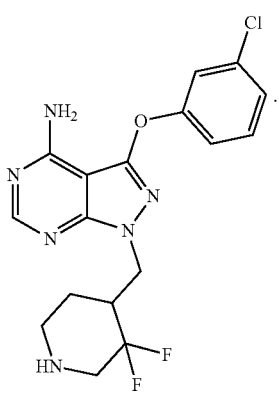 [SMILES: Nc1ncnc2c1c(Oc1cccc(Cl)c1)nn2CC1CCNCC1(F)F]
244
In embodiments, the compound is
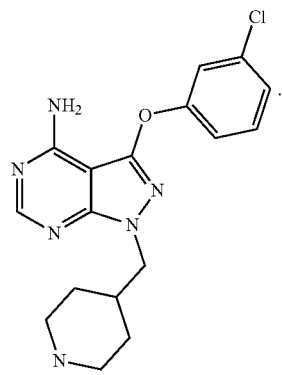
In embodiments, the compound is
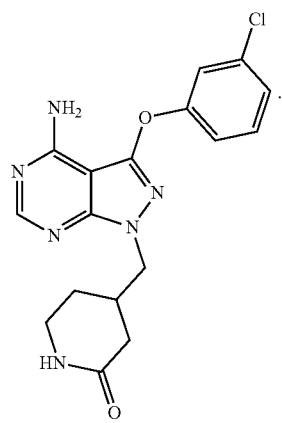 [SMILES: Nc1ncnc2c1c(Oc1cccc(Cl)c1)nn2CC1CCNC(=O)C1]
In embodiments, the compound is
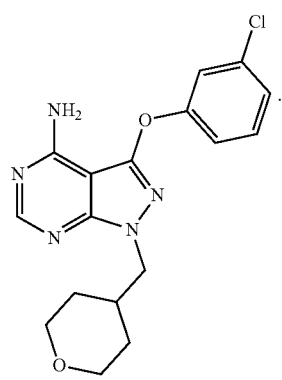 [SMILES: Nc1ncnc2c1c(Oc1cccc(Cl)c1)nn2CC1CCOCC1]

245
In embodiments, the compound is
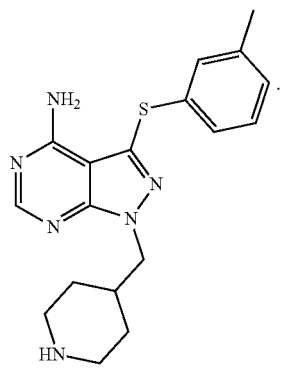 [SMILES: Cc1cccc(Sc2nn(CC3CCNCC3)c3ncnc(N)c23)c1]
In embodiments, the compound is
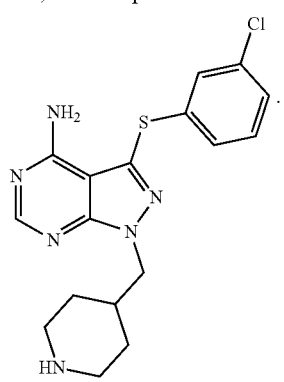
In embodiments, the compound is
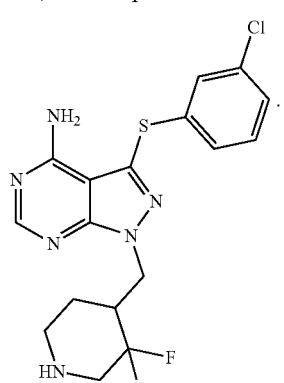
In embodiments, the compound is
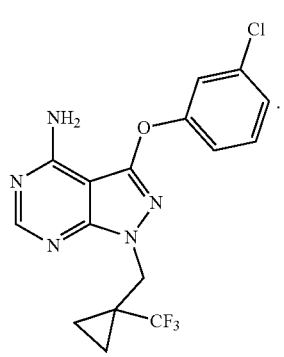 [SMILES: Nc1ncnc2c1c(Oc1cccc(Cl)c1)nn2CC1(C(F)(F)F)CC1]
246
In embodiments, the compound is
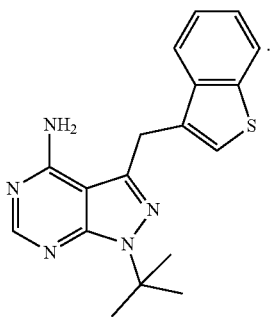 [SMILES: CC(C)(C)n1nc(Cc2csc3ccccc23)c2c(N)ncnc21]
In embodiments, the compound is
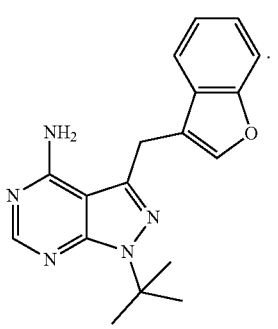 [SMILES: CC(C)(C)n1nc(Cc2coc3ccccc23)c2c(N)ncnc21]
In embodiments, the compound is
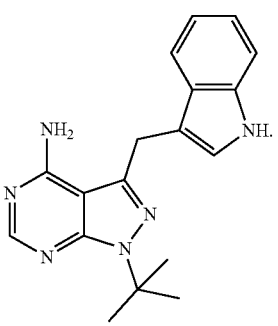 [SMILES: CC(C)(C)n1nc(Cc2c[nH]c3ccccc23)c2c(N)ncnc21]
In embodiments, the compound is
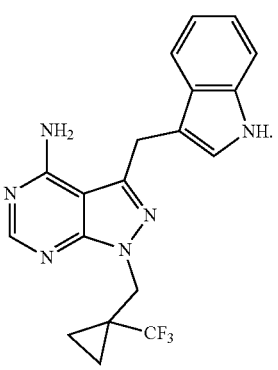 [SMILES: Nc1ncnc2c1c(Cc1c[nH]c3ccccc13)nn2CC1(C(F)(F)F)CC1]

In embodiments, the compound is
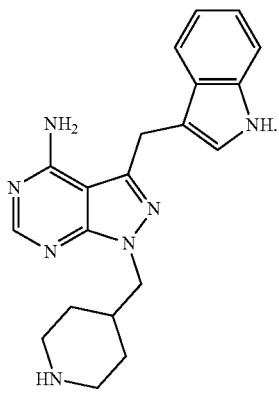 [SMILES: Nc1ncnc2c1c(Cc1c[nH]c3ccccc13)nn2CC1CCNCC1]
In embodiments, the compound is
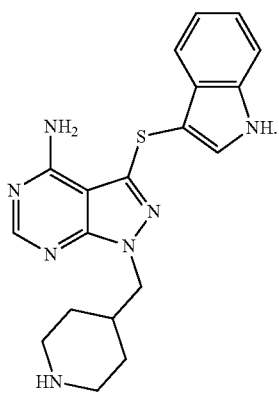
In embodiments, the compound is
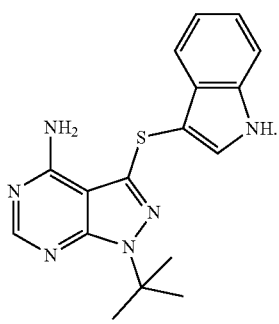 [SMILES: CC(C)(C)n1nc(Sc2c[nH]c3ccccc23)c2c(N)ncnc21]
In embodiments, the compound is
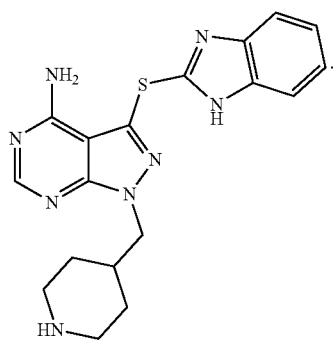 [SMILES: Nc1ncnc2c1c(Sc1nc3ccccc3[nH]1)nn2CC1CCNCC1]
In embodiments, the compound is
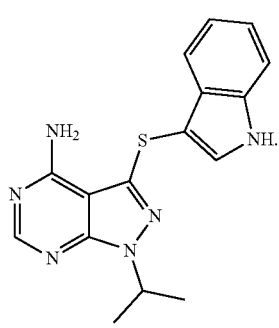 [SMILES: CC(C)n1nc(Sc2c[nH]c3ccccc23)c2c(N)ncnc21]
In embodiments, the compound is
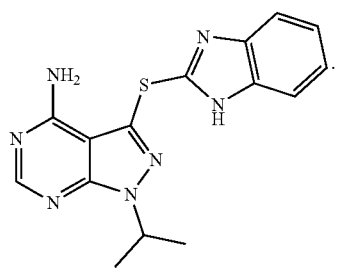
In embodiments, the compound is
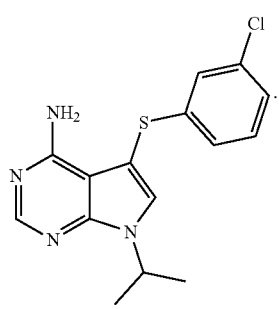 [SMILES: CC(C)n1cc(Sc2cccc(Cl)c2)c2c(N)ncnc21]
In embodiments, the compound is
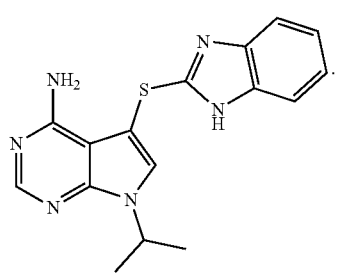

In embodiments, the compound is
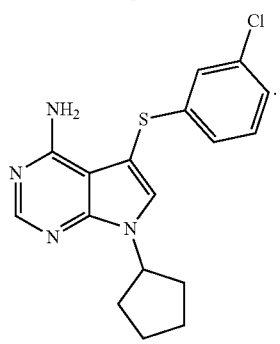 [SMILES: Nc1ncnc2c1c(Sc1cccc(Cl)c1)cn2C1CCCC1]
In embodiments, the compound is
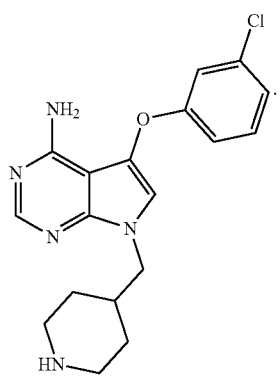 [SMILES: Nc1ncnc2c1c(Oc1cccc(Cl)c1)cn2CC1CCNCC1]
In embodiments, the compound is
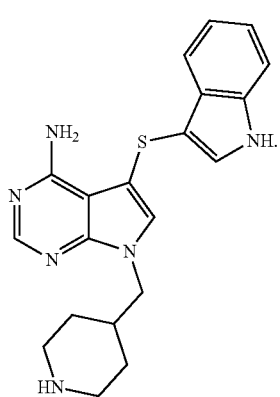 [SMILES: Nc1ncnc2c1c(Sc1c[nH]c3ccccc13)cn2CC1CCNCC1]
In embodiments, the compound is
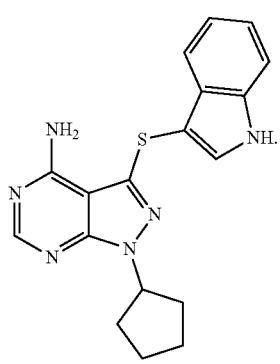 [SMILES: Nc1ncnc2c1c(Sc1c[nH]c3ccccc13)nn2C1CCCC1]
In embodiments, the compound is
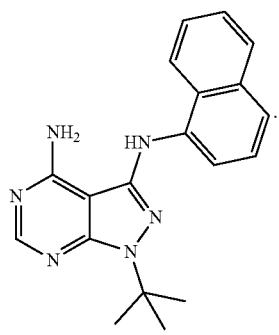
In embodiments, the compound is
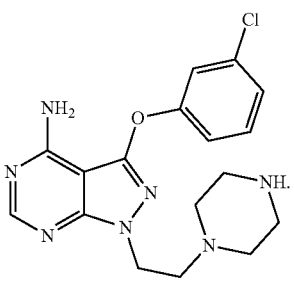 [SMILES: Nc1ncnc2c1c(Oc1cccc(Cl)c1)nn2CCN1CCNCC1]
In embodiments, the compound is
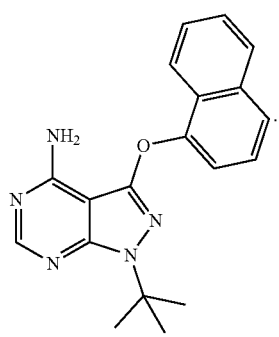 [SMILES: CC(C)(C)n1nc(Oc2cccc3ccccc23)c2c(N)ncnc21]
In embodiments, the compound is
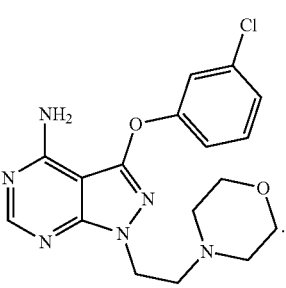 [SMILES: Nc1ncnc2c1c(Oc1cccc(Cl)c1)nn2CCN1CCOCC1]

In embodiments, the compound is
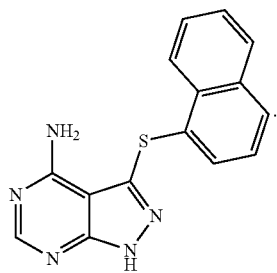 [SMILES: Nc1ncnc2[nH]nc(Sc3cccc4ccccc34)c12]
In embodiments, the compound is
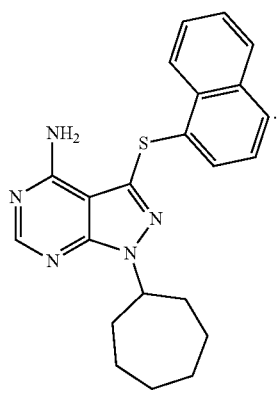 [SMILES: Nc1ncnc2c1c(Sc1cccc3ccccc13)nn2C1CCCCCC1]
In embodiments, the compound is
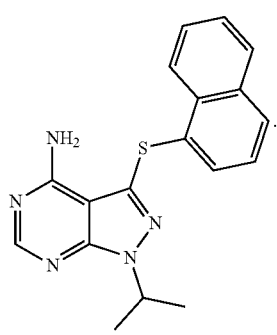 [SMILES: CC(C)n1nc(Sc2cccc3ccccc23)c2c(N)ncnc21]
In embodiments, the compound is
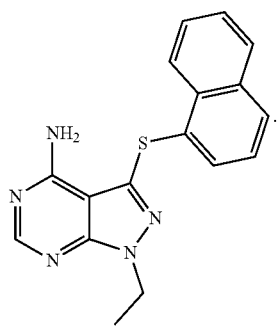 [SMILES: CCn1nc(Sc2cccc3ccccc23)c2c(N)ncnc21]
In embodiments, the compound is
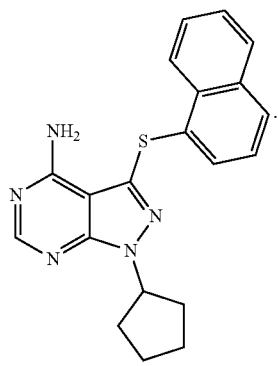 [SMILES: Nc1ncnc2c1c(Sc1cccc3ccccc13)nn2C1CCCC1]
In embodiments, the compound is
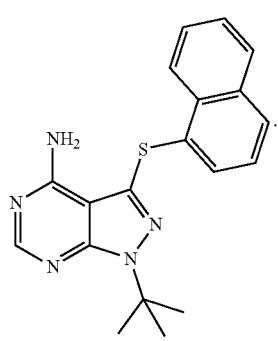 [SMILES: CC(C)(C)n1nc(Sc2cccc3ccccc23)c2c(N)ncnc21]
In embodiments, the compound is
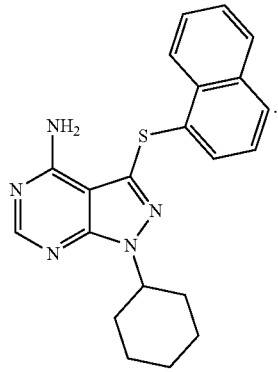 [SMILES: Nc1ncnc2c1c(Sc1cccc3ccccc13)nn2C1CCCCC1]
In embodiments, the compound is
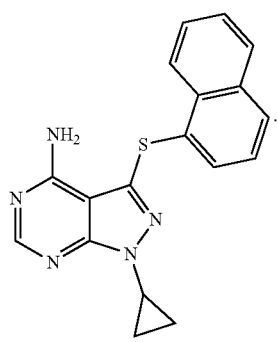 [SMILES: Nc1ncnc2c1c(Sc1cccc3ccccc13)nn2C1CC1]

In embodiments, the compound is

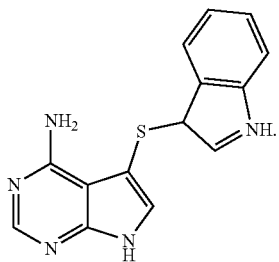

In embodiments, the compound is

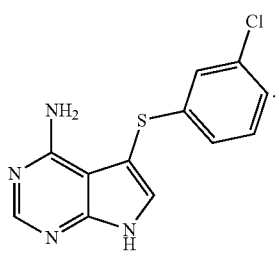 [SMILES: Nc1ncnc2[nH]cc(Sc3cccc(Cl)c3)c12]

In embodiments, the compound is

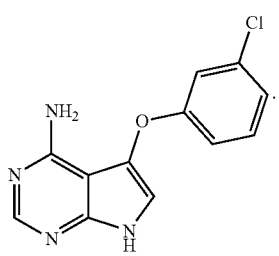 [SMILES: Nc1ncnc2[nH]cc(Oc3cccc(Cl)c3)c12]

In embodiments, the compound is

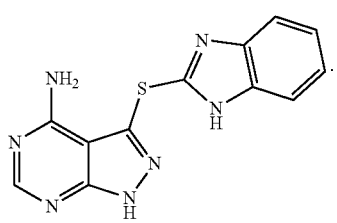 [SMILES: Nc1ncnc2[nH]nc(Sc3nc4ccccc4[nH]3)c12]

In embodiments, the compound is

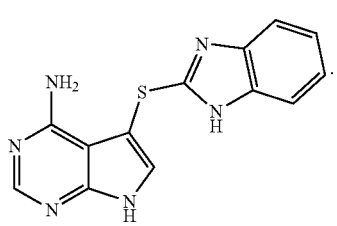 [SMILES: Nc1ncnc2[nH]cc(Sc3nc4ccccc4[nH]3)c12]

In embodiments, the compound is

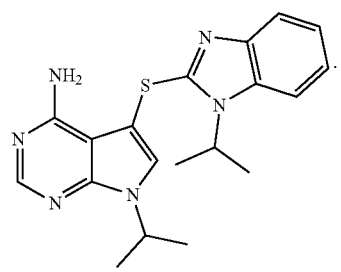 [SMILES: CC(C)n1cc(Sc2nc3ccccc3n2C(C)C)c2c(N)ncnc21]

In embodiments, the compound is

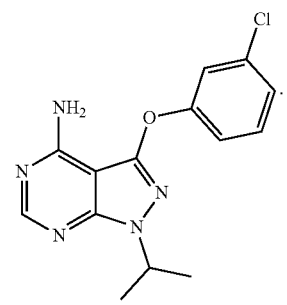

In some embodiments, the compound is a compound described herein (e.g., in an aspect, embodiment, example, claim, table, scheme, drawing, or figure).

In embodiments, $L^2$ is not a substituted $C_1$-$C_2$ alkylene. In embodiments, $L^2$ is not an oxo substituted methylene. In embodiments, $L^2$ is not a substituted methylene. In embodiments, $L^2$ is not a substituted ethylene. In embodiments, $L^2$ is not an unsubstituted $C_1$-$C_2$ alkylene. In embodiments, $L^2$ is not an unsubstituted methylene. In embodiments, $L^2$ is not an unsubstituted ethylene. In embodiments, $L^2$ is not an oxo substituted heteroalkylene. In embodiments, $L^2$ is not an oxo substituted 2 to 3 membered heteroalkylene. In embodiments, $L^2$ is not an oxo substituted 2 to 4 membered heteroalkylene. In embodiments, $L^2$ is not an oxo substituted 2 to 5 membered heteroalkylene. In embodiments, $L^2$ is not an oxo substituted 2 to 6 membered heteroalkylene. In embodiments, $R^2$ is not unsubstituted tert-butyl. In embodiments, $L^1$ is not methylene. In embodiments, when $L^1$ is an unsubstituted methylene, $L^2$ is not a bond. In embodiments, when $L^1$ is an unsubstituted methylene, $R^2$ is not a substituted or unsubstituted alkyl. In embodiments, when $L^1$ is an unsubstituted methylene, $R^2$ is not an unsubstituted alkyl. In embodiments, when $L^1$ is an unsubstituted methylene, $R^2$ is not an unsubstituted $C_1$-$C_4$ alkyl. In embodiments, when $L^1$ is an unsubstituted methylene, $R^2$ is not an unsubstituted tert-butyl.

In embodiments, the compound is not CZ43, LJQ-145, LJQ-138, 3ClB-PP1, or CZ75. In embodiments, the compound is not CZ43. In embodiments, the compound is not LJQ-145. In embodiments, the compound is not LJQ-138. In embodiments, the compound is not 3ClB-PP1. In embodiments, the compound is not CZ75.

In embodiments, the compound is not:

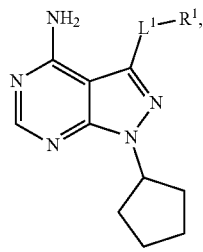

wherein L¹ is —O—, —NH—, —C(O)—, or unsubstituted methylene. In embodiments, L²-R² is not

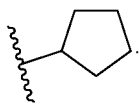 [SMILES: *C1CCCC1]

In embodiments, R¹ is not substituted or unsubstituted naphthyl. In embodiments, R¹ is not substituted naphthyl. In embodiments, R¹ is not unsubstituted naphthyl. In embodiments, L¹-R¹ is not

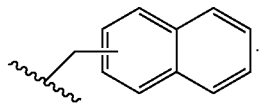

In embodiments, L¹-R¹ is not

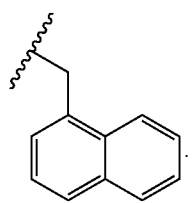 [SMILES: *Cc1cccc2ccccc12]

In embodiments, L¹R¹ is not

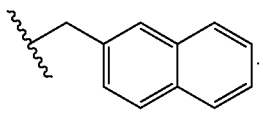 [SMILES: *Cc1ccc2ccccc2c1]

In embodiments, L¹-R¹ is not

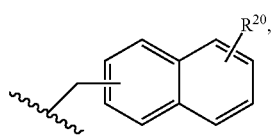

wherein R²⁰ is as described herein.

In embodiments, the compound is 3CIB-PP1, FUR6-157, CZ75, MLC468, LZH118, GXJ276, GXJ186, FUR7-68, FUR6-139, GXJ184, GXJ178, GXJ176, GXJ177, GXJ230, GXJ229, GXJ237, GXJ261, FUR6-6, FUR6-11, FUR6-13, FUR6-12, FUR7-27, FUR7-30, FUR7-36, FUR7-89, FUR7-77, FUR 5-56, FUR 7-76, or FUR7-2. In embodiments, the compound is 3CIB-PP1. In embodiments, the compound is FUR6-157. In embodiments, the compound is CZ75. In embodiments, the compound is MLC468. In embodiments, the compound is LZH118. In embodiments, the compound is GXJ276. In embodiments, the compound is GXJ186. In embodiments, the compound is FUR7-68. In embodiments, the compound is FUR 6-139. In embodiments, the compound is GXJ184. In embodiments, the compound is GXJ178. In embodiments, the compound is GXJ176. In embodiments, the compound is GXJ177. In embodiments, the compound is GXJ230. In embodiments, the compound is GXJ229. In embodiments, the compound is GXJ237. In embodiments, the compound is GXJ261. In embodiments, the compound is FUR6-6. In embodiments, the compound is FUR6-11. In embodiments, the compound is FUR6-13. In embodiments, the compound is FUR6-12. In embodiments, the compound is FUR7-27. In embodiments, the compound is FUR7-30. In embodiments, the compound is FUR7-36. In embodiments, the compound is FUR7-89. In embodiments, the compound is FUR7-77. In embodiments, the compound is FUR 5-56. In embodiments, the compound is FUR 7-76. In embodiments, the compound is FUR7-2.

In embodiments, the compound is CZ43, LJQ-145, LJQ-138, WXT-2, FUR6-95, FUR 5-57, or FUR6-159. In embodiments, the compound is the compound is CZ43. In embodiments, the compound is LJQ-145. In embodiments, the compound is LJQ-138. In embodiments, the compound is WXT-2. In embodiments, the compound is FUR6-95. In embodiments, the compound is FUR 5-57. In embodiments, the compound is FUR6-159.

In embodiments, the compound is FUR 6-161, FUR 6-142, FUR 6-160, FUR 6-140, FUR 6-162, FUR 6-140B, FUR 6-145, FUR 6-141, FUR 6-142B, FUR 6-124, FUR 6-123, FUR 6-99, FUR 6-15, FUR 6-100, FUR 6-106, FUR 6-102, FUR 6-107, FUR 6-104, FUR 6-111, FUR 6-105, FUR 6-103, FUR 6-133, FUR 6-132, FUR 6-144, FUR 6-146, FUR 6-147, FUR 6-162B, or HYC29. In embodiments, the compound is FUR 6-161. In embodiments, the compound is FUR 6-142. In embodiments, the compound is FUR 6-160. In embodiments, the compound is FUR 6-140. In embodiments, the compound is FUR 6-162. In embodiments, the compound is FUR 6-140B. In embodiments, the compound is FUR 6-145. In embodiments, the compound is FUR 6-141. In embodiments, the compound is FUR 6-142B. In embodiments, the compound is FUR 6-124. In embodiments, the compound is FUR 6-123. In embodiments, the compound is FUR 6-99. In embodiments, the compound is FUR 6-15. In embodiments, the compound is FUR 6-100. In embodiments, the compound is FUR 6-106. In embodiments, the compound is FUR 6-102. In embodiments, the compound is FUR 6-107. In embodiments, the compound is FUR 6-104. In embodiments, the compound is FUR 6-111. In embodiments, the compound is FUR 6-105. In embodiments, the compound is FUR 6-103. In embodiments, the compound is FUR 6-133. In embodiments, the compound is FUR 6-132. In embodiments, the compound is FUR 6-144. In embodiments, the compound is FUR 6-146. In embodiments, the compound is FUR 6-147. In embodiments, the compound is FUR 6-162B. In embodiments, the compound is HYC29.

III. Pharmaceutical Compositions

In another aspect is provided a pharmaceutical composition including a pharmaceutically acceptable excipient and a compound, or pharmaceutically acceptable salt thereof, as described herein, including embodiments (e.g. in an embodiment, example, figure, table, or claim).

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount.

In embodiments, the second agent is an antibiotic. In embodiments, the second agent is pyrimethanime. In embodiments, the second agent is a sulfonamide drug. In embodiments, the second agent is clindamycin. In embodiments, the sulfonamide drug is sulfadiazine. In embodiments, the secondary agent is artemisinin or atovaquone, or a derivative thereof. In embodiments, the sulfonamide drug is sulfamethoaxazole.

IV. Methods of Treatment

In an aspect is provided a method of treating an Apicomplexa infection (e.g., *Babesia* spp., *Plasmodium* spp., *Cryptosporidium parvum, Cyclospora cayetanensis, Cryptosporidium hominis, Isospora belli, Neospora caninum, Sarcicystis neurona*, or *Toxoplasma gondii*) infection, the method including administering to a subject in need thereof an effective amount of a compound described herein. In embodiments, the method further includes preventing reactivation of Apicomplexa tachyzoite, bradyzoite, oocysts, sporocyst, sporozoite, or enteroepithelial stage within tissue cysts. In embodiments, the method further includes preventing reactivation of Apicomplexa tachyzoite stage within tissue cysts. In embodiments, the method further includes preventing reactivation of Apicomplexa bradyzoite stage within tissue cysts. In embodiments, the method further includes preventing reactivation of Apicomplexa oocyst stage within tissue cysts. In embodiments, the method further includes preventing reactivation of Apicomplexa sporocyst stage within tissue cysts. In embodiments, the method further includes preventing reactivation of Apicomplexa sporozoite stage within tissue cysts. In embodiments, the method further includes preventing reactivation of Apicomplexa enteroepithelial stage within tissue cysts.

In an aspect is provided a compound as described herein for use as a medicament. In embodiments, the medicament is useful for treating a disease caused by an infectious agent (e.g., Apicomplexa, *Babesia* spp., *Plasmodium* spp., *Cryptosporidium hominis, Cryptosporidium parvum, Cyclospora cayetanensis, Isospora belli, Neospora caninum*, or *Toxoplasma gondii*).

In embodiments, the compound has the formula:
In embodiments, the compound is

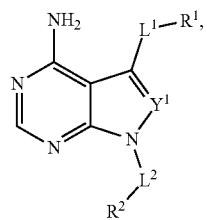

wherein $Y^1$ is —N= or —CH=; $R^1$ is substituted or unsubstituted aryl or substituted or unsubstituted heteroaryl; $R^2$ is hydrogen, substituted or unsubstituted heterocycloalkyl, substituted or unsubstituted heteroaryl, substituted or unsubstituted aryl, substituted or unsubstituted cycloalkyl, or substituted or unsubstituted alkyl; $L^1$ is —O—, —S—, or —N($R^3$)—; $L^2$ is a bond, substituted or unsubstituted alkylene, or substituted or unsubstituted heteroalkylene; $R^3$ is hydrogen, —CN, —COOH, —$CX^3_3$, substituted or unsubstituted alkyl, or substituted or unsubstituted heteroalkyl; and $X^3$ is independently halogen.

In an aspect is provided a compound as described herein for use in the treatment of a disease caused by an infectious agent (e.g., Apicomplexa, *Babesia* spp., *Plasmodium* spp., *Cryptosporidium parvum, Cryptosporidium hominis, Cyclospora cayetanensis, Isospora belli, Neospora caninum*, or *Toxoplasma gondii*).

In embodiments, the Apicomplexa infection is a systemic infection including the central nervous system, placenta, retina, and the brain. In embodiments, the Apicomplexa infection is in the central nervous system. In embodiments, the Apicomplexa infection is in the placenta. In embodiments, the Apicomplexa infection is in the retina. In embodiments, the Apicomplexa infection is in the brain. In embodiments, the method includes preventing chronic Apicomplexa infection. In embodiments, the method includes preventing reactivation of the Apicomplexa in tissue cysts. In embodiments, the method includes reducing Apicomplexa survival, relative to a control (e.g., the absence of the compound described herein). In embodiments, the method includes reducing Apicomplexa proliferation, relative to a control (e.g., the absence of the compound described herein). In embodiments, the method includes reducing Apicomplexa egress from a cell, relative to a control (e.g., Apicomplexa egress in the absence of the compound described herein). In embodiments, the method includes reducing Apicomplexa invasion of a cell, relative to a control (e.g., Apicomplexa invasion in the absence of the compound described herein). In embodiments, the method includes reducing Apicomplexa motility, relative to a control (e.g., Apicomplexa motility in the absence of the compound described herein). In embodiments, the method includes reducing microneme (e.g., organelles involved in motility and invasion) protein release, relative to a control (e.g., microneme protein releases in the absence of the compound described herein).

In embodiments, the Apicomplexa is *Babesia* spp., *Plasmodium* spp., *Cryptosporidium parvum, Cryptosporidium hominis, Cyclospora cayetanensis, Isospora belli, Neospora caninum*, or *Toxoplasma gondii*. In embodiments, the Apicomplexa is *Toxoplasma gondii*.

In embodiments, the Apicomplexa infection is a chronic infection (e.g., toxoplasmosis). In embodiments, the method includes reducing or eliminating Apicomplexa tissue cysts present during chronic infection. In embodiments, the Apicomplexa infection is an acute infection (e.g., toxoplasmosis). In embodiments, the Apicomplexa infection is a congenital infection (e.g., toxoplasmosis). In embodiments, the Apicomplexa infection is in a newborn (e.g., toxoplasmosis). In embodiments, the Apicomplexa infection is in an infant (e.g., toxoplasmosis). In embodiments, the method includes preventing chronic (e.g., recurring) Apicomplexa infection. Chronic toxoplasmosis has also been associated with bipolar disorder, obsessive compulsive disorder, and addiction, See Acta Psychiatr Scand. 2015 September; 132 (3):161-79. doi: 10.1111/acps.12423. Epub 2015 Apr. 15. In embodiments, the Apicomplexa infection is in an HIVpositive subject. In embodiments, the Apicomplexa infection is in an immunocompromised subject.

In an aspect is provided a method of treating an Apicomplexa associated disease, the method including administering to a subject in need thereof an effective amount of a compound described herein. In embodiments, the disease is encephalitis. In embodiments, the disease is schizophrenia. In embodiments, the disease is toxoplasmosis (e.g., chronic toxoplasmosis, acute toxoplasmosis, congenital toxoplasmosis, or toxoplasmosis in a newborn infant). In embodiments, the disease is toxoplasmic encephalitis. In embodiments, the disease is ocular toxoplasmosis. In embodiments, the disease is babesiosis, malaria, cryptosporidiosis, cyclosporiasis, isosporiasis, neosporosis, sarcocystosis, or toxoplasmosis. In embodiments, the disease is schizophrenia. In embodiments, the disease is bipolar disorder, obsessive compulsive disorder, or addiction.

In embodiments, the method further includes co-administering pyrimethanime, a sulfonamide drug, or clindamycin. In embodiments, the sulfonamide drug is sulfadiazine. In embodiments, the secondary agent is artemisinin or atovaquone. In embodiments, the sulfonamide drug is sulfamethoaxazole.

In embodiments, the treatment is prevention. In embodiments, the treatment does not include prevention. In embodiments, the compounds set forth herein are provided as pharmaceutical compositions including the compound and a pharmaceutically acceptable excipient. In embodiments, the disease is described herein, including in an aspect, embodiment, example, figure, table, definition, or claim.

V. Methods of Modulating Calcium Dependent Protein Kinase 1

In an aspect is provided a method of modulating calcium dependent protein kinase 1 (e.g., a parasite CDPK1, an Apicomplexa CDPK1, TgCDPK1, CpCDPK1) activity, the method including: contacting the calcium dependent protein kinase 1 with an effective amount of a compound described herein. In embodiments, the CDPK1 is a CDPK1 from *Toxoplasma gondii, Cryptosporidium parvum, Cryptosporidium hominis, Neospora caninum*, or *Sarcocystis* neurona. In embodiments, the CDPK1 is a CDPK1 from *Toxoplasma gondii*.

In embodiments, the compound has the formula:

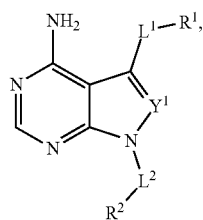

wherein $Y^1$ is —N= or —CH=; $R^1$ is substituted or unsubstituted aryl or substituted or unsubstituted heteroaryl; $R^2$ is hydrogen, substituted or unsubstituted heterocycloalkyl, substituted or unsubstituted heteroaryl, substituted or unsubstituted aryl, substituted or unsubstituted cycloalkyl, or substituted or unsubstituted alkyl; $L^1$ is —O—, —S—, or —N($R^3$)—; $L^2$ is a bond, substituted or unsubstituted alkylene, or substituted or unsubstituted heteroalkylene; $R^3$ is hydrogen, —CN, —COOH, —CX$^3_3$, substituted or unsubstituted alkyl, or substituted or unsubstituted heteroalkyl; and $X^3$ is independently halogen.

In an aspect is provided a method of inhibiting calcium dependent protein kinase (CDPK) activity, the method including contacting the calcium dependent protein kinase with an effective amount of a compound described herein. In embodiments the CDPK is *Toxoplasma gondii* CDPK1 (TgCDPK1). In embodiments the CDPK is *Cryptosporidium parvum* CDPK1 (CpCDPK1). In embodiments, the CDPK is a CDPK from *Toxoplasma gondii, Cryptosporidium parvum, Cryptosporidium hominis, Neospora caninum*, or *Sarcocystis* neurona. In embodiments, the CDPK is a CDPK from *Toxoplasma gondii*. In embodiments, the CDPK is *Toxoplasma gondii* CDPK1 (TgCDPK1), *N. caninum* Liverpool CDPK1 (NcCDPK1), *C. parvum* Iowa II CDPK1 (CpCDPK1), *P. falciparum* CDPK4 (PJCDPK4) *Toxoplasma gondi* mutant G128S CDPK1 (TgG128SCDPK1), *P. falciparum* 3d7 CDPK1 (PJCDPK1), *B. bovis* T2Bo CDPK4 (BbCDPK4), *E. tanella* CDPK1 (EtCDPK1), or *Toxoplasma gondi* mutant G128S CDPK1 (TgG128TCDPK1).

In an aspect is provided a method of inhibiting calcium dependent protein kinase 1 (e.g., a parasite CDPK1, an Apicomplexa CDPK1, or TgCDPK1) activity, the method including: contacting the calcium dependent protein kinase 1 with an effective amount of a compound described herein. In embodiments, inhibiting includes the reduction of calcium dependent protein kinase 1 (e.g., a parasite CDPK1, an Apicomplexa CDPK1, or TgCDPK1) activity relative to the absence of an effective amount of a compound described herein. In embodiments, the method includes inhibiting TgCDPK1 activity.

In embodiments, the calcium dependent protein kinase 1 is in a cell. In embodiments, the cell is an Apicomplexa cell (e.g., *Toxoplasma gondii* cell). In some embodiments, the cell is a mammalian cell, such as a human cell. The cell may be isolated in vitro, form part of a tissue in vitro, or may form part of an organism.

Modulating CDPK1 (e.g., TgCDPK1) activity includes directly or indirectly affecting one or more functions of calcium dependent protein kinase 1 and/or one or more downstream effects of calcium dependent protein kinase 1 activity.

VI. EMBODIMENTS

Embodiment P1

A compound having the formula:

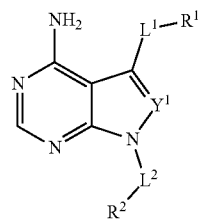

(I)

wherein, $Y^1$ is —N= or —CH=;

$R^1$ is substituted or unsubstituted aryl or substituted or unsubstituted heteroaryl;

$R^2$ is substituted or unsubstituted heterocycloalkyl or substituted or unsubstituted heteroaryl;

$L^1$ is —O—, —S—, or —N($R^3$)—;

$L^2$ is a substituted or unsubstituted alkylene, or substituted or unsubstituted heteroalkylene;

$R^3$ is hydrogen, —CN, —COOH, —CX$^3_3$, substituted or unsubstituted alkyl, or substituted or unsubstituted heteroalkyl; and $X^3$ is independently halogen.

Embodiment P2

The compound of embodiment P1, wherein $R^1$ is substituted or unsubstituted $C_6$-$C_{10}$ aryl or substituted or unsubstituted 5 to 10 membered heteroaryl.

Embodiment P3

The compound of one of embodiments P1 to P2, wherein $R^2$ is substituted or unsubstituted 3 to 7 membered heterocycloalkyl or substituted or unsubstituted 5 to 10 membered heteroaryl.

Embodiment P4

The compound of one of embodiments P1 to P3, wherein $L^2$ is a substituted or unsubstituted $C_1$-$C_5$ alkylene, or substituted or unsubstituted 2 to 5 membered heteroalkylene.

Embodiment P5

The compound of one of embodiments P1 to P3, wherein $L^2$ is a —CH$_2$—, —CH$_2$CH$_2$—, —CH$_2$O—, —CH$_2$S—, or —CH$_2$NH—.

Embodiment P6

The compound of one of embodiments P1 to P5, wherein $R^3$ is hydrogen, —CN, —COOH, —CX$^3_3$, substituted or unsubstituted $C_1$-$C_4$ alkyl, or substituted or unsubstituted 2 to 4 membered heteroalkyl.

Embodiment P7

The compound of one of embodiments P1 to P6, having the formula:

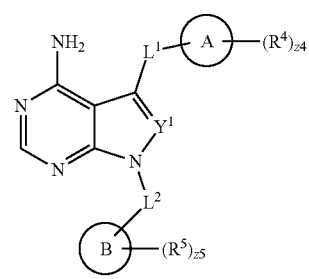

(I)

wherein,

Ring A is $C_6$-$C_{10}$ aryl or 5 to 10 membered heteroaryl;

Ring B is 3 to 7 membered heterocycloalkyl or 5 to 10 membered heteroaryl;

$R^4$ is halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is halogen, —CX$^5_3$, —CHX$^5_2$, —CH$_2$X$^5$, —OCX$^5_3$, —OCH$_2$X$^5$, —OCHX$^5_2$, —CN, —SO$_{n5}$R$^{5D}$, —SO$_{v5}$NR$^{5A}$R$^{5B}$, —NHC(O)NR$^{5A}$R$^{5B}$, —N(O)$_{m5}$, —NR$^{5A}$R$^{5B}$ C(O)R$^{5C}$, —C(O)—OR$^{5C}$, —C(O)NR$^{5A}$R$^{5B}$, —OR$^{5D}$, —NR$^{5A}$SO$_2$R$^{5D}$, —R$^{5A}$C(O)R$^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{4A}$, $R^{4B}$, $R^{4C}$, $R^{4D}$, $R^{5A}$, $R^{5B}$, $R^{5C}$, and $R^{5D}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl;

each X, $X^4$, and $X^5$ is independently —F, —Cl, —Br, or —I;

n4 and n5 are independently an integer from 0 to 4; and m4, m5, v4, and v5 are independently an integer from 1 to 2.

z4 is an integer from 0 to 9; and z5 is an integer from 0 to 6.

Embodiment P8

The compound of one of embodiments P1 to P7, wherein $L^1$ is —O—.

Embodiment P9

The compound of one of embodiments P1 to P7, wherein $L^1$ is —S—.

Embodiment P10

The compound of one of embodiments P1 to P7, wherein $L^1$ is —N($R^3$)—.

Embodiment P11

The compound of embodiment P10, wherein $R^3$ is hydrogen.

Embodiment P12

The compound of one of embodiments P7 to P11, wherein Ring A is phenyl.

Embodiment P13

The compound of one of embodiments P7 to P11, wherein Ring A is napththyl.

Embodiment P14

The compound of one of embodiments P7 to P11, wherein Ring A is 5 to 10 membered heteroaryl.

Embodiment P15

The compound of one of embodiments P7 to P11, wherein Ring A is benzofuranyl, isobenzofuranyl, indolyl, isoindolyl, benzothienyl, benzo[c]thienyl, benzimidazolyl, purinyl, indazolyl, benzoxazolyl, benzisoxazolyl, benzothiazolyl, quinolinyl, isoquinolinyl, quinoxalinyl, quinazolinyl, cinnolinyl, or phthalazinyl.

Embodiment P16

The compound of one of embodiments P7 to P11, wherein Ring A is 5 to 9 membered heteroaryl.

Embodiment P17

The compound of one of embodiments P7 to P11, wherein Ring A is 5 to 6 membered heteroaryl.

Embodiment P18

The compound of one of embodiments P7 to P11, wherein Ring A is furanyl, pyrrolyl, thienyl, imidazolyl, pyrazolyl, oxazolyl, isoxazolyl, thiazolyl, pyridinyl, pyrazinyl, pyrimidinyl, pyridazinyl, or triazinyl.

Embodiment P19

The compound of one of embodiments P7 to P18, wherein $R^4$ is independently —F, —Cl, —Br, —I, —CN, —NH$_2$, —OH, —SH, —COCH$_3$, —COOH, —COOCH$_3$, —CX$^4_3$, —CHX$^4_2$, —CH$_2$X$^4$, —OCX$^4_3$, —OCHX$^4_2$, —OCH$_2$X$^4$, —SCX$^4_3$, —SCHX$^4_2$, —SCH$_2$X$^4$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$CH$_3$.

Embodiment P20

The compound of one of embodiments P1 to P19, wherein z4 is 2.

Embodiment P21

The compound of one of embodiments P1 to P19, wherein z4 is 1.

Embodiment P22

The compound of one of embodiments P1 to P19, wherein z4 is 0.

Embodiment P23

The compound of one of embodiments P1 to P22, wherein $L^2$ is —CH$_2$—.

Embodiment P24

The compound of one of embodiments P1 to P22, wherein $L^2$ is —CH$_2$CH$_2$—.

Embodiment P25

The compound of one of embodiments P1 to 22, wherein $L^2$ is —CH$_2$O—.

Embodiment P26

The compound of one of embodiments P1 to P22, wherein $L^2$ is —CH$_2$S—.

Embodiment P27

The compound of one of embodiments P1 to P22, wherein $L^2$ is —CH$_2$NH—.

Embodiment P28

The compound of one of embodiments P7 to P27, wherein Ring B is 3 to 7 membered heterocycloalkyl.

Embodiment P29

The compound of one of embodiments P7 to 27, wherein Ring B is 3 to 6 membered heterocycloalkyl.

Embodiment P30

The compound of one of embodiments P7 to P27, wherein Ring B is aziridinyl, azirinyl, diaziridinyl, diazirinyl, oxaziridinyl, azetidinyl, azetyl, diazetidinyl, diazetyl, pyrrolidinyl, pyrazolidinyl, oxazolidinyl, isoxazolidinyl, thiazolidinyl, isothiazolidinyl, triazolyl, furazanyl, oxadiazolyl, thiadiazolyl, dithiazolyl, tetrazolyl, piperidinyl, piperazinyl, morpholinyl, or thiomorpholinyl.

Embodiment P31

The compound of one of embodiments P7 to P27, wherein Ring B is a 6 membered heterocycloalkyl.

Embodiment P32

The compound of one of embodiments P7 to P27, wherein Ring B is piperidinyl or piperazinyl.

Embodiment P33

The compound of one of embodiments P7 to P27, wherein Ring B is 5 to 10 membered heteroaryl.

Embodiment P34

The compound of one of embodiments P7 to P27, wherein Ring B is pyridinyl, pyrazinyl, pyrimidinyl, pyridazinyl, triazinyl, quinolinyl, isoquinolinyl, quinoxalinyl, quinazolinyl, cinnolinyl, or phthalazinyl.

Embodiment P35

The compound of one of embodiments P7 to P27, wherein Ring B is a 6 membered heteroaryl.

Embodiment P36

The compound of one of embodiments P7 to P27, wherein Ring B is pyridinyl, pyrazinyl, pyrimidinyl, or pyridazinyl.

Embodiment P37

The compound of one of embodiments P7 to P36, wherein $R^5$ is —F, —Cl, —Br, —I, —CN, —NH$_2$, —OH, —SH, —COCH₃, —COOH, —COOCH₃, —CX⁵₃, —CHX⁵₂, —CH₂X⁵, —OCX⁵₃, —OCHX⁵₂, —OCH₂X⁵, —SCX⁵₃, —SCHX⁵₂, —SCH₂X⁵, —CH₃, —CH₂CH₃, —OCH₃, —OCH₂CH₃, —NHCH₃, —N(CH₃)₂, —NHCH₂CH₃, —N(CH₃)(CH₂CH₃), —N(CH₂CH₃)₂, —SCH₃, or —SCH₂CH₃.

Embodiment P38

The compound of one of embodiments P7 to P37, wherein z5 is 2.

Embodiment P39

The compound of one of embodiments P7 to P37, wherein z5 is 1.

Embodiment P40

The compound of one of embodiments P7 to P37, wherein z5 is 0.

Embodiment P41

A pharmaceutical composition comprising a pharmaceutically acceptable excipient and a compound of one of embodiments P1 to P40, or a pharmaceutically acceptable salt thereof.

Embodiment P42

A method of inhibiting calcium dependent protein kinase 1 activity, said method comprising: contacting the calcium dependent protein kinase 1 with an effective amount of a compound having the formula:

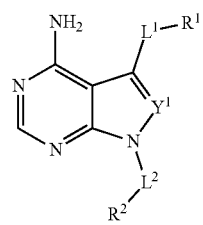

(I)

wherein,
Y¹ is —N= or —CH=;
R¹ is substituted or unsubstituted aryl or substituted or unsubstituted heteroaryl;
R² is substituted or unsubstituted heterocycloalkyl or substituted or unsubstituted heteroaryl;
L¹ is —O—, —S—, or —N(R³)—;
L² is a bond, substituted or unsubstituted alkylene, or substituted or unsubstituted heteroalkylene;
R³ is hydrogen, —CN, —COOH, —CX³₃, substituted or unsubstituted alkyl, or substituted or unsubstituted heteroalkyl; and
X³ is independently halogen.

Embodiment P43

A method of treating an Apicomplexa infection, said method comprising administering to a subject in need thereof an effective amount of a compound having the formula:

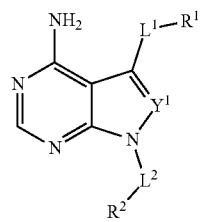

(I)

wherein,
Y¹ is —N= or —CH=;
R¹ is substituted or unsubstituted aryl or substituted or unsubstituted heteroaryl;
R² is substituted or unsubstituted heterocycloalkyl or substituted or unsubstituted heteroaryl;
L¹ is —O—, —S—, or —N(R³)—;
L² is a bond, substituted or unsubstituted alkylene, or substituted or unsubstituted heteroalkylene;
R³ is hydrogen, —CN, —COOH, —CX³₃, substituted or unsubstituted alkyl, or substituted or unsubstituted heteroalkyl; and
X³ is independently halogen.

Embodiment P44

The method of embodiment P43, wherein the Apicomplexa infection is in the brain.

Embodiment P45

The method of one of embodiments P43 to P44, comprising preventing chronic Apicomplexa infection.

Embodiment P46

The method of one of embodiments P43 to P44, comprising preventing reactivation of the Apicomplexa in cysts.

Embodiment P47

The method of one of embodiments P43 to P46, comprising reducing Apicomplexa survival.

Embodiment P48

The method of one of embodiments P43 to P46, comprising reducing Apicomplexa proliferation.

Embodiment P49

The method of one of embodiments P43 to P46, comprising reducing Apicomplexa egress from a cell.

Embodiment P50

The method of one of embodiments P43 to P46, comprising reducing Apicomplexa invasion of a cell.

Embodiment P51

The method of one of embodiments P43 to P46, comprising reducing Apicomplexa motility.

Embodiment P52

The method of one of embodiments P43 to P51, comprising reducing microneme protein release.

Embodiment P53

The method of one of embodiments P43 to P52, wherein the Apicomplexa is *Toxoplasma gondii*.

Embodiment P54

A method of treating an Apicomplexa associated disease, said method comprising administering to a subject in need thereof an effective amount of a compound having the formula:

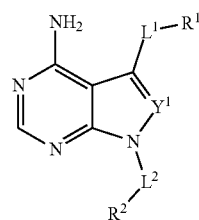

wherein,
$Y^1$ is —N= or —CH=;
$R^1$ is substituted or unsubstituted aryl or substituted or unsubstituted heteroaryl;
$R^2$ is substituted or unsubstituted heterocycloalkyl or substituted or unsubstituted heteroaryl;
$L^1$ is —O—, —S—, or —N($R^3$)—;
$L^2$ is a bond, substituted or unsubstituted alkylene, or substituted or unsubstituted heteroalkylene;
$R^3$ is hydrogen, —CN, —COOH, —$CX^3_3$, substituted or unsubstituted alkyl, or substituted or unsubstituted heteroalkyl; and
$X^3$ is independently halogen.

Embodiment P55

The method of embodiment P54, wherein the disease is encephalitis.

Embodiment P56

The method of embodiment P54, wherein the disease is schizophrenia.

Embodiment P57

The method of embodiment 54, wherein the disease is toxoplasmosis.

Embodiment P58

The method of embodiment P54, wherein the disease is toxoplasmic encephalitis.

Embodiment P59

The method of embodiment P54, wherein the disease is ocular toxoplasmosis.

Embodiment P60

The method of one of embodiments P57 to P59, further comprising co-administering pyrimethamine, a sulfonamide drug, or clindamycin.

Embodiment P61

The method of embodiment P60, wherein the sulfonamide drug is sulfadiazine.

Embodiment P62

The method of one of embodiments P42 to P61, wherein $R^1$ is substituted or unsubstituted $C_6$-$C_{10}$ aryl or substituted or unsubstituted 5 to 10 membered heteroaryl.

Embodiment P63

The method of one of embodiments P42 to P61, wherein $R^2$ is substituted or unsubstituted 3 to 7 membered heterocycloalkyl or substituted or unsubstituted 5 to 10 membered heteroaryl.

Embodiment P64

The method of one of embodiments P42 to P63, wherein $L^2$ is a bond, substituted or unsubstituted $C_1$-$C_5$ alkylene, or substituted or unsubstituted 2 to 5 membered heteroalkylene.

Embodiment P65

The method of one of embodiments P42 to P63, wherein $L^2$ is a bond, —$CH_2$—, —$CH_2CH_2$—, —$CH_2O$—, —$CH_2S$—, or —$CH_2NH$—.

Embodiment P66

The method of one of embodiments P42 to P65, wherein $R^3$ is hydrogen, —CN, —COOH, —$CX^3_3$, substituted or unsubstituted $C_1$-$C_4$ alkyl, or substituted or unsubstituted 2 to 4 membered heteroalkyl.

Embodiment P67

The method of one of embodiments P42 to P66, wherein the compound has the formula:

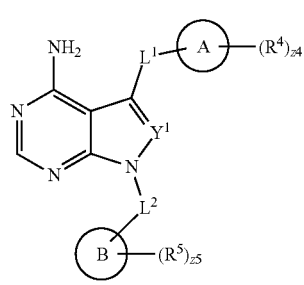

wherein,
Ring A is $C_6$-$C_{10}$ aryl or 5 to 10 membered heteroaryl;
Ring B is 3 to 7 membered heterocycloalkyl or 5 to 10 membered heteroaryl;

R$^4$ is halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is halogen, —CX$^5_3$, —CHX$^5_2$, —CH$_2$X$^5$, —OCX$^5_3$, —OCH$_2$X$^5$, —OCHX$^5_2$, —CN, —SO$_{n5}$R$^{5D}$, —SO$_{v5}$NR$^{5A}$R$^{5B}$, —NHC(O)NR$^{5A}$R$^{5B}$, —N(O)$_{m5}$, —NR$^{5A}$R$^{5B}$ C(O)R$^{5C}$, —C(O)—OR$^{5C}$, —C(O)NR$^{5A}$R$^{5B}$, —OR$^{5D}$, —NR$^{5A}$SO$_2$R$^{5D}$, —NR$^{5A}$C(O)R$^{5C}$, —NR AC(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{4A}$, R$^{4B}$, R$^{4C}$, R$^{4D}$, R$^{5A}$, R$^{5B}$, R$^{5C}$, and R$^{5D}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl;

each X, X$^4$, and X$^5$ is independently —F, —Cl, —Br, or —I;

n4 and n5 are independently an integer from 0 to 4; and m4, m5, v4, and v5 are independently an integer from 1 to 2.

z4 is an integer from 0 to 9; and z5 is an integer from 0 to 6.

Embodiment P68

The method of one of embodiments P42 to P67, wherein L$^1$ is —O—.

Embodiment P69

The method of one of embodiments P42 to P67, wherein L$^1$ is —S—.

Embodiment P70

The method of one of embodiments P42 to P67, wherein L$^1$ is —N(R$^3$)—.

Embodiment P71

The method of embodiment P70, wherein R$^3$ is hydrogen.

Embodiment P72

The method of one of embodiments P67 to P71, wherein Ring A is phenyl.

Embodiment P73

The method of one of embodiments P67 to P71, wherein Ring A is napththyl.

Embodiment P74

The method of one of embodiments P67 to P71, wherein Ring A is 5 to 10 membered heteroaryl.

Embodiment P75

The method of one of embodiments P67 to P71, wherein Ring A is benzofuranyl, isobenzofuranyl, indolyl, isoindolyl, benzothienyl, benzo[c]thienyl, benzimidazolyl, purinyl, indazolyl, benzoxazolyl, benzisoxazolyl, benzothiazolyl, quinolinyl, isoquinolinyl, quinoxalinyl, quinazolinyl, cinnolinyl, or phthalazinyl.

Embodiment P76

The method of one of embodiments P67 to P71, wherein Ring A is 5 to 9 membered heteroaryl.

Embodiment P77

The method of one of embodiments P67 to P71, wherein Ring A is 5 to 6 membered heteroaryl.

Embodiment P78

The method of one of embodiments P67 to P71, wherein Ring A is furanyl, pyrrolyl, thienyl, imidazolyl, pyrazolyl, oxazolyl, isoxazolyl, thiazolyl, pyridinyl, pyrazinyl, pyrimidinyl, pyridazinyl, or triazinyl.

Embodiment P79

The method of one of embodiments P67 to P78, wherein R$^4$ is independently —F, —Cl, —Br, —I, —CN, —NH$_2$, —OH, —SH, —COCH$_3$, —COOH, —COOCH$_3$, —CX$^4_3$, —CHX$^4_2$, —CH$_2$X$^4$, —OCX$^4_3$, —OCHX$^4_2$, —OCH$_2$X$^4$, —SCX$^4_3$, —SCHX$^4_2$, —SCH$_2$X$^4$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$CH$_3$.

Embodiment P80

The method of one of embodiments P42 to P79, wherein z4 is 2.

Embodiment P81

The method of one of embodiments P42 to P79, wherein z4 is 1.

Embodiment P82

The method of one of embodiments P42 to P79, wherein z4 is 0.

Embodiment P83

The method of one of embodiments P42 to P82, wherein L$^2$ is a bond.

Embodiment P84

The method of one of embodiments P42 to P82, wherein $L^2$ is —CH$_2$—.

Embodiment P85

The method of one of embodiments P42 to P82, wherein $L^2$ is —CH$_2$CH$_2$—.

Embodiment P86

The method of one of embodiments P42 to P82, wherein $L^2$ is —CH$_2$O—.

Embodiment P87

The method of one of embodiments P42 to P82, wherein $L^2$ is —CH$_2$S—.

Embodiment P88

The method of one of embodiments P42 to P82, wherein $L^2$ is —CH$_2$NH—.

Embodiment P89

The method of one of embodiments P67 to P88, wherein Ring B is 3 to 7 membered heterocycloalkyl.

Embodiment P90

The method of one of embodiments P67 to P88, wherein Ring B is 3 to 6 membered heterocycloalkyl.

Embodiment P91

The method of one of embodiments P67 to P88, wherein Ring B is aziridinyl, azirinyl, diaziridinyl, diazirinyl, oxaziridinyl, azetidinyl, azetyl, diazetidinyl, diazetyl, pyrrolidinyl, pyrazolidinyl, oxazolidinyl, isoxazolidinyl, thiazolidinyl, isothiazolidinyl, triazolyl, furazanyl, oxadiazolyl, thiadiazolyl, dithiazolyl, tetrazolyl, piperidinyl, piperazinyl, morpholinyl, or thiomorpholinyl.

Embodiment P92

The method of one of embodiments P67 to P88, wherein Ring B is a 6 membered heterocycloalkyl.

Embodiment P93

The method of one of embodiments P67 to P88, wherein Ring B is piperidinyl or piperazinyl.

Embodiment P94

The method of one of embodiments P67 to P88, wherein Ring B is 5 to 10 membered heteroaryl.

Embodiment P95

The method of one of embodiments P67 to P88, wherein Ring B is pyridinyl, pyrazinyl, pyrimidinyl, pyridazinyl, triazinyl, quinolinyl, isoquinolinyl, quinoxalinyl, quinazolinyl, cinnolinyl, or phthalazinyl.

Embodiment P96

The method of one of embodiments P67 to P88, wherein Ring B is a 6 membered heteroaryl.

Embodiment P97

The method of one of embodiments P67 to P88, wherein Ring B is pyridinyl, pyrazinyl, pyrimidinyl, or pyridazinyl.

Embodiment P98

The method of one of embodiments P67 to P97, wherein $R^5$ is —F, —Cl, —Br, —I, —CN, —NH$_2$, —OH, —SH, —COCH$_3$, —COOH, —COOCH$_3$, —CX$^5_3$, —CHX$^5_2$, —CH$_2$X$^5$, —OCX$^5_3$, —OCHX$^5_2$, —OCH$_2$X$^5$, —SCX$^5_3$, —SCHX$^5_2$, —SCH$_2$X$^5$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$CH$_3$.

Embodiment P99

The method of one of embodiments P67 to P98, wherein z5 is 2.

Embodiment P100

The method of one of embodiments P67 to P98, wherein z5 is 1.

Embodiment P101

The method of one of embodiments P67 to P98, wherein z5 is 0.

VII. ADDITIONAL EMBODIMENTS

Embodiment 1

A compound having the formula:

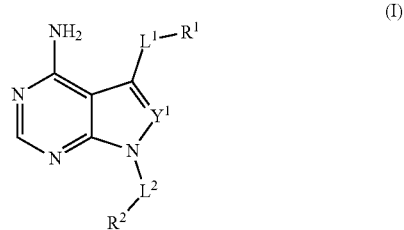

(I)

wherein,
  $Y^1$ is —N= or —CH=;
  $R^1$ is substituted or unsubstituted aryl or substituted or unsubstituted heteroaryl;
  $R^2$ is substituted or unsubstituted heterocycloalkyl, substituted or unsubstituted heteroaryl, or substituted or unsubstituted cycloalkyl;
  $L^1$ is —O—, —S—, or —N(R$^3$)—;
  $L^2$ is a substituted or unsubstituted alkylene, or substituted or unsubstituted heteroalkylene;
  $R^3$ is hydrogen, —CN, —COOH, —CX$^3_3$, substituted or unsubstituted alkyl, or substituted or unsubstituted heteroalkyl; and
  $X^3$ is independently halogen.

Embodiment 2

The compound of embodiment 1, wherein $R^1$ is substituted or unsubstituted $C_6$-$C_{10}$ aryl or substituted or unsubstituted 5 to 10 membered heteroaryl.

Embodiment 3

The compound of one of embodiments 1 to 2, wherein $R^2$ is substituted or unsubstituted 3 to 7 membered heterocycloalkyl, substituted or unsubstituted 5 to 10 membered heteroaryl, or substituted or unsubstituted $C_3$-$C_8$ cycloalkyl.

Embodiment 4

The compound of one of embodiments 1 to 3, wherein $L^2$ is a substituted or unsubstituted $C_1$-$C_5$ alkylene, or substituted or unsubstituted 2 to 5 membered heteroalkylene.

Embodiment 5

The compound of one of embodiments 1 to 3, wherein $L^2$ is a —CH$_2$—, —CH$_2$CH$_2$—, —CH$_2$O—, —CH$_2$S—, or —CH$_2$NH—.

Embodiment 6

The compound of one of embodiments 1 to 5, wherein $R^3$ is hydrogen, —CN, —COOH, —CX$^3{}_3$, substituted or unsubstituted $C_1$-$C_4$ alkyl, or substituted or unsubstituted 2 to 4 membered heteroalkyl.

Embodiment 7

The compound of one of embodiments 1 to 6, having the formula:

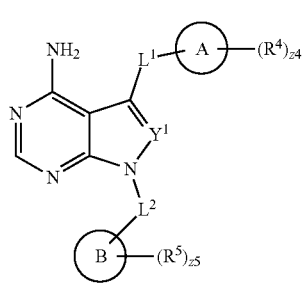

(I)

wherein,

Ring A is $C_6$-$C_{10}$ aryl or 5 to 10 membered heteroaryl;
Ring B is 3 to 7 membered heterocycloalkyl, 5 to 10 membered heteroaryl, or $C_3$-$C_8$ cycloalkyl;
$R^4$ is halogen, —CX$^4{}_3$, —CHX$^4{}_2$, —CH$_2$X$^4$, —OCX$^4{}_3$, —OCH$_2$X$^4$, —OCHX$^4{}_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is halogen, —CX$^5{}_3$, —CHX$^5{}_2$, —CH$_2$X$^5$, —OCX$^5{}_3$, —OCH$_2$X$^5$, —OCHX$^5{}_2$, —CN, —SO$_{n5}$R$^{5D}$, —SO$_{v5}$NR$^{5A}$R$^{5B}$, —NHC(O)NR$^{5A}$R$^{5B}$, —N(O)$_{m5}$, —NR$^{5A}$R$^{5B}$, C(O)R$^{5C}$, —C(O)—OR$^{5C}$, —C(O)NR$^{5A}$R$^{5B}$, —OR$^{5D}$, —NR$^{5A}$SO$_2$R$^{5D}$, —NR$^{5A}$C(O)R$^{5C}$, —NR$^{5A}$C(O)OR$^{5C}$, —N R$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{4A}$, $R^{4B}$, $R^{4C}$, $R^{4D}$, $R^{5A}$, $R^{5B}$, $R^{5C}$, and $R^{5D}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl;

each X, $X^4$, and $X^5$ is independently —F, —Cl, —Br, or —I;
n4 and n5 are independently an integer from 0 to 4; and
m4, m5, v4, and v5 are independently an integer from 1 to 2.
z4 is an integer from 0 to 9; and
z5 is an integer from 0 to 6.

Embodiment 8

The compound of one of embodiments 1 to 7, wherein $L^1$ is —O—.

Embodiment 9

The compound of one of embodiments 1 to 7, wherein $L^1$ is —S—.

Embodiment 10

The compound of one of embodiments 1 to 7, wherein $L^1$ is —N(R$^3$)—.

Embodiment 11

The compound of embodiment 10, wherein $R^3$ is hydrogen.

Embodiment 12

The compound of one of embodiments 7 to 11, wherein Ring A is phenyl.

Embodiment 13

The compound of one of embodiments 7 to 11, wherein Ring A is napththyl.

Embodiment 14

The compound of one of embodiments 7 to 11, wherein Ring A is 5 to 10 membered heteroaryl.

Embodiment 15

The compound of one of embodiments 7 to 11, wherein Ring A is benzofuranyl, isobenzofuranyl, indolyl, isoindolyl, benzothienyl, benzo[c]thienyl, benzimidazolyl, azaindolyl, benzoisoxazolyl, purinyl, indazolyl, benzoxazolyl, benzisoxazolyl, benzothiazolyl, quinolinyl, isoquinolinyl, quinoxalinyl, quinazolinyl, cinnolinyl, or phthalazinyl.

Embodiment 16

The compound of one of embodiments 7 to 11, wherein Ring A is 5 to 9 membered heteroaryl.

Embodiment 17

The compound of one of embodiments 7 to 11, wherein Ring A is 5 to 6 membered heteroaryl.

Embodiment 18

The compound of one of embodiments 7 to 11, wherein Ring A is furanyl, pyrrolyl, thienyl, imidazolyl, pyrazolyl, oxazolyl, isoxazolyl, thiazolyl, pyridinyl, pyrazinyl, pyrimidinyl, pyridazinyl, or triazinyl.

Embodiment 19

The compound of one of embodiments 7 to 18, wherein $R^4$ is independently —F, —Cl, —Br, —I, —CN, —NH$_2$, —OH, —SH, —COCH$_3$, —COOH, —COOCH$_3$, —CX$^4_3$, —CHX$^4_2$, —CH$_2$X$^4$, —OCX$^4_3$, —OCHX$^4_2$, —OCH$_2$X$^4$, —SCX$^4_3$, —SCHX$^4_2$, —SCH$_2$X$^4$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$CH$_3$.

Embodiment 20

The compound of one of embodiments 1 to 19, wherein z4 is 2.

Embodiment 21

The compound of one of embodiments 1 to 19, wherein z4 is 1.

Embodiment 22

The compound of one of embodiments 1 to 19, wherein z4 is 0.

Embodiment 23

The compound of one of embodiments 1 to 22, wherein $L^2$ is —CH$_2$—.

Embodiment 24

The compound of one of embodiments 1 to 22, wherein $L^2$ is —CH$_2$CH$_2$—.

Embodiment 25

The compound of one of embodiments 1 to 22, wherein $L^2$ is —CH$_2$O—.

Embodiment 26

The compound of one of embodiments 1 to 22, wherein $L^2$ is —CH$_2$S—.

Embodiment 27

The compound of one of embodiments 1 to 22, wherein $L^2$ is —CH$_2$NH—.

Embodiment 28

The compound of one of embodiments 7 to 27, wherein Ring B is 3 to 7 membered heterocycloalkyl.

Embodiment 29

The compound of one of embodiments 7 to 27, wherein Ring B is 3 to 6 membered heterocycloalkyl.

Embodiment 30

The compound of one of embodiments 7 to 27, wherein Ring B is aziridinyl, azirinyl, diaziridinyl, diazirinyl, oxaziridinyl, azetidinyl, azetyl, diazetidinyl, diazetyl, pyrrolidinyl, pyrazolidinyl, oxazolidinyl, isoxazolidinyl, thiazolidinyl, isothiazolidinyl, triazolyl, furazanyl, oxadiazolyl, thiadiazolyl, dithiazolyl, tetrazolyl, piperidinyl, piperazinyl, morpholinyl, or thiomorpholinyl.

Embodiment 31

The compound of one of embodiments 7 to 27, wherein Ring B is a 6 membered heterocycloalkyl.

Embodiment 32

The compound of one of embodiments 7 to 27, wherein Ring B is piperidinyl or piperazinyl.

Embodiment 33

The compound of one of embodiments 7 to 27, wherein Ring B is a $C_3$-$C_8$ substituted or unsubstituted cycloalkyl.

Embodiment 34

The compound of one of embodiments 7 to 27, wherein Ring B is substituted or unsubstituted cyclooctanyl, substituted or unsubstituted cycloheptanyl, substituted or unsubstituted cyclohexanyl, or substituted or unsubstituted cyclopentanyl.

Embodiment 35

The compound of one of embodiments 7 to 27, wherein Ring B is substituted or unsubstituted cyclopentanyl.

Embodiment 36

The compound of one of embodiments 7 to 27, wherein Ring B is 5 to 10 membered heteroaryl.

Embodiment 37

The compound of one of embodiments 7 to 27, wherein Ring B is pyridinyl, pyrazinyl, pyrimidinyl, pyridazinyl, triazinyl, quinolinyl, isoquinolinyl, quinoxalinyl, quinazolinyl, cinnolinyl, or phthalazinyl.

Embodiment 38

The compound of one of embodiments 7 to 27, wherein Ring B is a 6 membered heteroaryl.

Embodiment 39

The compound of one of embodiments 7 to 27, wherein Ring B is pyridinyl, pyrazinyl, pyrimidinyl, or pyridazinyl.

Embodiment 40

The compound of one of embodiments 7 to 39, wherein $R^5$ is —F, —Cl, —Br, —I, —CN, —NH$_2$, —OH, —SH, —COCH$_3$, —COOH, —COOCH$_3$, —CX$^5_3$, —CHX$^5_2$, —CH$_2$X$^5$, —OCX$^5_3$, —OCHX$^5_2$, —OCH$_2$X$^5$, —SCX$^5_3$, —SCHX$^5_2$, —SCH$_2$X$^5$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$CH$_3$.

Embodiment 41

The compound of one of embodiments 7 to 40, wherein z5 is 2.

Embodiment 42

The compound of one of embodiments 7 to 40, wherein z5 is 1.

Embodiment 43

The compound of one of embodiments 7 to 40, wherein z5 is 0.

Embodiment 44

The compound of embodiment 1, having the formula:

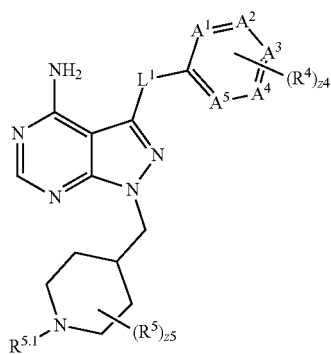

wherein, $A^1$, $A^2$, $A^3$, $A^4$, and $A^5$, are each independently —C($R^4$)= or —N=; $R^4$ is independently substituted or unsubstituted alkyl, substituted or unsubstituted cycloalkyl, halogen, —CF$_3$, —OCH$_3$, —CN, —SO$_2$CH$_3$, —SO$_2$NHR$^{4B}$, —OCF$_3$; $R^5$ is independently oxo, halogen, —COOH, or —C(O)NR$^{5A}$R$^{5B}$; $R^{51}$ is hydrogen, substituted or unsubstituted alkyl, substituted or unsubstituted cycloalkyl, —C(O)NR$^{5A}$R$^{5B}$,

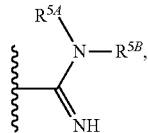

—C(N)-(substituted or unsubstituted alkyl), —C(N)-(substituted or unsubstituted cycloalkyl), —C(O)-(substituted or unsubstituted alkyl), or —C(O)-(substituted or unsubstituted cycloalkyl);

z4 and z5 are independently an integer from 0 to 2; and $R^{5A}$ and $R^{5B}$ are independently hydrogen or substituted or unsubstituted alkyl.

Embodiment 45

The compound of embodiment 44, wherein z5 is 2.

Embodiment 46

The compound of embodiment 44 or 45, wherein $R^{51}$ is substituted or unsubstituted cyclopropyl.

Embodiment 47

The compound of embodiment 1, wherein $L^2$-$R^2$ has the formula:

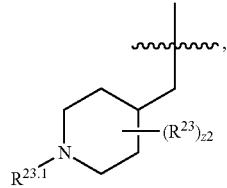

wherein $R^{23}$ is independently oxo, halogen, —CX$^{23}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{23}_3$, —OCHX$^{23}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{23.1}$ is hydrogen, substituted or unsubstituted alkyl, substituted or unsubstituted cyclopropyl, —C(O)-(substituted or unsubstituted alkyl), —C(O)-(substituted or unsubstituted cyclopropyl), —C(N)-alkyl, —C(N)-cyclopropyl; and z2 is an integer from 0 to 9.

Embodiment 48

The compound of embodiment 1, having the formula:

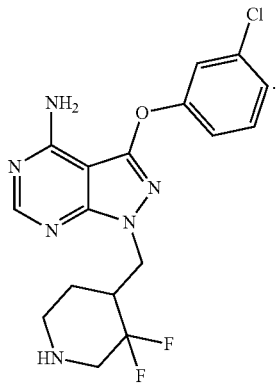

Embodiment 49

A pharmaceutical composition comprising a pharmaceutically acceptable excipient and a compound of one of embodiments 1 to 48, or a pharmaceutically acceptable salt thereof.

Embodiment 50

A method of inhibiting calcium dependent protein kinase 1 activity, said method comprising: contacting the calcium dependent protein kinase 1 with an effective amount of a compound having the formula:

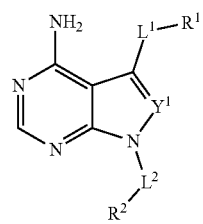

wherein,
$Y^1$ is —N= or —CH=;
$R^1$ is substituted or unsubstituted aryl or substituted or unsubstituted heteroaryl;
$R^2$ is substituted or unsubstituted heterocycloalkyl, substituted or unsubstituted heteroaryl, substituted or unsubstituted cycloalkyl, or substituted or unsubstituted alkyl;
$L^1$ is —O—, —S—, or —N($R^3$)—;
$L^2$ is a bond, substituted or unsubstituted alkylene, or substituted or unsubstituted heteroalkylene;
$R^3$ is hydrogen, —CN, —COOH, —$CX^3{}_3$, substituted or unsubstituted alkyl, or substituted or unsubstituted heteroalkyl; and
$X^3$ is independently halogen.

Embodiment 51

The method of embodiment 50, wherein $R^2$ is substituted or unsubstituted heterocycloalkyl, substituted or unsubstituted heteroaryl, or substituted or unsubstituted cycloalkyl.

Embodiment 52

A method of treating an Apicomplexa infection, said method comprising administering to a subject in need thereof an effective amount of a compound having the formula:

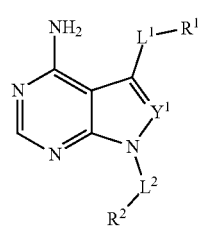

wherein,
$Y^1$ is —N= or —CH=;
$R^1$ is substituted or unsubstituted aryl or substituted or unsubstituted heteroaryl;
$R^2$ is substituted or unsubstituted heterocycloalkyl, substituted or unsubstituted heteroaryl, substituted or unsubstituted cycloalkyl, or substituted or unsubstituted alkyl;
$L^1$ is —O—, —S—, or —N($R^3$)—;
$L^2$ is a bond, substituted or unsubstituted alkylene, or substituted or unsubstituted heteroalkylene;
$R^3$ is hydrogen, —CN, —COOH, —$CX^3{}_3$, substituted or unsubstituted alkyl, or substituted or unsubstituted heteroalkyl; and
$X^3$ is independently halogen.

Embodiment 53

The method of embodiment 52, wherein $R^2$ is substituted or unsubstituted heterocycloalkyl, substituted or unsubstituted heteroaryl, or substituted or unsubstituted cycloalkyl.

Embodiment 54

The method of one of embodiments 50 or 52, further comprising preventing reactivation of Apicomplexa bradyzoite stages that exist within tissue cysts.

Embodiment 55

The method of one of embodiments 50 or 52, wherein the Apicomplexa infection is in central nervous system.

Embodiment 56

The method of one of embodiments 50 or 52, wherein the Apicomplexa infection is in the brain and the eye.

Embodiment 57

The method of one of embodiments 50 or 52, wherein the Apicomplexa infection is in the brain.

Embodiment 58

The method of one of embodiments 52 to 57, comprising preventing chronic Apicomplexa infection.

Embodiment 59

The method of one of embodiments 52 to 57, comprising reducing or eliminating Apicomplexa tissue cysts present during chronic infection.

Embodiment 60

The method of one of embodiments 52 to 57, comprising preventing reactivation of the Apicomplexa in cysts.

Embodiment 61

The method of one of embodiments 52 to 60, comprising reducing Apicomplexa survival.

Embodiment 62

The method of one of embodiments 52 to 60, comprising reducing Apicomplexa proliferation.

Embodiment 63

The method of one of embodiments 52 to 60, comprising reducing Apicomplexa egress from a cell.

Embodiment 64

The method of one of embodiments 52 to 60, comprising reducing Apicomplexa invasion of a cell.

Embodiment 65

The method of one of embodiments 52 to 60, comprising reducing Apicomplexa motility.

Embodiment 66

The method of one of embodiments 52 to 65, comprising reducing microneme protein release.

Embodiment 67

The method of one of embodiments 52 to 66, wherein the Apicomplexa is *Toxoplasma gondii*.

Embodiment 68

A method of treating an Apicomplexa associated disease, said method comprising administering to a subject in need thereof an effective amount of a compound having the formula:

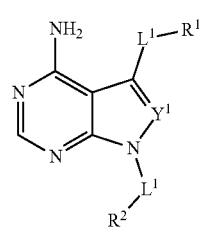

(I)

wherein,
$Y^1$ is —N= or —CH=;
$R^1$ is substituted or unsubstituted aryl or substituted or unsubstituted heteroaryl;
$R^2$ is substituted or unsubstituted heterocycloalkyl, substituted or unsubstituted heteroaryl, substituted or unsubstituted cycloalkyl, or substituted or unsubstituted alkyl;
$L^1$ is —O—, —S—, or —N($R^3$)—;
$L^2$ is a bond, substituted or unsubstituted alkylene, or substituted or unsubstituted heteroalkylene;
$R^3$ is hydrogen, —CN, —COOH, —$CX^3_3$, substituted or unsubstituted alkyl, or substituted or unsubstituted heteroalkyl; and
$X^3$ is independently halogen.

Embodiment 69

The method of embodiment 68, wherein $R^2$ is substituted or unsubstituted heterocycloalkyl, substituted or unsubstituted heteroaryl, or substituted or unsubstituted cycloalkyl.

Embodiment 70

The method of one of embodiments 68 to 69, wherein the disease is encephalitis.

Embodiment 71

The method of one of embodiments 68 to 69, wherein the disease is schizophrenia.

Embodiment 72

The method of one of embodiments 68 to 69, wherein the disease is toxoplasmosis.

Embodiment 73

The method of one of embodiments 68 to 69, wherein the disease is toxoplasmic encephalitis.

Embodiment 74

The method of one of embodiments 68 to 69, wherein the disease is ocular toxoplasmosis.

Embodiment 75

The method of one of embodiments 72 to 74, further comprising co-administering pyrimethamine, a sulfonamide drug, or clindamycin.

Embodiment 76

The method of embodiment 75, wherein the sulfonamide drug is sulfadiazine or sulfamethoxazole.

Embodiment 77

The method of one of embodiments 50 to 76, wherein $R^1$ is substituted or unsubstituted $C_6$-$C_{10}$ aryl or substituted or unsubstituted 5 to 10 membered heteroaryl.

Embodiment 78

The method of one of embodiments 50 to 76, wherein $R^2$ is substituted or unsubstituted 3 to 7 membered heterocycloalkyl or substituted or unsubstituted 5 to 10 membered heteroaryl.

Embodiment 79

The method of one of embodiments 50 to 78, wherein $L^2$ is a bond, substituted or unsubstituted $C_1$-$C_5$ alkylene, or substituted or unsubstituted 2 to 5 membered heteroalkylene.

Embodiment 80

The method of one of embodiments 50 to 78, wherein $L^2$ is a bond, —$CH_2$—, —$CH_2CH_2$—, —$CH_2O$—, —$CH_2S$—, or —$CH_2NH$—.

Embodiment 81

The method of one of embodiments 50 to 80, wherein $R^3$ is hydrogen, —CN, —COOH, —$CX^3{}_3$, substituted or unsubstituted $C_1$-$C_4$ alkyl, or substituted or unsubstituted 2 to 4 membered heteroalkyl.

Embodiment 82

The method of one of embodiments 50 to 81, wherein the compound has the formula:

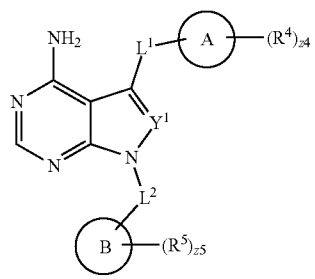

(I)

wherein,
Ring A is $C_6$-$C_{10}$ aryl or 5 to 10 membered heteroaryl;
Ring B is 3 to 7 membered heterocycloalkyl, 5 to 10 membered heteroaryl, or $C_3$-$C_5$ cycloalkyl;
$R^4$ is halogen, —$CX^4{}_3$, —$CHX^4{}_2$, —$CH_2X^4$, —$OCX^4{}_3$, —$OCH_2X^4$, —$OCHX^4{}_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is halogen, —$CX^5{}_3$, —$CHX^5{}_2$, —$CH_2X^5$, —$OCX^5{}_3$, —$OCH_2X^5$, —$OCHX^5{}_2$, —CN, —$SO_{n5}R^{5D}$, —$SO_5NR^{5A}R^{5B}$, —$NHC(O)NR^{5A}R^{5B}$, —$N(O)_{m5}$, —$NR^{5A}R^{5B}$ $C(O)R^{5C}$, —$C(O)$—$OR^{5C}$, —$C(O)NR^{5A}R^{5B}$, —$OR^{5D}$, —$NR^{5A}SO_2R^{5D}$, —$NR^{5A}C(O)R^{5C}$, —$NR^{5A}C(O)OR^{5C}$, —$NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
Each $R^{4A}$, $R^{4B}$, $R^{4C}$, $R^{4D}$, $R^{5A}$, $R^{5B}$, $R^{5C}$, and $R^{5D}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl;
each X, $X^4$, and $X^5$ is independently —F, —Cl, —Br, or —I;
n4 and n5 are independently an integer from 0 to 4; and
m4, m5, v4, and v5 are independently an integer from 1 to 2.
z4 is an integer from 0 to 9; and
z5 is an integer from 0 to 6.

Embodiment 83

The method of one of embodiments 50 to 82, wherein $L^1$ is —O—.

Embodiment 84

The method of one of embodiments 50 to 82, wherein $L^1$ is —S—.

Embodiment 85

The method of one of embodiments 50 to 82, wherein $L^1$ is —N($R^3$)—.

Embodiment 86

The method of embodiment 85, wherein $R^3$ is hydrogen.

Embodiment 87

The method of one of embodiments 82 to 86, wherein Ring A is phenyl.

Embodiment 88

The method of one of embodiments 82 to 86, wherein Ring A is napththyl.

Embodiment 89

The method of one of embodiments 82 to 86, wherein Ring A is 5 to 10 membered heteroaryl.

Embodiment 90

The method of one of embodiments 82 to 86, wherein Ring A is benzofuranyl, isobenzofuranyl, indolyl, isoindolyl, benzothienyl, benzo[c]thienyl, benzimidazolyl, azaindolyl, benzoisoxazolyl, purinyl, indazolyl, benzoxazolyl, benzisoxazolyl, benzothiazolyl, quinolinyl, isoquinolinyl, quinoxalinyl, quinazolinyl, cinnolinyl, or phthalazinyl.

Embodiment 91

The method of one of embodiments 82 to 86, wherein Ring A is 5 to 9 membered heteroaryl.

Embodiment 92

The method of one of embodiments 82 to 86, wherein Ring A is 5 to 6 membered heteroaryl.

Embodiment 93

The method of one of embodiments 82 to 86, wherein Ring A is furanyl, pyrrolyl, thienyl, imidazolyl, pyrazolyl, oxazolyl, isoxazolyl, thiazolyl, pyridinyl, pyrazinyl, pyrimidinyl, pyridazinyl, or triazinyl.

Embodiment 94

The method of one of embodiments 82 to 93, wherein $R^4$ is independently —F, —Cl, —Br, —I, —CN, —NH$_2$, —OH, —SH, —COCH$_3$, —COOH, —COOCH$_3$, —CX$^4_3$, —CHX$^4_2$, —CH$_2$X$^4$, —OCX$^4_3$, —OCHX$^4_2$, —OCH$_2$X$^4$, —SCX$^4_3$, —SCHX$^4_2$, —SCH$_2$X$^4$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$CH$_3$.

Embodiment 95

The method of one of embodiments 50 to 94, wherein z4 is 2.

Embodiment 96

The method of one of embodiments 50 to 94, wherein z4 is 1.

Embodiment 97

The method of one of embodiments 50 to 94, wherein z4 is 0.

Embodiment 98

The method of one of embodiments 50 to 97, wherein $L^2$ is a bond.

Embodiment 99

The method of one of embodiments 50 to 97, wherein $L^2$ is —CH$_2$—.

Embodiment 100

The method of one of embodiments 50 to 97, wherein $L^2$ is —CH$_2$CH$_2$—.

Embodiment 101

The method of one of embodiments 50 to 97, wherein $L^2$ is —CH$_2$O—.

Embodiment 102

The method of one of embodiments 50 to 97, wherein $L^2$ is —CH$_2$S—.

Embodiment 103

The method of one of embodiments 50 to 97, wherein $L^2$ is —CH$_2$NH—.

Embodiment 104

The method of one of embodiments 82 to 103, wherein Ring B is 3 to 7 membered heterocycloalkyl.

Embodiment 105

The method of one of embodiments 82 to 103, wherein Ring B is 3 to 6 membered heterocycloalkyl.

Embodiment 106

The method of one of embodiments 82 to 103, wherein Ring B is aziridinyl, azirinyl, diaziridinyl, diazirinyl, oxaziridinyl, azetidinyl, azetyl, diazetidinyl, diazetyl, pyrrolidinyl, pyrazolidinyl, oxazolidinyl, isoxazolidinyl, thiazolidinyl, isothiazolidinyl, triazolyl, furazanyl, oxadiazolyl, thiadiazolyl, dithiazolyl, tetrazolyl, piperidinyl, piperazinyl, morpholinyl, or thiomorpholinyl.

Embodiment 107

The method of one of embodiments 82 to 103, wherein Ring B is a 6 membered heterocycloalkyl.

Embodiment 108

The method of one of embodiments 82 to 103, wherein Ring B is piperidinyl or piperazinyl.

Embodiment 109

The method of one of embodiments 82 to 103, wherein Ring B is 5 to 10 membered heteroaryl.

Embodiment 110

The method of one of embodiments 82 to 103, wherein Ring B is pyridinyl, pyrazinyl, pyrimidinyl, pyridazinyl, triazinyl, quinolinyl, isoquinolinyl, quinoxalinyl, quinazolinyl, cinnolinyl, or phthalazinyl.

Embodiment 111

The method of one of embodiments 82 to 103, wherein Ring B is a $C_3$-$C_8$ substituted or unsubstituted cycloalkyl.

Embodiment 112

The method of one of embodiments 82 to 103, wherein Ring B is substituted or unsubstituted cyclooctanyl, substituted or unsubstituted cycloheptanyl, substituted or unsubstituted cyclohexanyl, or substituted or unsubstituted cyclopentanyl.

Embodiment 113

The method of one of embodiments 82 to 103, wherein Ring B is substituted or unsubstituted cyclopentanyl.

Embodiment 114

The method of one of embodiments 82 to 103, wherein Ring B is a 6 membered heteroaryl.

Embodiment 115

The method of one of embodiments 82 to 103, wherein Ring B is pyridinyl, pyrazinyl, pyrimidinyl, or pyridazinyl.

Embodiment 116

The method of one of embodiments 82 to 115, wherein $R^5$ is —F, —Cl, —Br, —I, —CN, —NH$_2$, —OH, —SH, —COCH$_3$, —COOH, —COOCH$_3$, —CX$^5_3$, —CHX$^5_2$, —CH$_2$X$^5$, —OCX$^5_3$, —OCHX$^5_2$, —OCH$_2$X$^5$, —SCX$^5_3$, —SCHX$^5_2$, —SCH$_2$X$^5$, —CH$_3$, —CH$_2$CH$_3$, —OCH$_3$, —OCH$_2$CH$_3$, —NHCH$_3$, —N(CH$_3$)$_2$, —NHCH$_2$CH$_3$, —N(CH$_3$)(CH$_2$CH$_3$), —N(CH$_2$CH$_3$)$_2$, —SCH$_3$, or —SCH$_2$CH$_3$.

Embodiment 117

The method of one of embodiments 82 to 116, wherein z5 is 2.

Embodiment 118

The method of one of embodiments 82 to 116, wherein z5 is 1.

Embodiment 119

The method of one of embodiments 82 to 116, wherein z5 is 0.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example A: Synthesis and Characterization

Materials obtained commercially were reagent grade and were used without further purification. Preparation of compounds begins from commercially available or prepared t-butyl protected pyrazolopyrimidine (See, for example Lourido Shokat and Sibley J Med Chem. 2013 Apr. 11; 56(7): 3068-77; Hanefeld, U., Rees, C. W., White, A. J. P. & Williams, D. J. *J. Am. Chem. Soc. Perkin Trans. 1* 1545-1552 (1996); Schenone, S., Radi, M., Musumeci, F., Brullo, C. & Botta, M. *Chem. Rev.* 114, 7189-7238 (2014); and Bulawa, C. E., Devit, M. & Elbaum, D. EP20080848219 (2010)) which are incorporated herein by reference in their entirety) or commercially available pyrrolopyrimidine which are briefly described here:

Scheme 1 Scaffold synthesis

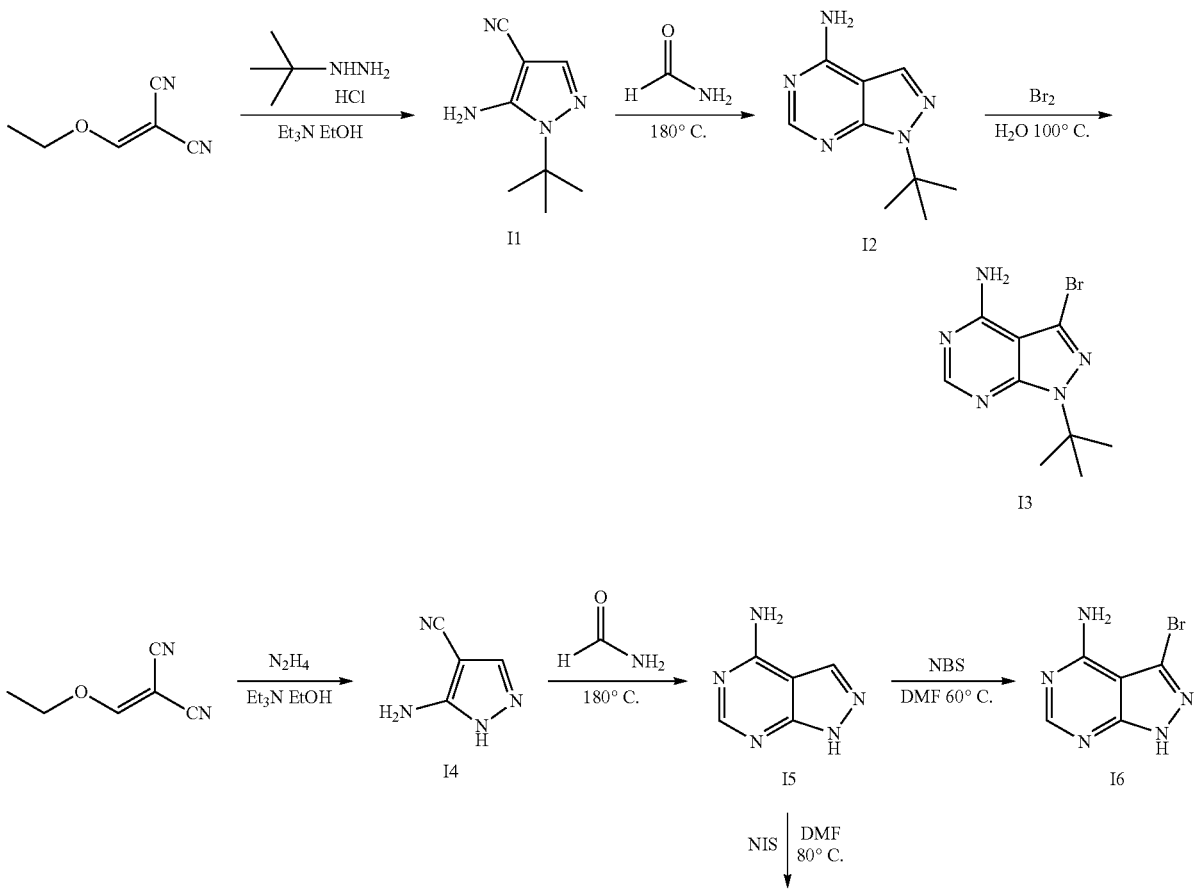

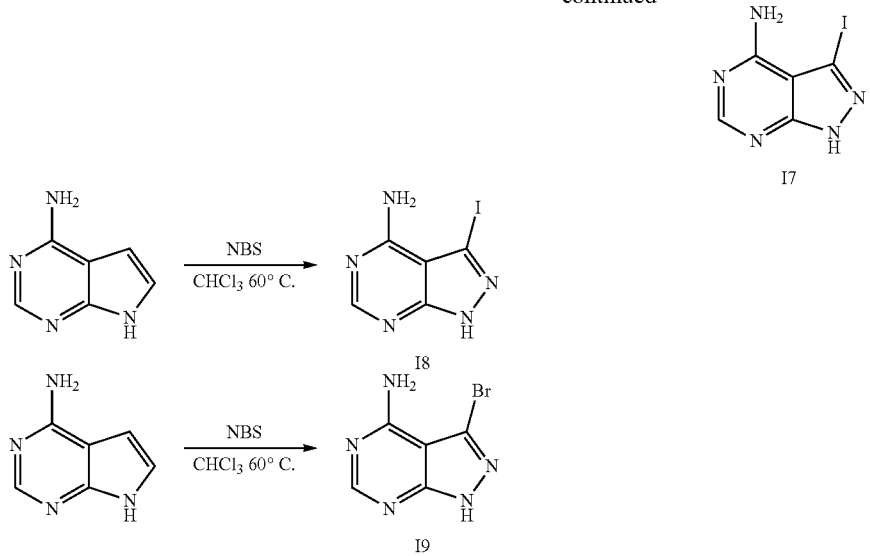

Example 1: 5-amino-1-(tert-butyl)-1H-pyrazole-4-carbonitrile (I1)

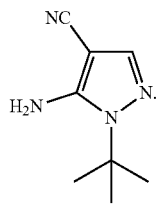

250 mL flame-dried argon purged round bottom flask, triethylamine (1.78 g, 17.7 mmol), and t-butyl hydrazine hydrochloride (1.56 g, 12.5 mmol) are dissolved in anhydrous ethanol (85 mL). Ethoxymethylenemalononitrile (1.98 g, 17.7 mmol) is added slowly and reaction mixture is brought to reflux at 82° C. for 3 hours. The solvent is removed in vacuo and 10% ethyl acetate/hexane is added (5 mL) and the mixture is sonicated (or simply utilize recrystallization from 10% ethyl acetate/hexane). The resulting crystalline solid is filtered, and washed with ether to yield I1. LC-MS (ES+) calcd for $C_8H_{12}N_4$ (M+H)$^+$ 165.11, found 165.05.

Example 2: 1-(tert-butyl)-1H-pyrazolo[3,4-d]pyrimidin-4-amine (I2)

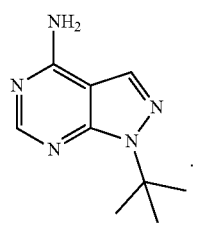

Formamide (35 mL) is added to intermediate I1 (~2.75 g) and the mixture is headed to 180° C. for 3 hours. Upon cooling, the mixture is added to water and extracted with ethyl acetate using sodium bicarbonate to wash the organic followed by a careful water wash as to avoid emulsion and lastly a wash with saturated brine. The organic layer is dried in vacuo and is recrystallized from a small amount of ether to yield intermediate I2. LC-MS (ES+) calcd for $C_9H_{13}N_5$ (M+H)$^+$192.12, found 192.21.

Example 3: 3-bromo-1-(tert-butyl)-1H-pyrazolo[3,4-d]pyrimidin-4-amine (I3)

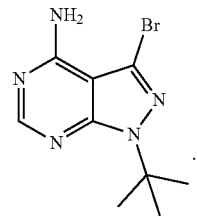

Intermediate I2 (~300 mgs) is suspended in water (7 mL) and bromine (188 uL, 2 equivalents) is added and the reaction mixture is stirred at room temperature for 1 hour followed by stirring at 100° C. for 1 hour. Upon cooling, the precipitated product is separated by filtration and the filtrate is stirred in 5% aqueous sodium hydrogen sulfite (12 mL) for 30 minutes and the solution is treated with 5 mL of saturated aqueous sodium bicarbonate. The precipitate is separated by filtration, washed with water and dried to yield brominated intermediate I3. LC-MS (ES+) calcd for $C_9H_{12}BrN_5$ (M+H)$^+$ 270.03, found 270.55, 272.40.

Synthesis of pyrazolopyrimidines without t-butyl modification at Ni proceeds similarly although hydrazine is utilized instead of a derivatized hydrazine reagent to yield intermediate I4 followed by similar procedures in generating intermediates I2 and I3 to yield intermediates I5 and I6.

Example 4: 3-bromo-1H-pyrazolo[3,4-d]pyrimidin-4-amine (I6)

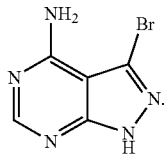

In a 250 mL argon purged, flame-dried flask, 50 mL DMF was added to dissolve 5 g (37 mmol) of starting material I5. NBS (6.5 g, 36.5 mmol) was added and the reaction heated to 60° C. overnight. Upon cooling, and completion of reaction monitored by TLC, precipitate was filtered to yield intermediate I6. LC-MS (ES+) calcd for $C_5H_4BrN_5$ $(M+H)^+$ 213.97, found 213.76, 215.71.

Example 5: 3-iodo-1H-pyrazolo[3,4-d]pyrimidin-4-amine (I7)

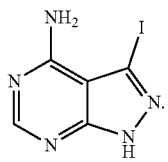

In a 100 mL argon purged, flame-dried flask, 30 mL DMF was added to dissolve 5 g (37 mmol) of starting material I5. NIS (12.3 g, 54.7 mmol) was added and the reaction was heated to 80° C. overnight. Upon cooling, and completion of reaction monitored by TLC, precipitate was filtered to yield intermediate I7. Water was added to filtrate and resulting precipitant was also filtered to yield a second batch of intermediate 17. LC-MS (ES+) calcd for $C_6H_4IN_5$ $(M+H)^+$ 261.95, found 261.87.

Example 6: 5-iodo-7H-pyrrolo[2,3-d]pyrimidin-4-amine (I8)

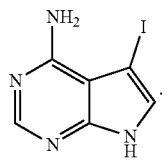 [SMILES: Nc1ncnc2[nH]cc(I)c12]

In a 20 mL scintillation vial, purchased pyrrolopyrimidine (1 g, 7.45 mmol) was dissolved in 7 mL of chloroform. NIS (2.18 g, 9.69 mmol) was added and reaction was refluxed for 2 hours. Upon cooling, precipitate was filtered to yield intermediate I8. LC-MS (ES+) calcd for $C_6H_5IN_4$ (M+H)+ 260.96, found 260.61.

Example 7: 5-bromo-7H-pyrrolo[2,3-d]pyrimidin-4-amine (I9)

In a 20 mL scintillation vial, purchased pyrrolopyrimidine (2 g, 14.9 mmol) was dissolved in 7 mL of chloroform. NBS (3.5 g, 19.38 mmol) was added and reaction was refluxed for 2 hours. As dibromination was observed in addition to desired intermediate I9, silica gel chromatography (DCM/MeOH) was required to obtain desired intermediate I9. LC-MS (ES+) calcd for $C_6H_5BrN_4$ (M+H)+212.97, found 212.68, 214.68. Subsequent reactions also utilized commercial sources of I9.

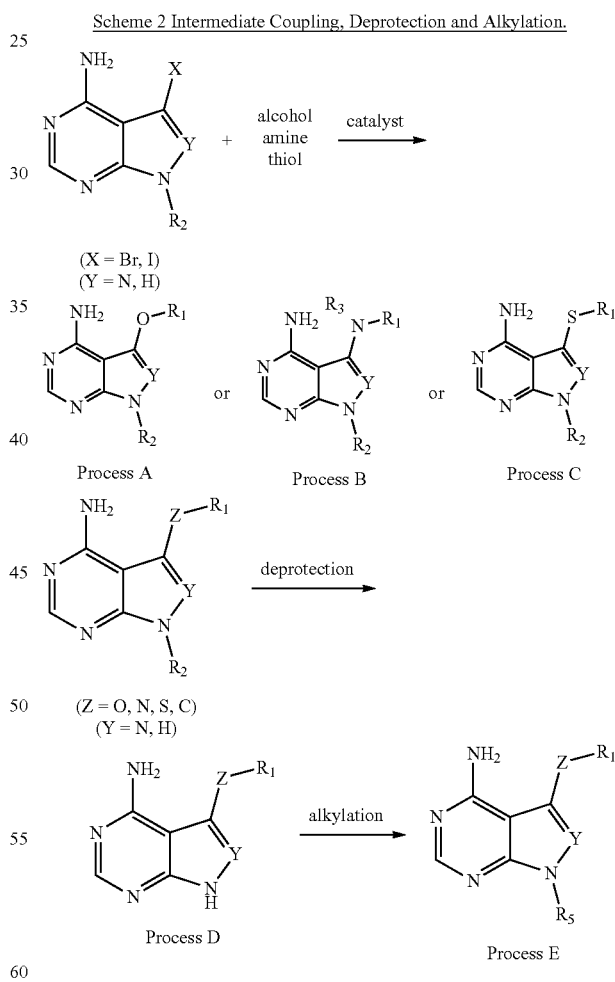

Scheme 2 Intermediate Coupling, Deprotection and Alkylation.

Addition of alcohol, amine or thiol in the presence of catalyst generates ether (Process A), amine (Process B) and thioether (Process C) linked compounds respectively. Deprotection of t-butyl (Process D) followed by alkylation (Process E) generates advanced compounds with diversity at $R_5$. Preparation can also proceed with $R_5$ already installed followed by catalyst assisted coupling. Representative procedures for each example follow.

Example 8: 1-(tert-butyl)-3-(3-chlorophenoxy)-1H-pyrazolo[3,4-d]pyrimidin-4-amine (GXJ-184)

Process A:

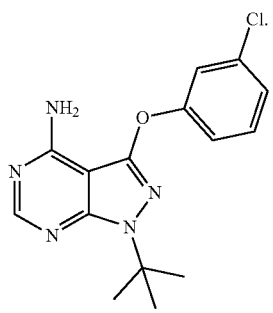 [SMILES: CC(C)(C)n1nc(Oc2cccc(Cl)c2)c2c(N)ncnc21]

Synthesis proceeds by Ullman coupling (Ma and Cai, Org Lett 2003). To an argon purged vial with magnetic stir bar is added intermediate 12 (85 mg, 0.315 mmol), 3-chlorophenol (60.7 mg, 0.473 mmol, 1.5 eq), N,N-dimethylglycine (19.5 mg, 0.189 mmol, 0.6 eq), and cesium carbonate (205.3 mg, 0.63 mmol, 2 eq) in 1 mL dioxane. After stirring for 5 minutes at room temperature is added copper iodide (12 mg, 0.063 mmol, 20 mol %) and reaction is heated to 120 C and stirred overnight. Reaction completion is monitored by LC/MS. After reaction is complete, water is added and compound is extracted with dichloromethane. Purification is conducted using silica column with ethyl acetate-hexane to yield GXJ184 (60 mgs, 60%). LC-MS (ES+) calcd for $C_{15}H_{16}ClN_5O$ (M+H)$^+$ 318.10, found 317.84. $^1$H NMR (400 MHz, DMSO-d$_6$) δ 8.17 (s, 1H), 7.55 (t, J=2.1 Hz, 1H), 7.47-7.36 (m, 2H), 7.23 (ddd, J=7.7, 2.0, 1.3 Hz, 1H), 1.66 (s, 9H).

Example 9: 1-(tert-butyl)-N$^3$-(naphthalen-1-yl)-1H-pyrazolo[3,4-d]pyrimidine-3,4-diamine Process B:

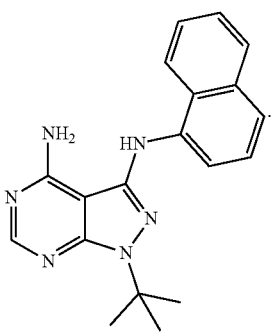

Synthesis proceeds via Pd-assisted Buchwald coupling (Fors et al. JACS 2009) due to electron-rich indole presenting difficulty with Ullman coupling. To an 1 dram argon purged vial with magnetic stir bar is added intermediate 12 (50 mg, 0.185 mmol), 1-napthylamine (32 mg, 0.223 mmol), potassium tert-butoxide (56 mg, 0.50 mmol), and Brett-PhosPd G3 (6 mg, 3.6 mol %) in 1 mL dioxane and stirred at 90° C. overnight. Reaction completion is monitored by LC/MS. After reaction is complete, reaction is purified by HPLC using acetonitrile-water in the presence of 0.1% formic acid yield product FUR 6-124 (<10%). LC-MS (ES+) calcd for $C_{19}H_{20}N_6$(M+H)$^+$ 333.17, found 333.00.

Example 10: 5-((3-chlorophenyl)thio)-7H-pyrrolo[2,3-d]pyrimidin-4-aminemine

Process C:

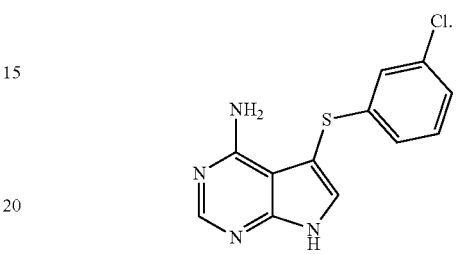

Synthesis proceeds via Ullman coupling. To a 20 mL argon purged scintillation vial with magnetic stir bar is added intermediate I8 (150 mg, 0.577 mmol), 3-chlorobenzenethiol (67 uL, 0.557 mmol), copper iodide (5.6 mg, 0.029 mmol), potassium carbonate (206 mg, 1.49 mmol), 2-propanol (1322 uL, 17.3 mmol), and ethylene glycol (166 uL, 3 mmol). Reaction is heated to 130° C. for 1 hour and then cooled to room temperature for one hour. Purification by HPLC using acetonitrile-water in the presence of 0.1% formic acid yields intermediate 5-((3-chlorophenyl)thio)-7H-pyrrolo[2,3-d]pyrimidin-4-aminemine (25.1 mg, 15.7%). LC-MS (ES+) calcd for $C_{12}H_9ClN_4S$ (M+H)$^+$ 277.02, found 277.40.

Example 11: 3-((1H-indol-3-yl)thio)-1-(tert-butyl)-1H-pyrazolo[3,4-d]pyrimidin-4-amine (FUR6-159)

Process C:

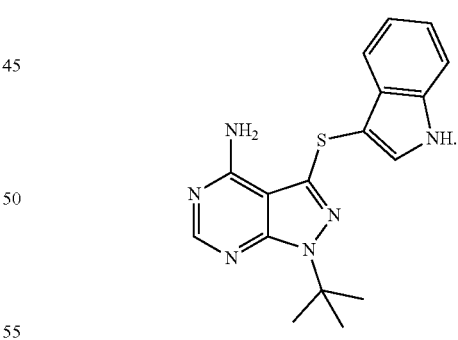

Synthesis proceeds via Pd-assisted Buchwald coupling. In a 20 mL argon-purged scintillation vial with magnetic stir bar was added intermediate 13 (100 mg, 0.370 mmol), N,N-diisopropylethylamine (129 uL, 0.740 mmol), Pd(dba)$_2$ (10.6 mg, 5 mol %), XantPhos (10.7 mg, 5 mol %), and 3-mercaptoindole (55.2 mg, 0.370 mmol) in 1.5 mL dioxane. Reaction was run overnight at 110° C. and then cooled to room temperature. Purification by HPLC using acetonitrile-water in the presence of 0.1% formic acid yields FUR6-159. LC-MS (ES+) calcd for $C_{17}H_{18}N_6S$ (M+H)$^+$ 339.13, found 339.53. $^1$H NMR (400 MHz, DMSO-d$_6$) δ 11.42 (s, 1H), 8.04 (s, 1H), 7.79 (d, J=2.6 Hz, 1H), 7.60 (d, J=7.9 Hz, 1H), 7.37-7.29 (m, 1H), 7.04 (ddd, J=8.2, 7.1, 1.3 Hz, 1H), 6.96 (ddd, J=8.0, 7.0, 1.0 Hz, 1H), 1.60 (s, 9H).

Example 12: 3-(3-chlorophenoxy)-1H-pyrazolo[3,4-d]pyrimidin-4-amine

Process D:

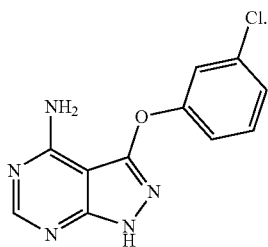 [SMILES: Nc1ncnc2[nH]nc(Oc3cccc(Cl)c3)c12]

Synthesis proceeds easily through acid deprotection of GXJ184. In a vial with magnetic stir bar is added 1-(tert-butyl)-3-(3-chlorophenoxy)-1H-pyrazolo[3,4-d]pyrimidin-4-amine (20 mgs, 0.63 mmol) formic acid (1 mL) and hydrochloric acid (0.1 mL). The solution is refluxed for 2 hours, cooled and intermediate 3-(3-chlorophenoxy)-1H-pyrazolo[3,4-d]pyrimidin-4-amine is purified by HPLC using acetonitrile-water with 0.1% formic acid. Yield 85% (14.2 mg) LC/MS ES+ calcd for $C_{11}H_5ClN_5O$ (M+H)+ 262.04, found 261.97.

Example 13: 3-(3-chlorophenoxy)-1-((3,3-difluoropiperidin-4-yl)methyl)-1H-pyrazolo[3,4-d]pyrimidin-4-amine (FUR7-27)

Process E:

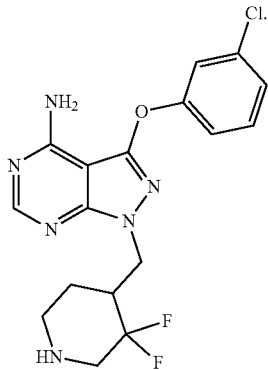 [SMILES: Nc1ncnc2c1c(Oc1cccc(Cl)c1)nn2CC1CCNCC1(F)F]

Synthesis proceeds by alkylation of pyrazolopyrimidine intermediate (Lourido Shokat and Sibley 2013 Journal of Medicinal Chemistry). In an argon purged 20 mL scintillation vial vial with magnetic stir bar is added 3-(3-chlorophenoxy)-1H-pyrazolo[3,4-d]pyrimidin-4-amine (225 mgs, 0.860 mmol), tert-butyl 4-(bromomethyl)-3,3-difluoropiperidine-1-carboxylate (311.6 mg, 0.946 mmol), and cesium carbonate (841 mg, 2.58 mmol) in 4.5 mL dry DMF. Reaction is heated to 80° C. overnight followed by cooling and the resulting tert-butyl 4-((4-amino-3-(3-chlorophenoxy)-1H-pyrazolo[3,4-d]pyrimidin-1-yl)methyl)-3,3-difluoropiperidine-1-carboxylate intermediate is purified by silica chromatography with hexanes and 3:1 ethylacetate:ethanol. Boc deprotection with trifluoroacetic acid followed by HPLC yields FUR 7-27 (116 mgs, 34.2%) LC/MS ES+ calcd for $C_{17}H_{17}ClF_2N_6O$ (M+H)+ 395.1, found 395.74. $^1$H NMR (400 MHz, DMSO-$d_6$) δ 8.13 (s, 1H), 7.48-7.26 (m, 3H), 7.19 (dd, J=7.7, 1.9 Hz, 1H), 4.38 (dd, J=14.1, 5.0 Hz, 1H), 4.12 (dd, J=14.1, 9.2 Hz, 1H), 3.14-2.96 (m, 1H), 2.88-2.63 (m, 2H), 1.31 (ddd, J=28.8, 10.4, 4.0 Hz, 2H), 1.10 (t, J=7.3 Hz, 1H).

Example 14: 3-(3-chlorophenoxy)-1-((1-methylpiperidin-4-yl)methyl)-1H-pyrazolo[3,4-d]pyrimidin-4-amine (FUR7-30)

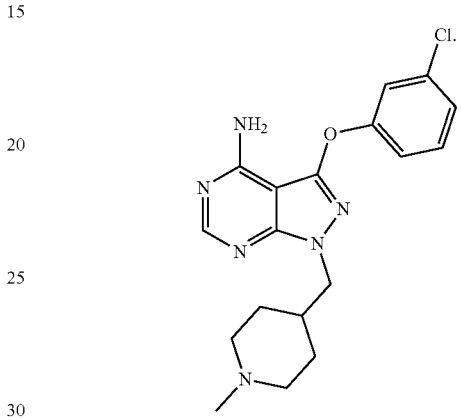

Synthesis proceeds by reductive alkylation of 3-(3-chlorophenoxy)-1-(piperidin-4-ylmethyl)-1H-pyrazolo[3,4-d]pyrimidin-4-amine (GXJ237). In a 1 dram vial with magnetic stir bar, GJX237 (25 mg, 0.070 mmol) was dissolved in methanol (200 uL). A solution of formaldehyde (52 uL of 37%, 0.70 mmol) in 2% acetic acid was added to the reaction and was stirred for 10 minutes at room temperature. Sodium cyanoborohydride (21.9 mg, 0.349 mmol) was added and the reaction was stirred for 3 hours at room temperature. Purification by HPLC using acetonitrile-water in the presence of 0.1% formic acid yields (FUR7-30). LC/MS ES+ calcd for $C_{18}H_{21}ClN_6O$ (M+H)+ 373.15, found 372.82. $^1$H NMR (400 MHz, DMSO-$d_6$) δ 8.10 (d, J=3.9 Hz, 2H), 7.41 (t, J=2.2 Hz, 1H), 7.35 (t, J=8.1 Hz, 1H), 7.30-7.25 (m, 1H), 7.21-7.14 (m, 1H), 3.97 (d, J=7.1 Hz, 2H), 2.74 (dt, J=12.2, 3.6 Hz, 2H), 2.14 (s, 3H), 2.01-1.84 (m, 2H), 1.84-1.62 (m, 1H), 1.45-1.33 (m, 2H), 1.24-1.09 (m, 2H).

Example 15: 1-(tert-butyl)-3-(3-chlorobenzyl)-1H-pyrazolo[3,4-d]pyrimidin-4-amine (3ClB-PP1)

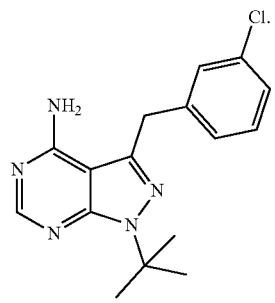 [SMILES: CC(C)(C)n1nc(Cc2cccc(Cl)c2)c2c(N)ncnc21]

Compound was previously published and characterized (Lourido Shokat and Sibley 2013).

Example 16: 3-(3-chlorobenzyl)-1-(piperidin-4-ylmethyl)-1H-pyrazolo[3,4-d]pyrimidin-4-amine (FUR6-157)

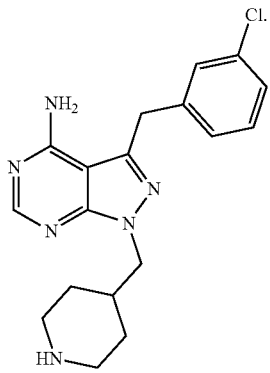 [SMILES: Nc1ncnc2c1c(Cc1cccc(Cl)c1)nn2CC1CCNCC1]

Compound was synthesized using processes D and E from 3ClB-PP1. LC/MS ES+ calcd for Chemical Formula: $C_{18}H_{21}ClN_6$ (M+H)$^+$ 357.15, found 357.57. $^1$H NMR (400 MHz, DMSO-d$_6$) δ 8.08 (d, J=2.3 Hz, 1H), 7.28-7.21 (m, 2H), 7.19 (dd, J=8.2, 1.8 Hz, 1H), 7.16-7.09 (m, 1H), 4.30 (s, 2H), 4.11 (d, J=7.0 Hz, 2H), 3.15 (dt, J=13.0, 3.3 Hz, 2H), 2.74 (td, J=12.7, 2.9 Hz, 2H), 2.12 (dtd, J=15.4, 7.7, 4.5 Hz, 1H), 1.54 (dd, J=14.2, 3.6 Hz, 2H), 1.39-1.20 (m, 2H).

Example 17: 1-(tert-butyl)-3-(3,5-difluorobenzyl)-1H-pyrazolo[3,4-d]pyrimidin-4-amine (CZ75)

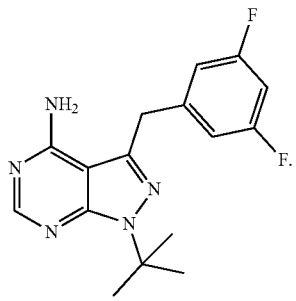 [SMILES: CC(C)(C)n1nc(Cc2cc(F)cc(F)c2)c2c(N)ncnc21]

Compound was previously published and characterized (Lourido Shokat and Sibley 2013).

Example 18: 3-(3,5-difluorobenzyl)-1-(piperidin-4-ylmethyl)-1H-pyrazolo[3,4-d]pyrimidin-4-amine (MLC468)

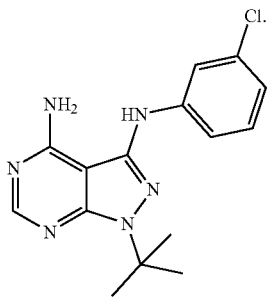 [SMILES: CC(C)(C)n1nc(Nc2cccc(Cl)c2)c2c(N)ncnc21]

Compound was synthesized using process D and E from CZ75. LC/MS ES+ calcd for Chemical Formula: $C_{18}H_{20}F_2N_6$ (M+H)$^+$ 359.17, found 359.27. $^1$H NMR (400 MHz, DMSO-d$_6$) δ 8.15 (s, 1H), 7.06 (tt, J=9.4, 2.4 Hz, 1H), 7.00-6.91 (m, 1H), 4.39 (s, 2H), 4.14 (d, J=7.1 Hz, 2H), 3.10-2.95 (m, 2H), 2.16-1.96 (m, 1H), 1.46 (d, J=13.0 Hz, 2H), 1.38 (d, J=1.9 Hz, 1H), 1.28-1.09 (m, 2H).

Example 19: 1-(tert-butyl)-N$^3$-(3-chlorophenyl)-1H-pyrazolo[3,4-d]pyrimidine-3,4-diamine (LZH118)

LC/MS ES+ calcd for Chemical Formula: $C_{15}H_{17}ClN_6$ (M+H)+317.12, found 317.35. $^1$H NMR (CDCl$_3$) δ 8.33 (1H), 7.20-7.17 (2H), 7.02-6.90 (2H), 6.78-6.76 (1H), 6.10 (1H), 5.28 (2H), 1.80 (9H).

Example 20: N³-(3-chlorophenyl)-1-(piperidin-4-ylmethyl)-1H-pyrazolo[3,4-d]pyrimidine-3,4-diamine (GXJ276)

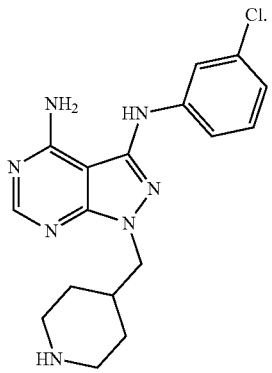 [SMILES: Nc1ncnc2c1c(Nc1cccc(Cl)c1)nn2CC1CCNCC1]

LC/MS ES+ calcd for Chemical Formula: $C_{17}H_{20}ClN_7$ (M+H) 358.15, found 358.06. ¹H NMR (400 MHz, DMSO-$d_6$) δ 8.76 (s, 1H), 8.11 (s, 1H), 7.83 (t, J=2.1 Hz, 1H), 7.62 (s, 2H), 7.58 (ddd, J=8.3, 2.2, 0.9 Hz, 1H), 7.28 (t, J=8.1 Hz, 1H), 6.89 (ddd, J=7.9, 2.1, 0.9 Hz, 1H), 4.09 (d, J=7.0 Hz, 2H), 3.14-3.02 (m, 2H), 2.64 (td, J=12.4, 2.7 Hz, 2H), 2.08 (ddt, J=11.4, 7.8, 3.8 Hz, 1H), 1.89 (s, 1H), 1.57 (d, J=12.8 Hz, 2H), 1.27 (dd, J=13.1, 3.8 Hz, 2H).

Example 21: 1-(tert-butyl)-3-((3-chlorophenyl)thio)-1H-pyrazolo[3,4-d]pyrimidin-4-amine (GXJ186)

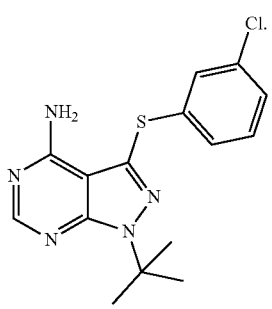 [SMILES: CC(C)(C)n1nc(Sc2cccc(Cl)c2)c2c(N)ncnc21]

LC/MS ES+ calcd for Chemical Formula: $C_{15}H_{16}ClN_5S$ (M+H)⁺ 334.08, found 333.98. ¹H NMR (400 MHz, DMSO-$d_6$) δ 8.23 (s, 1H), 7.38-7.26 (m, 3H), 7.09 (dt, J=7.7, 1.4 Hz, 1H), 1.75 (s, 9H).

Example 22: 1-(tert-butyl)-3-(m-tolylthio)-1H-pyrazolo[3,4-d]pyrimidin-4-amine (FUR7-68)

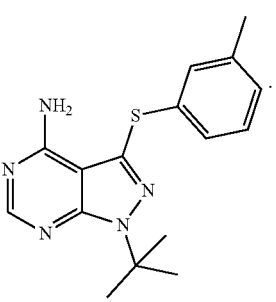 [SMILES: Cc1cccc(Sc2nn(C(C)(C)C)c3ncnc(N)c23)c1]

Compound was synthesized using process C from intermediate 13 similar to example 11. LC/MS ES+ calcd for Chemical Formula: $C_{16}H_{19}N_5S$ (M+H)⁺ 314.14, found 314.52. ¹H NMR (400 MHz, DMSO-$d_6$) δ 8.22 (s, 1H), 7.20 (t, J=7.7 Hz, 1H), 7.11 (d, J=1.8 Hz, 1H), 7.04 (ddt, J=7.6, 1.8, 0.9 Hz, 1H), 6.95 (ddt, J=7.8, 1.8, 0.8 Hz, 1H), 2.24 (s, 3H), 1.74 (s, 9H).

Example 23: 5-((3-chlorophenyl)thio)-7-(piperidin-4-ylmethyl)-7H-pyrrolo[2,3-d]pyrimidin-4-amine (FUR6-139)

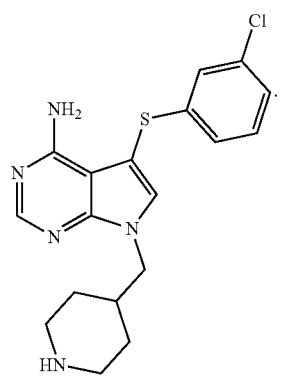

Compound was synthesized using Process E from intermediate in example 10. LC/MS ES+ calcd for Chemical Formula: $C_{18}H_{20}ClN_5S$ (M+H) 374.11, found 374.43. ¹H NMR (400 MHz, DMSO-$d_6$) δ 8.28 (s, 2H), 8.09 (s, 1H), 7.67 (s, 1H), 7.23 (t, J=7.9 Hz, 1H), 7.14 (dd, J=7.7, 2.0 Hz, 1H), 7.01 (t, J=1.9 Hz, 1H), 6.99-6.94 (m, 1H), 4.04 (d, J=7.2 Hz, 2H), 3.06 (d, J=12.1 Hz, 2H), 2.58 (t, J=11.9 Hz, 2H), 2.03 (s, 1H), 1.46 (d, J=13.0 Hz, 2H), 1.30-1.14 (m, 2H).

Example 24: 1-(tert-butyl)-3-(3-(trifluoromethyl)phenoxy)-1H-pyrazolo[3,4-d]pyrimidin-4-amine (GXJ178)

LC/MS ES+ calcd for Chemical Formula: $C_{16}H_{16}F_3N_5O$ (M+H)⁺ 352.13, found 351.94. ¹H NMR (400 MHz, DMSO-$d_6$) δ 8.18 (s, 1H), 7.90 (t, J=2.1 Hz, 1H), 7.77 (dd, J=8.3, 2.4 Hz, 1H), 7.65 (t, J=8.0 Hz, 1H), 7.57-7.51 (m, 1H), 1.66 (s, 9H).

Example 25: 1-(tert-butyl)-3-(m-tolyloxy)-1H-pyrazolo[3,4-d]pyrimidin-4-amine (GXJ176)

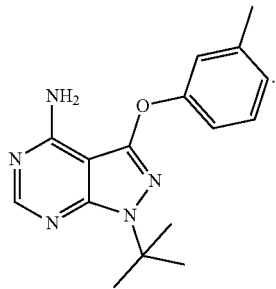 [SMILES: Cc1cccc(Oc2nn(C(C)(C)C)c3ncnc(N)c23)c1]

LC/MS ES+ calcd for Chemical Formula: $C_{16}H_{19}N_5O$ (M+H)+ 298.16, found 298.27. $^1$H NMR (400 MHz, DMSO-$d_6$) δ 8.17 (s, 1H), 7.28 (t, J=7.9 Hz, 1H), 7.20-7.07 (m, 2H), 6.98 (d, J=7.5 Hz, 1H), 2.32 (s, 3H), 1.65 (s, 9H).

Example 26: 3-(3-bromophenoxy)-1-(tert-butyl)-1H-pyrazolo[3,4-d]pyrimidin-4-amine (GXJ177)

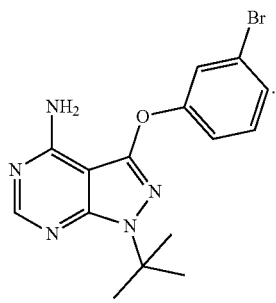

LC/MS ES+ calcd for Chemical Formula: $C_{15}H_{16}BrN_5O$ (M+H)+ 362.05, found 362.30, 364.11. $^1$H NMR (400 MHz, DMSO-$d_6$) δ 8.17 (s, 1H), 7.72-7.67 (m, 1H), 7.48-7.33 (m, 3H), 1.66 (s, 9H).

Example 27: 1-(tert-butyl)-3-(3-methoxyphenoxy)-1H-pyrazolo[3,4-d]pyrimidin-4-amine (GXJ230)

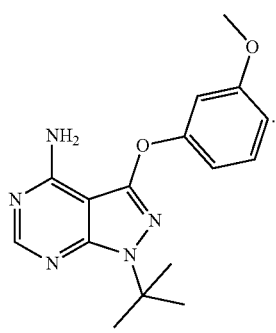 [SMILES: COc1cccc(Oc2nn(C(C)(C)C)c3ncnc(N)c23)c1]

LC/MS ES+ calcd for Chemical Formula: $C_{16}H_{19}N_5O_2$ (M+H)+ 314.15, found 314.13. $^1$H NMR (400 MHz, DMSO-$d_6$) δ 8.17 (s, 1H), 7.29 (t, J=8.2 Hz, 1H), 7.03 (t, J=2.4 Hz, 1H), 6.93 (ddd, J=8.2, 2.3, 0.8 Hz, 1H), 6.74 (ddd, J=8.3, 2.5, 0.8 Hz, 1H), 3.76 (s, 3H), 1.66 (s, 9H).

Example 28: 1-(tert-butyl)-3-(3,5-difluorophenoxy)-1H-pyrazolo[3,4-d]pyrimidin-4-amine (GXJ229)

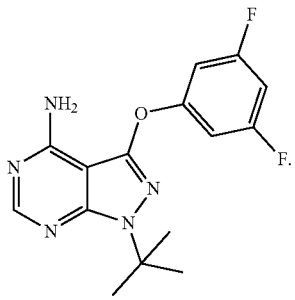

LC/MS ES+ calcd for Chemical Formula: $C_{15}H_{15}F_2N_5O$ (M+H)+ 320.12, found 320.20 $^1$H NMR (400 MHz, DMSO-$d_6$) δ 8.18 (s, 1H), 7.29-7.22 (m, 2H), 7.07 (d, J=2.3 Hz, 1H), 1.67 (s, 9H).

Example 29: 3-(3-chlorophenoxy)-1-(piperidin-4-ylmethyl)-1H-pyrazolo[3,4-d]pyrimidin-4-amine (GXJ237)

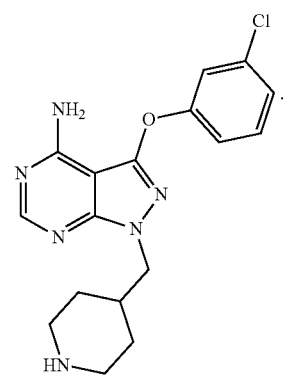

Compound was synthesized using Process E from intermediate in example 12. LC/MS ES+ calcd for Chemical Formula: $C_{17}H_{19}ClN_6O$ (M+H)+ 359.13, found 359.08. $^1$H NMR (400 MHz, DMSO-$d_6$) δ 8.13 (s, 1H), 7.46 (t, J=2.2 Hz, 1H), 7.38 (t, J=8.1 Hz, 1H), 7.31 (ddd, J=8.3, 2.4, 1.1 Hz, 1H), 7.20 (dt, J=8.0, 1.5 Hz, 1H), 4.04 (s, 2H), 3.15 (dt, J=13.0, 3.5 Hz, 2H), 2.73 (td, J=12.7, 3.0 Hz, 2H), 2.04 (dtt, J=14.9, 7.1, 2.9 Hz, 1H), 1.64-1.49 (m, 2H), 1.28 (qd, J=12.6, 4.0 Hz, 2H).

Example 30: 3-(3-chloro-4-fluorophenoxy)-1-(piperidin-4-ylmethyl)-1H-pyrazolo[3,4-d]pyrimidin-4-amine (GXJ261)

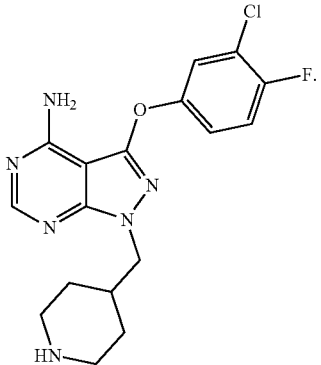 [SMILES: Nc1ncnc2c1c(Oc1ccc(F)c(Cl)c1)nn2CC1CCNCC1]

LC/MS ES+ calcd for Chemical Formula: $C_{17}H_{18}ClFN_6O$ (M+H)$^+$ 377.12, found 376.88. $^1$H NMR (400 MHz, DMSO-d$_6$) δ 9.03 (s, 2H), 8.19 (s, 1H), 7.79-7.71 (m, 1H), 7.53-7.44 (m, 2H), 4.08 (d, J=6.9 Hz, 2H), 3.18 (dt, J=11.5, 2.9 Hz, 2H), 2.77 (td, J=12.6, 3.0 Hz, 2H), 2.10 (dt, J=7.5, 3.7 Hz, 1H), 1.61 (dd, J=14.2, 3.5 Hz, 2H), 1.44 (tt, J=12.2, 6.3 Hz, 2H).

Example 31: 3-(3-chlorophenoxy)-1-(pyridin-4-ylmethyl)-1H-pyrazolo[3,4-d]pyrimidin-4-amine (FUR6-6)

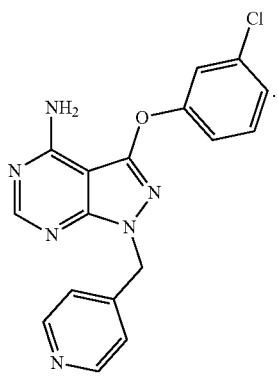 [SMILES: Nc1ncnc2c1c(Oc1cccc(Cl)c1)nn2Cc1ccncc1]

Compound was synthesized using process E from intermediate in example 12. LC/MS ES+ calcd for Chemical Formula: $C_{17}H_{13}ClN_6O$ (M+H)$^+$ 353.08, found 353.14. $^1$H NMR (400 MHz, DMSO-d$_6$) δ 8.42 (d, J=5.0 Hz, 2H), 8.15 (s, 1H), 7.45 (t, J=2.1 Hz, 1H), 7.40-7.29 (m, 2H), 7.19 (dt, J=7.8, 1.8 Hz, 1H), 7.08-7.01 (m, 2H), 5.38 (s, 2H).

Example 32: 3-(3-chlorophenoxy)-1-(piperidin-3-ylmethyl)-1H-pyrazolo[3,4-d]pyrimidin-4-amine (FUR6-11)

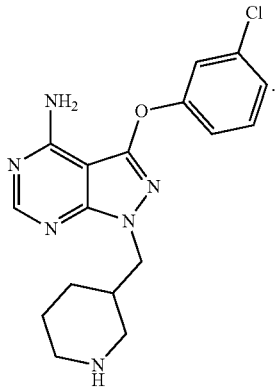 [SMILES: Nc1ncnc2c1c(Oc1cccc(Cl)c1)nn2CC1CCCNC1]

Compound was synthesized using process E from intermediate in example 12. LC/MS ES+ calcd for Chemical Formula: $C_{17}H_{19}ClN_6O$ (M+H)$^+$ 359.13, found 359.52. $^1$H NMR (400 MHz, DMSO-d$_6$) δ 8.13 (s, 1H), 7.46 (t, J=2.1 Hz, 1H), 7.43-7.30 (m, 2H), 7.20 (dt, J=7.8, 1.6 Hz, 1H), 4.15-3.97 (m, 2H), 3.13-2.90 (m, 2H), 2.71-2.49 (m, 2H), 2.15 (td, J=7.9, 4.2 Hz, 1H), 1.74-1.37 (m, 3H), 1.21-1.05 (m, 1H).

Example 33: 3-(3-chlorophenoxy)-1-(pyrrolidin-3-ylmethyl)-H-pyrazolo[3,4-d]pyrimidin-4-amine (FUR6-13)

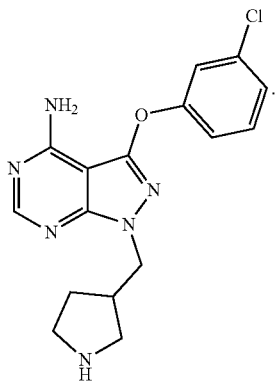 [SMILES: Nc1ncnc2c1c(Oc1cccc(Cl)c1)nn2CC1CCNC1]

Compound was synthesized using process E from intermediate in example 12. LC/MS ES+ calcd for Chemical Formula: $C_{16}H_{17}ClN_6O$ (M+H)$^+$ 345.11, found 345.43. $^1$H NMR (400 MHz, DMSO-d$_6$) δ 8.21 (s, 1H), 7.55 (t, J=2.2 Hz, 1H), 7.51-7.35 (m, 2H), 7.28 (dt, J=7.8, 1.5 Hz, 1H), 4.27 (qd, J=14.1, 7.0 Hz, 2H), 3.22 (td, J=11.2, 10.7, 6.2 Hz, 2H), 3.08 (dt, J=11.4, 7.9 Hz, 1H), 2.95 (dd, J=11.6, 7.9 Hz, 1H), 2.84-2.58 (m, 1H), 2.03-1.82 (m, 1H), 1.73-1.53 (m, 1H).

Example 34: 1-(azetidin-3-ylmethyl)-3-(3-chlorophenoxy)-1H-pyrazolo[3,4-d]pyrimidin-4-amine (FUR6-12)

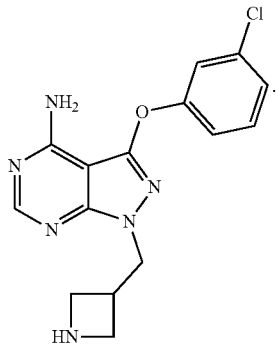 [SMILES: Nc1ncnc2c1c(Oc1cccc(Cl)c1)nn2CC1CNC1]

Compound was synthesized using process E from intermediate in example 12. LC/MS ES+ calcd for Chemical Formula: $C_{15}H_{15}ClN_6O$ (M+H)+ 331.10, found 331.44. $^1$H NMR (400 MHz, DMSO-$d_6$) δ 8.14 (s, 1H), 7.49 (t, J=2.1 Hz, 1H), 7.40-7.31 (m, 2H), 7.20 (dt, J=7.7, 1.6 Hz, 1H), 4.33 (d, J=6.6 Hz, 2H), 3.94-3.59 (m, 4H), 3.11 (s, 1H).

Example 35: 4-((4-amino-3-(3-chlorophenoxy)-1H-pyrazolo[3,4-d]pyrimidin-1-yl)methyl)piperidin-2-one (FUR7-36)

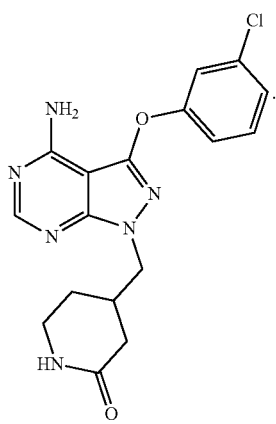 [SMILES: Nc1ncnc2c1c(Oc1cccc(Cl)c1)nn2CC1CCNC(=O)C1]

Compound was synthesized using process E from intermediate in example 12. LC/MS ES+ calcd for Chemical Formula: $C_{15}H_{15}ClN_6O$ (M+H)+ 373.11, found 373.23. $^1$H NMR (400 MHz, DMSO-$d_6$) δ 8.13 (s, 1H), 7.45 (t, J=2.2 Hz, 1H), 7.41-7.34 (m, 2H), 7.31 (dd, J=8.2, 2.3 Hz, 1H), 7.22-7.17 (m, 1H), 4.05 (d, J=7.0 Hz, 2H), 3.09 (ddt, J=12.3, 6.2, 3.6 Hz, 1H), 2.98 (td, J=11.4, 4.5 Hz, 1H), 2.32-2.18 (m, 1H), 2.01 (ddd, J=17.3, 5.4, 1.5 Hz, 1H), 1.86 (dd, J=17.3, 10.5 Hz, 1H), 1.58 (dd, J=13.4, 3.8 Hz, 1H), 1.29 (d, J=9.6 Hz, 1H).

Example 36: 3-(3-chlorophenoxy)-1-((tetrahydro-2H-pyran-4-yl)methyl)-1H-pyrazolo[3,4-d]pyrimidin-4-amine (FUR7-89)

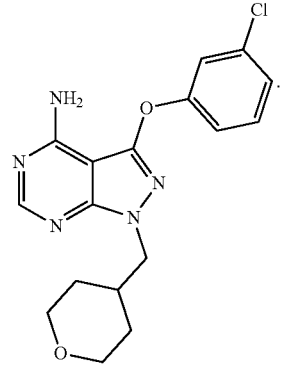 [SMILES: Nc1ncnc2c1c(Oc1cccc(Cl)c1)nn2CC1CCOCC1]

Compound was synthesized using process E from intermediate in example 12. LC/MS ES+ calcd for Chemical Formula: $C_{17}H_{18}ClN_5O_2$(M+H)+ 360.11, found 360.92. $^1$H NMR (400 MHz, DMSO-$d_6$) δ 8.12 (s, 1H), 7.50-7.26 (m, 3H), 7.19 (dt, J=8.0, 1.4 Hz, 1H), 4.00 (d, J=7.1 Hz, 2H), 3.73 (ddd, J=11.5, 4.5, 1.9 Hz, 2H), 3.15 (td, J=11.7, 2.1 Hz, 2H), 2.00 (ddq, J=11.3, 7.8, 3.9 Hz, 1H), 1.32 (dd, J=13.8, 3.3 Hz, 2H), 1.16 (qd, J=12.0, 4.4 Hz, 2H).

Example 37: 1-(piperidin-4-ylmethyl)-3-(m-tolylthio)-1H-pyrazolo[3,4-d]pyrimidin-4-amine (FUR7-77)

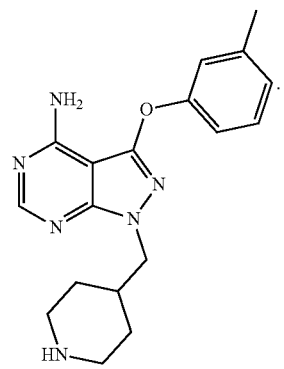

Compound was synthesized starting from intermediate 17 followed by Process C similar to Example 10 and followed by Process E similar to example 13. LC/MS ES+ calcd for Chemical Formula: $C_{18}H_{22}N_6S$ (M+H)+ 355.16, found 355.91. $^1$H NMR (400 MHz, DMSO-$d_6$) δ 8.17 (s, 1H), 7.14 (t, J=7.6 Hz, 1H), 7.09-6.89 (m, 2H), 4.21 (d, J=6.6 Hz, 1H), 3.14 (s, 2H), 2.72 (d, J=12.8 Hz, 2H), 2.16 (s, 3H), 1.54 (d, J=12.7 Hz, 2H), 1.37-1.21 (m, 3H).

Example 38: 3-((3-chlorophenyl)thio)-1-(piperidin-4-ylmethyl)-1H-pyrazolo[3,4-d]pyrimidin-4-amine (FUR5-56)

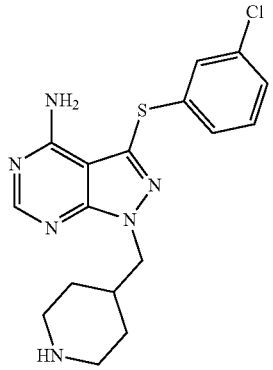

Compound was synthesized starting from intermediate 17 followed by Process C similar to Example 10 and followed by Process E similar to example 13. LC/MS ES+ calcd for Chemical Formula: $C_{17}H_{19}ClN_6S$ (M+H)+ 375.11, found 375.56. $^1$H NMR (400 MHz, DMSO-$d_6$) δ 8.57 (d, J=11.3 Hz, 1H), 8.26 (s, 1H), 7.32-7.22 (m, 3H), 7.13 (dt, J=7.6, 1.7 Hz, 1H), 4.26 (d, J=7.0 Hz, 2H), 3.19 (d, J=12.4 Hz, 2H), 2.87-2.71 (m, 2H), 2.18 (ddp, J=11.0, 7.2, 3.6 Hz, 1H), 1.64-1.54 (m, 2H), 1.33 (qd, J=12.5, 4.0 Hz, 2H)

Example 39: 3-((3-chlorophenyl)thio)-1-((3,3-difluoropiperidin-4-yl)methyl)-H-pyrazolo[3,4-d]pyrimidin-4-amine (FUR7-76)

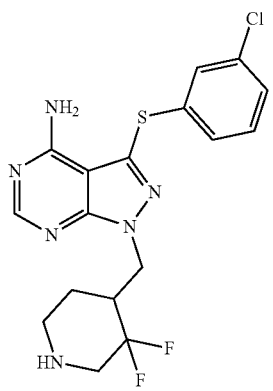

Compound was synthesized starting from intermediate 17 followed by Process C similar to Example 10 and followed by Process E similar to example 13. LC/MS ES+ calcd for Chemical Formula: $C_{17}H_{17}ClF_2N_6S$ (M+H)+ 411.09, found 411.88. $^1$H NMR (400 MHz, DMSO-$d_6$) δ 8.19 (s, 1H), 8.09 (s, 1H), 7.33-7.18 (m, 3H), 7.10 (dt, J=7.6, 1.6 Hz, 1H), 4.61 (dd, J=14.0, 5.3 Hz, 1H), 4.28 (dd, J=14.0, 8.9 Hz, 1H), 2.96 (td, J=12.6, 4.6 Hz, 1H), 2.83-2.51 (m, 3H), 1.30 (td, J=10.7, 9.8, 3.8 Hz, 2H).

Example 40: 3-(3-chlorophenoxy)-1-((1-(trifluoromethyl)cyclopropyl)methyl)-1H-pyrazolo[3,4-d]pyrimidin-4-amine (FUR7-2)

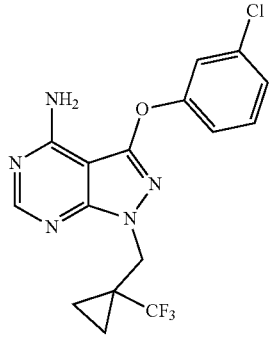

Compound was synthesized using process E from intermediate in example 12. LC/MS ES+ calcd for Chemical Formula: $C_{16}H_{13}ClF_3N_5O$ (M+H)+ 384.08, found 383.76. $^1$H NMR (400 MHz, DMSO-$d_6$) δ 8.15 (s, 1H), 7.46 (t, J=2.2 Hz, 1H), 7.39 (t, J=8.1 Hz, 1H), 7.31 (dd, J=8.2, 2.3 Hz, 1H), 7.23-7.16 (m, 1H), 4.38 (s, 2H), 1.05 (d, J=5.3 Hz, 2H), 0.96 (t, J=3.5 Hz, 2H).

Example 41: 3-(benzo[b]thiophen-3-ylmethyl)-1-(tert-butyl)-1H-pyrazolo[3,4-d]pyrimidin-4-amine (CZ43)

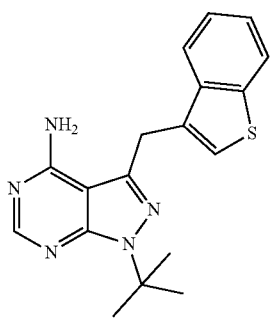

Compound was synthesized using synthetic methods previously described (Sebastian Sibley and Shokat 2013). LC/MS ES+ calcd for Chemical Formula: $C_{18}H_{19}N_5S$ (M+H)+ 338.14, found 338.29. $^1$H NMR (400 MHz, DMSO-$d_6$) δ 8.11 (s, 1H), 8.05-8.00 (m, 1H), 7.98-7.92 (m, 1H), 7.42 (d, J=1.1 Hz, 1H), 7.37 (tt, J=7.2, 5.5 Hz, 2H), 4.55 (d, J=1.2 Hz, 2H), 1.70 (s, 9H).

Example 42: 3-(benzofuran-3-ylmethyl)-1-(tert-butyl)-1H-pyrazolo[3,4-d]pyrimidin-4-amine (LJQ145)

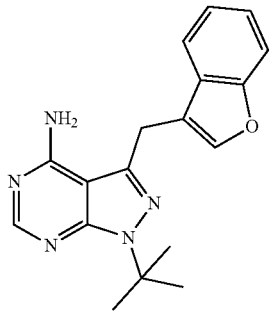

Compound was synthesized using synthetic methods previously described (Sebastian Sibley and Shokat 2013). LC/MS ES+ calcd for Chemical Formula: $C_{18}H_{19}N_5O$ (M+H)⁺ 321.16, found 321.36. ¹H NMR (400 MHz, DMSO-d₆) δ 8.10 (s, 1H), 7.91 (d, J=1.1 Hz, 1H), 7.61 (ddd, J=7.7, 1.4, 0.7 Hz, 1H), 7.52 (dt, J=8.2, 0.9 Hz, 1H), 7.27 (ddd, J=8.4, 7.2, 1.4 Hz, 1H), 7.19 (td, J=7.5, 1.0 Hz, 1H), 4.39 (d, J=1.2 Hz, 2H), 1.70 (s, 9H).

Example 43: 3-((1H-indol-3-yl)methyl)-1-(tert-butyl)-1H-pyrazolo[3,4-d]pyrimidin-4-amine (LJQ138)

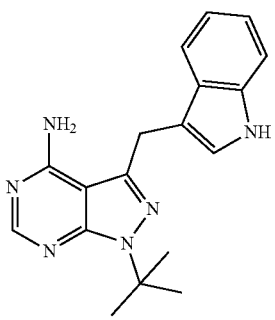

Compound was synthesized using synthetic methods previously described (Sebastian Sibley and Shokat 2013). LC/MS ES+ calcd for Chemical Formula: $C_{18}H_{20}N_6$ (M+H)⁺ 321.17, found 322.38. ¹H NMR (400 MHz, DMSO-d₆) δ 10.85 (s, 1H), 8.07 (s, 1H), 7.53 (d, J=8.0 Hz, 1H), 7.35-7.27 (m, 2H), 7.03 (ddd, J=8.1, 6.9, 1.2 Hz, 1H), 6.95-6.86 (m, 1H), 4.36 (s, 2H), 1.72 (s, 6H).

Example 44: 3-((1H-indol-3-yl)methyl)-1-((1-(trifluoromethyl)cyclopropyl)methyl)-1H-pyrazolo[3,4-d]pyrimidin-4-amine (WXT-2)

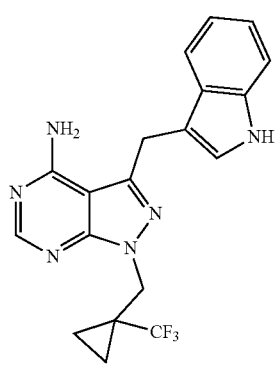

Compound was synthesized using processes D and E from LJQ138. LC/MS ES+ calcd for Chemical Formula: $C_{19}H_{17}F3N_6$ (M+H)+387.15. ¹H NMR (CDCl₃) δ 8.29 (1H), 7.55-7.53 (1H), 7.42-7.40 (1H), 7.25-7.23 (1H), 7.14-7.11 (1H), 6.97-6.96 (1H), 4.68 (2H), 4.42 (2H), 1.11-1.08 (4H)

Example 45: 3-((1H-indol-3-yl)methyl)-1-(piperidin-4-ylmethyl)-1H-pyrazolo[3,4-d]pyrimidin-4-amine (FUR6-95)

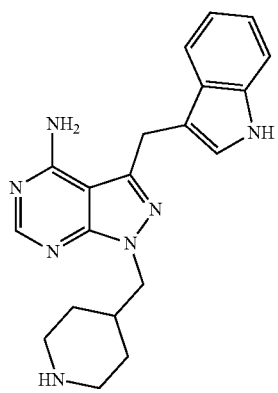

Compound was synthesized using processes D and E from LJQ138. LC/MS ES+ calcd for Chemical Formula: $C_{20}H_{23}N_7$(M+H)⁺362.20, found 362.64.

Example 46: 3-((1H-indol-3-yl)thio)-1-(piperidin-4-ylmethyl)-1H-pyrazolo[3,4-d]pyrimidin-4-amine (FUR5-57)

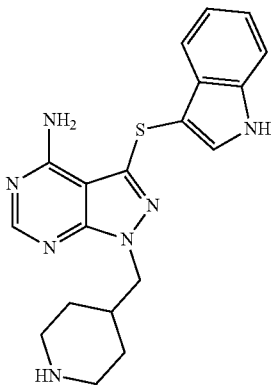

Compound was synthesized starting from intermediate 17 followed by Process C similar to Example 10 and followed by Process E similar to example 13. LC/MS ES+ calcd for Chemical Formula: $C_{19}H_{21}N_7S$ (M+H)$^+$ 380.16, found 380.48. $^1$H NMR (400 MHz, DMSO-d$_6$) δ 11.58 (s, 1H), 8.36 (s, 1H), 8.07 (s, 1H), 7.83 (d, J=1.4 Hz, 1H), 7.49 (d, J=7.9 Hz, 1H), 7.34 (d, J=8.1 Hz, 1H), 7.05 (ddd, J=8.1, 6.9, 1.2 Hz, 1H), 6.94 (td, J=7.5, 7.0, 0.9 Hz, 1H), 4.07 (d, 2H), 3.01 (d, J=12.3 Hz, 2H), 2.65-2.49 (m, 2H), 2.00 (dtd, J=11.1, 7.4, 3.7 Hz, 1H), 1.39 (d, J=13.3 Hz, 2H), 1.20 (tt, J=13.2, 7.0 Hz, 2H).

NMR data for FUR 6-160:

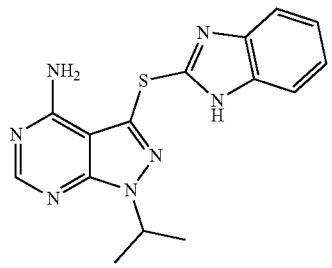

$^1$H NMR (400 MHz, DMSO-d$_6$) δ 11.42 (s, 1H), 8.04 (s, 1H), 7.79 (d, J=2.6 Hz, 1H), 7.60 (d, J=7.9 Hz, 1H), 7.37-7.29 (m, 1H), 7.04 (ddd, J=8.2, 7.1, 1.3 Hz, 1H), 6.96 (ddd, J=8.0, 7.0, 1.0 Hz, 1H), 1.60 (s, 9H).

NMR data for FUR 6NMR data for FUR 6-161

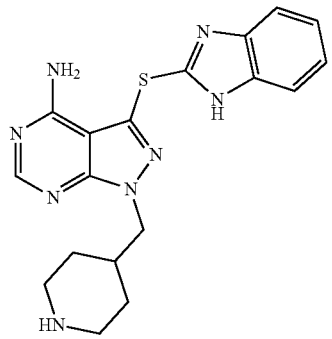

$^1$H NMR (400 MHz, DMSO-d$_6$) δ 8.33 (s, 1H), 8.18 (s, 1H), 7.47-7.34 (m, 2H), 7.17-7.04 (m, 2H), 4.19 (d, J=6.8 Hz, 2H), 3.16-2.97 (m, 2H), 2.62 (td, J=12.5, 2.8 Hz, 2H), 2.07 (qd, J=7.6, 4.1 Hz, 1H), 1.54 (dd, J=14.0, 3.5 Hz, 2H), 1.28 (qd, J=12.5, 3.9 Hz, 2H). NMR data for FUR 6-162

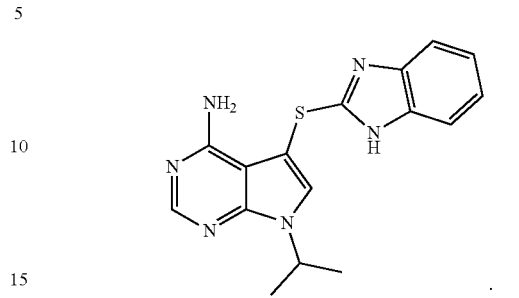

$^1$H NMR (400 MHz, DMSO-d$_6$) δ 8.07 (s, 1H), 7.78 (s, 1H), 7.35 (dt, J=6.0, 3.6 Hz, 2H), 7.09-6.98 (m, 2H), 4.87 (hept, J=6.6 Hz, 1H), 1.41 (d, J=6.8 Hz, 6H).

NMR data for FUR 6-162B:

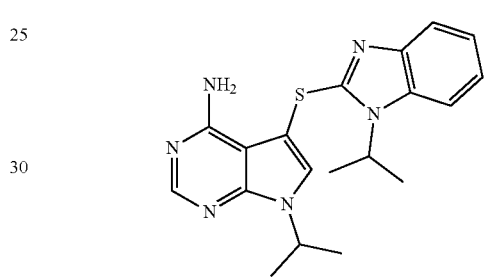

$^1$H NMR (400 MHz, DMSO-d$_6$) δ 8.02 (s, 1H), 7.91 (s, 1H), 7.71-7.61 (m, 1H), 7.55-7.46 (m, 1H), 7.13 (pd, J=7.2, 1.4 Hz, 2H), 6.97 (s, 2H), 5.24 (hept, J=6.8 Hz, 1H), 4.85 (p, J=6.7 Hz, 1H), 1.44 (d, J=6.9 Hz, 6H), 1.36 (d, J=6.8 Hz, 6H).

NMR data for FUR 6-141:

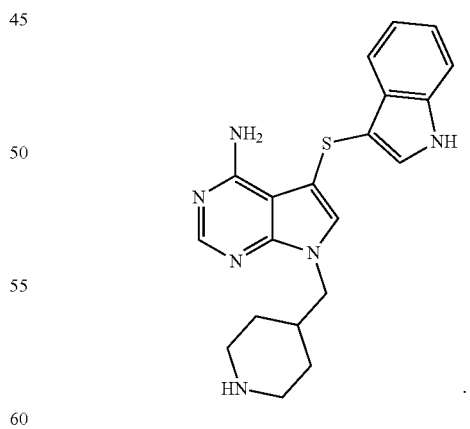

$^1$H NMR (400 MHz, DMSO-d$_6$) δ 11.32 (s, 1H), 8.22 (s, 1H), 7.95 (d, J=13.2 Hz, 1H), 7.70-7.53 (m, 2H), 7.45 (d, J=9.6 Hz, 1H), 7.31 (d, J=8.1 Hz, 1H), 7.10 (t, J=7.7 Hz, 1H), 3.96 (dd, J=29.9, 6.6 Hz, 2H), 3.06 (s, 2H), 2.66-2.54 (m, 2H), 1.93 (s, 1H), 1.46 (dd, J=25.1, 13.1 Hz, 2H), 1.21 (s, 2H).

NMR data for HYC29:

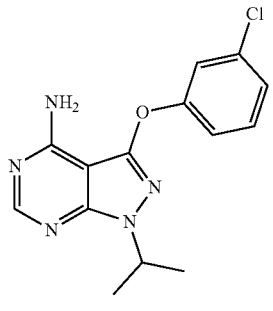

¹H NMR (400 MHz, DMSO-d₆) δ 8.18 (s, 1H), 7.51 (t, J=2.2 Hz, 1H), 7.44 (t, J=8.1 Hz, 1H), 7.37 (ddd, J=8.4, 2.4, 1.0 Hz, 1H), 7.25 (ddd, J=7.9, 2.0, 1.0 Hz, 1H), 4.93 (hept, J=6.6 Hz, 1H), 1.39 (d, J=6.7 Hz, 6H).

Compound FUR 6-157 was synthesized according to process E. NMR data for FUR 6-157:

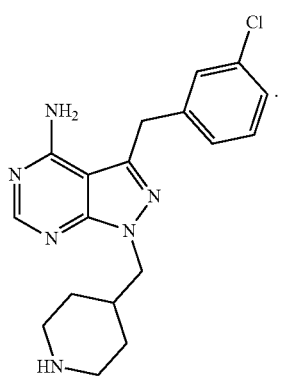

¹H NMR (400 MHz, DMSO-d₆) δ 8.08 (d, J=2.3 Hz, 1H), 7.28-7.21 (m, 2H), 7.19 (dd, J=8.2, 1.8 Hz, 1H), 7.16-7.09 (m, 1H), 4.30 (s, 2H), 4.11 (d, J=7.0 Hz, 2H), 3.15 (dt, J=13.0, 3.3 Hz, 2H), 2.74 (td, J=12.7, 2.9 Hz, 2H), 2.12 (dtd, J=15.4, 7.7, 4.5 Hz, 1H), 1.54 (dd, J=14.2, 3.6 Hz, 2H), 1.39-1.20 (m, 2H).

NMR data for compound FUR 6-139,

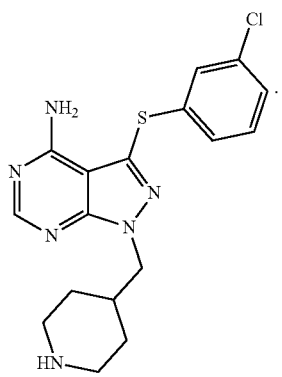

¹H NMR (400 MHz, DMSO-d₆) δ 8.28 (s, 2H), 8.09 (s, 1H), 7.67 (s, 1H), 7.23 (t, J=7.9 Hz, 1H), 7.14 (dd, J=7.7, 2.0 Hz, 1H), 7.01 (t, J=1.9 Hz, 1H), 6.99-6.94 (m, 1H), 4.04 (d, J=7.2 Hz, 2H), 3.06 (d, J=12.1 Hz, 2H), 2.58 (t, J=11.9 Hz, 2H), 2.03 (s, 1H), 1.46 (d, J=13.0 Hz, 2H), 1.30-1.14 (m, 2H).

Compound GXJ-184,

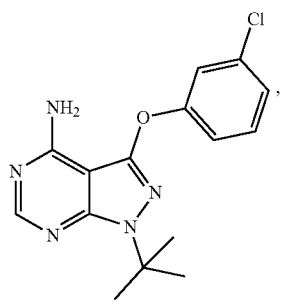 [SMILES: CC(C)(C)n1nc(Oc2cccc(Cl)c2)c2c(N)ncnc21]

was synthesized according to process A. The LC-MS ES⁺ for GXJ-184 was 318.10 (317.84) (observed).

The NMR data for compound GXJ-176,

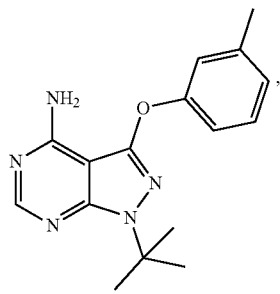

is ¹H NMR (400 MHz, DMSO-d₆) δ 8.17 (s, 1H), 7.28 (t, J=7.9 Hz, 1H), 7.20-7.07 (m, 2H), 6.98 (d, J=7.5 Hz, 1H), 2.32 (s, 3H), 1.65 (s, 9H).

The compound GXJ-237,

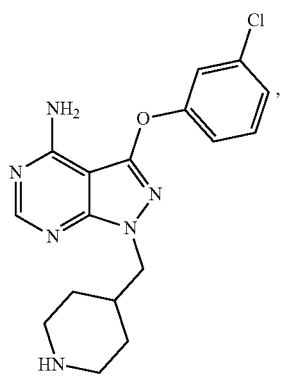

was synthesized according to process A (D, E). ¹H NMR (400 MHz, DMSO-d₆) δ 8.13 (s, 1H), 7.46 (t, J=2.2 Hz, 1H), 7.38 (t, J=8.1 Hz, 1H), 7.31 (ddd, J=8.3, 2.4, 1.1 Hz, 1H), 7.20 (dt, J=8.0, 1.5 Hz, 1H), 4.04 (s, 2H), 3.15 (dt, J=13.0, 3.5 Hz, 2H), 2.73 (td, J=12.7, 3.0 Hz, 2H), 2.04 (dtt, J=14.9, 7.1, 2.9 Hz, 1H), 1.64-1.49 (m, 2H), 1.28 (qd, J=12.6, 4.0 Hz, 2H).

The compound FUR 6-6,

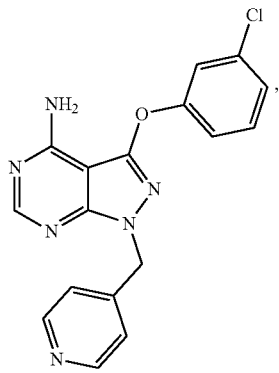

was synthesized according to process A (D, E). ¹H NMR (400 MHz, DMSO-d₆) δ 8.42 (d, J=5.0 Hz, 2H), 8.15 (s, 1H), 7.45 (t, J=2.1 Hz, 1H), 7.40-7.29 (m, 2H), 7.19 (dt, J=7.8, 1.8 Hz, 1H), 7.08-7.01 (m, 2H), 5.38 (s, 2H).

The compound FUR 6-11,

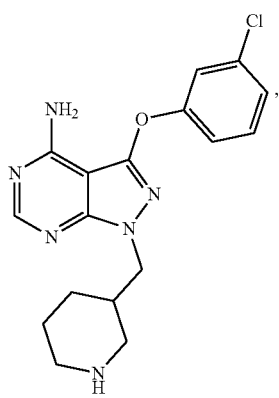

was synthesized according to process A (D, E). ¹H NMR (400 MHz, DMSO-d₆) δ 8.21 (s, 1H), 7.55 (t, J=2.2 Hz, 1H), 7.51-7.35 (m, 2H), 7.28 (dt, J=7.8, 1.5 Hz, 1H), 4.27 (qd, J=14.1, 7.0 Hz, 2H), 3.22 (td, J=11.2, 10.7, 6.2 Hz, 2H), 3.08 (dt, J=11.4, 7.9 Hz, 1H), 2.95 (dd, J=11.6, 7.9 Hz, 1H), 2.84-2.58 (m, 1H), 2.03-1.82 (m, 1H), 1.73-1.53 (m, 1H).

The compound FUR 6-13,

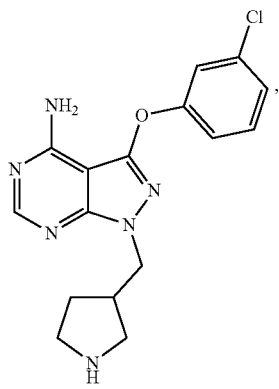 [SMILES: Nc1ncnc2c1c(Oc1cccc(Cl)c1)nn2CC1CCNC1]

was synthesized according to process A (D, E). ¹H NMR (400 MHz, DMSO-d₆) δ 8.21 (s, 1H), 7.55 (t, J=2.2 Hz, 1H), 7.51-7.35 (m, 2H), 7.28 (dt, J=7.8, 1.5 Hz, 1H), 4.27 (qd, J=14.1, 7.0 Hz, 2H), 3.22 (td, J=11.2, 10.7, 6.2 Hz, 2H), 3.08 (dt, J=11.4, 7.9 Hz, 1H), 2.95 (dd, J=11.6, 7.9 Hz, 1H), 2.84-2.58 (m, 1H), 2.03-1.82 (m, 1H), 1.73-1.53 (m, 1H).

The compound FUR 6-12,

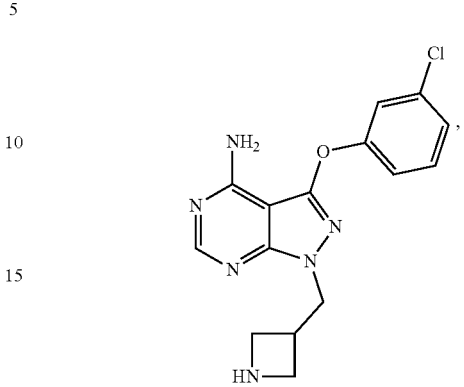

was synthesized according to process A (D, E). ¹H NMR (400 MHz, DMSO-d₆) δ 8.14 (s, 1H), 7.49 (t, J=2.1 Hz, 1H), 7.40-7.31 (m, 2H), 7.20 (dt, J=7.7, 1.6 Hz, 1H), 4.33 (d, J=6.6 Hz, 2H), 3.94-3.59 (m, 4H), 3.11 (s, 1H).

The compound FUR 7-27,

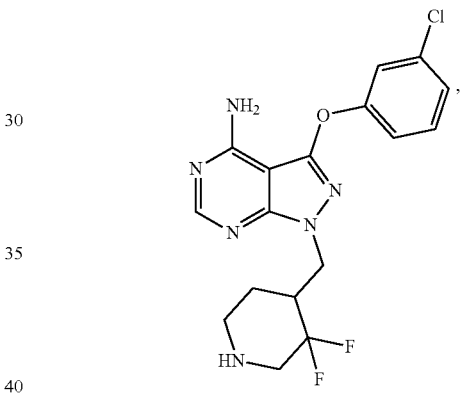

was synthesized according to process A (D, E). ¹H NMR (400 MHz, DMSO-d₆) δ 8.13 (s, 1H), 7.48-7.26 (m, 3H), 7.19 (dd, J=7.7, 1.9 Hz, 1H), 4.38 (dd, J=14.1, 5.0 Hz, 1H), 4.12 (dd, J=14.1, 9.2 Hz, 1H), 3.14-2.96 (m, 1H), 2.88-2.63 (m, 2H), 1.31 (ddd, J=28.8, 10.4, 4.0 Hz, 2H), 1.10 (t, J=7.3 Hz, 1H).

The compound 7-30,

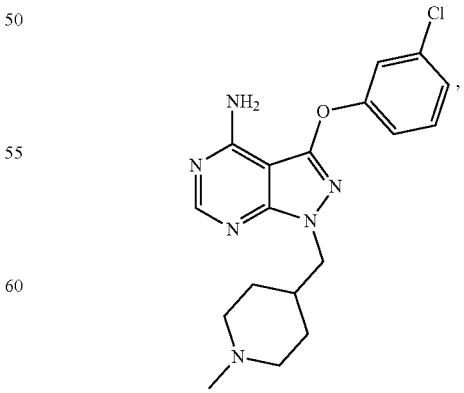

was synthesized according to process E. ¹H NMR (400 MHz, DMSO-d₆) δ 8.10 (d, J=3.9 Hz, 2H), 7.41 (t, J=2.2 Hz, 1H), 7.35 (t, J=8.1 Hz, 1H), 7.30-7.25 (m, 1H), 7.21-7.14 (m, 1H), 3.97 (d, J=7.1 Hz, 2H), 2.74 (dt, J=12.2, 3.6 Hz, 2H), 2.14 (s, 3H), 2.01-1.84 (m, 2H), 1.84-1.62 (m, 1H), 1.45-1.33 (m, 2H), 1.24-1.09 (m, 2H).

The compound FUR 7-36,

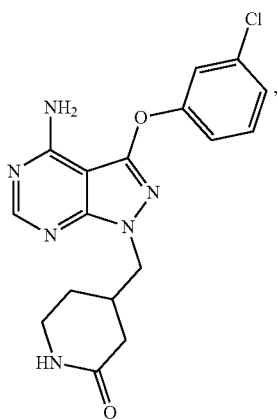 [SMILES: Nc1ncnc2c1c(Oc1cccc(Cl)c1)nn2CC1CCNC(=O)C1]

was synthesized according to process E.

The compound FUR 7-89,

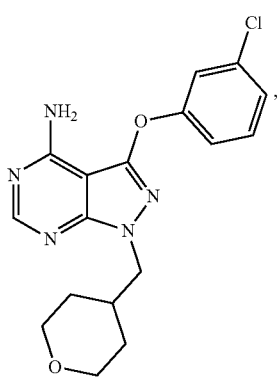

was synthesized according to process E. ¹H NMR (400 MHz, DMSO-d₆) δ 8.12 (s, 1H), 7.50-7.26 (m, 3H), 7.19 (dt, J=8.0, 1.4 Hz, 1H), 4.00 (d, J=7.1 Hz, 2H), 3.73 (ddd, J=11.5, 4.5, 1.9 Hz, 2H), 3.15 (td, J=11.7, 2.1 Hz, 2H), 2.00 (ddq, J=11.3, 7.8, 3.9 Hz, 1H), 1.32 (dd, J=13.8, 3.3 Hz, 2H), 1.16 (qd, J=12.0, 4.4 Hz, 2H).

The compound FUR 7-77,

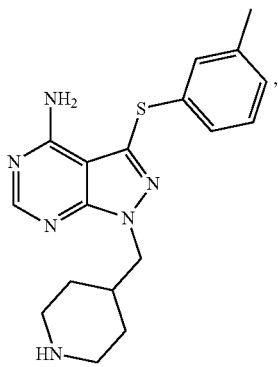 [SMILES: Cc1cccc(Sc2nn(CC3CCNCC3)c3ncnc(N)c23)c1]

was synthesized according to process C, E. ¹H NMR (400 MHz, DMSO-d₆) δ 8.17 (s, 1H), 7.14 (t, J=7.6 Hz, 1H), 7.09-6.89 (m, 2H), 4.21 (d, J=6.6 Hz, 1H), 3.14 (s, 2H), 2.72 (d, J=12.8 Hz, 2H), 2.16 (s, 3H), 1.54 (d, J=12.7 Hz, 2H), 1.37-1.21 (m, 3H).

The compound FUR 5-56,

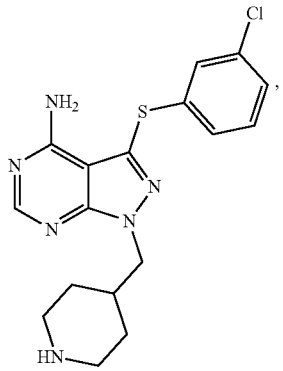 [SMILES: Nc1ncnc2c1c(Sc1cccc(Cl)c1)nn2CC1CCNCC1]

was synthesized according to process C, E. ¹H NMR (400 MHz, DMSO-d₆) δ 8.57 (d, J=11.3 Hz, 1H), 8.26 (s, 1H), 7.32-7.22 (m, 3H), 7.13 (dt, J=7.6, 1.7 Hz, 1H), 4.26 (d, J=7.0 Hz, 2H), 3.19 (d, J=12.4 Hz, 2H), 2.87-2.71 (m, 2H), 2.18 (ddp, J=11.0, 7.2, 3.6 Hz, 1H), 1.64-1.54 (m, 2H), 1.33 (qd, J=12.5, 4.0 Hz, 2H).

The compound FUR 7-76,

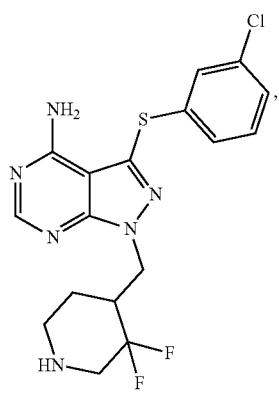

was synthesized according to process C, E. ¹H NMR (400 MHz, DMSO-d₆) δ 8.19 (s, 1H), 8.09 (s, 1H), 7.33-7.18 (m, 3H), 7.10 (dt, J=7.6, 1.6 Hz, 1H), 4.61 (dd, J=14.0, 5.3 Hz, 1H), 4.28 (dd, J=14.0, 8.9 Hz, 1H), 2.96 (td, J=12.6, 4.6 Hz, 1H), 2.83-2.51 (m, 3H), 1.30 (td, J=10.7, 9.8, 3.8 Hz, 2H).

The compound FUR 7-2,

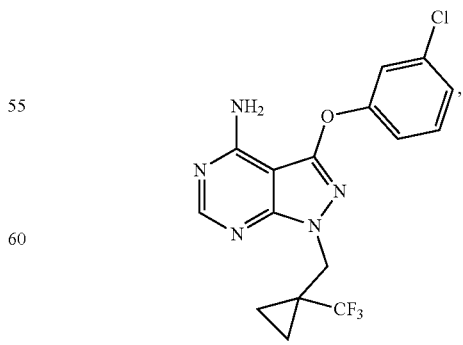

was synthesized according to process A. ¹H NMR (400 MHz, DMSO-d₆) δ 8.15 (s, 1H), 7.46 (t, J=2.2 Hz, 1H), 7.39

(t, J=8.1 Hz, 1H), 7.31 (dd, J=8.2, 2.3 Hz, 1H), 7.23-7.16 (m, 1H), 4.38 (s, 2H), 1.05 (d, J=5.3 Hz, 2H), 0.96 (t, J=3.5 Hz, 2H).

The NMR data for compound LJQ-138,

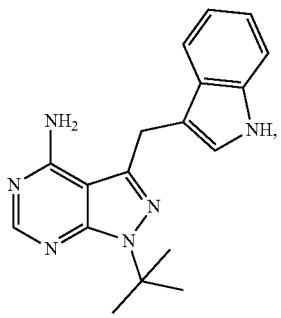 [SMILES: CC(C)(C)n1nc(Cc2c[nH]c3ccccc23)c2c(N)ncnc21]

is: ¹H NMR (400 MHz, DMSO-d₆) δ 10.85 (s, 1H), 8.07 (s, 1H), 7.53 (d, J=8.0 Hz, 1H), 7.35-7.27 (m, 2H), 7.03 (ddd, J=8.1, 6.9, 1.2 Hz, 1H), 6.95-6.86 (m, 1H), 4.36 (s, 2H), 1.72 (s, 6H).

The compound FUR 5-57,

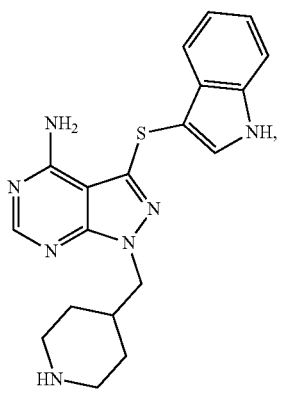 [SMILES: Nc1ncnc2c1c(Sc1c[nH]c3ccccc13)nn2CC1CCNCC1]

was synthesized according to process C, E. ¹H NMR (400 MHz, DMSO-d₆) δ 11.58 (s, 1H), 8.36 (s, 1H), 8.07 (s, 1H), 7.83 (d, J=1.4 Hz, 1H), 7.49 (d, J=7.9 Hz, 1H), 7.34 (d, J=8.1 Hz, 1H), 7.05 (ddd, J=8.1, 6.9, 1.2 Hz, 1H), 6.94 (td, J=7.5, 7.0, 0.9 Hz, 1H), 4.07 (d, 2H), 3.01 (d, J=12.3 Hz, 2H), 2.65-2.49 (m, 2H), 2.00 (dtd, J=11.1, 7.4, 3.7 Hz, 1H), 1.39 (d, J=13.3 Hz, 2H), 1.20 (tt, J=13.2, 7.0 Hz, 2H).

The compound FUR 6-159,

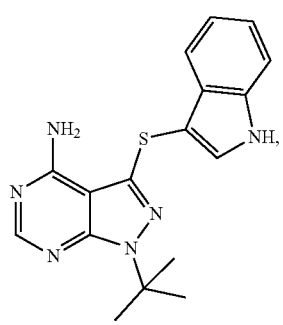

was synthesized according to process C. ¹H NMR (400 MHz, DMSO-d₆) δ 11.42 (s, 1H), 8.04 (s, 1H), 7.79 (d, J=2.6 Hz, 1H), 7.60 (d, J=7.9 Hz, 1H), 7.37-7.29 (m, 1H), 7.04 (ddd, J=8.2, 7.1, 1.3 Hz, 1H), 6.96 (ddd, J=8.0, 7.0, 1.0 Hz, 1H), 1.60 (s, 9H).

Compound and characterization table.

| Compound ID | Structure | LC-MS ES⁺ (observed) | ¹H NMR | Synthesis Process |
|---|---|---|---|---|
| 3 ClB-PP1 | (structure shown) | Cl | | Synthesized according to Lourido Shokat and Sibley J Med Chem. 2013 Apr 11;56(7):3068-77 |

| Compound ID | Structure | LC-MS ES+ (observed) | $^1$H NMR | Synthesis Process |
|---|---|---|---|---|
| FUR 6-157 | 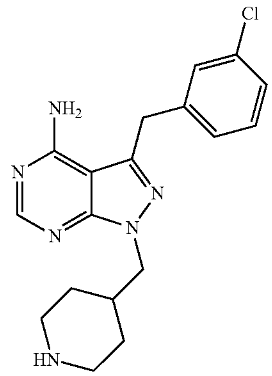 [SMILES: Nc1ncnc2c1c(Cc1cccc(Cl)c1)nn2CC1CCNCC1] | 357.15 (357.21) | $^1$H NMR (400 MHz, DMSO-$d_6$) δ 8.08 (d, J = 2.3 Hz, 1H), 7.28-7.21 (m, 2H), 7.19 (dd, J = 8.2, 1.8 Hz, 1H), 7.16-7.09 (m, 1H), 4.30 (s, 2H), 4.11 (d, J = 7.0 Hz, 2H), 3.15 (dt, J = 13.0, 3.3 Hz, 2H), 2.74 (td, J = 12.7, 2.9 Hz, 2H), 2.12 (dtd, J = 15.4, 7.7, 4.5 Hz, 1H), 1.54 (dd, J = 14.2, 3.6 Hz, 2H), 1.39-1.20 (m, 2H). | D, E |
| CZ75 | 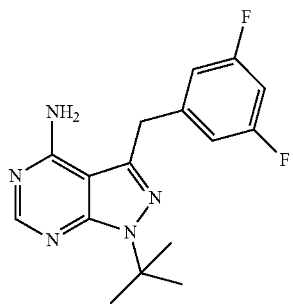 [SMILES: CC(C)(C)n1nc(Cc2cc(F)cc(F)c2)c2c(N)ncnc21] | Synthesized according to Lourido Shokat and Sibley J Med Chem. 2013 Apr 11;56(7):3068-77 | | |
| MLC468 | 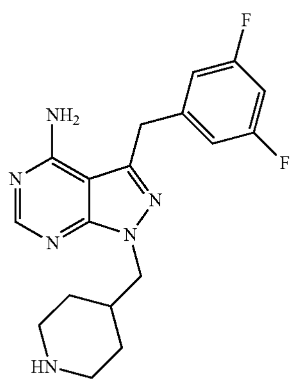 [SMILES: Nc1ncnc2c1c(Cc1cc(F)cc(F)c1)nn2CC1CCNCC1] | 359.17 (357.27) | $^1$H NMR (400 MHz, DMSO-$d_6$) δ 8.15 (s, 1H), 7.06 (tt, J = 9.4, 2.4 Hz, 1H), 7.00-6.91 (m, 1H), 4.39 (s, 2H), 4.14 (d, J = 7.1 Hz, 2H), 3.10-2.95 (m, 2H), 2.16-1.96 (m, 1H), 1.46 (d, J = 13.0 Hz, 2H), 1.38 (d, J = 1.9 Hz, 1H), 1.28-1.09 (m, 2H). | D, E |
| LZH-118 | 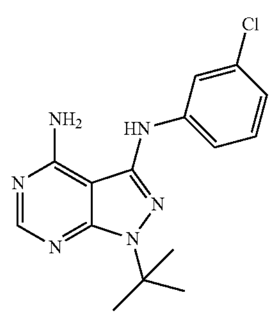 [SMILES: CC(C)(C)n1nc(Nc2cccc(Cl)c2)c2c(N)ncnc21] | 317.12 (317.35) | $^1$H NMR (CDCl$_3$) δ 8.33 (1H), 7.20-7.17 (2H), 7.02-6.90 (2H), 6.78-6.76 (1H), 6.10 (1H), 5.28 (2H), 1.80 (9H). | |

| Compound ID | Structure | LC-MS ES+ (observed) | ¹H NMR | Synthesis Process |
|---|---|---|---|---|
| GXJ-276 | 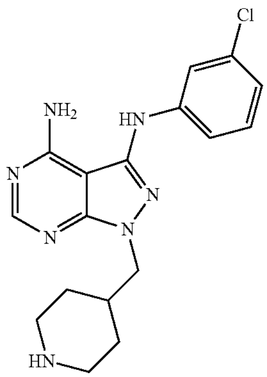 [SMILES: Nc1ncnc2c1c(Nc1cccc(Cl)c1)nn2CC1CCNCC1] | 358.15 (358.06) | ¹H NMR (400 MHz, DMSO-d₆) δ 8.76 (s, 1H), 8.11 (s, 1H), 7.83 (t, J = 2.1 Hz, 1H), 7.62 (s, 2H), 7.58 (ddd, J = 8.3, 2.2, 0.9 Hz, 1H), 7.28 (t, J = 8.1 Hz, 1H), 6.89 (ddd, J = 7.9, 2.1, 0.9 Hz, 1H), 4.09 (d, J = 7.0 Hz, 2H), 3.14-3.02 (m, 2H), 2.64 (td, J = 12.4, 2.7 Hz, 2H), 2.08 (ddt, J = 11.4, 7.8, 3.8 Hz, 1H), 1.89 (s, 1H), 1.57 (d, J = 12.8 Hz, 2H), 1.27 (dd, J = 13.1, 3.8 Hz, 2H). | |
| GXJ-186 | 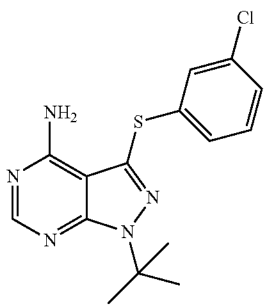 | 334.08 (333.98) | ¹H NMR (400 MHz, DMSO-d₆) δ 8.23 (s, 1H), 7.38-7.26 (m, 3H), 7.09 (dt, J = 7.7, 1.4 Hz, 1H), 1.75 (s, 9H). | |
| FUR 7-68 | 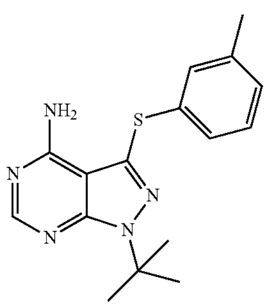 | 314.14 (314.52) | 1H NMR (400 MHz, DMSO-d6) δ 8.22 (s, 1H), 7.20 (t, J = 7.7 Hz, 1H), 7.11 (d, J = 1.8 Hz, 1H), 7.04 (ddt, J = 7.6, 1.8, 0.9 Hz, 1H), 6.95 (ddt, J = 7.8, 1.8, 0.8 Hz, 1H), 2.24 (s, 3H), 1.74 (s, 9H). | C |
| FUR 6-139 | 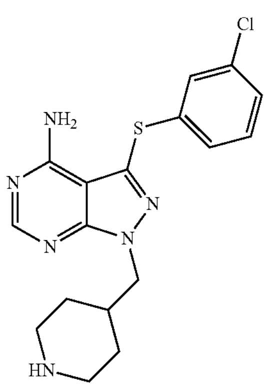 [SMILES: Nc1ncnc2c1c(Sc1cccc(Cl)c1)nn2CC1CCNCC1] | 374.11 (374.43) | 1H NMR (400 MHz, DMSO-d6) δ 8.28 (s, 2H), 8.09 (s, 1H), 7.67 (s, 1H), 7.23 (t, J = 7.9 Hz, 1H), 7.14 (dd, J = 7.7, 2.0 Hz, 1H), 7.01 (t, J = 1.9 Hz, 1H), 6.99-6.94 (m, 1H), 4.04 (d, J = 7.2 Hz, 2H), 3.06 (d, J = 12.1 Hz, 2H), 2.58 (t, J = 11.9 Hz, 2H), | E |

-continued

| Compound ID | Structure | LC-MS ES+ (observed) | ¹H NMR | Synthesis Process |
|---|---|---|---|---|
| | | | 2.03 (s, 1H), 1.46 (d, J = 13.0 Hz, 2H), 1.30-1.14 (m, 2H). | |
| GXJ-184 | 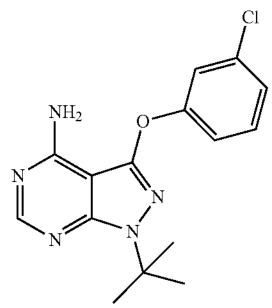 [SMILES: CC(C)(C)n1nc(Oc2cccc(Cl)c2)c2c(N)ncnc21] | 318.10 (317.84) | 1H NMR (400 MHz, DMSO-d6) δ 8.17 (s, 1H), 7.55 (t, J = 2.1 Hz, 1H), 7.47-7.36 (m, 2H), 7.23 (ddd, J = 7.7, 2.0, 1.3 Hz, 1H), 1.66 (s, 9H). | A |
| GXJ-178 | 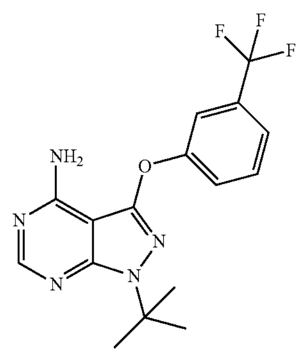 [SMILES: CC(C)(C)n1nc(Oc2cccc(C(F)(F)F)c2)c2c(N)ncnc21] | 352.13 (351.94) | 1H NMR (400 MHz, DMSO-d6) δ 8.18 (s, 1H), 7.90 (t, J = 2.1 Hz, 1H), 7.77 (dd, J = 8.3, 2.4 Hz, 1H), 7.65 (t, J = 8.0 Hz, 1H), 7.57-7.51 (m, 1H), 1.66 (s, 9H). | |
| GXJ-176 | 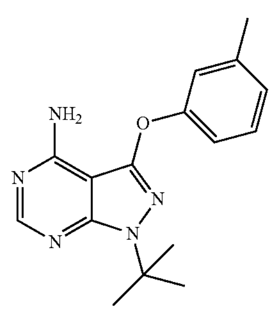 [SMILES: Cc1cccc(Oc2nn(C(C)(C)C)c3ncnc(N)c23)c1] | 298.16 (298.27) | 1H NMR (400 MHz, DMSO-d6) δ 8.17 (s, 1H), 7.28 (t, J = 7.9 Hz, 1H), 7.20-7.07 (m, 2H), 6.98 (d, J = 7.5 Hz, 1H), 2.32 (s, 3H), 1.65 (s, 9H). | |
| GXJ-177 | 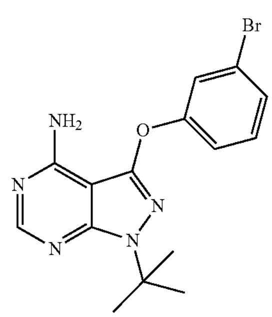 | 362.05 (362.30, 364.11) | 1H NMR (400 MHz, DMSO-d6) δ 8.17 (s, 1H), 7.72-7.67 (m, 1H), 7.48-7.33 (m, 3H), 1.66 (s, 9H). | |

| Compound ID | Structure | LC-MS ES⁺ (observed) | ¹H NMR | Synthesis Process |
|---|---|---|---|---|
| GXJ-230 | 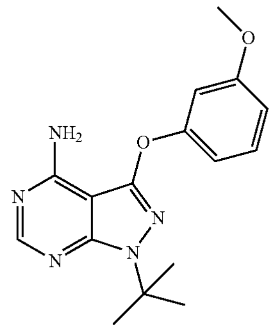 [SMILES: COc1cccc(Oc2nn(C(C)(C)C)c3ncnc(N)c23)c1] | 314.15 (314.13) | 1H NMR (400 MHz, DMSO-d6) δ 8.17 (s, 1H), 7.29 (t, J = 8.2 Hz, 1H), 7.03 (t, J = 2.4 Hz, 1H), 6.93 (ddd, J = 8.2, 2.3, 0.8 Hz, 1H), 6.74 (ddd, J = 8.3, 2.5, 0.8 Hz, 1H), 3.76 (s, 3H), 1.66 (s, 9H). | |
| GXJ-229 | 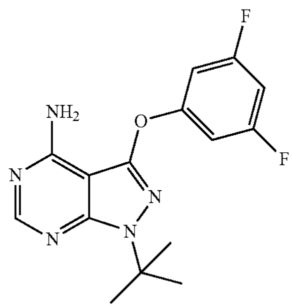 [SMILES: CC(C)(C)n1nc(Oc2cc(F)cc(F)c2)c2c(N)ncnc21] | 320.12 (320.20) | 1H NMR (400 MHz, DMSO-d6) δ 8.18 (s, 1H), 7.29-7.22 (m, 2H), 7.07 (d, J = 2.3 Hz, 1H), 1.67 (s, 9H). | |
| GXJ-237 | 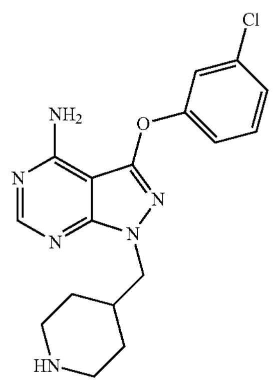 | 359.13 (359.08) | 1H NMR (400 MHz, DMSO-d6) δ 8.13 (s, 1H), 7.46 (t, J = 2.2 Hz, 1H), 7.38 (t, J = 8.1 Hz, 1H), 7.31 (ddd, J = 8.3, 2.4, 1.1 Hz, 1H), 7.20 (dt, J = 8.0, 1.5 Hz, 1H), 4.04 (s, 2H), 3.15 (dt, J = 13.0, 3.5 Hz, 2H), 2.73 (td, J = 12.7, 3.0 Hz, 2H), 2.04 (dtt, J = 14.9, 7.1, 2.9 Hz, 1H), 1.64-1.49 (m, 2H), 1.28 (qd, J = 12.6, 4.0 Hz, 2H). | E |
| GXJ-261 | 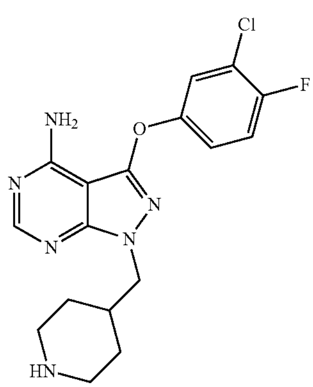 [SMILES: Nc1ncnc2c1c(Oc1ccc(F)c(Cl)c1)nn2CC1CCNCC1] | 377.12 (376.88) | 1H NMR (400 MHz, DMSO-d6) δ 9.03 (s, 2H), 8.19 (s, 1H), 7.79-7.71 (m, 1H), 7.53-7.44 (m, 2H), 4.08 (d, J = 6.9 Hz, 2H), 3.18 (dt, J = 11.5, 2.9 Hz, 2H), 2.77 (td, J = 12.6, 3.0 Hz, 2H), 2.10 (dt, J = 7.5, 3.7 Hz, 1H), 1.61 (dd, J = 14.2, 3.5 Hz, 2H), 1.44 (tt, J = 12.2, 6.3 Hz, 2H). | |

-continued

| Compound ID | Structure | LC-MS ES+ (observed) | ¹H NMR | Synthesis Process |
|---|---|---|---|---|
| FUR 6-6 | 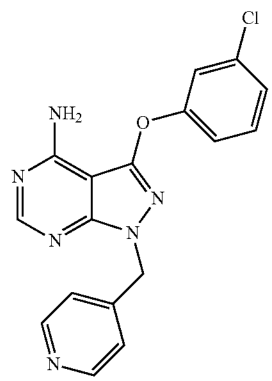 [SMILES: Nc1ncnc2c1c(Oc1cccc(Cl)c1)nn2Cc1ccncc1] | 353.08 (353.14) | 1H NMR (400 MHz, DMSO-d6) δ 8.42 (d, J = 5.0 Hz, 2H), 8.15 (s, 1H), 7.45 (t, J = 2.1 Hz, 1H), 7.40-7.29 (m, 2H), 7.19 (dt, J = 7.8, 1.8 Hz, 1H), 7.08-7.01 (m, 2H), 5.38 (s, 2H). | E |
| FUR 6-11 | 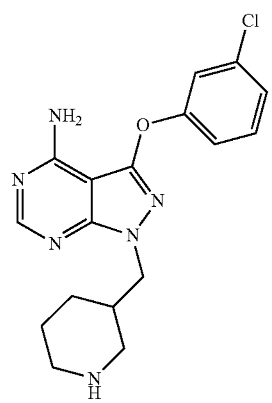 [SMILES: Nc1ncnc2c1c(Oc1cccc(Cl)c1)nn2CC1CCCNC1] | 359.13 (359.52) | 1H NMR (400 MHz, DMSO-d6) δ 8.13 (s, 1H), 7.46 (t, J = 2.1 Hz, 1H), 7.43-7.30 (m, 2H), 7.20 (dt, J = 7.8, 1.6 Hz, 1H), 4.15-3.97 (m, 2H), 3.13-2.90 (m, 2H), 2.71-2.49 (m, 2H), 2.15 (td, J = 7.9, 4.2 Hz, 1H), 1.74-1.37 (m, 3H), 1.21-1.05 (m, 1H). | E |
| FUR 6-13 | 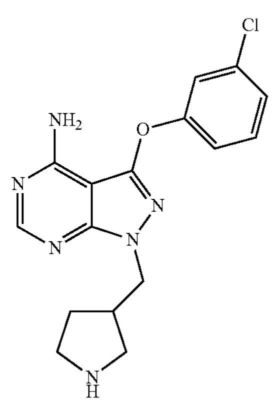 [SMILES: Nc1ncnc2c1c(Oc1cccc(Cl)c1)nn2CC1CCNC1] | 345.11 (345.43) | 1H NMR (400 MHz, DMSO-d6) δ 8.21 (s, 1H), 7.55 (t, J = 2.2 Hz, 1H), 7.51-7.35 (m, 2H), 7.28 (dt, J = 7.8, 1.5 Hz, 1H), 4.27 (qd, J = 14.1, 7.0 Hz, 2H), 3.22 (td, J = 11.2, 10.7, 6.2 Hz, 2H), 3.08 (dt, J = 11.4, 7.9 Hz, 1H), 2.95 (dd, J = 11.6, 7.9 Hz, 1H), 2.84-2.58 (m, 1H), 2.03-1.82 (m, 1H), 1.73-1.53 (m, 1H). | E |

-continued

| Compound ID | Structure | LC-MS ES+ (observed) | 1H NMR | Synthesis Process |
|---|---|---|---|---|
| FUR 6-12 | 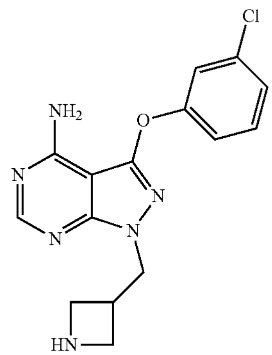 [SMILES: Nc1ncnc2c1c(Oc1cccc(Cl)c1)nn2CC1CNC1] | 331.10 (331.44) | 1H NMR (400 MHz, DMSO-d6) δ 8.14 (s, 1H), 7.49 (t, J = 2.1 Hz, 1H), 7.40-7.31 (m, 2H), 7.20 (dt, J = 7.7, 1.6 Hz, 1H), 4.33 (d, J = 6.6 Hz, 2H), 3.94-3.59 (m, 4H), 3.11 (s, 1H). | E |
| FUR 7-27 | 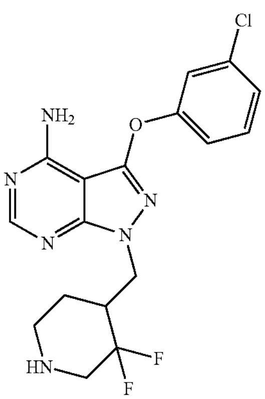 [SMILES: Nc1ncnc2c1c(Oc1cccc(Cl)c1)nn2CC1CCNCC1(F)F] | 395.11 (395.74) | 1H NMR (400 MHz, DMSO-d6) δ 8.13 (s, 1H), 7.48-7.26 (m, 3H), 7.19 (dd, J = 7.7, 1.9 Hz, 1H), 4.38 (dd, J = 14.1, 5.0 Hz, 1H), 4.12 (dd, J = 14.1, 9.2 Hz, 1H), 3.14-2.96 (m, 1H), 2.88-2.63 (m, 2H), 1.31 (ddd, J = 28.8, 10.4, 4.0 Hz, 2H), 1.10 (t, J = 7.3 Hz, 1H). | E |
| FUR 7-30 | 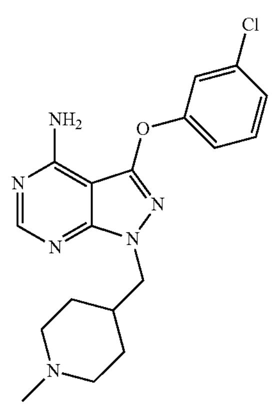 [SMILES: CN1CCC(Cn2nc(Oc3cccc(Cl)c3)c3c(N)ncnc32)CC1] | 373.15 (372.82) | 1H NMR (400 MHz, DMSO-d6) δ 8.10 (d, J = 3.9 Hz, 2H), 7.41 (t, J = 2.2 Hz, 1H), 7.35 (t, J = 8.1 Hz, 1H), 7.30-7.25 (m, 1H), 7.21-7.14 (m, 1H), 3.97 (d, J = 7.1 Hz, 2H), 2.74 (dt, J = 12.2, 3.6 Hz, 2H), 2.14 (s, 3H), 2.01-1.84 (m, 2H), 1.84-1.62 (m, 1H), 1.45-1.33 (m, 2H), 1.24-1.09 (m, 2H). | E |

-continued

| Compound ID | Structure | LC-MS ES+ (observed) | ¹H NMR | Synthesis Process |
|---|---|---|---|---|
| FUR 7-36 | 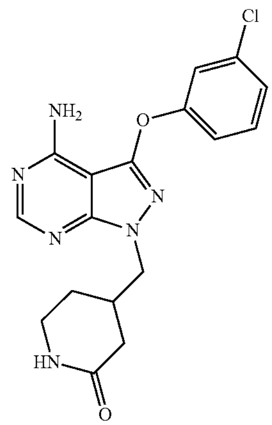 [SMILES: Nc1ncnc2c1c(Oc1cccc(Cl)c1)nn2CC1CCNC(=O)C1] | 373.11 (373.23) | 1H NMR (400 MHz, DMSO-d6) δ 8.13 (s, 1H), 7.45 (t, J = 2.2 Hz, 1H), 7.41-7.34 (m, 2H), 7.31 (dd, J = 8.2, 2.3 Hz, 1H), 7.22-7.17 (m, 1H), 4.05 (d, J = 7.0 Hz, 2H), 3.09 (ddt, J = 12.3, 6.2, 3.6 Hz, 1H), 2.98 (td, J = 11.4, 4.5 Hz, 1H), 2.32-2.18 (m, 1H), 2.01 (ddd, J = 17.3, 5.4, 1.5 Hz, 1H), 1.86 (dd, J = 17.3, 10.5 Hz, 1H), 1.58 (dd, J = 13.4, 3.8 Hz, 1H), 1.29 (d, J = 9.6 Hz, 1H). | E |
| FUR 7-89 | 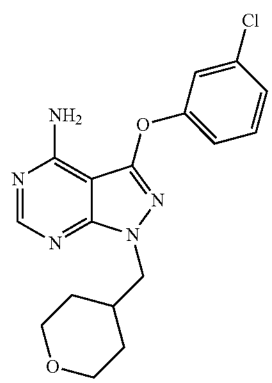 [SMILES: Nc1ncnc2c1c(Oc1cccc(Cl)c1)nn2CC1CCOCC1] | 360.11 (360.92) | 1H NMR (400 MHz, DMSO-d6) δ 8.12 (s, 1H), 7.50-7.26 (m, 3H), 7.19 (dt, J = 8.0, 1.4 Hz, 1H), 4.00 (d, J = 7.1 Hz, 2H), 3.73 (ddd, J = 11.5, 4.5, 1.9 Hz, 2H), 3.15 (td, J = 11.7, 2.1 Hz, 2H), 2.00 (ddq, J = 11.3, 7.8, 3.9 Hz, 1H), 1.32 (dd, J = 13.8, 3.3 Hz, 2H), 1.16 (qd, J = 12.0, 4.4 Hz, 2H). | E |
| FUR 7-77 | 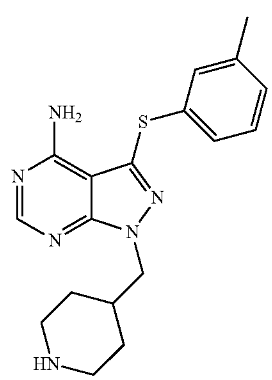 [SMILES: Cc1cccc(Sc2nn(CC3CCNCC3)c3ncnc(N)c23)c1] | 355.16 (355.91) | 1H NMR (400 MHz, DMSO-d6) δ 8.17 (s, 1H), 7.14 (t, J = 7.6 Hz, 1H), 7.09-6.89 (m, 2H), 4.21 (d, J = 6.6 Hz, 1H), 3.14 (s, 2H), 2.72 (d, J = 12.8 Hz, 2H), 2.16 (s, 3H), 1.54 (d, J = 12.7 Hz, 2H), 1.37-1.21 (m, 3H). | C, E |

-continued

| Compound ID | Structure | LC-MS ES+ (observed) | ¹H NMR | Synthesis Process |
|---|---|---|---|---|
| FUR 5-56 | 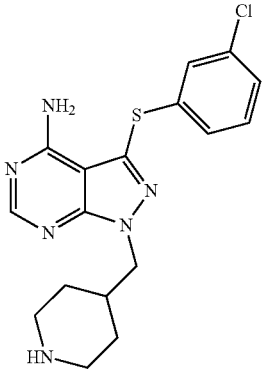 | 375.11 (375.56) | 1H NMR (400 MHz, DMSO-d6) δ 8.57 (d, J = 11.3 Hz, 1H), 8.26 (s, 1H), 7.32-7.22 (m, 3H), 7.13 (dt, J = 7.6, 1.7 Hz, 1H), 4.26 (d, J = 7.0 Hz, 2H), 3.19 (d, J = 12.4 Hz, 2H), 2.87-2.71 (m, 2H), 2.18 (ddp, J = 11.0, 7.2, 3.6 Hz, 1H), 1.64-1.54 (m, 2H), 1.33 (qd, J = 12.5, 4.0 Hz, 2H) | C, E |
| FUR 7-76 | 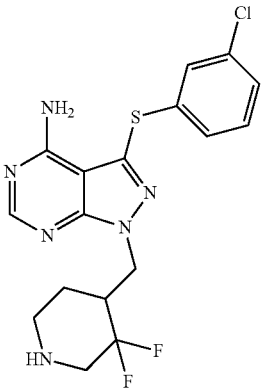 | 411.09 (411.88) | 1H NMR (400 MHz, DMSO-d6) δ 8.19 (s, 1H), 8.09 (s, 1H), 7.33-7.18 (m, 3H), 7.10 (dt, J = 7.6, 1.6 Hz, 1H), 4.61 (dd, J = 14.0, 5.3 Hz, 1H), 4.28 (dd, J = 14.0, 8.9 Hz, 1H), 2.96 (td, J = 12.6, 4.6 Hz, 1H), 2.83-2.51 (m, 3H), 1.30 (td, J = 10.7, 9.8, 3.8 Hz, 2H). | C, E |
| FUR 7-2 | 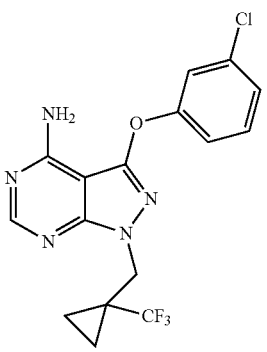 | 384.08 (383.76) | 1H NMR (400 MHz, DMSO-d6) δ 8.15 (s, 1H), 7.46 (t, J = 2.2 Hz, 1H), 7.39 (t, J = 8.1 Hz, 1H), 7.31 (dd, J = 8.2, 2.3 Hz, 1H), 7.23-7.16 (m, 1H), 4.38 (s, 2H), 1.05 (d, J = 5.3 Hz, 2H), 0.96 (t, J = 3.5 Hz, 2H). | E |
| CZ43 | 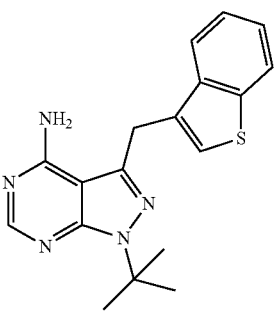 | 338.14 (338.29) | 1H NMR (400 MHz, DMSO-d6) δ 8.11 (s, 1H), 8.05-8.00 (m, 1H), 7.98-7.92 (m, 1H), 7.42 (d, J = 1.1 Hz, 1H), 7.37 (tt, J = 7.2, 5.5 Hz, 2H), 4.55 (d, J = 1.2 Hz, 2H), 1.70 (s, 9H). | Synthesized according to Lourido Shokat and Sibley J Med Chem. 2013 Apr 11;56(7):3068-77 |

| Compound ID | Structure | LC-MS ES+ (observed) | ¹H NMR | Synthesis Process |
|---|---|---|---|---|
| LJQ-145 | 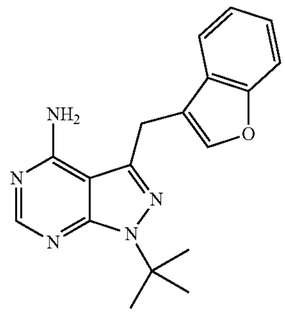 [SMILES: CC(C)(C)n1nc(Cc2coc3ccccc23)c2c(N)ncnc21] | 321.16 (321.36) | 1H NMR (400 MHz, DMSO-d6) δ 8.10 (s, 1H), 7.91 (d, J = 1.1 Hz, 1H), 7.61 (ddd, J = 7.7, 1.4, 0.7 Hz, 1H), 7.52 (dt, J = 8.2, 0.9 Hz, 1H), 7.27 (ddd, J = 8.4, 7.2, 1.4 Hz, 1H), 7.19 (td, J = 7.5, 1.0 Hz, 1H), 4.39 (d, J = 1.2 Hz, 2H), 1.70 (s, 9H). | Synthesized according to Lourido Shokat and Sibley J Med Chem. 2013 Apr 11;56(7):3068-77 |
| LJQ-138 | 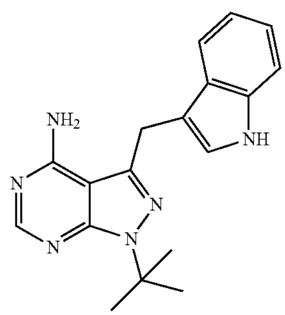 [SMILES: CC(C)(C)n1nc(Cc2c[nH]c3ccccc23)c2c(N)ncnc21] | 321.17 (322.38) | 1H NMR (400 MHz, DMSO-d6) δ 10.85 (s, 1H), 8.07 (s, 1H), 7.53 (d, J = 8.0 Hz, 1H), 7.35-7.27 (m, 2H), 7.03 (ddd, J = 8.1, 6.9, 1.2 Hz, 1H), 6.95-6.86 (m, 1H), 4.36 (s, 2H), 1.72 (s, 6H). | Synthesized according to Lourido Shokat and Sibley J Med Chem. 2013 Apr 11;56(7):3068-77 |
| WXT-2 | 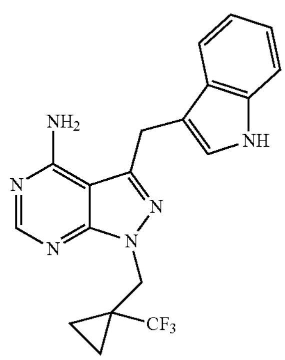 [SMILES: Nc1ncnc2c1c(Cc1c[nH]c3ccccc13)nn2CC1(C(F)(F)F)CC1] | 387.15 (387.10) | 1H NMR (CDCl3) δ 8.29 (1H), 7.55-7.53 (1H), 7.42-7.40 (1H), 7.25-7.23 (1H), 7.14-7.11 (1H), 6.97-6.96 (1H), 4.68 (2H), 4.42 (2H), 1.11-1.08 (4H) | D, E |
| FUR 6-95 | 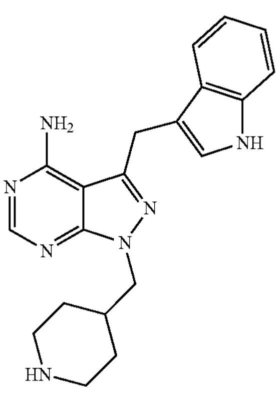 | 362.20 (362.64) | | D, E |

-continued

| Compound ID | Structure | LC-MS ES+ (observed) | ¹H NMR | Synthesis Process |
|---|---|---|---|---|
| FUR 5-57 | 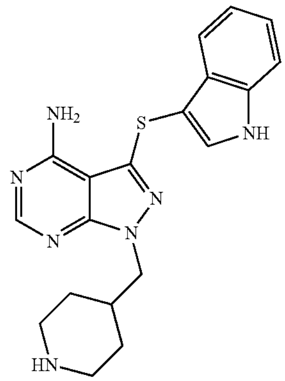 [SMILES: Nc1ncnc2c1c(Sc1c[nH]c3ccccc13)nn2CC1CCNCC1] | 380.16 (380.48) | 1H NMR (400 MHz, DMSO-d6) δ 11.58 (s, 1H), 8.36 (s, 1H), 8.07 (s, 1H), 7.83 (d, J = 1.4 Hz, 1H), 7.49 (d, J = 7.9 Hz, 1H), 7.34 (d, J = 8.1 Hz, 1H), 7.05 (ddd, J = 8.1, 6.9, 1.2 Hz, 1H), 6.94 (td, J = 7.5, 7.0, 0.9 Hz, 1H), 4.07 (d, 2H), 3.01 (d, J = 12.3 Hz, 2H), 2.65-2.49 (m, 2H), 2.00 (dtd, J = 11.1, 7.4, 3.7 Hz, 1H), 1.39 (d, J = 13.3 Hz, 2H), 1.20 (tt, J = 13.2, 7.0 Hz, 2H). | C, E |
| FUR 6-159 | 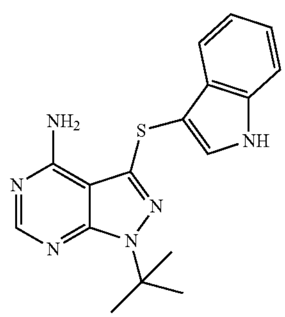 [SMILES: CC(C)(C)n1nc(Sc2c[nH]c3ccccc23)c2c(N)ncnc21] | 339.13 (339.53) | 1H NMR (400 MHz, DMSO-d6) δ 11.42 (s, 1H), 8.04 (s, 1H), 7.79 (d, J = 2.6 Hz, 1H), 7.60 (d, J = 7.9 Hz, 1H), 7.37-7.29 (m, 1H), 7.04 (ddd, J = 8.2, 7.1, 1.3 Hz, 1H), 6.96 (ddd, J = 8.0, 7.0, 1.0 Hz, 1H), 1.60 (s, 9H). | C |

Example B: Expression and Purification of Active Kinases

Full length CDPK1 was PCR amplified from a *T. gondii* RH cDNA library generated using the SMART cDNA synthesis kit (Clontech). The primers contained restriction sites that were used to directionally clone the PCR product, NdeI to XhoI, into the pET-22b(+) vector, in frame with a C-terminal hexahistidine tag. Single mutation of the codon corresponding to glycine 128 was achieved using the QuikChange II Site-Directed Mutagenesis Kit (Agilent Technologies), with specific primers designed according to manufacturer instructions. Plasmids were transformed into BL21(DE3)V2RpAcYc-LIC+LamP *E. coli*, which express the LamP phosphatase, as described previously. Following overnight growth in Terrific Broth at 37° C., cells were diluted 1:50 in fresh medium and cultured for 3 h at 37° C., then cooled to 15° C., induced by addition of 1 mM IPTG, and cultured overnight. Cells were lysed in CelLyticB solution (Sigma Aldrich), and proteins purified using HIS-select Nickel Affinity Gel following manufacturers instructions (Sigma-Aldrich). Purified proteins were dialyzed (50 mM Tris-HCl, pH 7.5, 150 mM NaCl, 0.125% Chelex 100) and stored in 20% glycerol at −80° C. Protein purity and concentration were determined by SDS-PAGE followed by staining with SYPRO Ruby (Invitrogen).

Kinase assays were conducted using a peptide-based ELISA based on the syntide-2 peptide (Calbiochem). Syntide-2 peptide (10 mg/ml) was used to coat 96-well plates by overnight incubation in carbonate coating buffer (pH 9.6) at 4° C. Following washing in Tris tween (50 mM Tris-HCl, pH 7.5, 0.2% Tween20), plates were blocked with 3% BSA in Tris-tween for 2 h at room temperature, and further washing steps were conducted with Tris-tween. Kinase reactions were conducted at 30° C. for 20 min in kinase buffer (20 mM HEPES, pH 7.5, 10 mM MgCl2, 1 mM DTT, 2.5 mM CaCl2, 0.1 mM EGTA, 0.005% Tween20) containing appropriate amounts of ATP (Km for each enzyme) and enzyme dilutions (see below). Phosphorylated syntide peptides were detected with mAb MS-6E6 (MBL Intl. Corp.), followed by peroxidase-conjugated goat-anti-mouse IgG, developed with the substrate 3,3',5,5'-Tetramethylbenzidine (TMB) and detected by absorbance at 450 nm. The activity of human calmodulin dependent kinase II alpha (aCaMKII) was tested using the CaM Kinase II Assay CycLex kit (MBL Intl. Corp.).

For testing CDPK1, purified enzymes were tested with increasing amounts of purified enzyme added to establish their half-maximal activity from a dose-response curve. The Km for ATP was determined for each enzyme tested at its half-maximum and by serial dilution of ATP. The sensitivity of CDPK1 forms were tested at their individual half-maximal activities and Km values for ATP. Samples were conducted in triplicate for all assays. For screening different compounds, serial dilutions of compounds were under the optimized conditions for CDPK1. Data were analyzed using Prism (GraphPad) to determine $IC_{50}$ values by plotting normalized, log-transformed data (X axis), using non-linear regression analysis as a sigmoidal dose response curve with variable slope.

CDPKs are a plant-like family of kinases that is not found in humans, but found in a variety of apicomplexan parasites. CDPK1 is one member of the kinase family and it is an essential gene in *T. gondii*. CDPK1 is a target of inhibitors of the compounds as described herein because it has a glycine gatekeeper. Other CDPKs may also show sensitivity to some of these inhibitors and thus may be targets for treatment of parasitic infection. For example, *T. gondii* (TgCDPK1), *N. caninum* Liverpool (NcCDPK1), *C. parvum* Iowa II (CpCDPK1), all have glycine gatekeepers. Additional CDPK targets include *P. falciparum* (PJCDPK4) and *Toxo. gondi* mutant G128S (TgG128SCDPK1), both of which have serine gatekeeper residues. Targets with Threonine gatekeepers include *P. falciparum* 3d7 (PJCDPK1), *B. bovis* T2Bo (BbCDPK4), *E. tanella* (EtCDPK1), and *Toxo. gondi* mutant G128S (TgG128TCDPK1).

For example, CDPK1 in *Cryptosporidium parvum*, *Cryptosporidium hominis*, *Neospora caninum*, and *Sarcocystis neurona*, share features of the ATP binding pocket with CDPK1 in *Toxoplasma gondii* and thus are likely to be inhibited by the compounds described here. Other CDPKs that are important in parasite biology and which may also be susceptible include: CPKD1 in *Plasmodium falciparum*, this enzyme is important in red cell invasion by merozpotes as well as development of ookinetes on the mosquito. CDPK6 in *Toxoplasma gondii*, this enzyme is important in cell division. CPKD2 in *Toxoplasma gondii*, this enzyme is important in carbohydrate metabolism in bradyzoites.

Example C: Inhibition of Parasite Growth In Vitro

Inhibition of parasite growth was determined using the 2F clone of the type I RH strain that expresses the *E. coli* P3-galactoside enzyme (13-Gal), as described previously. Compounds were dissolved in DMSO at 10 mM stock and diluted in medium containing 1% DMSO, which also served as a no compound control. Freshly harvested parasites were mixed with compounds and preincubated for 20 min at room temperature before being used to challenge confluent monolayers of human foreskin fibroblasts (HFF) grown in 96-well plates containing DMEM supplemented with 10% FBS. All samples were tested in triplicate. Following addition of $5 \times 10^2$ parasites/well containing dilutions of compounds and/or 1% DMSO, plates were centrifuged at 300 g for 5 min and returned to culture at 37° C., 5% $CO_2$. HFF cultures were challenged with parasites and compound dilutions, washed in warm PBS after 2, 4, 24 and 48 hours, and returned to culture in DMEM supplemented with 10% FBS at 37° C., 5% $CO_2$. To compare the effects of different compounds, HFF cultures were challenged with parasites and compound dilutions, washed in warm PBS after 4 h, and returned to culture in DMEM supplemented with 10% FBS at 37° C., 5% $CO_2$. Replication was stopped at 72 h by addition of 1% Triton X-100 and 3-gal activity was determined following addition of 1 mM chlorophenol red-β-D-galactopyranoside and monitoring of absorbtion at 570 nm, as described previously. Data were analyzed using Prism (GraphPad) to determine $EC_{50}$ values by plotting normalized, log-transformed data (X axis), using non-linear regression analysis as a sigmoidal dose response curve with variable slope.

A conditional knockout strain of CDPK1 (CDPK1-cKO), which expresses CDP1 under control of a tet-off promoter, complemented with either wild type or $G^{128}M$ CDPK1 expressed under its endogenous promoter, is used to assess the specificity of compounds. Parasite strains are grown for 72 h in the presence of 1 µg/ml anhydrotetracycline (ATc; Clontech), and kept in the presence of ATc for the course of the assay. Parasites are harvested and incubated 20 min at 37° C. in DMEM containing 10% FBS and different compound concentrations or vehicle control (1% DMSO). Confluent monolayers of HFF cells in 96-well plates are infected with the pre-treated parasites at a concentration of $10^5$ per well, and sedimented onto the host cells by centrifugation at 300 g for 2 minutes. Infection is allowed to proceed at 37° C., 5% $CO_2$, for 1 hour, prior to rinsing the monolayers 5 times with 37° C. PBS to remove extracellular parasites. DMEM containing 10% FBS and 1 µg/ml ATc is added to all wells, and parasites are allowed to replicate for 72 hours. Host cell lysis is quantified by staining monolayers with crystal violet and measuring the absorbance at 570 nm.

The stability of compounds in vitro was tested in using rat liver microsomes as performed by Absorption Systems Inc (Exton, Pa.). In brief, compounds were mixed with rat liver microsomes activated with 1 mM NADPH and loss of compound was followed at 10, 20, 30 and 60 min. The percentages of remaining compounds were calculated from the peak area ratio vs. standard for each starting compound by LC-MS. The half-life was estimated as $t_{1/2} = 0.693/K$, where K is the slope of a plot of the natural log of percent of remaining compound vs. time. The intrinsic clearance ($Cl_{int}$) was calculated as k/D, where K is defined above and D is the protein concentration in the microsome preparation. Log P was estimated using ChemDraw Ultra.

TABLE 1

Physical parameters and in vitro activities of select compounds.

| Compound | ClogP | tPSA | pKa | Protein binding | Papp $10^{-6}$ cs/s A to B[1] | Papp $10^{-6}$ cs/s B to A[2] | Efflux ratio[3] | Microsomes $CL_{int}$[4] mL/min/mg | Cell toxicity[5] |
|---|---|---|---|---|---|---|---|---|---|
| 3CLB | 3.15 | 66.34 | — | 99.2% | 42.9 | 28.7 | 0.7 | 0.452 | >10 mM |
| GXJ184 | 3.48 | 75.57 | — | 99.8% | 34.8 | 30.6 | 0.9 | 0.281 | >10 mM |
| GXJ176 | 3.41 | 75.57 | — | 98.4% | 15.0 | 14.6 | 1.0 | 1.240 | >10 mM |
| GXJ237 | 2.57 | 87.6 | 10.4 | 73.5% | 1.07 | 9.58 | 8.9 | 0.019 | >10 mM |

TABLE 1-continued

Physical parameters and in vitro activities of select compounds.

| Compound | ClogP | tPSA | pKa | Protein binding | Papp $10^{-6}$ cs/s A to B[1] | Papp $10^{-6}$ cs/s B to A[2] | Efflux ratio[3] | Microsomes $CL_{int}$[4] mL/min/mg | Cell toxicity[5] |
|---|---|---|---|---|---|---|---|---|---|
| FUR7-27 | 3.0 | 87.6 | 7.1 | 88.3% | 22.8 | 21.2 | 0.9 | 0.694 | >10 mM |
| FUR5-56 | 3.25 | 78.37 | 10.4 | 87.5% | 2.76 | 25.6 | 9 | 0.072 | >10 mM |
| FUR7-76 | 3.57 | 78.37 | 7.1 | 91.8% | 27.1 | 25.3 | .9 | 0.887 | >10 mM |

[1]Apparent permeability (Papp), apical to basolateral (A-B).
[2]Apparent permeability (Papp) basolateral to apical (B-A).
[3]Papp (B to A)/Papp (A to B).
[4]$CL_{int}$ = k/P, where k is the elimination rate constant and P is the protein concentration in the assay.
[5]Inhibition of replication of human HFF cells.

TABLE 2

In vivo pharmacokinetic properties of select compounds.

| Cmpd | Route | Dose mg/kg | Tmax hr | Co/Cmax[1] ng/ml | AUC $_{last}$ ng/ml hr | AUC $_{inf}$ ng/ml hr | T1/2 hr | CL[2] ml/min/kg | Vss[3] L/kg | % F[4] |
|---|---|---|---|---|---|---|---|---|---|---|
| 3CLB | iv | 3 | — | 6892.94 | 1075.29 | 1081.76 | 2.06 | 46.22 | 1.09 | — |
|  | po | 10 | 0.25 | 585.42 | 918.80 | 930.88 | — | — | — | 26 |
| GXJ184 | iv | 3 | — | 5471.09 | 1146.49 | 1149.99 | 1.56 | 43.48 | 1.10 | — |
|  | po | 10 | 0.25 | 1136.36 | 1172.75 | 1279.20 | — | — | — | 31 |
| GXJ176 | iv | 3 | — | 2741.80 | 619.33 | 625.04 | 1.74 | 80 | 2.32 | — |
|  | po | 10 | 0.25 | 76.69 | 85.47 | 91.42 | — | — | — | 4 |
| GXJ237 | iv | 3 | — | 535.79 | 449.57 | 523.99 | 3.68 | 95.42 | 19.59 | — |
|  | po | 10 | 2.00 | 182.56 | 757.85 | 891.24 | — | — | — | 51 |
| FUR7-27 | iv | 3 | — | 1205.19 | 975.90 | 988.58 | 1.56 | 50.58 | 3.68 | — |
|  | po | 10 | 0.25 | 1048.80 | 3058.44 | 3547.95 | — | — | — | 94 |

[1] Cmax for po route, Co (initial conc.);
[2]CL, clearance;
[3]Vss steady-state volume of distribution;
[4]Oral availability determined from $AUC_{last}$.

TABLE 3

Compound analogs and activity.

| Cmpd | Structure | TgCDPK1 Inhibition IC$_{50}$ (uM) | Para-site Growth EC$_{50}$ (uM) | Microsome Half-Life (min) | Src % Inhibition | Src IC50 uM | cLogP |
|---|---|---|---|---|---|---|---|
| 3CIB-PP1 | 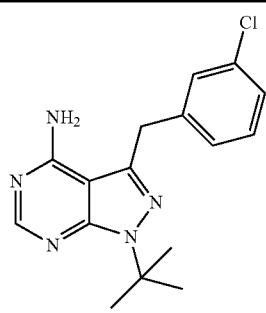 | 0.00338 | 0.167 | 4 | 18.48 | 0.607 | 3.15 |

TABLE 3-continued
Compound analogs and activity.
| Cmpd | Structure | TgCDPK1 Inhibition IC$_{50}$ (uM) | Para-site Growth EC$_{50}$ (uM) | Microsome Half-Life (min) | Src % Inhibition | Src IC50 uM | cLogP |
|---|---|---|---|---|---|---|---|
| FUR6-157 | 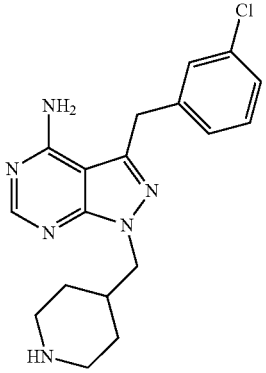 | 0.01453 | 0.799 | >60 | 87.11 | >10 | 2.31 |
| CZ75 | 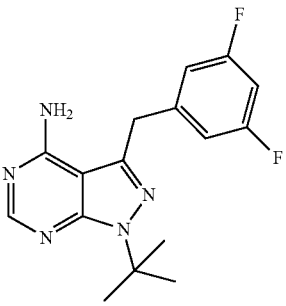 [SMILES: CC(C)(C)n1nc(Cc2cc(F)cc(F)c2)c2c(N)ncnc21] | 0.03186 | 0.613 | 10.6 | 91.31 | >10 | 2.91 |
| MLC468 | 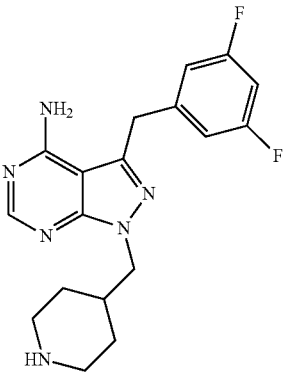 [SMILES: Nc1ncnc2c1c(Cc1cc(F)cc(F)c1)nn2CC1CCNCC1] | 0.17330 | 5.976 | >60 | 94.97 | >10 | 1.88 |
| LZH118 | 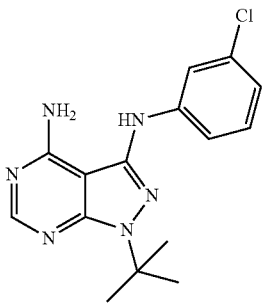 [SMILES: CC(C)(C)n1nc(Nc2cccc(Cl)c2)c2c(N)ncnc21] | 0.01032 | 0.190 | 19.6 | 21.86 | 0.828 | 3.96 |

TABLE 3-continued
Compound analogs and activity.
| Cmpd | Structure | TgCDPK1 Inhibition IC$_{50}$ (uM) | Para-site Growth EC$_{50}$ (uM) | Micro-some Half-Life (min) | Src % Inhibi-tion | Src IC50 uM | cLogP |
|---|---|---|---|---|---|---|---|
| GXJ276 | 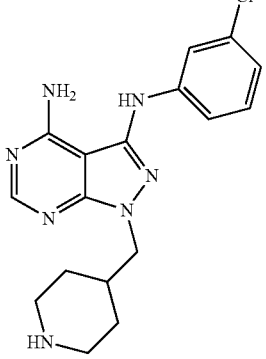 | 0.01639 | 3.476 | 20 | 24.50 | 0.901 | 2.95 |
| GXJ186 | 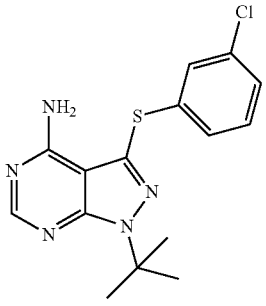 [SMILES: CC(C)(C)n1nc(Sc2cccc(Cl)c2)c2c(N)ncnc21] | 0.01379 | 1.131 | 2.4 | 72.84 | >10 | 4.00 |
| FUR7-68 | 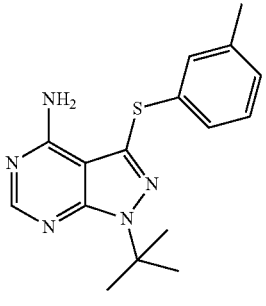 | 0.02290 | 0.376 | 1 | 64.39 | >10 | 3.78 |
| FUR 6-139 | 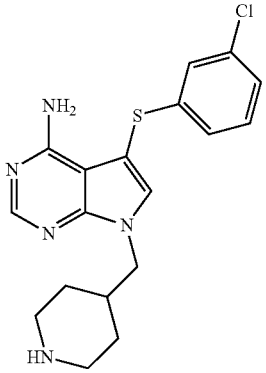 [SMILES: Nc1ncnc2c1c(Sc1cccc(Cl)c1)cn2CC1CCNCC1] | 0.01353 | 0.367 | 9.6 | 97.49 | >10 | 3.82 |

TABLE 3-continued

Compound analogs and activity.

| Cmpd | Structure | TgCDPK1 Inhibition IC$_{50}$ (uM) | Para-site Growth EC$_{50}$ (uM) | Microsome Half-Life (min) | Src % Inhibition | Src IC50 uM | cLogP |
|---|---|---|---|---|---|---|---|
| GXJ184 | (3-chlorophenoxy pyrazolopyrimidine, t-butyl) | 0.00999 | 0.343 | 15.7 | 79.94 | >10 | 3.48 |
| GXJ178 | (3-trifluoromethylphenoxy pyrazolopyrimidine, t-butyl) | 0.03512 | 0.537 | 16.8 | 79.53 | >10 | 3.74 |
| GXJ176 | (3-methylphenoxy pyrazolopyrimidine, t-butyl) | 0.01356 | 0.163 | 4.2 | 84.24 | >10 | 3.36 |
| GXJ177 | (3-bromophenoxy pyrazolopyrimidine, t-butyl) | 0.00749 | 0.246 | 6.2 | 73.35 | >10 | 3.72 |

TABLE 3-continued

Compound analogs and activity.

| Cmpd | Structure | TgCDPK1 Inhibition IC$_{50}$ (uM) | Para-site Growth EC$_{50}$ (uM) | Microsome Half-Life (min) | Src % Inhibition | Src IC50 uM | cLogP |
|---|---|---|---|---|---|---|---|
| GXJ230 | 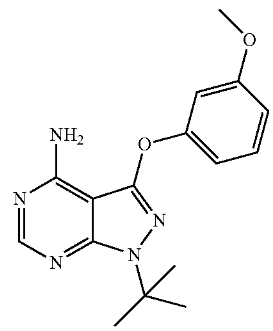 [SMILES: COc1cccc(Oc2nn(C(C)(C)C)c3ncnc(N)c23)c1] | 0.00894 | 0.305 | 2.7 | 77.53 | >10 | 2.78 |
| GXJ229 | 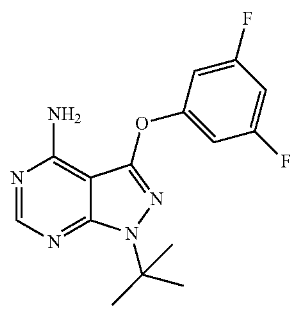 | 0.04698 | 1.897 | 33 | 87.48 | >10 | 3.15 |
| GXJ237 | 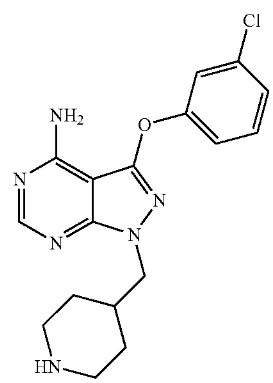 | 0.01415 | 0.437 | >60 | 87.87 | >10 | 2.57 |
| GXJ261 | 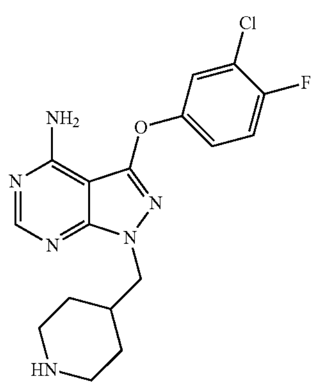 [SMILES: Nc1ncnc2c1c(Oc1ccc(F)c(Cl)c1)nn2CC1CCNCC1] | 0.06754 | 2.979 | >60 | 78.16 | >10 | 2.71 |

TABLE 3-continued

Compound analogs and activity.

| Cmpd | Structure | TgCDPK1 Inhibition IC$_{50}$ (uM) | Para-site Growth EC$_{50}$ (uM) | Microsome Half-Life (min) | Src % Inhibition | Src IC50 uM | cLogP |
|---|---|---|---|---|---|---|---|
| FUR6-6 | 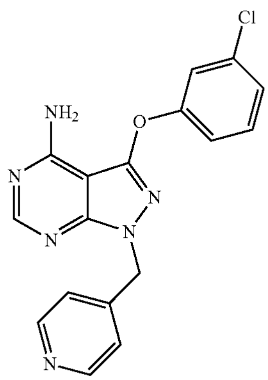 [SMILES: Nc1ncnc2c1c(Oc1cccc(Cl)c1)nn2Cc1ccncc1] | 0.27185 | >10 | 14 | 93.91 | >10 | 2.79 |
| FUR6-11 | 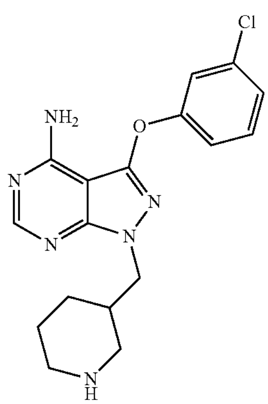 [SMILES: Nc1ncnc2c1c(Oc1cccc(Cl)c1)nn2CC1CCCNC1] | 0.07309 | 1.821 | >60 | 90.05 | >10 | 2.57 |
| FUR6-13 | 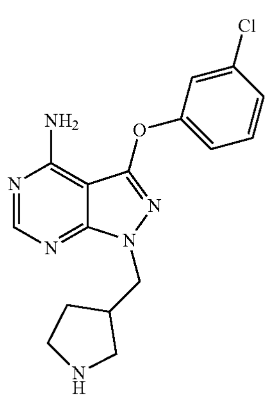 [SMILES: Nc1ncnc2c1c(Oc1cccc(Cl)c1)nn2CC1CCNC1] | 0.11861 | 4.091 | >60 | 99.50 | >10 | 2.01 |

TABLE 3-continued

Compound analogs and activity.

| Cmpd | Structure | TgCDPK1 Inhibition IC$_{50}$ (uM) | Para-site Growth EC$_{50}$ (uM) | Microsome Half-Life (min) | Src % Inhibition | Src IC50 uM | cLogP |
| --- | --- | --- | --- | --- | --- | --- | --- |
| FUR6-12 | 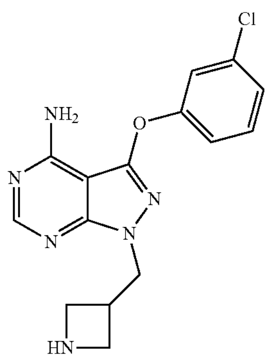 [SMILES: Nc1ncnc2c1c(Oc1cccc(Cl)c1)nn2CC1CNC1] | 0.19055 | >10 | >60 | 91.81 | >10 | 1.45 |
| FUR7-27 | 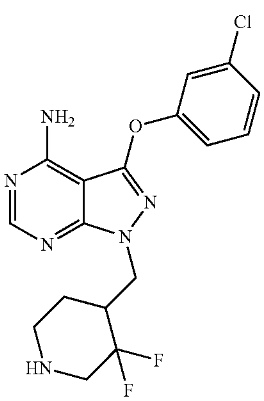 [SMILES: Nc1ncnc2c1c(Oc1cccc(Cl)c1)nn2CC1CCNCC1(F)F] | 0.01094 | 0.272 | 8.8 | 87.87 | >10 | 2.85 |
| FUR7-30 | 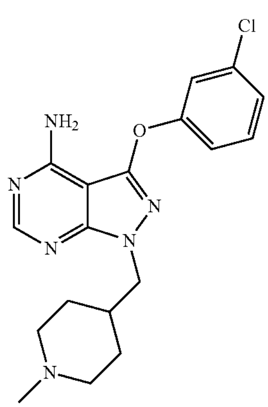 [SMILES: CN1CCC(Cn2nc(Oc3cccc(Cl)c3)c3c(N)ncnc32)CC1] | 0.07749 | 1.803 | >60 | 96.94 | >10 | 3.01 |

TABLE 3-continued

Compound analogs and activity.

| Cmpd | Structure | TgCDPK1 Inhibition IC$_{50}$ (uM) | Para-site Growth EC$_{50}$ (uM) | Micro-some Half-Life (min) | Src % Inhibi-tion | Src IC50 uM | cLogP |
|---|---|---|---|---|---|---|---|
| FUR7-36 | 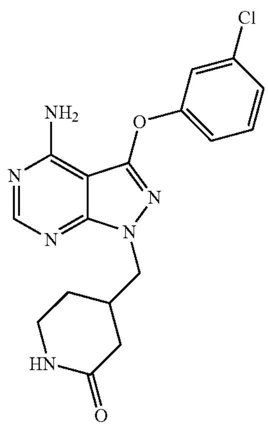 [SMILES: Nc1ncnc2c1c(Oc1cccc(Cl)c1)nn2CC1CCNC(=O)C1] | 0.09534 | >10 | >60 | 96.13 | >10 | 1.22 |
| FUR7-89 | 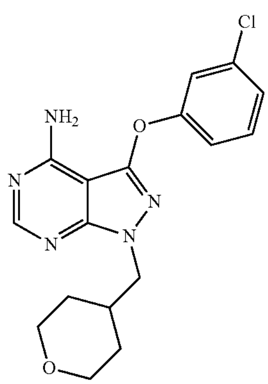 [SMILES: Nc1ncnc2c1c(Oc1cccc(Cl)c1)nn2CC1CCOCC1] | 0.21845 | 2.653 | 14 | 77.33 | >10 | 2.59 |
| FUR7-77 | 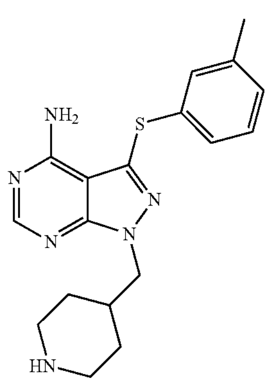 [SMILES: Cc1cccc(Sc2nn(CC3CCNCC3)c3ncnc(N)c23)c1] | 0.51670 | 0.729 | 26 | 80.21 | >10 | 2.78 |

TABLE 3-continued

Compound analogs and activity.

| Cmpd | Structure | TgCDPK1 Inhibition IC$_{50}$ (uM) | Para-site Growth EC$_{50}$ (uM) | Microsome Half-Life (min) | Src % Inhibition | Src IC50 uM | cLogP |
|---|---|---|---|---|---|---|---|
| FUR 5-56 | 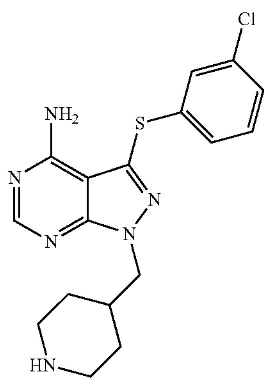 [SMILES: Nc1ncnc2c1c(Sc1cccc(Cl)c1)nn2CC1CCNCC1] | 0.01920 | 0.242 | 11 | 102.82 | >10 | 3.00 |
| FUR 7-76 | 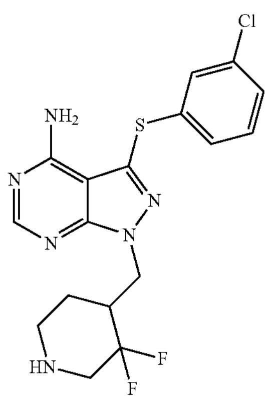 | 0.04700 | 1.517 | 2.5 | 76.47 | >10 | 3.28 |
| FUR7-2 | 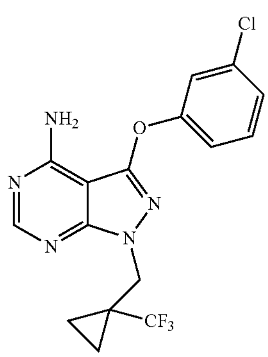 [SMILES: Nc1ncnc2c1c(Oc1cccc(Cl)c1)nn2CC1(C(F)(F)F)CC1] | 0.01022 | 1.004 | 11 | 91.63 | >10 | 3.45 |
| CZ43 | 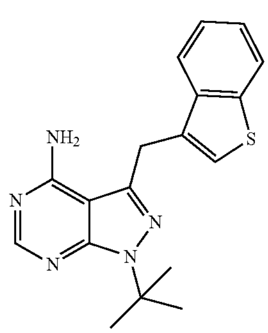 | 0.00745 | 0.135 | 2.5 | 28.21 | 0.014 | 3.86 |

TABLE 3-continued

Compound analogs and activity.

| Cmpd | Structure | TgCDPK1 Inhibition IC$_{50}$ (uM) | Para-site Growth EC$_{50}$ (uM) | Microsome Half-Life (min) | Src % Inhibition | Src IC50 uM | cLogP |
|---|---|---|---|---|---|---|---|
| LJQ-145 | 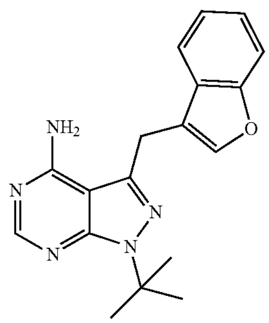 [SMILES: CC(C)(C)n1nc(Cc2coc3ccccc23)c2c(N)ncnc21] | 0.02372 | 2.027 | 1.7 | 36.04 | 1.57 | 3.16 |
| LJQ-138 | 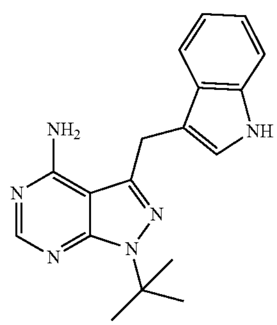 [SMILES: CC(C)(C)n1nc(Cc2c[nH]c3ccccc23)c2c(N)ncnc21] | 0.01234 | 0.177 | 2.0 | 74.94 | >10 | 2.59 |
| WXT-2 | 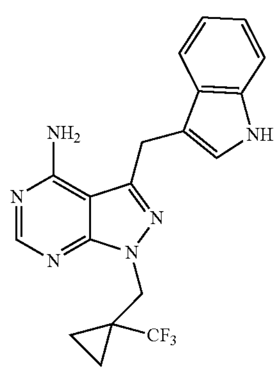 [SMILES: Nc1ncnc2c1c(Cc1c[nH]c3ccccc13)nn2CC1(C(F)(F)F)CC1] | 0.03811 | 0.206 | 4.7 | 96.00 | >10 | 2.47 |
| FUR6-95 | 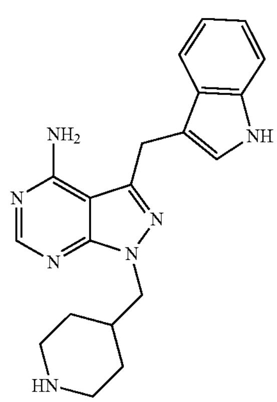 | 0.023875 | >10 | >60 | 92.70 | >10 | 1.58 |

TABLE 3-continued
Compound analogs and activity.
| Cmpd | Structure | TgCDPK1 Inhibition IC$_{50}$ (uM) | Para-site Growth EC$_{50}$ (uM) | Microsome Half-Life (min) | Src % Inhibition | Src IC50 uM | cLogP |
|---|---|---|---|---|---|---|---|
| FUR 5-57 | 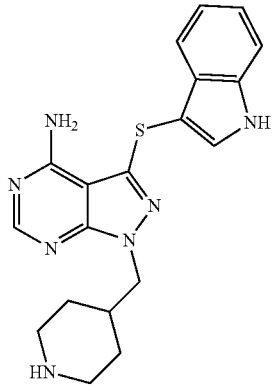 [SMILES: Nc1ncnc2c1c(Cc1c[nH]c3ccccc13)nn2CC1CCNCC1] | 0.32485 | >10 | 12 | 96.99 | >10 | 2.27 |
| FUR6-159 | 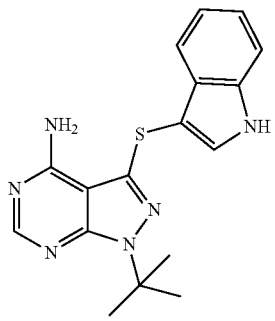 [SMILES: CC(C)(C)n1nc(Sc2c[nH]c3ccccc23)c2c(N)ncnc21] | 0.202200 | >10 | 2.6 | 97.66 | >10 | 3.27 |
TABLE 4
Compound analogs and cLogP characterization.
| Cmpd ID | Structure | cLogP LC/MS (obs) | Cmpd ID | Structure | cLogP LC/MS (obs) |
|---|---|---|---|---|---|
| FUR 6-161 | 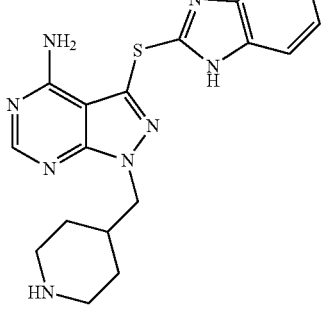 | 2.16 381.15 (381.59) | FUR-6-142 | 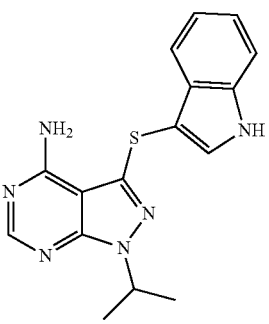 [SMILES: CC(C)n1nc(Sc2c[nH]c3ccccc23)c2c(N)ncnc21] | 2.87 325.12 (325.20) |

TABLE 4-continued

Compound analogs and cLogP characterization.

| Cmpd ID | Structure | cLogP LC/MS (obs) | Cmpd ID | Structure | cLogP LC/MS (obs) |
|---|---|---|---|---|---|
| FUR 6-160 | 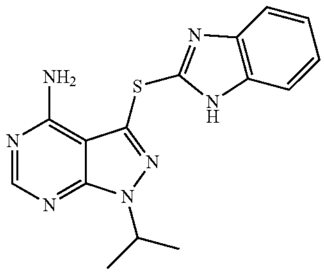 [SMILES: CC(C)n1nc(Sc2nc3ccccc3[nH]2)c2c(N)ncnc21] | 2.77 326.10 (326.51) | FUR 6-140 | 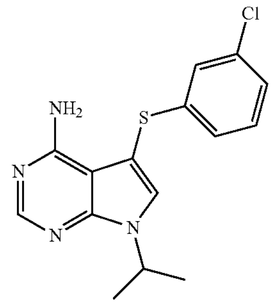 [SMILES: CC(C)n1cc(Sc2cccc(Cl)c2)c2c(N)ncnc21] | 4.42 319.07 (319.40) |
| FUR 6-162 | 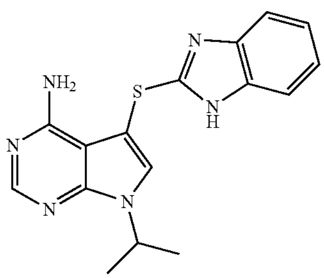 [SMILES: CC(C)n1cc(Sc2nc3ccccc3[nH]2)c2c(N)ncnc21] | 3.59 325.11 (325.51) | FUR 6-140B | 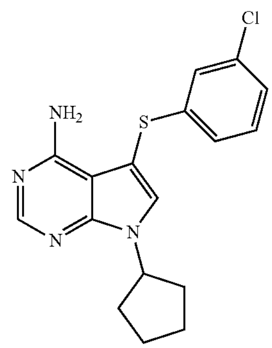 [SMILES: Nc1ncnc2c1c(Sc1cccc(Cl)c1)cn2C1CCCC1] | 5.06 345.09 (345.43) |
| FUR 6-145 | 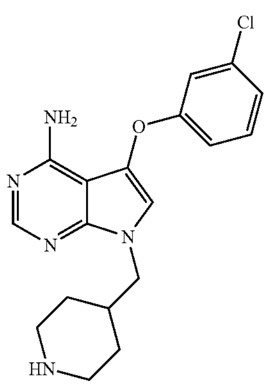 [SMILES: Nc1ncnc2c1c(Oc1cccc(Cl)c1)cn2CC1CCNCC1] | 3.39 358.14 (358.60) | FUR 6-141 | 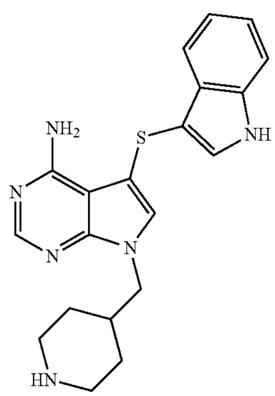 [SMILES: Nc1ncnc2c1c(Sc1c[nH]c3ccccc13)cn2CC1CCNCC1] | 3.09 379.16 (379.54) |
| FUR 6-142B | 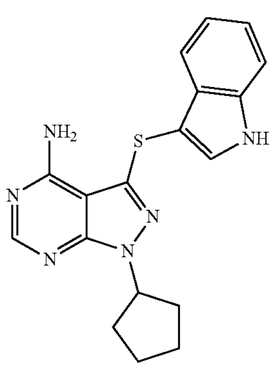 [SMILES: Nc1ncnc2c1c(Sc1c[nH]c3ccccc13)nn2C1CCCC1] | 3.51 351.13 (350.99) | FUR 6-124 | 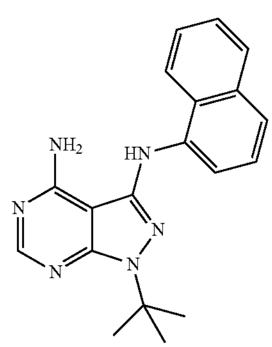 [SMILES: CC(C)(C)n1nc(Nc2cccc3ccccc23)c2c(N)ncnc21] | 4.42 333.17 (333.00) |

TABLE 4-continued

Compound analogs and cLogP characterization.

| Cmpd ID | Structure | cLogP LC/MS (obs) | Cmpd ID | Structure | cLogP LC/MS (obs) |
|---|---|---|---|---|---|
| FUR 6-123 | 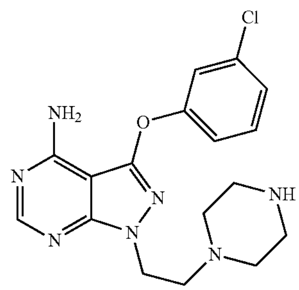 [SMILES: Nc1ncnc2c1c(Oc1cccc(Cl)c1)nn2CCN1CCNCC1] | 1.99 374.14 (374.68) | FUR 6-99 | 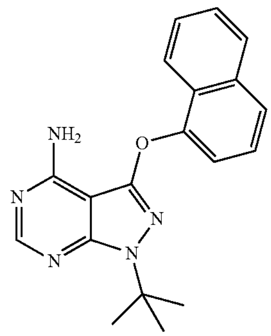 [SMILES: CC(C)(C)n1nc(Oc2cccc3ccccc23)c2c(N)ncnc21] | 4.04 334.16 (334.56) |
| FUR 6-15 | 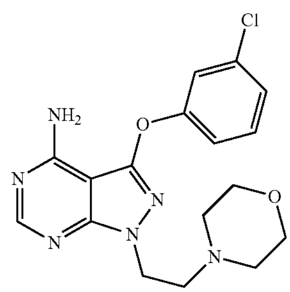 [SMILES: Nc1ncnc2c1c(Oc1cccc(Cl)c1)nn2CCN1CCOCC1] | 2.39 375.13 (375.56) | FUR 6-100 | 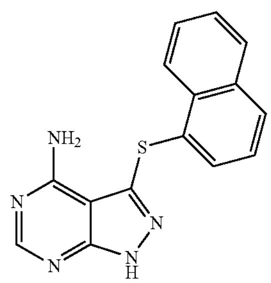 [SMILES: Nc1ncnc2[nH]nc(Sc3cccc4ccccc34)c12] | 3.57 294.07 (294.58) |
| FUR 6-106 | 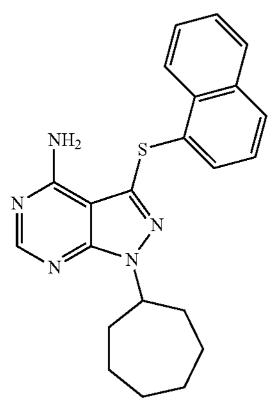 [SMILES: Nc1ncnc2c1c(Sc1cccc3ccccc13)nn2C1CCCCCC1] | 5.81 390.17 (390.47) | FUR 6-102 | 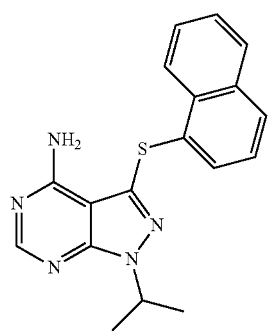 [SMILES: CC(C)n1nc(Sc2cccc3ccccc23)c2c(N)ncnc21] | 4.06 336.12 (336.36) |
| FUR 6-107 | 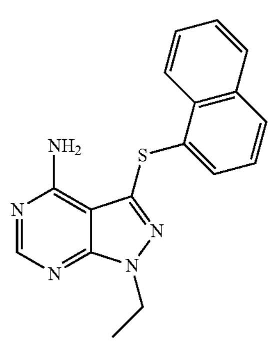 [SMILES: CCn1nc(Sc2cccc3ccccc23)c2c(N)ncnc21] | 3.75 322.10 (322.62) | FUR 6-104 | 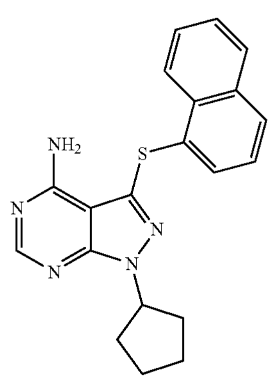 [SMILES: Nc1ncnc2c1c(Sc1cccc3ccccc13)nn2C1CCCC1] | 4.69 362.14 (362.50) |

TABLE 4-continued

Compound analogs and cLogP characterization.

| Cmpd ID | Structure | cLogP LC/MS (obs) | Cmpd ID | Structure | cLogP LC/MS (obs) |
|---|---|---|---|---|---|
| FUR 6-111 | 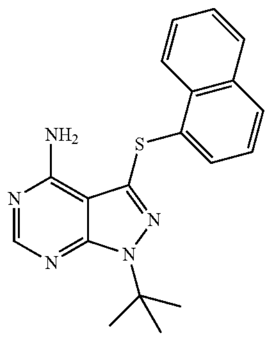 [SMILES: CC(C)(C)n1nc(Sc2cccc3ccccc23)c2c(N)ncnc21] | 4.46 350.14 (350.65) | FUR 6-105 | 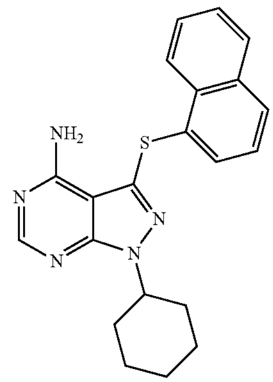 [SMILES: Nc1ncnc2c1c(Sc1cccc3ccccc13)nn2C1CCCCC1] | 5.25 376.15 (376.58) |
| FUR 6-103 | 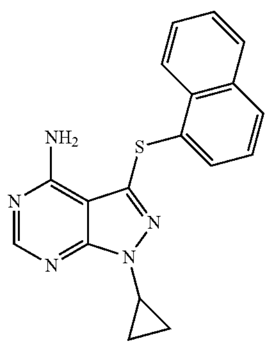 [SMILES: Nc1ncnc2c1c(Sc1cccc3ccccc13)nn2C1CC1] | 3.80 334.10 (334.41) | FUR 6-133 | 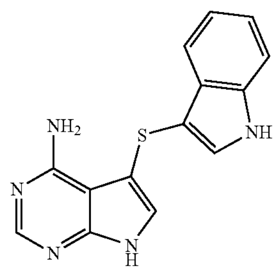 [SMILES: Nc1ncnc2[nH]cc(Sc3c[nH]c4ccccc34)c12] | 2.91 282.07 (282.40) |
| FUR 6-132 | 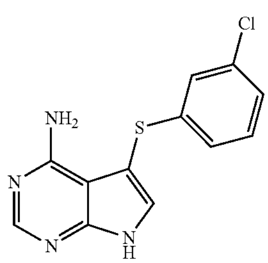 [SMILES: Nc1ncnc2[nH]cc(Sc3cccc(Cl)c3)c12] | 3.64 277.02 (277.40) | FUR 6-144 | 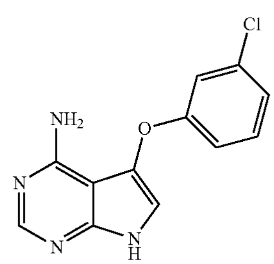 | 3.21 261.05 (261.39) |
| FUR 6-146 | 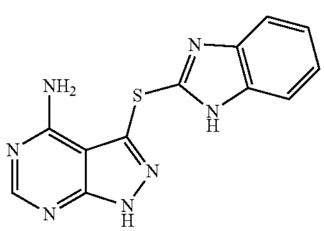 | 2.36 284.06 (284.35) | FUR 6-147 | 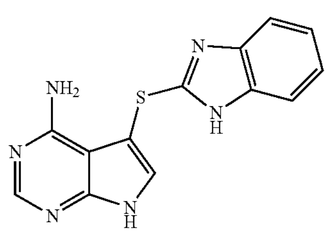 [SMILES: Nc1ncnc2[nH]cc(Sc3nc4ccccc4[nH]3)c12] | 2.80 283.07 (282.93) |
| FUR 6-162B | 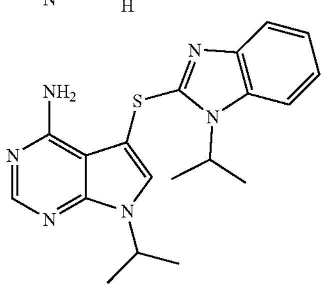 | 4.45 367.16 (367.69) | HYC29 | 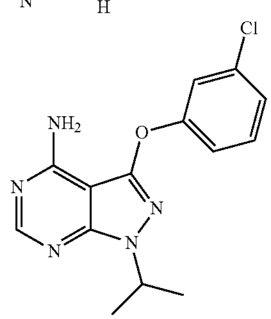 | 3.18 |

Example D: Murine Infection Model of Toxoplasmosis

To assess the ability of compounds to protect against lethal infection in vivo, a murine model is used and challenged with lethal doses of a type II strain of *T. gondii*, similar to previously described protocols. Balb/C female mice at 8 to 10 weeks of age are injected i.p. with $10^4$ PRU-Luc-GFP parasites per animal. Compounds are reconstituted in dimethyl sulfoxide (DMSO) and diluted in PBS prior to injection into mice. Mice are treated beginning on the day of infection and continuing for ten days with daily i.p. injections of the specified compound at 1-5 mg/kg containing 5% DMSO, or DMSO control. Survival is monitored for 30 days following infection. After 30 days, animals are sacrificed, brains removed and homogenized, and tissue cysts are enumerated by microscopic examination after staining with fluorescently labeled lectin (*Dolichos biflorus*) as described previously. Animals are maintained in an AAALAC-approved facility overseen by the Institutional Animal Care Committee at Washington University.

Additionally, apicomplexans contain from 6-11 related CDPKs, depending on the species (Cell Host Microbe 2009 Jun. 18; 5(6):612-22), which is incorporated herein by reference in its entirety. *Toxoplasma gondii* contains 14 CDPKs (Infect Immun. 2016 Apr. 22; 84(5): 1262-73. doi: 10.1128/IAI.01173-15). In addition to TgCDPK1, which controls invasion and egress, TgCDPK2 and TgCPDK6 have also been shown to play essential roles in bradyzoite development and cell division, respectively. Although these enzymes differ slightly from TgCDPK1 in the ATP binding pocket, which is targeted by the inhibitors described herein, some of these compounds may also serve as potent inhibitors of these other CDPKs. *Plasmodium* also contains a number of CDPKs, including an enzyme called CDPK1 (although it is not a direct ortholog of TgCDPK1, it is a member of this kinase family), which is important in infection of red blood cells, as well as development of ookinetes in the mosquito during development. Additional roles for CDPKs in parasites may be defined by future studies and some of these enzymes may also be inhibited by the compounds described herein.

What is claimed is:
1. A compound having the formula:

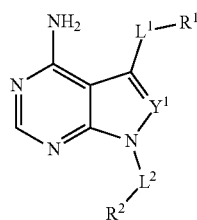

(I)

wherein,
 $Y^1$ is N= or CH=;
 $R^1$ is substituted or unsubstituted aryl or substituted or unsubstituted heteroaryl;
 $R^2$ is substituted or unsubstituted heterocycloalkyl or substituted or unsubstituted single ring heteroaryl;
 $L^1$ is —O—, —S—, or —N($R^3$)—;
 $L^2$ is a substituted or unsubstituted alkylene, or substituted or unsubstituted heteroalkylene;
 $R^3$ is hydrogen, —CN, —COOH, —$CX^3_3$, substituted or unsubstituted alkyl, or substituted or unsubstituted heteroalkyl; and
 $X^3$ is independently halogen.

2. The compound of claim 1, wherein $R^1$ is substituted or unsubstituted $C_6$-$C_{10}$ aryl or substituted or unsubstituted 5 to 10 membered heteroaryl.

3. The compound of claim 1, wherein $R^2$ is substituted or unsubstituted 3 to 7 membered heterocycloalkyl or substituted or unsubstituted 5 to 10 membered single ring heteroaryl.

4. The compound of claim 1, wherein $L^2$ is a substituted or unsubstituted $C_1$-$C_5$ alkylene, or substituted or unsubstituted 2 to 5 membered heteroalkylene.

5. The compound of claim 1, wherein $L^2$ is a —$CH_2$—, —$CH_2CH_2$—, —$CH_2O$—, —$CH_2S$—, or —$CH_2NH$—.

6. The compound of claim 1, wherein $R^3$ is hydrogen, —CN, —COOH, —$CX^3_3$, substituted or unsubstituted $C_1$-$C_4$ alkyl, or substituted or unsubstituted 2 to 4 membered heteroalkyl.

7. The compound of claim 1, having the formula:

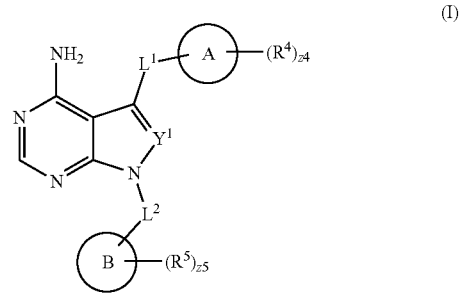

(I)

wherein,
 Ring A is $C_6$-$C_{10}$ aryl or 5 to 10 membered heteroaryl;
 Ring B is 3 to 7 membered heterocycloalkyl or 5 to 10 membered single ring heteroaryl;
 $R^4$ is halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —NHC(O)$NR^{4A}R^{4B}$, —N(O)$_{m4}$, —$NR^{4A}R^{4B}$, —C(O)$R^{4C}$, —C(O)—$OR^{4C}$, —C(O)$NR^{4A}R^{4B}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
 $R^5$ is halogen, —$CX^5_3$, —$CHX^5_2$, —$CH_2X^5$, —$OCX^5_3$, —$OCH_2X^5$, —$OCHX^5_2$, —CN, —$SO_{n5}R^{5D}$, —$SO_{v5}NR^{5A}R^{5B}$, —NHC(O)$NR^{5A}R^{5B}$, —N(O)$_{m5}$, —$NR^{5A}R^{5B}$, —C(O)$R^{5C}$, —C(O)—$OR^{5C}$, —C(O)$NR^{5A}R^{5B}$, —$OR^{5D}$, —$NR^{5A}SO_2R^{5D}$, —$NR^{5A}C(O)R^{5C}$, —$NR^{5A}C(O)OR^{5C}$, —$NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
 each $R^{4A}$, $R^{4B}$, $R^{4C}$, $R^{4D}$, $R^{5A}$, $R^{5B}$, $R^{5C}$, and $R^{5D}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl;

each X, $X^4$, and $X^5$ is independently —F, —Cl, —Br, or —I;

n4 and n5 are independently an integer from 0 to 4;

m4, m5, v4, and v5 are independently an integer from 1 to 2;

z4 is an integer from 0 to 9; and z5 is an integer from 0 to 6.

8. The compound of claim 1, having the formula:

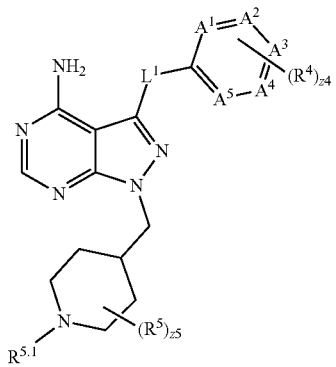

wherein, $A^1$, $A^2$, $A^3$, $A^4$, and $A^5$, are each independently —C($R^4$)= or —N=;

$R^4$ is independently substituted or unsubstituted alkyl, substituted or unsubstituted cycloalkyl, halogen, —CF$_3$, —OCH$_3$, —CN, —SO$_2$CH$_3$, —SO$_2$NHR$^{4B}$, —OCF$_3$;

$R^5$ is independently oxo, halogen, —COOH, or —C(O)NR$^{5A}$R$^{5B}$;

$R^5$ is hydrogen, substituted or unsubstituted alkyl, substituted or unsubstituted cycloalkyl, —C(O)NR$^{5A}$R$^{5B}$,

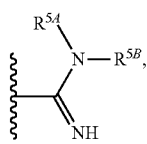

—C(N)-(substituted or unsubstituted alkyl), —C(N)-(substituted or unsubstituted cycloalkyl), —C(O)-(substituted or unsubstituted alkyl), or —C(O)-(substituted or unsubstituted cycloalkyl);

z4 and z5 are independently an integer from 0 to 2; and $R^{5A}$ and $R^{5B}$ are independently hydrogen or substituted or unsubstituted alkyl.

9. The compound of claim 1, wherein $L^2$-$R^2$ has the formula:

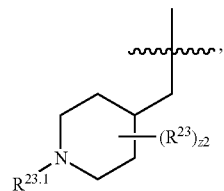

wherein $R^{23}$ is independently oxo, halogen, —CX$^{23}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{23}$$_3$, —OCHX$^{23}$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{23.1}$ is hydrogen, substituted or unsubstituted alkyl, substituted or unsubstituted cyclopropyl, —C(O)-(substituted or unsubstituted alkyl), —C(O)-(substituted or unsubstituted cyclopropyl), —C(N)-cyclopropyl; and z2 is an integer from 0 to 9.

10. The compound of claim 1, having the formula:

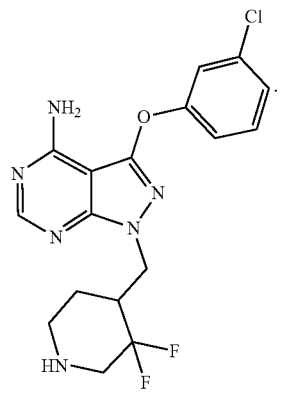 [SMILES: Nc1ncnc2c1c(Oc1cccc(Cl)c1)nn2CC1CCNCC1(F)F]

11. A pharmaceutical composition comprising a pharmaceutically acceptable excipient and a compound of claim 1, or a pharmaceutically acceptable salt thereof.

12. A method of inhibiting calcium dependent protein kinase 1 activity, said method comprising contacting the calcium dependent protein kinase 1 with an effective amount of a compound having the formula:

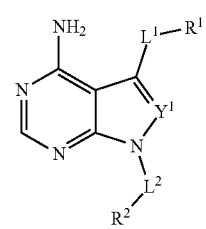

(I)

wherein,

Y¹ is —N= or —CH=;

R¹ is substituted or unsubstituted aryl or substituted or unsubstituted heteroaryl;

R² is substituted or unsubstituted heterocycloalkyl, substituted or unsubstituted heteroaryl, substituted or unsubstituted cycloalkyl, or substituted or unsubstituted alkyl;

L¹ is —O—, —S—, or —N(R³)—;

L² is a bond, substituted or unsubstituted alkylene, or substituted or unsubstituted heteroalkylene;

R³ is hydrogen, —CN, —COOH, —CX³$_3$, substituted or unsubstituted alkyl, or substituted or unsubstituted heteroalkyl; and X³ is independently halogen.

13. The method of claim 12, wherein the calcium dependent protein kinase 1 is *Toxoplasmosis gondii* calcium dependent protein kinase 1.

14. A method of treating an Apicomplexa infection, said method comprising administering to a subject in need thereof an effective amount of a compound having the formula:

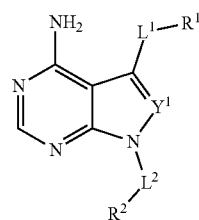

(I)

wherein,

Y¹ is —N= or —CH=;

R¹ is substituted or unsubstituted aryl or substituted or unsubstituted heteroaryl;

R² is substituted or unsubstituted heterocycloalkyl, substituted or unsubstituted heteroaryl, substituted or unsubstituted cycloalkyl, or substituted or unsubstituted alkyl;

L¹ is —O—, —S—, or —N(R³)—;

L² is a bond, substituted or unsubstituted alkylene, or substituted or unsubstituted heteroalkylene;

R³ is hydrogen, —CN, —COOH, —CX³$_3$, substituted or unsubstituted alkyl, or substituted or unsubstituted heteroalkyl; and X³ is independently halogen.

15. The method of claim 14, further comprising preventing reactivation of Apicomplexa bradyzoite stages that exist within tissue cysts.

16. The method of claim 14, wherein the Apicomplexa infection is in central nervous system.

17. The method of claim 14, wherein the compound has the formula:

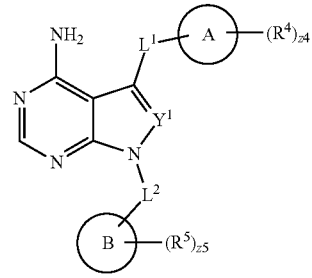

(I)

wherein,

Ring A is $C_6$-$C_{10}$ aryl or 5 to 10 membered heteroaryl;

Ring B is 3 to 7 membered heterocycloalkyl, 5 to 10 membered heteroaryl, or $C_3$-$C_8$ cycloalkyl;

R⁴ is halogen, —CX⁴$_3$, —CHX⁴$_2$, —CH$_2$X⁴, —OCX⁴$_3$, —OCH$_2$X⁴, —OCHX⁴$_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁵ is halogen, —CX⁵$_3$, —CHX⁵$_2$, —CH$_2$X⁵, —OCX⁵$_3$, —OCH$_2$X⁵, —OCHX⁵$_2$, —CN, —SO$_{n5}$R$^{5D}$, —SO$_{v5}$NR$^{5A}$R$^{5B}$, —NHC(O)NR$^{5A}$R$^{5B}$, —N(O)$_{m5}$, —NR$^{5A}$R$^{5B}$, —C(O)R$^{5C}$, —C(O)—OR$^{5C}$, —C(O)NR$^{5A}$R$^{5B}$, —OR$^{5D}$, —NR$^{5A}$SO$_2$R$^{5D}$, —NR$^{5A}$C(O)R$^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each R$^{4A}$, R$^{4B}$, R$^{4C}$, R$^{4D}$, R$^{5A}$, R$^{5B}$, R$^{5C}$, and R$^{5D}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl;

each X, X⁴, and X⁵ is independently —F, —Cl, —Br, or —I;

n4 and n5 are independently an integer from 0 to 4;

m4, m5, v4, and v5 are independently an integer from 1 to 2;

z4 is an integer from 0 to 9; and z5 is an integer from 0 to 6.

18. A method of treating an Apicomplexa associated disease, said method comprising administering to a subject in need thereof an effective amount of the compound of claim 1.

19. The method of claim 18, wherein the disease is encephalitis, schizophrenia, or toxoplasmosis.

20. The method of claim 19, further comprising co-administering pyrimethamine, a sulfonamide drug, or clindamycin.

\* \* \* \* \*